US009486541B2

(12) United States Patent
Hutton et al.

(10) Patent No.: US 9,486,541 B2
(45) Date of Patent: Nov. 8, 2016

(54) DETECTING AND TREATING DEMENTIA

(71) Applicants: Mayo Foundation for Medical Education and Research, Rochester, MN (US); VIB VZW, Ghent (BE); Universiteit Antwerpen, Antwerpen (BE); The University of British Columbia, Vancouver (CA); The University of Manchester, Manchester (GB)

(72) Inventors: Michael L. Hutton, Newton, MA (US); Matthew Charles Baker, Jacksonville, FL (US); Jennifer Mae Gass, Atlantic Beach, FL (US); Rosa Rademakers, Ponte Vedra, FL (US); Jason Eriksen, Houston, TX (US); Stuart M. Pickering-Brown, Derbyshire (GB); Ian Reid Alexander Mackenzie, Vancouver (CA); Howard Feldman, Vancouver (CA); Samir Kumar-Singh, Edegem (BE); Christine Van Broeckhoven, Edegem (BE); Marc Cruts, Antwerpen (BE); Ashley Diane Cannon, Jacksonville, FL (US)

(73) Assignees: Mayo Foundation for Medical Education and Research, Rochester, MN (US); VIB VZW, Ghent (BE); Universteit Antwerpen, Antwerp (BE); The University of British Columbia, Vancouver (CA); The University of Manchester, Manchester (GB)

( * ) Notice: Subject to any disclaimer, the term of this patent is extended or adjusted under 35 U.S.C. 154(b) by 363 days.

(21) Appl. No.: 13/932,727

(22) Filed: Jul. 1, 2013

(65) Prior Publication Data

US 2013/0345142 A1 Dec. 26, 2013

Related U.S. Application Data

(63) Continuation of application No. 12/302,691, filed as application No. PCT/US2007/070008 on May 30, 2007, now Pat. No. 8,486,635.

(60) Provisional application No. 60/848,711, filed on Oct. 2, 2006, provisional application No. 60/818,604, filed on Jul. 5, 2006, provisional application No. 60/818,601, filed on Jul. 5, 2006, provisional application No. 60/818,000, filed on Jun. 29, 2006, provisional application No. 60/809,904, filed on May 30, 2006.

(30) Foreign Application Priority Data

Jul. 4, 2006 (EP) .................... 06116589
Jul. 4, 2006 (EP) .................... 06116591

(51) Int. Cl.
*A61K 48/00* (2006.01)
*C07K 14/435* (2006.01)
*C12Q 1/68* (2006.01)

(52) U.S. Cl.
CPC .......... *A61K 48/005* (2013.01); *C07K 14/435* (2013.01); *C12Q 1/6809* (2013.01); *C12Q 1/6883* (2013.01); *C12Q 2600/118* (2013.01); *C12Q 2600/136* (2013.01); *C12Q 2600/156* (2013.01); *C12Q 2600/158* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| 5,508,167 | A | 4/1996 | Roses et al. |
|---|---|---|---|
| 5,877,399 | A | 3/1999 | Hsiao et al. |
| 5,976,872 | A | 11/1999 | Tao et al. |
| 6,066,726 | A | 5/2000 | Farb et al. |
| 6,558,668 | B2 | 5/2003 | Liau |
| 8,486,635 | B2 | 7/2013 | Hutton |
| 2002/0001586 | A1 | 1/2002 | Liau |
| 2004/0131618 | A1 | 7/2004 | Serrero |
| 2005/0069881 | A1 | 3/2005 | Poirier et al. |
| 2005/0071608 | A1 | 3/2005 | Landfield et al. |
| 2005/0074497 | A1 | 4/2005 | Schultz |
| 2005/0123962 | A1 | 6/2005 | Gan et al. |

FOREIGN PATENT DOCUMENTS

| WO | WO 99/57318 | 11/1999 |
|---|---|---|
| WO | WO 2004/047871 | 6/2004 |
| WO | WO2004078782 A1 | 9/2004 |

OTHER PUBLICATIONS

Bartus et al. Parkinson's disease gene therapy: success by design meets failure by efficacy. Molecular Therapy 22(3):487-497 (2014).*

(Continued)

*Primary Examiner* — Samuel Woolwine
(74) *Attorney, Agent, or Firm* — Fish & Richardson P.C.

(57) ABSTRACT

This document relates to methods and materials for detecting mutations that can be linked to dementia. For example, methods and materials for detecting one or more mutations within PGRN nucleic acid are provided. This document also provides methods and materials for detecting the level of progranulin expression. In addition, this document relates to methods and materials for treating mammals having a neurodegenerative disorder (e.g., dementia). For example, methods and materials for increasing PGRN polypeptide levels in mammals are provided, as are methods and materials for identifying agents that can be used to increase PGRN polypeptide levels in mammals.

6 Claims, 34 Drawing Sheets

(56) References Cited

OTHER PUBLICATIONS

Office Action in European Application No. 07840211.2, dated Oct. 2, 2013, 6 pages.
Office Action in European Application No. 07840211.2, dated Aug. 4, 2011, 6 pages.
Office Action in Japanese Application No. 2009-513441, mailed Apr. 23, 2012, 8 pages.
Huey et al., "A systematic review of neurotransmitter deficits and treatments in frontotemporal dementia," Neurology, 66(1)17-22, Jan. 10, 2006.
Qin et al., "Effects of Progranulin on Blastocyst Hatching and Subsequent Adhesion and Outgrowth in the Mouse," Biol Reprod., 73(3):434-442, Epub May 18, 2005.
European Search Report and Opinion for Application No. 13174869, mailed Dec. 20, 2013, 10 pages.
Office Action in European Application No. 13174869.1 dated May 12, 2015, 6 pages.
GenBank® Accession No. AC003043 dated Nov. 3, 2006.
GenBank® Accession No. M75161 dated Dec. 31, 1994.
GenBank® Accession No. NM_002087.2 dated Feb. 15, 2009.
GenBank® GI No. 113171578 dated Aug. 28, 2006.
GenBank® GI No. 47086537 dated Mar. 29, 2008.
GenBank® GI No. 47086569 dated Feb. 17, 2008.
GenBank® GI No. 66472848 dated Mar. 8, 2007.
GenBank® GI No. 73665551 dated Aug. 23, 2006.
GenBank® GI No. 77797837 Mar. 29, 2008.
GenBank® GI No. 6680107 dated Feb. 1, 2009.
GenPept® Accession No. NP_002078.1 (GI:4504151) dated Feb. 15, 2009.
"Clinical and neuropathological criteria for frontotemporal dementia," The Lund and Manchester Groups, *J. Neurol. Neurosurg. Psychiatry*, 1994, 57:416-418.
Abe et al., "Cognitive function in amyotrophic lateral sclerosis," *J. Neurol. Sci.*, 1997, 148:95-100.
Baines and Thorpe, "Purification of Immunoglobulin G (IgG)," *Meth. Mol. Biol.*, 1992, 10:79-104.
Baker and Manuelidis, "Unique inflammatory RNA profiles of microglia in Creutzfeldt-Jakob disease," *Proc. Natl. Acad. Sci. USA*, 2003, 100:675-679.
Baker et al., "Mutations in proguanulin cause tau-negative frontotemporal dementia linked to chromosome 17," *Nature*, 2006, 442:916-919.
Baker et al., "Association of an extended haplotype in the tau gene with progressive supranuclear palsy," *Hum. Mol. Genet.*, 1999, 8:711-715.
Barrett et al., "Haploview: analysis and visualization of LD and haplotype 2005, 21(2):263-265 maps," *Bioinformatics*, 2005, 21(2):263-265.
Bhandari et al., "Structural and functional analysis of a promoter of the human granulin/epithelin gene," *Biochem. J.*, 1996, 319:441-447.
Bhandari et al., "The Complementary Deoxyribonucleic Acid Sequence, Tissue Distribution, and Cellular Localization of the Rat Granulin Precursor," *Endocrinology*, 1993, 133(6):2682-2689.
Bird et al., "Chromosome 17 and hereditary dementia: Linkage studies in three non-Alzheimer families and kindreds with late-onset FAD," *Neurology*, 1997, 48:949-954.
Brenner et al., "Mutations in GFAP, encoding glial fibrillary acidic protein, are associated with Alexander disease," *Nat. Genet.*, 2001, 27:117-120.
Brown et al., "Familial non-specific dementia maps to chromosome 3," 4(9):1625-1628 *Hum. Mol. Genet.*, 1995, 4(9):1625-1628.
Buée and Delacourte, "Comparative Biochemistry of Tau in Progressive Supranuclear Palsy, Corticobasal Degeneration, FTDP-17 and Pick's Disease," *Brain Pathol.*, 1999, 9:681-693.
Capsoni et al., "Alzheimer-like neurodegeneration in aged antinerve growth factor transgenic mice," *Proc. Natl. Acad. Sci. USA*, 2000, 97:6826-6831.

Cartharius et al., "MatInspector and beyond: promoter analysis based on transcription factor binding sites," *Bioinformatics*, 2005, 21(13):2933-2942.
Chen et al., "Identification of a peroxisome in mouse plasminogen activator inhibitor-1 2006, 347:821-826 proliferator responsive element (PPRE)-like *cis*-element gene promoter," *Biochem. Biophys. Res. Commun.*, 2006, 347:821-826.
Cheung et al., "Granulin-epithelin precursor overexpression promotes growth and invasion of hepatocellular carcinoma," *Clin. Cancer Res.*, 2004, 10:7629-7636.
Chow et al., "Inheritance of frontotemporal dementia," *Arch. Neurol.*, 1999, 56:817-822.
Christopherson et al., "Thrombospondins Are Astrocyte-Secreted Proteins that Promote CNS Synaptogenesis," *Cell*, 2005, 120:421-433.
Cibelli et al., "Cloned Transgenic Calves Produced from Nonquiescent Fetal Fibroblasts," *Science*, 1998, 280:1256-1258.
Coligan et al., "Production of Polyclonal Antisera in Rabbits, Rats, Mice and Hamsters," *Current Protocols in Immunology*, 1992, sections 2.4.1, 2.5.1, 2.6.7, 2.7.1, 2.7.12, 2.9.1, 2.9.3, Unit 9.
Conrad et al., "Genetic evidence for the involvement of tau in progressive supranuclear palsy," *Ann. Neurol.*, 1997, 41:277-281.
Cruts et al., "Null mutations in progranulin cause ubiquitin-positive frontotemporal dementia linked to chromosome 17q21," *Nature*, 2006, 442(7105):920-924.
Cruts et al., "Genomic architecture of human 17q21 linked to frontotemporal dementia uncovers a highly homologous family of low-copy repeats in the tau region," *Hum. Mol. Genet.*, 2005, 14:1753-1762.
Czaplewski et al., "Prediction of the structures of proteins with the UNRES force field, including dynamic formation and breaking of disulfide bonds," *Protein Eng. Des. Sel.*, 2004, 17(1):29-36.
Daniel et al., "Cellular localization of gene expression for progranulin," *J. Histochem. Cytochem.*, 2000, 48:999-1009.
Daniel et al., "Progranulin (Acrogranin/PC Cell-Derived Growth Factor/Granulin-Epithelin Precursor) Is Expressed in the Placenta, Epidermis, Microvasculature, and Brain During Murine Development," *Dev. Dyn.*, 2003, 227:593-599.
Dayanandan et al., "Mutations in tau reduce its microtubule binding properties in intact cells and affect its phosphorylation," *FEBS Lett.*, 1999, 446:228-232.
De Deyn et al., "The Middelheim Frontality Score: a behavioural assessment scale that discriminates frontotemporal dementia from Alzheimer's disease," *Int. J. Geriatr. Psychiatry*, 2005, 20:70-79.
Dermaut et al., "A Novel Presenilin 1 Mutation Associated with Pick's Disease but Not β-Amyloid Plaques," *Ann. Neurol.*, 2004, 55:617-626.
Dickey et al., "Selectively reduced expression of synaptic plasticity-related genes in amyloid precursor protein + presenilin-1 transgenic mice," *J. Neurosci.*, 2003, 23:5219-5226.
Dickson, "Neurodegenerative diseases with cytoskeletal pathology: a biochemical classification," *Ann. Neurol.*, 1997, 42:541-544.
Dickson, "Neuropathology of Pick's disease," *Neurology*, 2001, 56(Suppl 4):S16-S20.
Dohna et al., "A CDE/CHR tandem element regulates cell cycle-dependent repression of *cuclin B2* transcription," *FEBS Lett.*, 2000, 484:77-81.
Dokmeci, "Ibuprofen and Alzheimer's disease," *Folia Med (Plovdiv).*, 2004, 46(2):5-10.
Dresbach et al., "Functional regions of the presynaptic cytomatrix protein Bassoon: significance for synaptic targeting and cytomatrix anchoring," *Mol. Cell. Neurosci.*, 2003, 23:279-291.
D'Souza and Schellenberg, "Determinants of 4-repeat tau expression. Coordination between enhancing and inhibitory splicing sequences for exon 10 inclusion," *J. Biol. Chem.*, 2000, 275:17700-17709.
D'Souza and Schellenberg, "tau Exon 10 expression involves a bipartite intron 10 regulatory sequence and weak 5' and 3' splice sites," *J. Biol. Chem.*, 2002, 277:26587-26599.
D'Souza et al., "Missense and silent tau gene mutations cause frontotemporal dementia with parkinsonism-chromosome 17 type, by affecting multiple alternative RNA splicing regulatory elements," *Proc. Natl. Acad. Sci. USA*, 1999, 96:5598-5603.

(56) References Cited

OTHER PUBLICATIONS

Ebneth et al., "Overexpression of Tau Protein Inhibits Kinesin-dependent Trafficking of Vesicles, Mitochondria, and Endoplasmic Reticulum: Implications for Alzheimer's Disease," *J. Cell Biol.*, 1998, 143(3):777-794.
Engelborghs et al., "Diagnostic performance of a CSF-biomarker panel in autopsy-confirmed dementia," *Neurobiol. Aging*, 2008, 29:1143-1159.
Engelborghs et al., "Dose dependent effect of APOE §4 on behavioral symptoms in frontal lobe dementia," *Neurobiol. Aging*, 2006, 27:285-292.
Engelborghs et al., "Prospective Belgian study of neurodegenerative and vascular dementia: APOE genotype effects," *J. Neurol. Neurosurg. Psychiatry*, 2003, 74:1148-1151.
Evdokimidis et al., "Frontal lobe dysfunction in amyotrophic lateral sclerosis," *J. Neurol. Sci.*, 2002, 195:25-33.
Finck and Kelly, "PGC-1 coactivators: inducible regulators of energy metabolism in health and disease," *J. Clin. Invest.*, 2006, 116(3):615-622.
Fiser and Sali, *Meth. Enzymol.*, 2003, 374:461-491.
Folstein et al., "Mini-Mental State. A Practical Method for Grading the Cognitive State of Patients for the Clinician," *J. Psychiatr. Res*, 1975, 12:189-198.
Forman et al., "Frontotemporal Dementia: Clinicopathological Correlations," *Ann. Neurol.*, 2006, 59:952-962.
Foster et al., "Frontotemporal dementia and parkinsonism linked to chromosome 17: a consensus conference. Conference Participants," *Ann Neurol.*, 1997, 41:706-715.
Froelich et al., "Mapping of a Disease Locus for Familial Rapidly Progressive Frontotemporal Dementia to Chromosome 17q12-21," *Am. J. Med. Genet.*, 1997, 74:380-385.
Gähwiler et al., "Organotypic slice cultures: a technique has come of age," *Trends Neurosci.*, 1997, 20:471-477.
Gan et al., "Multicolor "DiOlistic" Labeling of the Nervous System Using Lipophilic Dye Combinations," *Neuron*, 2000, 27:219-225.
Gass et al., "Mutations in *progranulin* are a major cause of ubiquitin-positive frontotemporal lobar degeneration," *Hum. Mol. Genet.*, 2006, 15(20):2988-3001.
Ghetti et al., "Mutations in the *Tau* gene cause frontotemporal dementia," *Brain Res. Bull.*, 1999, 50:471-472.
Ghetti et al., "Progress in Hereditary Tauopathies: A Mutation in the *Tau* Gene (G389R) Causes a Pick Disease-like Syndrome," *Ann. N Y Acad. Sci.*, 2000, 920:52-62.
Goedert et al., "Cloning and sequencing of the cDNA encoding an isoform of microtubule-associated protein tau containing four tandem repeats: differential expression of tau protein mRNAs in human brain," *EMBO J*, 1989, 8:393-399.
Goedert et al., "Multiple isoforms of human microtubule-associated protein tau: sequences and localization in neurofibrillary tangles of Alzheimer's disease," *Neuron*, 1989, 3:519-526.
Green and Manson, "Production of Polyclonal Antisera," *Immunochemical Protocols*, 1992, Manson. (ed.), pp. 1-5, Humana Press.
Greenway et al., "*ANG* mutations segregate with familial and 'sporadic' amyotrophic lateral sclerosis," *Nat. Genet.*, 2006, 38(4):411-413.
Grover et al., "5' splice site mutations in *tau* associated with the inherited dementia FTDP-17 affect stem-loop structure that regulates alternative a splicing of exon 10," *J. Biol. Chem.*, 1999, 274(21):15134-15143.
Guerreiro et al. A thorough assessment of benign genetic variability in GRN and MAPT. Human Mutation; Mutation in Brief 31 :E1126-E1140 (2010).
Guex and Peitsch, "SWISS-MODEL and the Swiss-PdbViewer: An environment for comparative protein modeling," *Electrophoresis*, 1997, 18(15):2714-2723.
Hall et al., "Relationship of Oxygen Radical-Induced Lipid Peroxidative Damage to Disease Onset and Progression in a Transgenic Model of Familial ALS," *J. Neurosci. Res.*, 1998, 53:66-77.

Hardy et al., "Genetic dissection of Alzheimer's disease and related dementias: amyloid and its relationship to tau," *Nat. Neurosci.*, 1998, 1(5):355-358.
Harlow et al., *Antibodies: A Laboratory Manual*, 1988, p. 726, Cold Spring Harbor Pub.
Hasegawa et al., "Tau proteins with FTDP-17 mutations have a reduced ability to promote microtubule assembly," *FEBS Lett.*, 1998, 437:207-210.
Hayashi et al., "Late-onset frontotemporal dementia with a novel exon 1 (Arg5His) tau gene mutation," *Ann. Neurol.*, 2002, 51:525-530.
He and Bateman, "Progranulin (granulin-epithelin precursor, PC-cell-derived growth factor, acrogranin) mediates tissue repair and tumorigenesis," *J. Mol. Med.*, 2003, 81:600-612.
He et al., "Progranulin (PC-cell-derived growth factor/acrogranin) regulates invasion and cell survival," *Cancer Res.*, 2002, 62:5590-5596.
He et al., "Progranulin is a mediator of the wound response," *Nat. Med.*, 2003, 9(2):225-229.
Henderson et al., "Apolipoprotein E4 and tau allele frequencies among Choctaw Indians," *Neurosci. Lett.*, 2002, 324:77-79.
Heneka et al., "Acute treatment with the PPARγ agonist pioglitazone and ibuprofen reduces glial inflammation and Aβ1-42 levels in APPV7171 transgenic mice," *Brain*, 2005, 128:1442-1453.
Hong et al., "Mutation-specific functional impairments in distinct tau isoforms of hereditary FTDP-17," *Science*, 1998, 282:1914-1917.
Hosler et al., "Linkage of Familial Amyotrphic Laterla Sclerosis With Frontotemporal Dementia to Chromosome 9q21-q22," *JAMA*, 2000, 284(13):1664-1669.
Houlden et al., "Corticobasal degeneration and progressive supranuclear palsy share a common tau haplotype," *Neurology*, 2001, 56:1702-1706.
Houlden et al., "Frequency of *tau* mutations in three series of non-Alzheimer's degenerative dementia," *Ann. Neurol.*, 1999, 46:243-248.
Huang et al., "*Salacia oblonga* root improves cardiac lipoid metabolism in Zucker diabetic fatty rats: Modulation of cardiac PPAR-α-mediated transcription of fatty acid metabolic genes," *Toxicol. Appl. Pharmacol*, 2006, 210:78-85.
Hudson, "Amyotrophic lateral sclerosis and its association with dementia, parkinsonism and other neurological disorders: a review," *Brain*, 1981, 104:217-247.
Hutton et al., "Association of missense and 5'-splice-site mutations in tau with the inherited dementia FTDP-17," *Nature*, 1998, 393:702-705.
Hutton, "Missense and splice site mutations in tau associated with FTDP-17: Multiple pathogenic mechanisms," *Neurology*, 2001, 56(Suppl 4):S21-S25.
Ingram and Spillantini, "*Tau* gene mutations: dissecting the pathogenesis of FTDP-17," *Trends Mol. Med.*, 2002, 8(12):555-562.
Jaradat et al., "Activation of peroxisome proliferator-activated receptor isoforms and inhibition of prostaglandin $H_2$ synthases by ibuprofen, naproxen, and indomethacin," *Biochem. Pharmacol.*, 2001, 62:1587-1595.
Jeanmougin et al., "Multiple sequence alignment with Clustal X," *Trends Biochem. Sci.*, 1998, 23(10):403-405.
Jiang et al., "Aberrant splicing of tau pre-mRNA caused by intronic mutations associated with the inherited dementia frontotemporal dementia with parkinsonism linked to chromosome 17," *Mol. Cell Biol.*, 2000, 20:4036-4048.
Jones et al., "The Granulin-Epithelin Precursor Is a Steroid-Regulated Growth Factor in Endometrial Cancer," *J. Soc. Gynecol. Investig.*, 2006, 13(4):304-311.
Kamrava et al., "Lysophosphatidic acid and endothelin-induced proliferation of ovarian cancer cell lines is mitigated by neutralization of granulin-epithelin precursor (GEP), a prosurvival factor for ovarian cancer," *Oncogene*, 2005, 24:7084-7093.
Katsuse et al., "Neurofibrillary tangle-related synaptic alterations of spinal motor neurons of P301L tau transgenic mice," *Neurosci. Lett.*, 2006, 409:95-99.
Kertesz et al., "Familial frontotemporal dementia with ubiquitin-positive, tau-negative inclusions," *Neurology*, 2000, 54:818-827.

(56) References Cited

OTHER PUBLICATIONS

Köhler and Milstein, "Continuous cultures of fused cells secreting antibody of predefined specificity," *Nature*, 1975, 256:495.

Kojo et al., "Evaluation of Human Peroxisome Proliferator-Activated Receptor (PPAR) Subtype Selectivity of a Variety of Anti-inflammatory Drugs Based on a Novel Assay for PPARδ(β)," *J. Pharmacol. Sci.*, 2003, 93:347-355.

Kruglvak and Lander, "Complete multipoint sib-pair analysis of qualitative and quantitative traits," *Am. J. Hum. Genet.*, 1995, 57:439-454.

Lander and Kruglyak, "Genetic dissection of complex traits: guidelines for interpreting and reporting linkage results," *Nat. Genet.*, 1995, 11:241-247.

Landreth, "PPARγ agonists as new therapeutic agents for the treatment of Alzheimer's disease," *Exp. Neurol.*, 2006, 199(2):245-248.

Lathrop and Lalouel, "Easy calculations of lod scores and genetic risks on small computers," *Am. J. Hum. Genet.*, 1984, 36:460-465.

Le Ber et al., "Demographic, neurological and behavioural characteristics and brain perfusion SPECT in frontal variant o f frontotemporal dementia," *Brain*, 2006, 129:3051-3065.

Le Ber et al., "Progranulin Null Mutationsin Both Sporadic and Familiar Frontotemporal Dementia," *Human Mutat.*, 2007, 28(9):846-855.

Lee et al., "Effects of Perinatal Exposure to Phthalate/Adipate Esters on Hypothalamic Gene Expression and Sexual Behavior in Rats," *J. Reprod. Dev.*, 2006, 52(3):343-352.

Lee et al., "Ginsenoside Rf, a component of ginseng, regulates lipoprotein metabolism through peroxisome proliferator-activated receptor α," *Biochem. Biophys. Res. Commun.*, 2006, 339:196-203.

Lee et al., "The microtubule binding domain of tau protein," *Neuron*, 1989, 2:1615-1624.

Leesnitzer et al., "Functional Consequences of Cysteine Modification in the Ligand Binding Sites of Peroxisome Proliferator Activated Receptors by GW9662," *Biochemistry*, 2002, 41:6640-6650.

Lehmann et al., "Peroxisome Proliferator-activated Receptors α and γ Are Activated by Indomethacin and Other Non-steroidal Anti-inflammatory Drugs," *J. Biol. Chem.*, 1997, 272(6):3406-3410.

Lendon et al., "Hereditary dysphasic disinhibition dementia: a frontotemporal dementia linked to 17q21-22," *Neurology*, 1998, 50:1546-1555.

Lewis et al., "Neurofibrillary tangles, amyotrophy and progressive motor disturbance in mimce expressing mutant (P301L) tau protein," *Nat. Genet.*, 2000, 25(4):402-405.

Li et al., "Inhibition of COXs and 5-LOX and activation of PPARs by Australian *Clematis* species (Ranunculaceae)," *J. Ethnopharmacol.*, 2006, 104:138-143.

LoPresti et al., "Functional implications for the microtubule-associated protein tau: localization in oligodendrocytes," *Proc. Natl. Acad. Sci. USA*, 1995, 92:10369-10373.

Lu and Serrero, "Inhibition of PC cell-derived growth factor (PCDGF, epithelin/granulin precursor) expression by antisense PCDGF cDNA transfection inhibits tumorigenicity of the human breast carcinoma cell line MDA-MB-468," *Proc. Natl. Acad. Sci. USA*, 2000, 97(8):3993-3998.

Lu and Serrero, "Mediation of estrogen mitogenic effect in human breast cancer MCF-7 cells by PC-cell-derived growth factor (PCDGF/granulin precursor)," *Proc. Natl. Acad. Sci. USA*, 2001, 98:142-147.

Lu and Serrero, "Stimulation of PC Cell-Derived Growth Factor (Epithelin/Granulin Precursor) Expression by Estradiol in Human Breast Cancer Cells," *Biochem. Biophys. Res. Commun.*, 1999, 256:204-207.

Mackenzie and Feldman, "Neuronal intranuclear inclusions distinguish familial FTD-MND type from sporadic cases," *Acta Neuropathol.*, 2003, 105:543-548.

Mackenzie and Feldman, "The relationship between extramotor ubiquitin-immunoreactive neuronal inclusions and dementia in motor neuron disease," *Acta Neuropathol.*, 2003, 105:98-102.

Mackenzie and Feldman, "Ubiquitin immunohistochemistry suggests classic motor neuron disease, motor neuron disease with dementia, and frontotemporal dementia of the motor neuron disease type represent a clinicopathologic spectrum," *J. Neuropathol. Exp. Neurol.*, 2005, 64:730-739.

Mackenzie et al., "The neuropathology of frontotemporal lobar degeneration caused by mutations in the progranulin gene," *Brain*, 2006, 129(Pt 11):3081-3090.

Mackenzie et al., "A family with tau-negative frontotemporal dementia and neuronal intranuclear inclusions linked to chromosome 17," *Brain*, 2006, 129(4):853-867.

Malaspina et al., "Differential expression of 14 genes in amyotrophic lateral sclerosis spinal cord detected using gridded cDNA arrays," *J. Neurochem.*, 2001, 77:132-145.

Mann et al., "Molecular classification of the dementias," *Lancet*, 2000, 355:626.

Mann, "Dementia of Frontal Type and Dementias with Subcortical Gliosis," *Brain Pathol.*, 1998, 8:325-338.

Maquat, "Nonsense-mediated mRNA decay: splicing, translation and mRNP dynamics," *Nat Rev. Mol. Cell Biol.*, 2004, 5:89-99.

McKee et al., "Regulation of expression of early growth response transcription factors in rat primary cortical neurons by extracellular ATP," *Brain Res.*, 2006, 1088:1-11.

McKhann et al., "Clinical and pathological diagnosis of frontotemporal dementia. Report of the Work Group on Frontotemporal Dementia and Pick's Disease," *Arch. Neurol.*, 2001, 58:1803-1809.

McKhann et al., "Clinical diagnosis of Alzheimer's disease: Report of the NINCDS-ADRDA Work Group under the auspices of Department of Health and Human Services Task Force on Alzheimer's Disease," *Neurology*, 1984, 34:939-944.

Møller et al., "Efficient estimation of cell volume and number using the nucleator and the dissector," *J. Microsc.*, 1990, 159 (Pt 1):61-71.

Moorefield et al., "Sp2 DNA Binding Activity and *trans*-Activation Are Negatively Regulated in Mammalian Cells," *J. Biol. Chem.*, 2004, 279(14):13911-13924.

Morita et al., "A locus on chromosome 9p confers susceptibility to ALS and frontotemporal dementia," Neurology, 2006, 66:839-844.

Nacharaju et al., "Accelerated filament formation from tau protein with specific FTDP-17 missense mutations," *FEBS Lett.*, 1999, 447:195-199.

Neary et al., "Classification and Description of Frontotemporal Dementias," *Ann. N Y Acad. Sci.*, 2000, 920:46-51.

Neary et al., "Cognitive change in motor neurone disease/amyotrophic lateral sclerosis (MND/ALS)," *J. Neurol. Sci.*, 2000, 180:15-20.

Neary et al., "Frontal lobe dementia and motor neuron disease," *J. Neurol. Neurosurg. Psychiatry*, 1990, 53:23-32.

Neary et al., "Frontotemporal lobar degeneration: a consensus on clinical diagnostic criteria," *Neurology*, 1998, 51:1546-1554.

Neumann et al., "Ubiquitinated TDP-43 in Frontotemporal Lobar Degeneration and Amyotrophic Lateral Sclerosis," *Science*, 2006, 314:130-133.

Ng and Henikoff, "Accounting for Human Polymorphisms predicted to Affect Protein Function," *Genome Res.*, 2002, 12(3):436-446.

Ng and Henikoff, "SIFT: predicting amino acid changes that affect protein function," *Nucleic Acids Res.*, 2003, 31(13):3812-3814.

Nishio and Walsh, "CCAAT displacement protein/*cut* homolog recruits G9a histone lysine methyltransferase to repress transcription," *Proc. Natl. Acad. Sci. USA*, 2004, 101(31):11257-11262.

Nishiyama et al., "Curcuminoids and Sesquiterpenoids in Turmeric (*Curcuma longa* L.) Suppress an Increase in Blood Glucose Level in Type 2 Diabetic KK-A$^y$ Mice," *J. Agric. Food Chem.*, 2005, 53:959-963.

Oddo et al., "Triple-Transgenic Model of Alzheimer's Disease with Plaques and Tangles: Intracellular Aβ and Synaptic Dysfunction," *Neuron*, 2003, 39(3):409-421.

Okamoto et al., "Ubiquitin-positive intraneuronal inclusions in the extramotor cortices of presenile dementia patients with motor neuron disease," *J. Neurol.*, 1992, 239:426-430.

(56) References Cited

OTHER PUBLICATIONS

Ong et al., "Regulation of progranulin expression in nyeloid cells," *Am J Physiol Regul Integr Comp Physiol.*, 2006, 291(6):R1602-1612

Oosthuyse et al., "Deletion of the hypoxia-response element in the vascular endothelial growth factor promoter causes motor neuron degeneration," *Nat. Genet.*, 2001, 28:131-138.

Pals et al., "Case-control study of environmental risk factors for Parkinson's disease in Belgium," *Eur. J. Epidemiol.*, 2003, 18:1133-1142.

Pickering-Brown et al., "Evidence of a Founder Effect in Families With Frontotemporal Dementia That Harbor the tau +16 Splice Mutation," *Am. J. Med. Genet.*, 2004, 125B:79-82.

Pickering-Brown et al., "Frontotemporal dementia with Pick-type histology associated with Q336R mutation in the tau gene," *Brain*, 2004, 127:1415-1426.

Pickering-Brown et al., "Inherited frontotemporal dementia in nine British families associated with intronic mutations in the tau gene," *Brain*, 2002, 125:732-751.

Pickering-Brown et al., "Pick's disease is associated with mutations in the tau gene," *Ann. Neurol.*, 2000, 48:859-867.

Pirici et al., "Characterization of Ubiquitinated Intraneuronal Inclusions in a Novel Belgian Frontotemporal Lobar Degeneration Family," *J. Neuropathol. Exp. Neurol.*, 2006, 65(3):289-301.

Pittman et al., "The structure of the tau haplotype in controls and in progressive supranuclear palsy," *Hum. Mol. Genet.*, 2004, 13:1267-1274.

Poorkaj et al., "An $R5^L$ τ Mutation in a Subject with a Progressive Supranuclear Palsy Phenotype," *Ann. Neurol.*, 2002, 52:511-516.

Poorkaj et al., "Frequency of tau gene mutations in familial and sporadic cases of non-Alzheimer dementia," *Arch. Neurol.*, 2001, 58:383-387.

Poorkaj et al., "Tau is a candidate gene for chromosome 17 frontotemporal dementia," *Ann. Neurol.*, 1998, 43:815-825.

Prince et al., "Robust and Accurate Single Nucleotide Polymorphism Genotyping by Dynamic Allele-Specific Hybridization (DASH): Design Criteria and Assay Validation," *Genome Res.*, 2001, 11(1):152-162.

Pritchard et al., "Inference of Population Structure Using Multilocus Genotype Data," *Genetics*, 2000, 155(2):945-959.

Rademakers et al., "Chromosome 17-linked Frontotemporal dementia with Ubiquitin-Positive, Tau-Negative Inclusions," *Genotype-Proteotype-Phenotype: Relationships in Neurodegenerative diseases*, 2005, Springer-Verlag, Berlin, pp. 119-139.

Rademakers et al., "Hiqh-density SNP haplotyping suggests altered regulation of tau gene expression in progressive supranuclear palsy," *Hum. Mol. Genet.*, 2005, 14:3281-3292.

Rademakers et al., "Tau negative frontal lobe dementia at 17q21: significant finemapping of the candidate region to a 4.8 cM interval," *Mol. Psychiatry*, 2002, 7:1064-1074.

Ramsden et al., "Age-Dependent Neurofibrillary Tangle Formation, Neuron Loss, and Memory Impairment in a Mouse Model of Human Tauopathy (P301L)," *J. Neurosci.*, 2005, 25:10637-10647.

Ratnavalli et al., "The prevalence of frontotemporal dementia," *Neurology*, 2002, 58:1615-1621.

Rau et al., "Screening of herbal extracts for activation of the human oeroxisome proliferator-activated receptor," *Pharmazie*, 2006, 61:952-956.

Reed et al., "Phenotypic correlations in FTDP-17," *Neurobiol. Aging*, 2001, 22:89-107.

Reumers et al., "SNPeffect v2.0: a new step in investigating the molecular phenotypic effects of human non-synonymous SNPs," *Bioinformatics*, 2006, 22(17):2183-2185.

Rizzini et al., "*Tau* Gene Mutation K257T Causes a Tauopathy Similar to Pick's Disease," *J. Neuropathol. Exp. Neurol.*, 2000, 59(11):990-1001.

Rizzu et al., "High Prevalence of Mutations in the Microtubule-Associated Protein Tau in a Population Study of Frontotemporal Dementia in the Netherlands," *Am. J. Hum. Genet.*, 1999, 64:414-421.

Rogers et al., "Behavioral and functional analysis of mouse phenotype: SHIRPA, a proposed protocol for comprehensive phenotype assessment," *Mamm. Genome*, 1997, 8:711-713.

Rosso et al., "Familial frontotemporal dementia with ubiquitin-positive inclusions is linked to chromosome 17q21-22," *Brain*, 2001, 124:1948-1957.

Rozen and Skaletsky, "Primer3 on the WWW for General Users and for Biologist Programmers," *Meth. Mol. Biol.*, 2000, 132:365-386.

Salehi et al., "Alzheimer's disease and NGF signaling," *J. Neural Transm.*, 2004, 111:323-345.

Sambrook et al., *Molecular Cloning, A Laboratory Manual*, 1989, second edition, Section 9.37-9.52, Cold Spring Harbor Press, Plainview, NY.

SantaCruz et al., "Tau Suppression in a Neurodegenerative Mouse Model Improves Memory Function," *Science*, 2005, 309(5733):476-481.

Schachtrup et al., "Functional analysis of peroxisome-proliferator-responsive element motifs in genes of fatty acid-binding proteins," *Biochem. J.*, 2004, 382:239-245.

Schafer et al., "DNA variation and the future of human genetics," *Nat. Biotechnol.*, 1998, 15:33-39.

Schaid et al., "Score Tests for Association between Traits and Haplotypes when Linkage Phase is Ambiguous," *Am. J. Hum. Genet.*, 2002, 70(2):425-434.

Schymkowitz et al., "The FoldX web server: an online force field," *Nucleic Acids Res.*, 2005, 33(Web Server issue):W382-W388.

Short et al., "Differences in tau and apolipoprotein E polymorphism frequencies in sporadic frontotemporal lobar degeneration syndromes," *Arch Neurol.*, 2002, 59:611-615.

Siegel and Chauhan, "Neurotrophic factors in Alzheimer's and Parkinson's disease brain," *Brain Res. Rev.*, 2000, 33:199-227.

Skibinski et al., "Mutations in the endosomal ESCRTIII-complex subunit CHMP2B in frontotemporal dementia," *Nat. Genet.*, 2005, 37(8):806-808.

Skipper et al., "Linkage disequilibrium and association of MAPT H1 in Parkinson disease," *Am. J. Hum. Genet.*, 2004, 75:2005:669-677.

Sleegers et al., "*APP* duplication is sufficient to cause early onset Alzheimer's dementia with cerebral amyloid angiopathy," *Brain*, 2006, 129:2977-2983.

Snowden et al., "Frontotemporal dementia," *Br. J. Psychiatry*, 2002, 180:140-143.

Sobel and Lange, "Descent graphs in pedigree analysis: applications to haplotyping, location scores, and marker-sharing statistics," *Am. J. Hum. Genet.*, 1996, 58:1323-1337.

Spillantini and Goedert, "Tau gene mutations and tau pathology in frontotemporal dementia and parkinsonism linked to chromosome 17," *Neuropathology and Genetics of Dementia.*, 2001, 487:21-37.

Spillantini and Goedert, "Tau protein pathology in neurodegenerative diseases," *Trends Neurosci.*, 1998, 21:428-334.

Spillantini et al., "Frontotemporal dementia and Parkinsonism linked to chromosome 17: a new group of tauopathies," *Brain Pathol.*, 1998, 8:387-402.

Spillantini et al., "Mutation in the tau gene in familial multiple system tauopathy with presenile dementia," *Proc. Natl. Acad. Sci. USA*, 1998, 95:7737-7741.

Spillantini et al., "Tau pathology in two Dutch families with mutations in the microtubule-binding region of tau," *Am. J. Pathol.*, 1998, 153:1359-6313.

Stanford et al., "Mutations in the tau gene that cause an increase in three repeat tau and frontotemporal dementia," *Brain*, 2003, 126:814-826.

Stefansson et al., "A common inversion under selection in Europeans," *Nat. Genet.*, 2005, 37(2):129-137.

Steinbach et al., "Overexpression of PAX5 is not sufficient for neoplastic transformation of mouse neuroectoderm," *Int. J. Cancer*, 2001, 93:459-467.

Stevens et al., "Familial aggregation in frontotemporal dementia," *Neurology*, 1998, 50:1541-1545.

Stoneking et al., "Population variation of Human mtDNA Control Region Sequences Detected by Enzymatic Amplification and sequence-Specific Oligonucleotide Probes," *Am. J. Hum. Genet.*, 1991, 48:370-382.

(56) References Cited

OTHER PUBLICATIONS

Suls et al., "Microdeletions Involving the *SCN1A* Gene May Be Common in *SCN1A*-Mutation-Negative SMEI Patients," *Hum. Mutat.*, 2006, 27(9):914-920.

Suzuki and Nishiahara, "Granulin Precursor Gene: A Sex Steroid-Inducible Gene Involved in Sexual Differentiation of the Rat Brain," *Mol. Genet. Metab.*, 2002, 75:31-37.

Suzuki et al., "Identification of a sex steroid-inducible gene in the neonatal rat hypothalamus," *Neurosci. Lett.*, 1998, 242(3):127-130.

Suzuki et al., "Induction of granulin precursor gene expression by estrogen treatment in neonatal rat hypothalamus," *Neurosci. Lett.*, 2001, 297(3):199-202.

Suzuki et al., "Suppression of copulatory behavior by intracerebroventricular infusion of antisense oligodeoxynucleotide of granulin in neonatal male rats," *Physiol. Behav.*, 2000, 68(5):707-713.

Talbot et al., "Inter-relation between "classic" motor neuron disease and frontotemporal dementia: neuropsychological and single photon emission computed tomography study," *J Neurol Neurosurg Psychiatry*, 1995, 58:541-547.

Tangkeangsirisin and Serrero, "PC cell-derived growth factor (PCDGF/GP88, progranulin)stimulates migration, invasiveness and VEGF expression in breast cancer cells," *Carcinogenesis*, 2004, 25:1587-1592.

Taniguchi et al., "The neuropathology of frontotemporal lobar degeneration with respect to the cytological and biochemical characteristics of tau protein," *Neuropathol. Appl. Neurobiol.*, 2004, 30:1-18.

Tolkatchev et al., "Design and Solution Structure of a Well-Folded Stack of Two β-Hairpins Based on the Amino-Terminal Fragment of Human Granulin A," *Biochemistry*, 2000, 39(11):2878-2886.

Tolnay and Probst, "Frontotemporal lobar degeneration—tau as a pied piper?" *Neurogenetics*, 2002, 4:63-75.

Trojanowski and Dickson, "Update on the Neuropathological Diagnosis of Frontotemporal Dementias," *J. Neuropathol. Exp. Neurol.*, 2001, 60(12):1123-1126.

Ulrich et al., "Peroxisome Proliferator-Activated Receptor γ as a Molecular Target of Resveratrol-Induced Modulation of Polyamine Metabolism," *Cancer Res.*, 2006, 66(14):7348-7354.

Underhill et al., "Detection of Numerous Y chromosome Biallelic Polymorphisms by Denaturing High-Performance Liquid Chromatography," *Genome Res.*, 1997, 7:996-1005.

van der Zee et al., "A Belgian ancestral haplotype harbours a highly prevalent mutation for 17q21-linked tau-negative FTLD," *Brain*, 2006, 129:841-852.

van der Zee et al., "Mutations Other Than Null Mutations Producing a Pathogenic Loss of Progranulin in Frontotemporal Dementia," *Hum. Mutat.*, 2007, 28:416.

Vance et al., "Familial amyotrophic lateral sclerosis with frontotemporal dementia is linked to a locus on chromosome 9p13.2-21.3," *Brain*, 2006, 129:868-876.

Vardy et al., "Emerging therapeutics for Alzheimer's disease," *Expert Rev. Neurother.*, 2006, 6:695-704.

Vinciguerra and Stutz, "mRNA export: an assembly line from genes to nuclear pores," *Curr. Opin. Cell Biol.*, 2004, 16:285-292.

Wakayama et al., "Full-term development of mice from enucleated oocytes injected with cumulus cell nuclei," *Nature*, 1998, 394(6691):369-374.

Wallner and Elofsson, "Can correct protein models be identified?" *Protein Sci.*, 2003, 12(5):1073-1086.

Wang et al., "PC Cell-Derived Growth Factor Confers Resistance to Dexamethasone and Promotes Tumorigenesis in Human Multiple Myeloma," *Clin. Cancer Res.*, 2006, 12(1):49-56.

Weckx et al., "novoSNP, a novel computational tool for sequence variation discovery," *Genome. Res.*, 2005, 15:436-442.

Wheeler et al., "Database resources of the National Center for Biotechnology Information: update," *Nucleic Acids Res.*, 2004, 32 Database issue:D35-D40.

Wheeler et al., "Database resources of the National Center for Biotechnology Information," *Nucleic. Acids Res.*, 2006, 34(Database issue):D173-D180.

Wilhelmsen, "Disinhibition-Dementia-Parkinsonism-Amyotrophy Complex (DDPAC) is a non-Alzheimer's frontotemporal dementia," *J. Neural. Transm. Suppl.*, 1997, 49:269-275.

Wilmut et al., "Viable offspring derived from fetal and adult mammalian cells," *Nature*, 1997, 385(6619):810-813.

Wong et al., "A Comprehensive Analysis of Common Copy-Number Variations in the Human Genome," *Am. J. Hum. Genet.*, 2007, 80:91-104.

Woulfe et al., "Frontotemporal dementia with ubiquitinated cytoplasmic and intranuclear inclusions," *Acta Neuropathol.*, 2001, 102:94-102.

Xia et al., "Anthocyanins Induce Cholesterol Efflux from Mouse Peritoneal Macrophages," *J. Biol. Chem.*, 2005, 280:36792-36801.

Xiang et al., "Long-term maintenance of mature hippocampal slices in vitro," *J. Neurosci. Meth.*, 2000, 98:145-154.

Zanocco-Marani et al., "Biological activities and signaling pathways of the granulin/epithelin precursor," *Cancer Res.*, 1999, 59:5331-5340.

Zhukareva et al., "Loss of brain tau defines novel sporadic and familial tauopathies with frontotemporal dementia," *Ann. Neurol.*, 2001, 49:165-175.

Zhukareva et al., "Selective reduction of soluble Tau proteins in sporadic and familial frontotemporal dementias: an international follow-up study," *Acta Neuropathol.*, 2003, 105:469-476.

Zhukareva et al., "Sporadic Pick's disease: a tauopathy characterized by a spectrum of pathological τ isoforms in gray and white matter," *Ann. Neurol.*, 2002, 51:730-739.

European Search Report for Application No. 07840211.2, dated May 27, 2010, 7 pages.

International Preliminary Report on Patentability for PCT/US2007/070008, issued Dec. 3, 2008, 7 pages.

International Search Report for PCT/US2007/070008, mailed Mar. 4, 2008, 11 pages.

Capell et al., "Rescue of progranulin deficiency associated with frontotemporal lobar degeneration by alkalizing reagents and inhibition of vacuolar ATPase," *J Neurosci.*, 31(5):1885-1894, Feb. 2, 2011.

Lee et al., "Targeted manipulation of the sortilin-progranulin axis rescues progranulin haploinsufficiency," Hum Mol Genet., 23(6):1467-1478, Epub Oct. 26, 2013.

Raitano et al., "Restoration of progranulin expression rescues cortical neuron generation in an induced pluripotent stem cell model of frontotemporal dementia," Stem Cell Reports., 4(1):16-24. Epub Dec. 31, 2014.

Van Kampen et al., "Progranulin gene delivery protects dopaminergic neurons in a mouse model of Parkinson's disease," PLoS One., 9(5):e97032, May 7, 2014.

\* cited by examiner

Figure 3
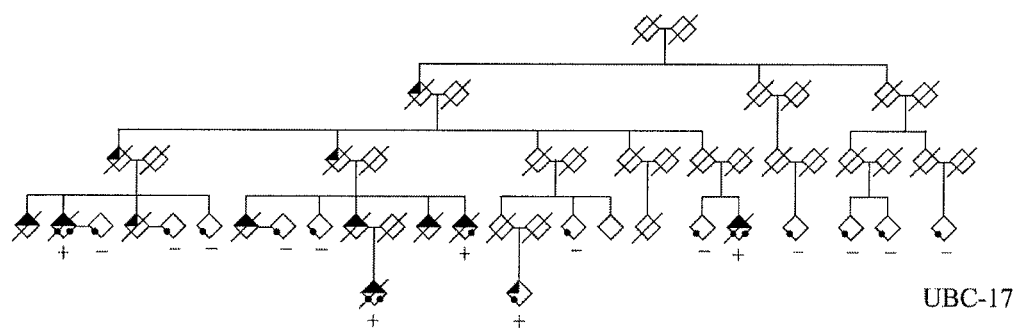
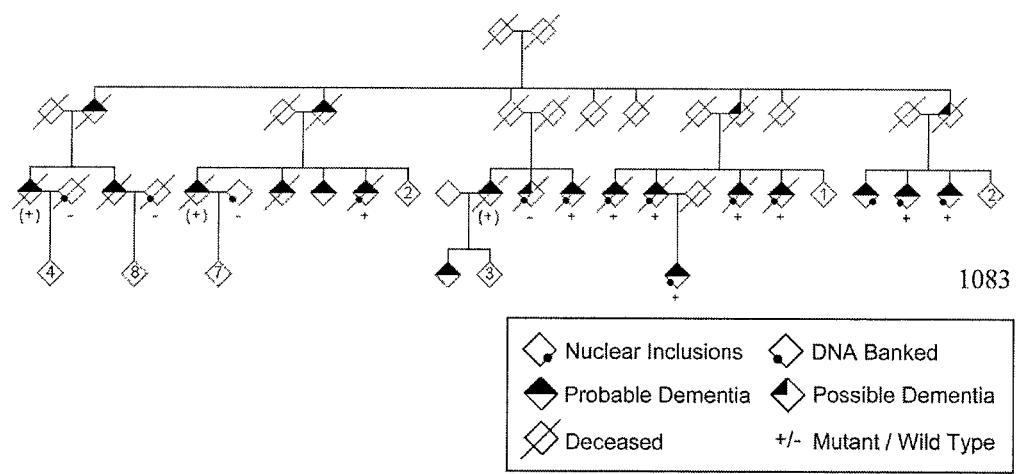

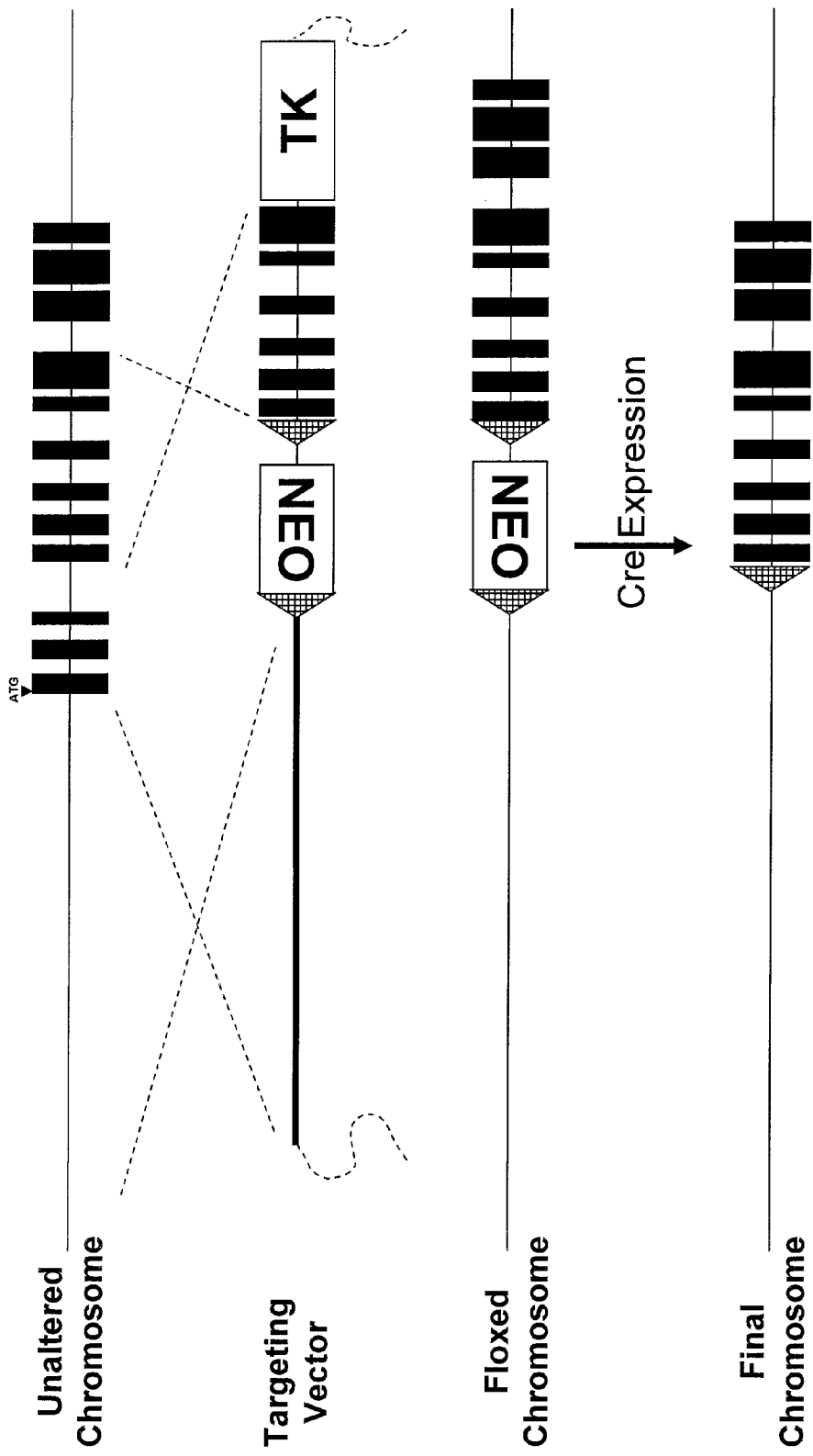

Figure 10

MWTLVSWVALTAGLVAGTRCPDGQFCPVACCLDPGGASYSCCRPLLDKWPTTLSRHLGGPCQVDAHCSAGH
SCIFTVSGTSSCCPFPEAVACGDGHHCCPRGFHCSADGRSCFQRSGNNSVGAIQCPDSQFECPDFSTCCVM
VDGSWGCCPMPQASCCEDRVHCCPHGAFCDLVHTRCITPTGTHPLAKKLPAQRTNRAVALSSSVMCPDARS
RCPDGSTCCELPSGKYGCCPMPNATCCSDHLHCCPQDTVCDLIQSKCLSKENATTDLLTKLPAHTVGDVKC
DMEVSCPDGYTCCRLQSGAWGCCPFTQAVCCEDHIHCCPAGFTCDTQKGTCEQGPHQVPWMEKAPAHLSLP
DPQALKRDVPCDNVSSCPSSDTCCQLTSGEWGCCPIPEAVCCSDHQHCCPQRYTCVAEGQCQRGSEIVAGL
EKMPARRGSLSHPRDIGCDQHTSCPVGGTCCPSQGGSWACCQLPHAVCCEDRQHCCPAGYTCNVKARSCEK
EVVSAQPATFLARSPHVGVKDVECGEGHFCHDNQTCCRDNRQGWACCPYAQGVCCADRRHCCPAGFRCARR
GTKCLRREAPRWDAPLRDPALRQLL
(SEQ ID NO:1)

```
cgcaggcaga ccatgtggac cctggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgcccttc ccagaggccg tggcatgcgg ggatggccat
cactgctgcc cacggggctt ccactgcagt gcagacgggc gatcctgctt ccaaagatca
ggtaacaact ccgtgggtgc catccagtgc cctgatagtc agttcgaatg cccggacttc
tccacgtgct gtgttatggt cgatggctcc tggggtgct gccccatgcc ccaggcttcc
tgctgtgaag acagggtgca ctgctgtccg cacggtgcct tctgcgacct ggttcacacc
cgctgcatca cacccacggg caccccaccc ctggcaaaga agctccctgc ccagaggact
aacagggcag tggccttgtc cagctcggtc atgtgtccgg acgcacggtc ccgtgccct
gatggttcta cctgctgtga gctgccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctataccctgc
tgccgtctac agtcgggggc ctggggctgc tgccctttta cccaggctgt gtgctgtgag
gaccacatac actgctgtcc cgcgggggttt acgtgtgaca cgcagaaggg tacctgtgaa
cagggggcccc accaggtgcc ctggatggag aaggcccag ctcacctcag cctgccagac
ccacaagcct tgaagagaga tgtccctgt gataatgtca gcagctgtcc ctcctccgat
acctgctgcc aactcacgtc tggggagtgg ggctgctgtc caatcccaga ggctgtctgc
tgctcggacc accagcactg ctgccccag cgatacacgt gtgtagctga ggggcagtgt
cagcgaggaa gcgagatcgt ggctggactg gagaagatgc ctgcccgccg cggttcctta
tcccaccccca gagacatcgg ctgtgaccag cacaccagct gcccggtggg cggaacctgc
tgcccgagcc agggtgggag ctgggcctgc tgccagttgc cccatgctgt gtgctgcgag
gatcgccagc actgctgccc ggctggctac acctcaacg tgaaggctcg atcctgcgag
aaggaagtgg tctctgccca gcctgccacc ttcctggccc gtagccctca cgtgggtgtg
aaggacgtgg agtgtggga aggacacttc tgccatgata accagacctg ctgccgagac
aaccgacagg gctgggcctg ctgtccctac gccagggcg tctgttgtgc tgatcggcgc
cactgctgtc ctgctggctt ccgctgcgca cgcagggta ccaagtgttt gcgcagggag
gccccgcgct gggacgcccc tttgagggac ccagccttga gacagctgct gtgagggaca
gtactgaaga ctctgcagcc ctcgggaccc cactcggagg gtgccctctg ctcaggcctc
cctagcacct ccccctaacc aaattctccc tggaccccat tctgagctcc ccatcaccat
gggaggtggg gcctcaatct aaggcccttc cctgtcagaa ggggttgag gcaaaagccc
attacaagct gccatcccct ccccgtttca gtggaccctg tggccaggtg cttttcccta
tccacagggg tgtttgtgtg ttgggtgtgc tttcaataaa gtttgtcact ttctt
(SEQ ID NO:2)
```

Figure 11A

```
N-terminal    MWTLVSWVALTAGLVAG
Paragranulin  TRCPDGQF--CPVA---CCLDPGGASYSCCRPLLDKWPTTLSRHLG
Granulin G    GPC-QVDAHCSAGHSCIFTVSG-TSSCCPFPEAVACGDGHHCCPRGFHCSADGRSCFQRSGNNSVGA
Granulin F    IQCPDSQFECCPDFSTCCELPSG-KYGCCPMPQAS-SWGCCPMPQASCCEDRVHCCPHGAFCCDLVHTRCITPTGTHPLAKKLPAQRTNRAVALSSS
Granulin B    VMCPDARSRQPDGSTCCELPSG-KYGCCPMPNATCSDHLHCCPQDTVCDLIQSKELSKENATTDLLTKLPAHTVGD
Granulin A    VKC-DMEVSCPDGYTCCRLQSG-AWGCCPFTQAVCCEDHIHCCPAGFTCDTQKGIEQGPHQVPWMEKAPAHLSLPDPQALKRD
Granulin C    VPC-DNVSSCPSSDTCCQLTSG-EWGCCPIPEAVCCSDHQHCCPQRYTCVAEG-QCRGSEIVAGLEKMPARASLSHPRD
Granulin D    IGC-DQHTSCPVGQTCCPSLGG-SWACCQLPHAVCCEDRQHCCPAGYTCNVKARSCEKEVVSAQPATFLARSPHYGVKD
Granulin E    VECGEGHF-CHDNQTCCRDNRQ-GWACCPYRQGVCCADRRHCCPAGFRCAARGTKCLRREAPRWDAPLRDALRQLL
```

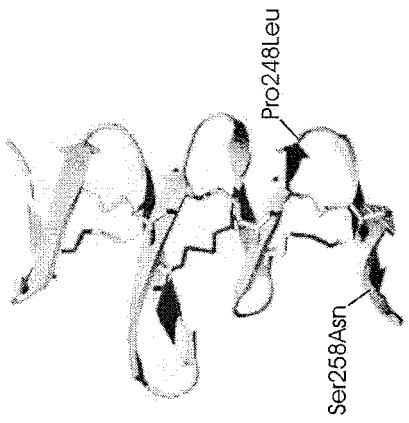

Figure 11B

Pro248Leu

Ser258Asn

DETECTING AND TREATING DEMENTIA

CROSS-REFERENCE TO RELATED APPLICATIONS

This application is a continuation application of U.S. application Ser. No. 12/302,691, filed Dec. 15, 2009 (now U.S. Pat. No. 8,486,635), which is a National Stage application under 35 U.S.C. §371 of International Application No. PCT/US2007/070008 having an International Filing Date of May 30, 2007, which claims the benefit of priority of European Patent Application Nos. 06116591.6 and 06116589.0 having filing dates of Jul. 4, 2006, and claiming the benefit of U.S. Provisional Application Ser. No. 60/848,711, filed Oct. 2, 2006; U.S. Provisional Application Ser. No. 60/818,604, filed Jul. 5, 2006; U.S. Provisional Application Ser. No. 60/818,601, filed Jul. 5, 2006; U.S. Provisional Application Ser. No. 60/818,000, filed Jun. 29, 2006; and U.S. Provisional Application Ser. No. 60/809,904, filed May 30, 2006.

STATEMENT AS TO FEDERALLY SPONSORED RESEARCH

This invention was made with government support under AG026251 and AG016574 awarded by National Institutes of Health. The government has certain rights in the invention.

BACKGROUND

1. Technical Field

This document relates to methods and materials involved in detecting mutations linked to dementia (e.g., frontotemporal dementia) as well as methods and materials involved in detecting reduced progranulin expression. This document also relates to methods and materials involved in treating mammals having or being susceptible to developing neurodegenerative disorders (e.g., frontotemporal dementia). For example, this document relates to methods and materials involved in using a nucleic acid encoding a progranulin polypeptide or an agent that increases progranulin polypeptide levels to treat a mammal (e.g., human) having a neurodegenerative disorder.

2. Background Information

Frontotemporal dementia (FTD) is the second most common cause of dementia in people under 65 years (Clinical and neuropathological criteria for frontotemporal dementia. The Lund and Manchester Groups. *J. Neurol. Neurosurg. Psychiatry,* 57:416-8 (1994)). A large proportion of FTD patients (35-50%) have a family history of dementia consistent with a strong genetic component to the disease (Chow et al., *Arch. Neurol.,* 56:817-22 (1999); Stevens et al., *Neurology,* 50:1541-5 (1998); and Mann, *Brain Pathol.,* 8:325-38 (1998)). Mutations in the gene encoding the microtubule associated protein tau (MAPT) were shown to cause familial FTD with Parkinsonism linked to chromosome 17q21 (FTDP-17; Hutton et al., *Nature,* 393:702-5 (1998)). The neuropathology of patients with defined MAPT mutations is characterized by the presence of cytoplasmic neurofibrillary inclusions composed of hyperphosphorylated tau (Hutton et al., *Nature,* 393:702-5 (1998) and Ghetti et al., *Brain Res. Bull.,* 50:471-2 (1999)).

In an increasing number of FTD families with significant evidence for linkage to the same region on chromosome 17q21 (D17S1787-D17S806), the disease can not be explained by mutations in MAPT, and patients also consistently lack tau-immunoreactive inclusion pathology (Rademakers et al., *Mol. Psychiatry,* 7:1064-74 (2002); Rosso et al., *Brain,* 124:1948-57 (2001); Lendon et al., *Neurology,* 50:1546-55 (1998); Kertesz et al., *Neurology,* 54:818-27 (2000); Froelich et al., *Am. J. Med. Genet.,* 74:380-5 (1997); Bird et al., *Neurology,* 48:949-54 (1997); and Rademakers et al., (ed. Cummings, J. L. e.) 119-139 (Springer-Verlag, Berlin, 2005)). In contrast, tau-negative FTD-17 patients have ubiquitin-immunoreactive (ub-ir) neuronal cytoplasmic inclusions (NCI) and characteristically lentiform ub-ir neuronal intranuclear inclusions (NII; Rademakers et al., (ed. Cummings, J. L. e.) 119-139 (Springer-Verlag, Berlin, 2005)).

SUMMARY

This document relates to methods and materials for detecting mutations that are linked to dementia. The methods and materials provided herein are based, in part, on the discovery that mutations within progranulin (PGRN) nucleic acid are linked to dementia (e.g., FTD). The human PGRN gene is located at chromosome 17q21, and its coding sequence is available at GenBank® Accession Number M75161 (GI:183612). The PGRN gene is also known as epithelin precursor, proepithelin, PEPI, acrogranin, and granulin. A PGRN gene can have 12 exons that together can encode a polypeptide with a molecular weight of 68.5 kDa. Granulins form a family of cysteine-rich polypeptides, some of which have growth modulatory activity. The widespread occurrence of PGRN mRNA in cells from the hematopoietic system and in epithelia implies functions in these tissues. At least four different human granulin polypeptides can be processed from a single PGRN precursor which can contain 7.5 repeats that each contain 12 conserved cysteine residues. Both the PGRN precursor and processed PGRN polypeptides can have biological activity. The term "PGRN polypeptide" as used herein includes, without limitation, human PGRN polypeptides (e.g., human PGRN polypeptides set forth in GenBank® under GI numbers 183612, 4504151, and 77416865), mouse PGRN polypeptides (e.g., the mouse PGRN polypeptide set forth in GenBank® under GI number 6680107), zebrafish PGRN polypeptides (e.g., zebrafish PGRN polypeptides set forth in GenBank® under GI numbers 66472848, 77797837, 47086569, and 47086537), and fish PGRN polypeptides (e.g., Mozambique tilapia PGRN polypeptides set forth in GenBank® under GI numbers 113171578 and 73665551), as well as fragments thereof that are at least 40 amino acids in length such as granulin A, granulin B, granulin C, granulin D, granulin E, granulin F, granulin G, and granulin P. A human progranulin polypeptide can be a 593-amino acid glycosylated polypeptide having a consensus sequence that is repeated seven and a half times.

This document provides methods and materials for detecting PGRN nucleic acid containing one or more mutations that can be linked to dementia. For example, standard PCR techniques can be used to amplify a fragment of a patient's PGRN nucleic acid. The amplified fragment can be sequenced or probed using standard techniques to determine whether or not the fragment contains one or more mutations such as a truncation mutation. Detecting such mutations can allow clinicians to assess patients for disease risk and plan treatment options for the patient.

This document also provides methods and materials for detecting the level of PGRN expression. As described herein, a mammal having reduced levels of PGRN mRNA or PGRN polypeptide expression can be identified as having or as being likely to develop dementia.

This document also relates to methods and materials for treating a mammal having or being likely to develop a neurodegenerative disorder (e.g., dementia). For example, this document relates to methods and materials for treating a neurodegenerative disorder in a mammal by administering a nucleic acid encoding a PGRN polypeptide to the mammal such that the level of a PGRN polypeptide is increased in the mammal. This document also relates to methods and materials for treating a neurodegenerative disorder in a mammal using an agent such as a non-steroidal anti-inflammatory drug (NSAID) or a PPAR agonist or a combination of such agents. While not being limited to any particular mode of action, administering an agent such as an NSAID or a PPAR agonist to a mammal can treat neurodegeneration, as described herein, by producing an increased level of a progranulin (PGRN) polypeptide in the mammal. Having the ability to treat neurodegenerative disorders can help clinicians reduce the considerable morbidity and mortality associated with such disorders, and can also reduce health care expenditures. Methods and materials for identifying agents that can be used to treat neurodegenerative disorders as well as non-human models of dementia also are provided herein.

In general, one aspect of this document features a method for diagnosing dementia in a mammal suspected of having dementia. The method comprises, or consists essentially of, determining whether or not the mammal comprises PGRN nucleic acid containing a mutation, where the presence of the PGRN nucleic acid containing a mutation indicates that the mammal has dementia. The mammal can be a human. The dementia can be frontotemporal lobar degeneration. The dementia can be frontotemporal dementia. The PGRN nucleic acid can encode a sequence of a PGRN polypeptide. The PGRN nucleic acid can be a cis-acting regulatory element that regulates expression of a PGRN polypeptide. The mutation can be a nucleotide addition. The mutation can be a nucleotide deletion. The mutation can be a nucleotide substitution. The mutation can cause reduced expression of a PGRN polypeptide in the mammal. The mammal can be a human, and the mutation can cause expression of a PGRN polypeptide having the amino acid sequence set forth in SEQ ID NO:1 while containing at least one mutation in the amino acid sequence. The PGRN polypeptide can be shorter than 593 amino acid residues in length. The mutation can cause expression of a truncated PGRN polypeptide in the mammal.

In another aspect, this document features a method for classifying a mammal as being at risk of developing dementia. The method comprises, or consists essentially of, determining whether or not a mammal comprises PGRN nucleic acid containing a mutation, where the presence of the PGRN nucleic acid containing a mutation indicates that the mammal is at risk of developing dementia. The mammal can be a human. The dementia can be frontotemporal lobar degeneration. The dementia can be frontotemporal dementia. The PGRN nucleic acid can encode a sequence of a PGRN polypeptide. The PGRN nucleic acid can be a cis-acting regulatory element that regulates expression of a PGRN polypeptide. The mutation can be a nucleotide addition. The mutation can be a nucleotide deletion. The mutation can be a nucleotide substitution. The mutation can cause reduced expression of a PGRN polypeptide in the mammal. The mammal can be a human, and the mutation can cause expression of a PGRN polypeptide having the amino acid sequence set forth in SEQ ID NO:1 while containing at least one mutation in the amino acid sequence. The PGRN polypeptide can be shorter than 593 amino acid residues in length. The mutation can cause expression of a truncated PGRN polypeptide in the mammal.

In another aspect, this document features a method for diagnosing dementia in a mammal suspected of having dementia. The method comprises, or consists essentially of, determining whether or not the mammal comprises a reduced level of a PGRN polypeptide or a PGRN mRNA, where the presence of the reduced level indicates that the mammal has dementia. The mammal can be a human. The dementia can be frontotemporal lobar degeneration. The dementia can be frontotemporal dementia. The mammal can be a human, and the PGRN polypeptide can comprise the amino acid sequence set forth in SEQ ID NO:1. The method can comprise determining whether or not the mammal comprises a reduced level of a PGRN polypeptide. The method can comprise determining whether or not the mammal comprises a reduced level of a PGRN mRNA.

In another aspect, this document features a method for classifying a mammal as being at risk of developing dementia. The method comprises, or consists essentially of, determining whether or not a mammal comprises a reduced level of a PGRN polypeptide or a PGRN mRNA, where the presence of the reduced level indicates that the mammal is at risk of developing dementia. The mammal can be a human. The dementia can be frontotemporal lobar degeneration. The dementia can be frontotemporal dementia. The mammal can be a human, and the PGRN polypeptide can comprise the amino acid sequence set forth in SEQ ID NO:1. The method can comprise determining whether or not the mammal comprises a reduced level of a PGRN polypeptide. The method can comprise determining whether or not the mammal comprises a reduced level of a PGRN mRNA.

In another aspect, this document features an isolated nucleic acid molecule. The isolated nucleic acid molecule comprises, or consists essentially of, a nucleic acid sequence that encodes at least ten contiguous amino acids set forth in SEQ ID NO:1 provided that the at least ten contiguous amino acids contains at least one mutation with respect to the sequence set forth in SEQ ID NO:1, where the isolated nucleic acid molecule is at least 30 nucleotides in length. The isolated nucleic acid molecule can result from a polymerase chain reaction. The isolated nucleic acid molecule can be DNA. The nucleic acid sequence can encode at least 20 contiguous amino acids set forth in SEQ ID NO:1 provided that the at least 20 contiguous amino acids contains at least one mutation with respect to the sequence set forth in SEQ ID NO:1. The nucleic acid sequence can encode at least 40 contiguous amino acids set forth in SEQ ID NO:1 provided that the at least 40 contiguous amino acids contains at least one mutation with respect to the sequence set forth in SEQ ID NO:1. The isolated nucleic acid molecule can be at least 50 nucleotides in length. The isolated nucleic acid molecule can be at least 100 nucleotides in length. The mutation can be an amino acid substitution.

In another aspect, this document features an isolated nucleic acid molecule. The isolated nucleic acid molecule comprises, or consists essentially of, a nucleic acid sequence having at least 15 contiguous nucleotides set forth in SEQ ID NO:2 provided that the at least 15 contiguous nucleotides contains at least one mutation with respect to the sequence set forth in SEQ ID NO:2. The isolated nucleic acid molecule can result from a polymerase chain reaction. The isolated nucleic acid molecule can be DNA. The nucleic acid sequence can comprise at least 25 contiguous nucleotides set forth in SEQ ID NO:2 provided that the at least 25 contiguous nucleotides contains at least one mutation with respect to the sequence set forth in SEQ ID NO:2. The nucleic acid sequence can comprise at least 50 contiguous nucleotides set forth in SEQ ID NO:2 provided that the at least 50 contiguous nucleotides contains at least one mutation with respect to the sequence set forth in SEQ ID NO:2. The isolated nucleic acid molecule can be at least 50 nucleotides in length. The isolated nucleic acid molecule can be at least 100 nucleotides in length. The mutation can be a nucleotide addition. The mutation can be a nucleotide deletion. The mutation can be a nucleotide substitution. The mutation, when present within an endogenous PGRN nucleic acid within a mammal, can cause reduced expression of a PGRN polypeptide in the mammal. The mutation, when present within an endogenous PGRN nucleic acid within a human, can cause expression of a PGRN polypeptide having the amino acid sequence set forth in SEQ ID NO:1 while containing at least one mutation in the amino acid sequence.

In another aspect, this document features a method for treating a mammal having a neurodegenerative disorder or suspected to develop the neurodegenerative disorder. The method comprises, or consists essentially of, administering, to the mammal, a PGRN polypeptide or a nucleic acid comprising a nucleic acid sequence that encodes the PGRN polypeptide. The mammal can be a human. The mammal can have a neurodegenerative disorder. The PGRN polypeptide or the nucleic acid can be administered to the mammal under conditions where a symptom of the neurodegenerative disorder improves. The symptom can improve by at least 25 percent. The mammal can be suspected to develop the neurodegenerative disorder. The PGRN polypeptide or the nucleic acid can be administered to the mammal under conditions where the onset of symptoms of the neurodegenerative disorder is delayed. The onset can be delayed at least five years. The neurodegenerative disorder can be selected from the group consisting of frontotemporal dementia, Alzheimer's disease, and motor neuron disease. The method can comprise administering the PGRN polypeptide to the mammal. The PGRN polypeptide can comprise the amino acid sequence set forth in SEQ ID NO:1. The method can comprise administering the nucleic acid to the mammal. The nucleic acid can comprise the nucleotide sequence set forth in SEQ ID NO:2. The PGRN polypeptide can comprise the amino acid sequence set forth in SEQ ID NO:1. The nucleic acid can be administered using a viral vector. The viral vector can be selected from the group consisting of an adeno-associated virus vector, a lentivirus vector, and an adenovirus vector.

In another aspect, this document features a method for treating a mammal having a neurodegenerative disorder or suspected to develop the neurodegenerative disorder. The method comprises, or consists essentially of, (a) obtaining a mammal comprising (i) PGRN nucleic acid containing a mutation or (ii) a reduced level of a PGRN polypeptide or a PGRN mRNA, and (b) administering, to the mammal, an agent that increases the level of a PGRN polypeptide in the mammal. The mammal can be a human. The mammal can have a neurodegenerative disorder. The agent can be administered to the mammal under conditions where a symptom of the neurodegenerative disorder improves. The symptom can improve by at least 25 percent. The mammal can be suspected to develop the neurodegenerative disorder. The agent can be administered to the mammal under conditions where the onset of symptoms of the neurodegenerative disorder is delayed. The onset can be delayed at least five years. The neurodegenerative disorder can be selected from the group consisting of frontotemporal dementia, Alzheimer's disease, and motor neuron disease. The agent can be selected from the group consisting of 17β-estradiol, endothelin, testosterone propionate, lysophosphatidic acid, cAMP, and ethinyl estradiol. The agent can be a non-steroidal anti-inflammatory drug. The non-steroidal anti-inflammatory drug can be selected from the group consisting of ibuprofen, indomethacin, diclofenac, naproxen, and aspirin. The agent can be a PPAR agonist. The PPAR agonist can be selected from the group consisting of gemfibrozil, fenofibrate, clofibrate, rosaglitazone, pioglitazone, troglitazone, ciglitazone, and L165,041.

In another aspect, this document features a method for identifying an agent for treating a neurodegenerative disorder in a mammal. The method comprises, or consists essentially of, (a) administering a test agent to a non-human mammal comprising somatic and germ cells that are heterozygous or homozygous for a disrupted PGRN sequence, and (b) determining whether or not (i) a symptom of a neurodegenerative disorder improves in the non-human mammal or (ii) the level of PGRN polypeptide or PGRN mRNA expression is increased in the non-human mammal, where the presence of the improvement or the increased level indicates that the test agent is the agent for treating a neurodegenerative disorder. The non-human mammal can be a mouse. The non-human mammal can comprise exogenous nucleic acid encoding a polypeptide selected from the group consisting of microtubule associated protein tau, TAR DNA binding protein 43, and amyloid precursor protein. The non-human mammal can be a transgenic mouse whose somatic and germ cells comprise the exogenous nucleic acid. The non-human mammal can comprise exogenous nucleic acid encoding a polypeptide having the amino acid sequence set forth in SEQ ID NO:1 while containing at least one mutation in the amino acid sequence. The non-human mammal can be a transgenic mouse whose somatic and germ cells comprise the exogenous nucleic acid. The non-human mammal can comprise somatic and germ cells that are homozygous for the disrupted PGRN sequence.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 contains family pedigrees revealing the segregation of PGRN mutations C31LfsX34 and Q125X with disease in the UBC17 (A) and 1083 (B) families, respectively. Affected individuals are indicated by filled or partially filled diamonds. Presence (+) or absence (−) of the mutation is shown for each individual with available DNA. Only affected members of the youngest generation are shown to protect the identity of the families.

FIG. 9 is a schematic diagram depicting a targeting nucleic acid construct to create PGRN knockout animals.

FIG. 10 contains an amino acid sequence (SEQ ID NO:1) of a human PGRN polypeptide and a nucleic acid sequence (SEQ ID NO:2) that encodes a human PGRN polypeptide.

FIG. 11A is an alignment of the amino acid sequences of individual granulin domains of a PGRN polypeptide: N-terminal (SEQ ID NO:76), Paragranulin (SEQ ID NO:77), Granulin G (SEQ ID NO:78), Granulin F (SEQ ID NO:79), Granulin B (SEQ ID NO:80), Granulin A (SEQ ID NO:81), Granulin C (SEQ ID NO:82), Granulin D (SEQ ID NO:83), and Granulin E (SEQ ID NO:84). Conserved Cys residues are darkly shaded, and other conserved amino acids are lightly shaded. PGRN missense mutations are indicated with shaded circles. FIG. 11B is a molecular model of granulin domains. The complete structure of a granulin domain was reconstructed based on the crystal structure of the N-terminal module of Granulin A (PDB 1g26; Tolkatchev et al., *Biochemistry*, 39:2878-2886 (2000)), and the inherent symmetry of the disulfide-dominated structure. The structure comprises six disulfide bonds and can be split into three self-similar overlapping modules. The two missense mutations located in a granulin domain were mapped on the reconstructed model.

FIG. 22B also contains a Western blot analyzing GAPDH (GAP) polypeptide expression in cell lysates from M17 cells treated with the indicated concentrations of ciglitazone (bottom row).

FIG. 24B also contains a Western blot analyzing GAPDH (GAP) polypeptide expression in cell lysates from human lymphoblast cells treated with the indicated concentrations of L165,041 (bottom row).

DETAILED DESCRIPTION

Figure 1:
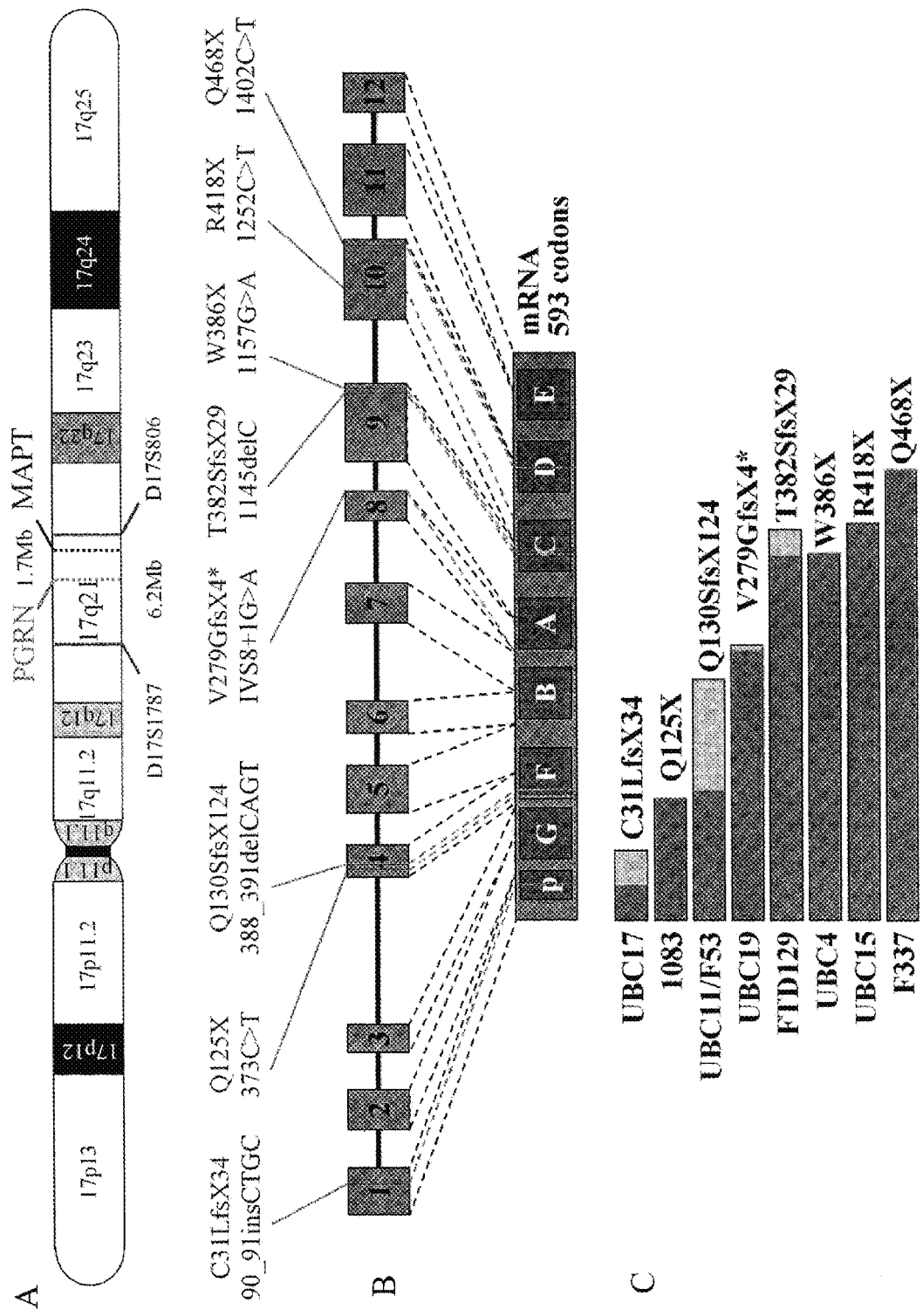
FIG. 1A is a schematic representation of chromosome 17. PGRN is located 1.7 Mb from MAPT, which is mutated in FTDP-17.
FIG. 1B is a schematic representation of a PGRN gene and mRNA encoding a PGRN polypeptide with positions of tau-negative FTD-17 mutations indicated. Lettered boxes refer to individual granulin cysteinyl repeats.
FIG. 1C is a graphic representation of the locations of premature termination codons created by this group of mutations in PGRN RNA. The truncated RNAs can be subjected to nonsense mediated decay resulting in null alleles, thereby representing at least one pathogenic mechanism for PGRN mutations. The IVS8+1G>A mutation (*) is predicted to cause skipping of exon 8 and a frameshift (V279 GfsX4); however, RNA was not available to confirm the effect of this mutation.

This description provides methods and materials related to detecting one or more mutations in PGRN nucleic acid. For example, this description provides methods and materials for determining whether or not a mammal contains PGRN nucleic acid having a mutation such as a mutation that results in premature termination of the coding sequence. This document also provides methods and materials for detecting the level of PGRN expression. For example, this description provides methods and materials for determining whether or not a mammal contains a reduced level of PGRN mRNA or PGRN polypeptide expression. As described herein, a mammal having reduced PGRN mRNA or PGRN polypeptide expression can be identified as having or as being likely to develop dementia.

The mammal can be any type of mammal including, without limitation, a mouse, rat, dog, cat, horse, sheep, goat, cow, pig, monkey, or human. The term "PGRN nucleic acid" as used herein refers to a nucleic acid that extends from 5 kb upstream of the transcription start site of PGRN mRNA to 5 kb downstream of the transcription termination site of PGRN mRNA. In some cases, a PGRN nucleic acid can be (1) any nucleic acid that encodes a PGRN polypeptide, (2) any fragment of a nucleic acid that encodes a PGRN polypeptide, (3) any intronic sequences located between exon sequences that encode a portion of a PGRN polypeptide, (4) any 5' flanking sequence within 5 kb of the transcription start site of PGRN mRNA, (5) any 3' flanking sequence within 5 kb of the transcription termination site of PGRN mRNA, (6) any sequence located between the transcription start site of PGRN mRNA and the first exon that encodes a portion of a PGRN polypeptide, (7) any sequence located between the last exon that encodes a portion of a PGRN polypeptide and the transcription termination site of PGRN mRNA, or (8) any cis-acting regulatory sequence of PGRN mRNA. A PGRN nucleic acid that encodes a PGRN polypeptide can be, for example, a PGRN mRNA or a PGRN cDNA. In some cases, a PGRN nucleic acid can be exon 1, exon 2, exon 3, exon 4, exon 5, exon 6, exon 7, exon 8, exon 9, exon 10, exon 11, or exon 12 of PGRN. In some cases, a PGRN nucleic acid can include a PGRN exon, a PGRN intron, a PGRN 5' UTR, a PGRN 3' UTR, and a PGRN promoter sequence as well as sequences encompassing 4 kb, 3 kb, 2 kb, 1 kb, 0.8 kb, 0.5 kb, 0.3 kb, or 0.1 kb upstream of the transcription start site for PGRN mRNA expression and 4 kb, 3 kb, 2 kb, 1 kb, 0.8 kb, 0.5 kb, 0.3 kb, or 0.1 kb downstream of the transcription termination site for PGRN mRNA expression. Examples of PGRN nucleic acid include, without limitation, the nucleic acid sequence set forth in SEQ ID NO:2 and the nucleic acid sequence set forth in GenBank® Accession Number M75161 (GI:183612).

The methods and materials provided herein can be used to determine whether or not a PGRN nucleic acid of a mammal (e.g., human) contains a mutation or combination of mutations (e.g., one or more mutations identified herein). In some cases, the methods and materials provided herein can be used to determine whether both alleles containing PGRN nucleic acid of a mammal contain one or more mutations in PGRN nucleic acid (e.g., either the same mutation(s) in both alleles, or separate mutations in each allele), or whether only a single allele containing PGRN nucleic acid of the mammal contains one or more PGRN mutations. The identification of one or more PGRN mutations (e.g., one or more mutations listed in Table 1) in an allele can be used to diagnose dementia in a mammal, typically when known clinical symptoms of a neurological disorder also are present. The identification of a PGRN mutation in only one allele can indicate that the mammal is a carrier.

A mutant PGRN nucleic acid is any PGRN nucleic acid containing a mutation as compared to a wild type PGRN nucleic acid for a particular species. For example, a mutant human PGRN nucleic acid can be a nucleic acid having the nucleotide sequence set forth in SEQ ID NO:2 provided that the sequence contains at least one mutation. The term "mutation" as used herein with respect to nucleic acid includes insertions of one or more nucleotides, deletions of one or more nucleotides, nucleotide substitutions, and combinations thereof, including mutations that occur in coding and non-coding regions (e.g., exons, introns, untranslated sequences, sequences upstream of the transcription start site of PGRN mRNA, and sequences downstream of the transcription termination site of PGRN mRNA). For example, a mutation in a PGRN nucleic acid can cause decreased PGRN expression (e.g., due to nonsense-mediated PGRN mRNA decay). In some cases, a mutation in a PGRN nucleic acid can result in premature termination of the coding sequence through the introduction of a stop codon. In some cases, a mutation can be a frame-shift mutation. For example, a nucleic acid can contain a mutation (e.g., an insertion or deletion) that shifts the reading frame such that the encoded polypeptide starts with the amino acid sequence of a PGRN polypeptide and then switches to an amino acid sequence that is different from that found in a PGRN polypeptide. In some cases, a mutation in a PGRN nucleic acid can cause mis-folding or aberrant processing of the encoded polypeptide. Examples of mutations in PGRN nucleic acid include, without limitation, the mutations listed in Table 1. Nucleotides are referred to herein by the standard one-letter designation (A, C, G, or T). Other mutations in PGRN nucleic acid can be identified as described herein. In some cases, a mutation in a non-coding region of a PGRN nucleic acid that may not cause dementia, be linked to dementia, or be responsible for reduced PGRN polypeptide levels can co-segregate with one or more mutations that do cause dementia, that are linked to dementia, or that result in reduced PGRN polypeptide levels. It will be appreciated that such co-segregating mutations can be used as markers for one or more mutations that do cause dementia, that are linked to dementia, or that result in reduced PGRN polypeptide levels.

A mutant PGRN polypeptide is any PGRN polypeptide containing a mutation as compared to a wild type PGRN polypeptide for a particular species. For example, a mutant human PGRN polypeptide can be a polypeptide having the amino acid sequence set forth in SEQ ID NO:1 provided that the sequence contains at least one mutation. In some cases, a mutant PGRN polypeptide can be a polypeptide that contains fewer amino acids than a wild type PGRN polypeptide for a particular species (e.g., a truncated PGRN polypeptide), or a polypeptide that contains at least one amino acid that differs from a wild type PGRN polypeptide for a particular species.

TABLE 1

PGRN mutations linked to dementia, FTLD, AD, PD, and ALS

| Mutation (cDNA)[1] | Mutation (genomic DNA)[2] | Mutation (Polypeptide)[3] |
|---|---|---|
| c.-8 + 3A > T (IVS0 + 3A > T) | g.-3828A > T | p.0 |
| c.-8 + 5G > C (IVS0 + 5G > C) | g.-3826G > C | p.0 |
| c.2T > C | g.2T > C | p.0 |
| c.3G > A | g.3G > A | p.0 |
| c.26C > A | g.26C > A | p.A9D |
| c.63_64insC | g.63_64insC | p.Asp22fs |
| c.90_91insCTGC | g.90_91insCTGC | p.Cys31fs |
| c.102delC | g.102delC | p.Gly35fs |
| c.138 + 1G > A (IVS1 + 1G > A) | g.139G > A | p.0 |
| c.154delA | g.277delA | p.Thr52fs |
| c.234_235delAG | g.357_358delAG | p.Gly79fs |
| c.347C > A | g.585C > A | p.Ser116X |
| c.361delG | g.1075delG | p.Val121fs |
| c.373C > T | g.1087C > T | p.Gln125X |
| c.380_381delCT | g.1094_1095delCT | p.Pro127fs |
| c.384_387delTAGT | g.1098_1101delTAGT | p.Gln130fs |
| c.388_391delCAGT | g.1102_1105delCAGT | p.Gln130fs |
| c.415T > C | g.1129T > C | p.Cys139Arg |
| c.463-1G > A (IVS4-1G > A) | g.1277G > A | p.Ala155fs |
| c.468_474delCTGCTGT | g.1283_1289delCTGCTGT | p.Cys157fs |
| c.472_496dup | g.1287_1311dup | p.Pro166fs |
| c.675_676delCA | g.1603_1604delCA | p.Ser226fs |
| c.708 + 1G > C (IVS6 + 1G > C) | g.1637G > C | p.Val200fs |
| c.708 + 6_708 + 9delTGAG (IVS6 + 6_+ 9delTGAG) | g.1642_1645delTGAG | p.Val200fs (predicted) |
| c.743C > T | g.1907C > T | p.Pro248Leu |
| c.759_760delTG | g.1923_1924delTG | p.Cys253X |
| c.835_835 + 1insCTGA | g.1999_2000insCTGA | p.Ala237fs |
| c.836-1G > C (IVS7-1G > C) | g.2198G > C | p.Val279fs |
| c.911G > A | g.2274G > A | p.Trp304X |
| c.910_911insTG | g.2273_2274insTG | p.Trp304fs |
| c.933 + 1G > A (IVS8 + 1G > A) | g.2297G > A | p.Val279fs |
| c.942C > A | g.2394C > A | p.Cys314X |
| c.998delG | g.2450delG | p.Gly333fs |
| c.1095_1096delCT | g.2547_2548delCT | p.Cys366fs |
| c.1145delC | g.2597delC | p.Thr382fs |
| c.1157G > A | g.2609G > A | p.Trp386X |
| c.1201C > T | g.2872C > T | p.Gln401X |
| c.1232_1233insGT | g.2903_2904insGT | p.Ala412fs |
| c.1243C > T | g.2914C > T | p.Gln415X |
| c.1252C > T | g.2923C > T | p.Arg418X |
| c.1294C > T | g.2965C > T | p.Arg432Cys |
| c.1354delG | g.3025delG | p.Val452fs |
| c.1395_1396insC | g.3066_3067insC | p.Cys466fs |
| c.1402C > T | g.3073C > T | p.Gln468fs |

TABLE 1-continued

PGRN mutations linked to dementia, FTLD, AD, PD, and ALS

| | | |
|---|---|---|
| c.1414-2A > G (IVS10-2 A > G) | g.3175A > G | p.Ala472__491Lysdel |
| c.1477C > T | g.3240C > T | p.Arg493X |
| c.1414-15__1590del (IVS10-15__EX11 + 177del; Δ11) | g.3162__3354del | p.Ala472__Gln548del |

| Genome[4] | Predicted RNA[5] | Predicted polypeptide[6] | Patients N | Control individuals N (%) | Clinical diagnosis | Pathological diagnosis |
|---|---|---|---|---|---|---|
| *PGRN null mutations in FTLD* | | | | | | |
| g.96241G > C | — | p.0 | 1 | 0 | FTD | FTLD-U |
| g.96241G > C | — | p.0 | 1 | 0 | FTD | FTLD-U |
| g.96241G > C | — | p.0 | 1 | 0 | FTLD (FTD) | FTLD-U |
| g.96241G > C | — | p.0 | 1 | 0 | PPA/ FTLD (FTD) | |
| g.96241G > C | — | p.0 | 1 | 0 | FTD | FTLD-U |
| g.96241G > C | — | p.0 | 1 | 0 | FTD | FTLD-U |
| g.96241G > C | — | p.0 | 1 | 0 | FTLD (PPA) | FTLD-U |
| g.96241G > C | — | p.0 | 1 | 0 | FTD:PNFA | |
| g.100069G > A | c.3G > A | p.Met1? | 1 | 0 | FTLD (FTD) | |
| g.101160__101161 delCT | c.380__381 delCT | p.Pro127Arg fsX2 | 1 | 0 | FTD:PNFA | |
| g.102065__102066 insCTGA | c.709__835 del | p.Ala237Trp fsX4 | 1 | 0 | FTD | FTLD-U |
| *PGRN missense mutations in FTLD* | | | | | | |
| g.103031C > T | c.1294C > T | p.Arg432Cys | 1 | 0 | FTLD (FTD) | |
| *PGRN 5' regulatory region variations in FTLD* | | | | | | |
| g.96172G > T | — | — | 1 | 0 | FTD | FTLD-U |
| g.96282G > T | — | — | 1 | 0 | FTLD (possible FTD) | |
| g.96425C > T | — | — | 1 | 0 | FTLD (FTD) | |
| *PGRN null mutations in AD* | | | | | | |
| g.96241G > C | — | p.0 | 2 | 0 | probable AD | |
| g.103432C > T | c.1690C > T | p.Arg535X | 1 | 0 | probable AD | |
| *PGRN missense mutations in AD* | | | | | | |
| g.100165C > A | c.99C > A | p.Asp33Glu | 1 | 0 | probable AD | |
| g.101195T > C | c.415T > C | p.Cys139Arg | 1 | 0 | probable AD | |
| g.102488G > A | c.970G > A | p.Ala324Thr | 1 | 0 | probable AD | |
| g.103089C > T | c.1352C > T | p.Pro451Leu | 1 | 0 | probable AD | |
| g.103369G > A | c.1540G > A | p.Val514Met | 1 | 0 | probable AD | |
| g.103373G > C | c.1544G > C | p.Gly515Ala | 2 | 0 | probable AD | |
| g.103608C > T | c.1690C > T | p.Arg564Cys | 1 | 0 | probable AD | |
| *PGRN regulatory region variations in AD* | | | | | | |
| g.95991C > T | — | — | 1 | 0 | probable AD | |
| g.96135C > T | — | — | 1 | 0 | probable AD | |
| g.96188T > G | — | — | 1 | 0 | probable AD | |
| g.96282G > T | — | — | 1 | 0 | probable AD | |
| g.96385G > A | — | — | 1 | 0 | probable AD | |
| g.96425C > T | — | — | 1 | 0 | probable AD | |

TABLE 1-continued

PGRN mutations linked to dementia, FTLD, AD, PD, and ALS

| | | | | | |
|---|---|---|---|---|---|
| g.96906A > C | — | — | 1 | 0 | probable AD |
| g.103941delT | c.2023delT | — | 1 | 0 | possible AD |
| g.103976G > A | c.2058G > A | — | 1 | 0 | probable AD |

PGRN null mutations in PD

| | | | | | | |
|---|---|---|---|---|---|---|
| g.96241G > C | — | p.0 | 1 | 0 | PD/FTD | FTLD-U/ diffuse LBD |

PGRN missense mutations in PD

| | | | | | |
|---|---|---|---|---|---|
| g.100165C > A | c.99C > A | p.Asp33Glu | 1 | 0 | PD |
| g.102488G > A | c.970G > A | p.Ala324Thr | 1 | 0 | PD |
| g.103369G > A | c.1540G > A | p.Val514Met | 1 | 0 | PD |

PGRN 5' regulatory region variations in PD

| | | | | | |
|---|---|---|---|---|---|
| g.96282G > T | — | — | 2 | 0 | PD |
| g.96707G > A | — | — | 1 | ? | PD |

PGRN missense mutations in ALS

| | | | | | |
|---|---|---|---|---|---|
| g.100633G > A | c.329G > A | p.Arg110Gln | 1 | 0 | ALS |
| g.101151T > C | c.371T > C | p.Ile124Thr | 1 | 0 | ALS |
| g.102488G > A | c.970G > A | p.Ala324Thr | 2 | 0 | ALS |
| g.102990G > A | c.1253G > A | p.Arg418Gln | 1 | 0 | ALS |

PGRN 5' regulatory region variations in ALS

| | | | | | |
|---|---|---|---|---|---|
| g.96061A > G | — | — | 1 | 0 | ALS |

[1]Numbering relative to GenBank® accession number NM_02087.2 (GI: 60498993) and starting at the translation initiation codon, which is nucleotide position 220.
[2]Numbering according to the reverse complement of GenBank® accession number AC003043.1 (GI: 117414200) with 1 as nucleotide 100067.
[3]Numbering according to GenPept® accession number NP_002078.1 (GI: 4504151).
Exon numbering starts with non-coding first exon EX 0;
[4]Numbering relative to the reverse complement of GenBank® Accession Number AC003043 and starting at nt 1;
[5]Numbering according to the largest PGRN transcript (GenBank® Accession Number NM_002087.2) and starting at the translation initiation codon;
[6]Numbering according to the largest PGRN isoform (GenPept® Accession Number NP_002078.1).
FTLD: frontotemporal lobar degeneration;
FTD: frontotemporal dementia;
PPA: primary progressive aphasia;
PNFA: progressive non-fluent aphasia;
FTLD-U frontotemporal lobar degeneration with ubiquitin positive inclusions;
AD: Alzheimer's Disease;
MCI: mild cognitive impairment;
PD: Parkinson's Disease;
DLB: dementia with Lewy bodies;
LBD: Lewy body disease Any appropriate method can be used to detect a mutation in PGRN nucleic acid. For example, mutations can be detected by sequencing cDNA, exons, introns, or untranslated sequences, denaturing high performance liquid chromatography (DHPLC; Underhill et al., *Genome Res.*, 7:996-1005 (1997)), allele-specific hybridization (Stoneking et al., *Am. J. Hum. Genet.*, 48:370-382 (1991); and Prince et al., *Genome Res.*, 11(1):152-162 (2001)), allele-specific restriction digests, mutation specific polymerase chain reactions, single-stranded conformational polymorphism detection (Schafer et al., *Nat. Biotechnol.*, 15:33-39 (1998)), infrared matrix-assisted laser desorption/ionization mass spectrometry (WO 99/57318), and combinations of such methods.

In some cases, genomic DNA can be used to detect one or more mutations in PGRN nucleic acid. Genomic DNA typically is extracted from a biological sample such as a peripheral blood sample, but can be extracted from other biological samples, including tissues (e.g., mucosal scrapings of the lining of the mouth or from renal or hepatic tissue). Any appropriate method can be used to extract genomic DNA from a blood or tissue sample, including, for example, phenol extraction. In some cases, genomic DNA can be extracted with kits such as the QIAamp® Tissue Kit (Qiagen, Chatsworth, Calif.), the Wizard® Genomic DNA purification kit (Promega, Madison, Wis.), the Puregene DNA Isolation System (Gentra Systems, Minneapolis, Minn.), or the A.S.A.P.3 Genomic DNA isolation kit (Boehringer Mannheim, Indianapolis, Ind.).

An amplification step can be performed before proceeding with the detection method. For example, exons or introns of a PGRN nucleic acid can be amplified and then directly sequenced. Dye primer sequencing can be used to increase the accuracy of detecting heterozygous samples.

Mutations in PGRN nucleic acid can be detected by, for example, DHPLC analysis of PGRN nucleic acid. Genomic DNA can be isolated from a mammal (e.g., a human), and sequences from one or more regions of a PGRN nucleic acid can be amplified (e.g., by PCR) using pairs of oligonucleotide primers. The primer pairs listed in Table 2, for example, can be used to amplify sequences of human PGRN nucleic acid. After amplification, PCR products can be denatured and reannealed, such that an allele containing a mutation can reanneal with a wild-type allele to form a heteroduplex (i.e., a double-stranded nucleic acid with a mismatch at one or more positions). The reannealed products then can be subjected to DHPLC, which detects heteroduplexes based on their altered melting temperatures, as compared to homoduplexes that do not contain mismatches.

Samples containing heteroduplexes can be sequenced by standard methods to identify mutant nucleotides. Examples of specific PGRN mutations are provided in Table 1.

Allele specific hybridization also can be used to detect mutations in PGRN nucleic acid, including complete haplotypes of a mammal. For example, samples of DNA or RNA from one or more mammals can be amplified using pairs of primers, and the resulting amplification products can be immobilized on a substrate (e.g., in discrete regions). Hybridization conditions can be selected such that a nucleic acid probe specifically binds to the sequence of interest, e.g., a PGRN nucleic acid containing a particular mutation. Such hybridizations typically are performed under high stringency, as some nucleotide mutations include only a single nucleotide difference. High stringency conditions can include the use of low ionic strength solutions and high temperatures for washing. For example, nucleic acid molecules can be hybridized at 42° C. in 2×SSC (0.3 M NaCl/0.03 M sodium citrate/0.1% sodium dodecyl sulfate (SDS)) and washed in 0.1×SSC (0.015 M NaCl/0.0015 M sodium citrate) with 0.1% SDS at 65° C. Hybridization conditions can be adjusted to account for unique features of the nucleic acid molecule, including length and sequence composition. Probes can be labeled (e.g., fluorescently) to facilitate detection. In some cases, one of the primers used in the amplification reaction can be biotinylated (e.g., 5' end of reverse primer), and the resulting biotinylated amplification product can be immobilized on an avidin or streptavidin coated substrate.

Allele-specific restriction digests can be performed in the following manner. For mutations that introduce a restriction site into PGRN nucleic acid, a restriction digest with the particular restriction enzyme can differentiate alleles.

Other methods also can be used to detect PGRN mutations. For example, conventional and field-inversion electrophoresis can be used to visualize base pair changes. In addition, Southern blotting and hybridization can be used to detect larger rearrangements such as large deletions (e.g., 74.3 kb, 69.1 kb, 62.9 kb, 29.6 kb, 11.5 kb, or 3.6 kb) and insertions. In some cases, quantitative PCR analysis of the genomic copy number for PGRN exons (e.g., all PGRN exons) can be used to detect deletion or duplication mutations in PGRN nucleic acid.

A mutation in PGRN nucleic acid of a mammal also can be detected by analyzing a PGRN polypeptide in a sample from a mammal. Any appropriate method can be used to analyze PGRN polypeptides including, without limitation, immunological methods, chromatographic methods, and spectroscopic methods. For example, a mutation in PGRN nucleic acid that results in expression of a mutant PGRN polypeptide can be detected in a sample from a mammal using an antibody that recognizes the mutant PGRN polypeptide but not wild-type PGRN polypeptide. Such an antibody can, for example, recognize a truncated PGRN polypeptide, or a mutant PGRN polypeptide, that differs from a wild-type PGRN polypeptide by one or more amino acid residues, without recognizing a wild-type PGRN polypeptide. A mutation in PGRN nucleic acid that results in expression of a truncated PGRN polypeptide also can be detected using an antibody that recognizes the truncated PGRN polypeptide as well as wild-type PGRN polypeptide. For example, such an antibody can be used to analyze PGRN polypeptides in a sample from a mammal by Western blotting, which can allow truncated and wild-type PGRN polypeptides to be distinguished by size. Any appropriate sample from a mammal can be used to analyze a PGRN polypeptide including, without limitation, a sample of peripheral blood lymphocytes.

As described herein, the presence of PGRN nucleic acid containing one or more mutations (e.g., one or more mutations listed in Table 1) in a mammal (e.g., human) can indicate that that mammal has dementia. In some cases, the presence of PGRN nucleic acid containing one or more mutations in a human can indicate that that human has dementia, especially when that human is between the ages of 35 and 75, has a family history of dementia, and/or presents symptoms of dementia. Symptoms of dementia can include changes in behavior such as changes that result in impulsive, repetitive, compulsive, or even criminal behavior. For example, changes in dietary habits and personal hygiene can be symptoms of dementia. Symptoms of dementia also can include language dysfunction, which can present as problems in expression of language, such as problems using the correct words, naming objects, or expressing oneself. Difficulties reading and writing can also develop. In some cases, the presence of PGRN nucleic acid containing one or more mutations in a mammal, together with positive results of other diagnostic tests, can indicate that the mammal has dementia. For example, the presence of a mutation in PGRN nucleic acid together with results from a neurological exam, neurophysical testing, cognitive testing, and/or brain imaging can indicate that a mammal has dementia. Other diagnostic tests can include, without limitation, tests for mutations in MAPT and/or apolipoprotein E (APOE) nucleic acid. In some cases, the presence of PGRN nucleic acid containing one or more mutations in a mammal can indicate that the mammal has neuropathy (e.g., ub-ir lentiform neuronal intranuclear inclusions (NII) in the neocortex and striatum, moderate to severe superficial laminar spongiosis in the neocortex, chronic degenerative changes in the neocortex, ub-ir neurites in the neocortex, well-defined ub-ir neuronal cytoplasmic inclusions (NCI) in the neocortex, numerous ub-ir neurites in the striatum, NCI in the hippocampus with a granular appearance, or any combination thereof; Mackenzie et al., *Brain,* 129(Pt 11):3081-90 (2006)).

In some cases, any mammal containing a mutation in PGRN nucleic acid can be classified as having an elevated risk of developing dementia. For example, a human having one or more than one mutation in PGRN nucleic acid (e.g., one or more than one mutation set forth in Table 1) can be classified as having an elevated risk of developing dementia when the human is any age (e.g., less than 65, 60, 55, 50, 45, 40, or 35 years old), does or does not appear to have symptoms of dementia, or has or has not had a positive or negative diagnostic test for dementia. In some cases, a human having one or more mutations in PGRN nucleic acid can be classified as having an elevated risk of developing dementia when the human also has one or more mutations in MAPT or APOE nucleic acid and is less than, for example, 35 years old or does not appear to have symptoms of dementia.

In addition to providing methods and materials for identifying mammals as having dementia, or as having an elevated risk of developing dementia, by analyzing a PGRN nucleic acid or a PGRN polypeptide for mutations, this document provides methods and materials for identifying mammals as having dementia, or as having an elevated risk of developing dementia, by measuring a level of PGRN expression (e.g., a level of PGRN RNA or PGRN polypeptide). For example, a mammal identified as having a reduced level of PGRN expression can be identified as having dementia or can be identified as having an elevated risk of developing dementia. The level of PGRN expression in a sample (e.g., blood sample, plasma sample, cerebral spinal fluid sample, or tissue biopsy sample such as a skin biopsy) from a mammal can be determined by measuring the level of a wild-type PGRN polypeptide, a mutant PGRN polypeptide, or any fragment of a wild type or mutant PGRN polypeptide. Examples of wild-type PGRN polypeptides include, without limitation, a human PGRN polypeptide having the amino acid sequence set forth in SEQ ID NO:1. In some cases, the level of PGRN expression can be determined by measuring the level of RNA encoding a wild-type PGRN polypeptide, a mutant PGRN polypeptide, or a fragment of a wild type or mutant PGRN polypeptide.

A level of PGRN expression (e.g., a level of wild-type PGRN RNA or polypeptide) can be reduced due to a mutation in a PGRN nucleic acid that results in little or no expression of PGRN RNA or PGRN polypeptide. In some cases, a level of PGRN expression can be reduced due to a mutation in a PGRN nucleic acid that results in expression of a mutant PGRN mRNA that is susceptible to nonsense mediated decay. In some cases, a level of wild-type PGRN polypeptide expression can be reduced due to a mutation in a PGRN nucleic acid that results in expression of a mutant PGRN polypeptide. The presence of such a mutation in only one PGRN allele can result in a level of wild-type PGRN polypeptide that is intermediate between the level of wild-type PGRN polypeptide typically observed when both PGRN alleles are wild-type and the level typically observed when both alleles contain the mutation.

The term "reduced level" as used herein with respect to a level of PGRN expression is any level of PGRN expression that is less than a median level of wild-type PGRN polypeptide or PGRN RNA expression in a random population of mammals (e.g., a random population of 10, 20, 30, 40, 50, 100, 500, 1000 or more mammals) having homozygous wild-type PGRN alleles. In some cases, a "reduced level" of PGRN expression can be any level of wild-type PGRN polypeptide or PGRN RNA expression that is less than a median level of wild-type PGRN polypeptide or RNA expression, respectively, in a random population of mammals (e.g., a random population of 10, 20, 30, 40, 50, 100, 500, 1000 or more mammals) not having been diagnosed with dementia. In some cases, a reduced level of PGRN expression can be a level of wild-type PGRN expression that is at least one (e.g., at least 1.0, 1.2, 1.4, 1.6, 1.8, 2.0, or 2.2) standard deviation less than a mean level of wild-type PGRN expression in a random population of mammals (e.g., having homozygous wild-type PGRN alleles and/or not having been diagnosed with dementia).

In some cases, a reduced level of PGRN expression can be a level of wild-type PGRN expression that is less than a median level of wild-type PGRN expression in a random population of mammals (e.g., a random population of 10, 20, 30, 40, 50, 100, 500, 1000 or more mammals) that are age-matched and/or, in the case of humans, who are race-matched to the mammal being evaluated. Mammals that are age-matched can be the same age or can be in the same age range (e.g., 15 to 35 years of age, 35 to 75 years of age, 75 to 100 years of age, 35 to 45 years of age, 60 to 80 years of age, 20 to 35 years of age, or 40 to 50 years of age). In some case, a reduced level of PGRN expression can be a level of wild-type PGRN expression that is less than a median level of wild-type PGRN expression in a random population of mammals (e.g., a random population of 10, 20, 30, 40, 50, 100, 500, 1000 or more mammals) having homozygous wild-type PGRN alleles that are age-matched and/or, in the case of humans, who are race-matched to the mammal being evaluated. In some cases, a reduced level of PGRN expression can be little or no detectable wild-type PGRN expression.

It will be appreciated that PGRN expression levels from comparable samples (e.g., blood samples) are used when determining whether or not a particular PGRN expression level is a reduced level. For example, an mRNA level of PGRN expression in a skin biopsy from a particular species of mammal is compared to the median mRNA level of PGRN expression in skin biopsies from a random population of mammals (e.g., having homozygous wild-type PGRN alleles and/or not having been diagnosed with dementia) of the same species. In addition, PGRN expression levels are compared to a median PGRN expression level measured using the same or a comparable method.

Any appropriate method can be used to determine a PGRN expression level. For example, Northern blotting, RT-PCR, or quantitative PCR can be used to determine a level of RNA molecules encoding a wild-type PGRN polypeptide. In some cases, mass spectrometry can be used to determine a level of a wild-type PGRN polypeptide. In some cases, a level of PGRN polypeptide can be detected using a method that relies on an anti-PGRN polypeptide antibody. Such methods include, without limitation, FACS, Western blotting, ELISA, immunohistochemistry, and immunoprecipitation. Antibody based assays (e.g., sandwich enzyme-linked immunosorbent assays) can include using combinations of antibodies that bind to one or more sites of the amino-terminal, central, and carboxy-terminal portions of a PGRN polypeptide or a fragment thereof. An anti-PGRN polypeptide antibody can be labeled for detection. For example, an anti-PGRN polypeptide antibody can be labeled with a radioactive molecule, a fluorescent molecule, or a bioluminescent molecule. PGRN polypeptides can also be detected indirectly using a labeled antibody that binds to an anti-PGRN polypeptide antibody that binds to a PGRN polypeptide.

An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. An anti-PGRN polypeptide antibody can bind to a PGRN polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

An anti-PGRN polypeptide antibody provided herein can be prepared using any appropriate method. For example, any substantially pure PGRN polypeptide, or fragment thereof (e.g., a truncated PGRN polypeptide encoded by a PGRN nucleic acid containing a mutation), can be used as an immunogen to elicit an immune response in an animal such that specific antibodies are produced. Thus, a human PGRN polypeptide or a fragment thereof can be used as an immunizing antigen. In addition, the immunogen used to immunize an animal can be chemically synthesized or derived from translated cDNA. Further, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1-5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, CURRENT PROTOCOLS IN IMMUNOLOGY, Wiley Interscience, 1994).

The preparation of monoclonal antibodies also is well-known to those skilled in the art. See, e.g., Kohler & Milstein, Nature 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, Vol. 10, pages 79-104 (Humana Press 1992).

Once hybridoma clones that produce antibodies to an antigen of interest (e.g., a PGRN polypeptide containing a mutation) have been selected, further selection can be performed for clones that produce antibodies having a particular specificity. For example, clones can be selected that produce antibodies that preferentially bind to a PGRN polypeptide that is truncated versus a PGRN polypeptide that is a full-length, wild type polypeptide. Such antibodies can recognize epitopes that are exposed in the truncated region of the PGRN polypeptide, for example, but that are not accessible in the full-length, wild type polypeptide. In some cases, a hybridoma clone can be selected that produces antibodies that bind to a PGRN polypeptide differing from a corresponding wild-type PGRN polypeptide by one or more amino acids with a higher affinity than the affinity of binding to a wild-type PGRN polypeptide.

The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

This document also provides kits that can be used to perform a method provided herein (e.g., to determine whether or not a PGRN nucleic acid contains a mutation). Such kits can include nucleic acid molecules (e.g., primer pairs or probes), antibodies (e.g., anti-PGRN polypeptide antibodies), secondary antibodies, control nucleic acid molecules (e.g., PGRN nucleic acids that do or do not contain a mutation), control polypeptides (e.g., wild type or mutant PGRN polypeptides), DNA aptamers, microarrays, ELISA plates, or data analysis software optionally together with any other appropriate reagent, tool, or instruction for performing the methods described herein. Appropriate informational material can be descriptive, instructional, marketing or other material that relates to the methods described herein and/or the use of the reagents for the methods described herein. For example, the informational material can relate to performing a genetic analysis on a human and subsequently diagnosing the human as being at risk (or not) for dementia, and/or delivering a prognosis of the human relating to survival time, likelihood of responding to therapy, or quality of life. In addition, or in an alternative, the informational material of a kit can be contact information, e.g., a physical address, email address, website, or telephone number, where a user of the kit can obtain substantive information about performing a genetic analysis and interpreting the results, particularly as they apply to a human's likelihood of developing dementia and a subsequent prognosis.

The informational material of the kits can be in any form. In many cases, the informational material, e.g., instructions, can be provided in printed matter, e.g., a printed text, drawing, and/or photograph, e.g., a label or printed sheet. Informational material can be provided in other formats, such as Braille, computer readable material, video recording, or audio recording. Informational material can also be provided in any combination of formats.

The kit can include one or more containers for the reagents for performing a genetic analysis, such as reagents for performing PCR, FISH, CGH, or any other method described herein. The kit can contain separate containers, dividers, or compartments for the reagents and informational material. A container can be labeled for use for the diagnosis and/or prognosis of a human relating to the development and treatment of dementia.

This document also provides methods and materials to assist medical or research professionals in determining whether or not a mammal has a mutation in a PGRN nucleic acid. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the presence or absence of a mutation in a PGRN nucleic acid in a sample, and (2) communicating information about the presence or absence of that mutation to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides isolated nucleic acids having a nucleotide sequence of at least about 20 contiguous nucleotides (e.g., at least about 20, 25, 30, 40, 50, 75, 100, 150, 300, 500, or more nucleotides) from a PGRN nucleic acid (e.g., a PGRN nucleic acid having the nucleic acid sequence set forth in SEQ ID NO:2). In some cases, an isolated nucleic acid provided herein can have a nucleotide sequence of at least about 20 contiguous nucleotides (e.g., at least about 20, 25, 30, 40, 50, 75, 100, 150, 300, 500, or more nucleotides) from a PGRN nucleic acid having the nucleic acid sequence set forth in SEQ ID NO:2 while having one or more (e.g., two, three, four, five, six, seven, eight, nine, ten, or more) mutations as compared to the nucleic acid sequence set forth in SEQ ID NO:2. Such mutations can be as set forth in Table 1. For example, an isolated nucleic acid can contain 30 nucleotides of human PGRN nucleic acid with one of the mutations set forth in Table 1. In some cases, a PGRN nucleic acid provided herein can contain a mutation that results in expression of a truncated polypeptide. In some cases, a PGRN nucleic acid provided herein can contain a mutation that prevents splicing out of the first intron of a PGRN nucleic acid, intron 0, causing nuclear retention and degradation of the mutant transcript. In some cases, a PGRN nucleic acid provided herein can contain a mutation that prevents or reduces transcription of PGRN nucleic acid.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

Typically, isolated nucleic acids provided herein are at least about 20 nucleotides in length. For example, a nucleic acid can be about 20-30 (e.g., 20, 21, 22, 23, 24, 25, 26, 27, 28, 29, or 30 nucleotides in length), 20-50, 50-100, or greater than 100 nucleotides in length (e.g., greater than 150, 200, 250, 300, 350, 400, 450, 500, 750, or 1000 nucleotides in length). Isolated nucleic acids provided herein can be in a sense or antisense orientation, can be single-stranded or double-stranded, can be complementary to a PGRN nucleic acid sequence (e.g., SEQ ID NO:2), and can be DNA, RNA, or nucleic acid analogs. Nucleic acid analogs can be modified at the base moiety, sugar moiety, or phosphate backbone to improve, for example, stability, hybridization, or solubility of the nucleic acid.

Isolated nucleic acids can be produced by standard techniques, including, without limitation, common molecular cloning and chemical nucleic acid synthesis techniques. For example, polymerase chain reaction techniques can be used to obtain an isolated nucleic acid containing a fragment of PGRN nucleic acid with one or more mutations.

Isolated nucleic acids provided herein can be used for diagnostic purposes. For example, an isolated nucleic acid comprising a portion of a PGRN nucleic acid (e.g., a PCR amplicon comprising one or more than one mutation provided herein) can be used in DHPLC or allele specific hybridization analyses. An isolated nucleic acid containing a mutation also can be used in the form of a PCR primer that is about 20 nucleotides in length to amplify a region of a PGRN nucleic acid containing the mutation. In addition, an isolated nucleic acid containing a mutation can be labeled (e.g., with a fluorescent label) and used to detect a PGRN nucleic acid containing the mutation.

An isolated nucleic acid provided herein also can be used to produce an immunogen to elicit an immune response in an animal such that specific antibodies are produced. For example, a PGRN nucleic acid containing a mutation that results in expression of a truncated PGRN polypeptide can be cloned into an expression vector, and the vector can be transfected into cells (e.g., insect cells or bacterial cells) to express the truncated polypeptide. The truncated polypeptide can then be purified from cell extracts and used to immunize animals such as rabbits. Serum from the animals can then be screened for polyclonal antibodies, and monoclonal antibodies can be obtained as described herein.

This document also provides methods and materials related to treating mammals (e.g., humans) having or being likely to develop (e.g., having an elevated risk of developing) a neurodegenerative disorder such as dementia. A mammal can be identified as having or being likely to develop a neurodegenerative disorder (e.g., frontotemporal dementia) if it is determined that the mammal contains a PGRN nucleic acid having one or more mutations such as the mutations described herein. A neurodegenerative disorder can be any condition in which neurons are damaged. Examples of neurodegenerative disorders include, without limitation, Alzheimer's disease, dementia, frontotemporal dementia (FTD), frontotemporal lobar degeneration (FTLD), Parkinson's disease, Huntington's disease, stroke, and motor neuron disease.

As described herein, a mammal identified as having or being susceptible to developing a neurodegenerative disorder can be treated by administering a nucleic acid encoding a PGRN polypeptide to the mammal such that the level of a PGRN polypeptide in the mammal is increased. In addition, a mammal identified as having or being susceptible to developing a neurodegenerative disorder can be treated using an agent that increases a PGRN polypeptide level in the mammal, a combination of agents that increase the level of a PGRN polypeptide, or a combination of nucleic acid encoding a PGRN polypeptide and one or more agents that increase the level of a PGRN polypeptide.

The level of a PGRN polypeptide can be increased in a mammal having or being susceptible to developing a neurodegenerative disorder by administering a nucleic acid encoding a PGRN polypeptide to the mammal. Such a nucleic acid can encode a full-length PGRN polypeptide such as a human PGRN polypeptide having the amino acid sequence set forth in SEQ ID NO:1, or a biologically active fragment of a PGRN polypeptide (e.g., granulin A (SEQ ID NO:81), granulin B (SEQ ID NO:80), granulin C (SEQ ID NO:82), granulin D (SEQ ID NO:83), granulin E (SEQ ID NO:84), granulin F (SEQ ID NO:79), granulin G (SEQ ID NO:78), or granulin P (SEQ ID NO:77)). A nucleic acid encoding a PGRN polypeptide can be administered to a mammal using any appropriate method. For example, a nucleic acid can be administered to a mammal using a vector such as a viral vector.

Vectors for administering nucleic acids (e.g., a nucleic acid encoding a PGRN polypeptide) to a mammal are known in the art and can be prepared using standard materials (e.g., packaging cell lines, helper viruses, and vector constructs). See, for example, *Gene Therapy Protocols (Methods in Molecular Medicine)*, edited by Jeffrey R. Morgan, Humana Press, Totowa, N.J. (2002) and *Viral Vectors for Gene Therapy: Methods and Protocols*, edited by Curtis A. Machida, Humana Press, Totowa, N.J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses.

Lentiviruses are a genus of retroviruses that can be used to infect neuronal cells and non-dividing cells. Adenoviruses contain a linear double-stranded DNA genome that can be engineered to inactivate the ability of the virus to replicate in the normal lytic life cycle. Adenoviruses can be used to infect dividing and non-dividing cells. Adenoviral vectors can be introduced and efficiently expressed in cerebrospinal fluid and in brain. Adeno-associated viruses also can be used to infect non-dividing cells. Muscle cells and neurons can be efficient targets for nucleic acid delivery by adeno-associated viruses. Additional examples of viruses that can be used as viral vectors include herpes simplex virus type 1 (HSV-1). HSV-1 can be used as a neuronal gene delivery vector to establish a lifelong latent infection in neurons. HSV-1 can package large amounts of foreign DNA (up to about 30-40 kb). The HSV latency-associated promoter can be used to allow high levels of expression of nucleic acids during periods of viral latency.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a PGRN polypeptide. A viral vector can be replication-competent or replication-defective, and can contain fewer viral genes than a corresponding wild-type virus or no viral genes at all.

In addition to nucleic acid encoding a PGRN polypeptide, a viral vector can contain regulatory elements operably linked to a nucleic acid encoding a PGRN polypeptide. Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a PGRN polypeptide. A promoter can be constitutive or inducible (e.g., in the presence of tetracycline), and can affect the expression of a nucleic acid encoding a PGRN polypeptide in a general or tissue-specific manner. Tissue-specific promoters include, without limitation, enolase promoter, prion protein (PrP) promoter, and tyrosine hydroxylase promoter.

As used herein, "operably linked" refers to positioning of a regulatory element in a vector relative to a nucleic acid in such a way as to permit or facilitate expression of the encoded polypeptide. For example, a viral vector can contain a neuronal-specific enolase promoter and a nucleic acid encoding a PGRN polypeptide. In this case, the enolase promoter is operably linked to a nucleic acid encoding a PGRN polypeptide such that it drives transcription in neuronal tissues.

A nucleic acid encoding a PGRN polypeptide also can be administered to a mammal using non-viral vectors. Methods of using non-viral vectors for nucleic acid delivery are known to those of ordinary skill in the art. See, for example, *Gene Therapy Protocols (Methods in Molecular Medicine)*, edited by Jeffrey R. Morgan, Humana Press, Totowa, N.J. (2002). For example, a nucleic acid encoding a PGRN polypeptide can be administered to a mammal by direct injection of nucleic acid molecules (e.g., plasmids) comprising nucleic acid encoding a PGRN polypeptide, or by administering nucleic acid molecules complexed with lipids, polymers, or nanospheres.

A nucleic acid encoding a PGRN polypeptide can be produced by standard techniques, including, without limitation, common molecular cloning, polymerase chain reaction (PCR), chemical nucleic acid synthesis techniques, and combinations of such techniques. For example PCR or RT-PCR can be used with oligonucleotide primers designed to amplify nucleic acid (e.g., genomic DNA or RNA) encoding a PGRN polypeptide.

In some cases, a nucleic acid encoding a PGRN polypeptide can be isolated from a healthy mammal, a mammal having a neurodegenerative disorder, or a mammal being susceptible to developing a neurodegenerative disorder. For example, a nucleic acid that encodes a wild type PGRN polypeptide such as a PGRN polypeptide having the amino acid sequence set forth in SEQ ID NO:1 can be isolated from a mammal that is homozygous or heterozygous for such a nucleic acid. The isolated nucleic acid can then be used to generate a viral vector, for example, which can be administered to a mammal so that the level of a PGRN polypeptide in the mammal is increased. In some cases, a nucleic acid encoding a PGRN polypeptide containing one or more mutations can be isolated from a mammal, and the one or more mutations can be altered by site-directed mutagenesis to remove the mutations prior to administering the nucleic acid to a mammal.

This document also provides methods and materials for treating a mammal having or being susceptible to developing a neurodegenerative disorder using an agent that increases the level of a PGRN polypeptide. Any appropriate agent that increases the level of any PGRN polypeptide can be used to treat a mammal having or being likely to develop a neurodegenerative disorder. Suitable agents include chemical compounds, mixtures of chemical compounds, polypeptides, lipids, carbohydrates, amino acid analogs, nucleic acid analogs, and extracts isolated from bacterial, plant, fungal, or animal matter. Examples of agents that can increase PGRN polypeptide levels in mammals include estrogen, 17β-estradiol (E2), ethinyl estradiol, androgen, testosterone propionate, endothelin (ET-1), lysophosphatidic acid (LPA), and cAMP (Lu and Serrero, *Proc Natl Acad Sci USA*, 97(8):3993-8 (2000); Lu and Serrero, *Biochem Biophys Res Commun*, 256(1):204-7 (1999); Jones et al., *J Soc Gynecol Investig*, 13(4):304-11 (2006); Lee et al., *J Reprod Dev* (2006); Ong et al., *Am J Physiol Regul Integr Comp Physiol*, 291(6):R1602-12 (2006); Lu and Serrero, *Proc Natl Acad Sci USA*, 98(1):142-7 (2001); Suzuki et al., *Physiol Behav*, 68(5):707-13 (2000); Suzuki and Nishiahara, *Mol Genet Metab*, 75(1):31-7 (2002); Suzuki et al., *Neurosci Leu*, 297(3):199-202 (2001); Suzuki et al., *Neurosci Lett*, 242(3):127-30 (1998); Wang et al., *Clin Cancer Res*, 12(1): 49-56 (2006); Kamrava et al., *Oncogene*, 24(47):7084-93 (2005)). In some cases, an agent that can increase PGRN polypeptide levels in mammals can be an agent that can increase the activity of the Golgi apparatus in mammalian cells.

Agents that can increase PGRN polypeptide levels in mammals also include non-steroidal anti-inflammatory drugs (NSAID), NSAID derivatives, and NSAID analogs that target (e.g., inhibit) cyclooxygenase enzymes. For example, agents that can increase PGRN polypeptide levels in mammals include aryl propionic acid derivatives, aryl acetic acid derivatives, and amino carboxylic acid derivatives. In some cases, an agent that can increase PGRN polypeptide levels can be ibuprofen, flufenamic acid, indomethacin, diclofenac, naproxen, or a salicylate such as aspirin.

An agent that can increase PGRN polypeptide levels can be an agent that activates a PPARα, PPARβ (also called PPARδ), and/or a PPARγ receptor (Heneka et al., *Brain*, 128:1442-1453 (2005)). A variety of PPAR agonists that are specific for PPARα, PPARβ, and PPARγ receptor subtypes have been reported. Examples of such agents include, without limitation, PPARα fibrate compounds (e.g., gemfibrozil, clofibrate, fenofibrate, and GW7647), PPARγ compounds such as thiazolidinediones (e.g., rosaglitazone, pioglitazone, troglitazone, ciglitazone, and GW1929), PPARδ agonists such as L-165,041 and GW501516, and pan-PPAR agonists such as LY171883.

Agents that can increase PGRN polypeptide levels can be natural or synthesized molecules that can alter the activity of cellular components in the PPAR receptor pathway. Such agents can, for example, increase activation of PPAR receptors, either directly or indirectly through PPAR agonists. In some cases, agents can increase PGRN polypeptide levels by increasing a level of one or more PPAR receptor subtypes. In some cases, agents can increase PGRN polypeptide levels by serving as a PPAR receptor co-factor, or by altering the activity of a PPAR receptor co-factor. Examples of agents that can affect PPAR activity include compounds such as retinoic acid and vitamin A (a retinoic acid precursor), and polypeptide co-factors such as PPARγ co-activator 1 alpha (PCG-1α) and PPARγ co-activator 1β (PCG-1β; Finck and Kelly, *J Clin Invest*, 116:615-622 (2006)). Without being bound by any particular mechanism of action, agents such as retinoic acid and vitamin A can potentiate PPAR activity by binding to and activating retinoic-acid activated receptors (e.g., RAR and RXR), which can heterodimerize with PPAR receptors to promote their activity. In some cases, expression of PCG-1α or PCG-1β can be increased to enhance expression of PPAR targets such as a PGRN polypeptide. Co-factor activity can be upregulated by administering a pharmacological agent or a nucleic acid. For example, a viral vector, such as an adeno-associated virus or a lentivirus vector described herein, containing a sequence encoding a PPAR receptor or PPAR receptor co-activator, can be used to overexpress the receptor or co-activator by administering (e.g., through injection) recombinant viral particles to a mammal. In some cases, PGRN polypeptide levels can be increased in mammals by direct administration of PGRN polypeptides (e.g., one or more biologically active PGRN polypeptide fragments or synthetic PGRN polypeptides). For example, a mammal (e.g., a human) having a neurodegenerative disorder or having an elevated risk for developing a neurodegenerative disorder can be treated with PGRN polypeptides or a cocktail of different PGRN polypeptides. Such a cocktail can include two or more of the following: a PGRN polypeptide having the amino acid sequence set forth in SEQ ID NO:1, SEQ ID NO:77, SEQ ID NO:78, SEQ ID NO:79, SEQ ID NO:80, SEQ ID NO:81, SEQ ID NO:82, SEQ ID NO:83, or SEQ ID NO:84.

Agents that can increase PGRN polypeptide levels can be natural products or can be derived or synthesized from existing compounds. For example, agents that can increase PGRN polypeptide levels can be derived from natural or synthetic product libraries where compounds from these products are known to have activity against peroxisome proliferation activating receptor pathways. These products may activate PPAR receptors, or may increase the expression of one or more PPAR receptors. Examples of natural products that can activate PPAR receptors or increase their expression include curcuminoids and sesquiterpenoids in turmeric, omega-3 fatty acids, resveratrol and anthocyanins in grape extract, ginsenoside from ginseng, extract of *Salacia oblonga* root, extracts of *Alisma plantago* aquatica (ze xie/european waterplantain), extract of *Catharanthus roseus* (madagascar periwinkle), extract of *Acorns calamus* (sweet calamus), extract of *Euphorbia balsamifera* (balsam spurge), extract of *Jatropha curcas* (barbados nut), extract of *Origanum majorana* (marjoram), extract of *Zea mays* (corn silk), extract of *Capsicum frutescens* (chili), extract of *Australian Clematis* species (Ranunculaceae), and extract of *Urtica dioica* (stinging nettle). See, for example, Rau et al., *Pharmazie*, 61:952-956 (2006); Lee et al., *Biochem Biophys Res Commun*, 339:196-203 (2006); Li et al., *J Ethnopharmacol*, 104:138-143 (2006); Nishiyama et al., *J Agric Food Chem*, 53:959-963 (2005); Huang et al., *Toxicol Appl Pharmacol*, 210:78-85 (2006); Xia et al., *J Biol Chem*, 280: 36792-36801 (2005); Ulrich et al., *Cancer Res*, 66:7348-7354 (2006).

Agents that can increase PGRN polypeptide levels can be obtained from any appropriate commercial source. For example, agents such as PPAR activators, NSAIDs, NSAID derivatives, NSAID analogues, 17β-estradiol (E2), lysophosphatidic acid, ET-1, cAMP, and various analogues thereof can be obtained from Sigma-Aldrich (Saint Louis, Mo.), Calbiochem (San Diego, Calif.), Biomol (Plymouth Meeting, Pa.), Cayman Chemical (Ann Arbor, Mich.), MP Biomedicals (Solon, Ohio), or through the Chemnavigator website. Agents that can increase PGRN polypeptide levels also can be chemically synthesized using methods that are known to those of skill in the art. For example, NSAIDs, NSAID derivatives, and NSAID analogues can be chemically synthesized using standard methods. Agents that can increase PGRN polypeptide levels also can be designed using in silico models and the chemical structures of other agents that increase PGRN polypeptide levels. Agents identified as having the ability to increase the level of PGRN polypeptide in cells can be optimized for properties such as potency, selectivity, and pharmacokinetic properties, e.g., by synthesizing variations of the agents using methods known to those of skill in the art. For example, NSAIDs, NSAID derivatives, and NSAID analogues having altered potency for COX-1 and COX-2 receptors can be synthesized.

Agents that can increase the level of a PGRN polypeptide in cells can be identified by screening candidate agents (e.g., from synthetic compound libraries and/or natural product libraries). Candidate agents can be obtained from any commercial source and can be chemically synthesized using methods that are known to those of skill in the art. Candidate agents can be screened and characterized using in vitro cell-based assays, cell free assays, and/or in vivo animal models.

For example, cell cultures can be contacted with various amounts of a candidate agent (e.g., a synthetic or natural agent, an extract containing a natural agent, or an active fraction of such an extract). Prior to contacting cells with a candidate agent, the candidate agent can be dissolved in a suitable vehicle for in vitro cell culture studies such as water, dimethyl sulfoxide, ethanol, or ethyl acetate. The level of a PGRN polypeptide, which can be the level of a PGRN polypeptide having the amino acid sequence set forth in SEQ ID NO:1 or a fragment thereof (or any combination thereof), in the cells or secreted from the cells can be monitored to determine whether or not treatment with the candidate agent causes an increase in the level of a PGRN polypeptide. For example, the level of PGRN polypeptide in cultured cells treated with a candidate agent can be compared with the level of PGRN polypeptide in untreated cells or cells treated with vehicle alone, and comparisons can be made at different time points. The effective concentration(s) of the candidate agent also can be determined. An effective concentration of agent can be a concentration that increases the level of PGRN polypeptide in or secreted from a cell by at least 10% (e.g., at least 20%, 25%, 30%, 40%, 50%, 60%, 70%, 80%, or 90%) compared to the corresponding level in or secreted from a cell not treated with the agent.

PGRN polypeptide levels can be detected using any standard antibody based assays such as immunoprecipitation, western hybridization, and sandwich enzyme-linked immunosorbent assays (ELISA). Antibody based assays can utilize combinations of antibodies that bind to one or more sites of the amino-terminal, central, and carboxy-terminal portions of PGRN polypeptides or fragments thereof. Different PGRN polypeptide forms also can be detected by mass spectrometry. The level of a PGRN polypeptide also can be determined by measuring PGRN RNA using any appropriate method such as northern blotting, quantitative RT-PCR, microarray analysis, or in situ hybridization.

In some cases, candidate agents for increasing the level of a PGRN polypeptide can be identified and/or characterized using cells such as lymphoblasts from a mammal having or being likely to develop a neurodegenerative disorder. In some cases, cells in which a nucleic acid encoding a PGRN polypeptide is expressed (e.g., overexpressed) or in which a nucleic acid encoding a PGRN polypeptide is underexpressed can be used to identify or characterize agents that can increase a PGRN polypeptide level. For example, a vector containing a nucleic acid encoding a PGRN polypeptide (e.g., a human PGRN polypeptide having the amino acid sequence set forth in SEQ ID NO:1 with or without a mutation) can be used to stably or transiently express the polypeptides in cells (e.g., human cells or non-human mammalian cells that do or do not normally express a PGRN polypeptide), and the cells can then be used to identify and characterize agents that can increase the level of a PGRN polypeptide. In some cases, a vector containing a nucleic acid encoding an interfering RNA targeted to a nucleic acid encoding a PGRN polypeptide, or to a regulatory region of a nucleic acid encoding a PGRN polypeptide, can be used to decrease the level of expression of a nucleic acid encoding a PGRN polypeptide in cells. Cells in which a PGRN polypeptide is underexpressed can be used to identify and characterize agents that can increase the level of a PGRN polypeptide.

Any appropriate cell type can be used to identify or characterize agents that can increase the level of a PGRN polypeptide. For example, mammalian cells such as Chinese hamster ovary (CHO) cells, fibroblast cells, neuronal cells, lymphoblast cells, or neuroglioma cells can be used. A mammalian cell can be one that does or that does not naturally produce, process, or catabolize a PGRN polypeptide.

Examples of vectors that can be used to express or inhibit expression of a nucleic acid encoding a PGRN polypeptide in cells include, without limitation, non-viral vectors and viral vectors such as adeno-associated virus and lentivirus vectors. For example, a nucleic acid encoding a mouse PGRN polypeptide having the amino acid sequence set forth in GenBank® under GI number 6680107 can be cloned into the multiple cloning site (MCS) of the pAAV NEW vector. A helper AAV system, of any described serotype, can be used to package the pAAV vector, and a sufficient titer of infectious particles can be used to transduce cells with the nucleic acid encoding the PGRN polypeptide. In some cases, a biological tag that does not interfere with the biological activity of a PGRN polypeptide can be added to the amino- or carboxy-terminus of the polypeptide to monitor expression of the transgene. Examples of commonly used tags include myc, polyhistidine, FLAG, and GFP.

An agent that can increase the level of a PGRN polypeptide can exert an effect at any of a number of steps along the PGRN pathway. The level of PGRN polypeptide can depend not only on its production, but also on the mechanisms responsible for its removal. Without being bound by a particular mechanism, increases in the level of PGRN polypeptide can be due to the activity of binding polypeptides that sequester a PGRN polypeptide, or to other cellular mechanisms such as increased transcription, increased translation, increased secretion, or decreased catabolism of a PGRN polypeptide. By way of example, the level of a PGRN polypeptide can involve both intracellular (e.g., acting at the site of PGRN polypeptide generation and/or within the secretory pathway) and extracellular (e.g., cell-surface, secreted, endosomal and/or lysosomal) protease mediated degradation.

An agent that can increase the level of a PGRN polypeptide also can be identified and characterized using a cell free assay. For example, a cell free assay can be used to identify and characterize agents that can alter PGRN polypeptide processing (e.g., processing of a PGRN polypeptide into various forms, such as a biologically active fragment) or catabolism. Such a cell free assay can be performed using a purified or partially purified enzyme preparation or a lysate from cells able to catabolize PGRN polypeptides or process PGRN polypeptides into fragments. Cell lysates can be prepared using known methods such as, for example, sonication or detergent-based lysis. The cell-free biological sample (e.g., enzyme preparation or cell lysate) having an activity that can catabolize a PGRN polypeptide or process a PGRN polypeptide can be incubated with substrate PGRN polypeptide under conditions in which the substrate PGRN polypeptide is catabolized or processed. To determine whether a candidate agent for increasing the level of PGRN polypeptide has an effect on processing or catabolism of a PGRN polypeptide, two reactions can be compared. In one reaction, the candidate agent can be included in the processing or catabolic reaction, while in a second reaction, the candidate agent can be excluded from the processing or catabolic reaction. Levels of polypeptides in the reaction containing the candidate agent can be compared with the levels in the reaction that does not contain the agent to determine if the level of a PGRN polypeptide is increased.

Agents that can increase the level of a PGRN polypeptide also can be identified by screening candidate agents (e.g., from compound libraries) in non-human mammals (e.g., PGRN transgenic or PGRN knockout non-human mammals). For example, PGRN polypeptide levels can be assessed in a first group of such non-human mammals in the presence of an agent, and compared with PGRN polypeptide levels in a corresponding control group in the absence of the agent to determine whether or not administration of the agent results in an increase in the level of a PGRN polypeptide.

Non-human mammals include, for example, rodents such as rats, guinea pigs, and mice, and farm animals such as pigs, sheep, goats, horses, and cattle. Non-human mammals can be designed to contain exogenous nucleic acid that encodes a human PGRN polypeptide having the amino acid sequence set forth in SEQ ID NO:1 with or without a mutation. Non-human mammals also can be designed to lack endogenous nucleic acid encoding a PGRN polypeptide or to contain truncated or disrupted endogenous PGRN nucleic acid (e.g., knockout animals).

To create non-human mammals having a particular gene (e.g., a PGRN gene) inactivated in all cells, a knockout construct can be introduced into the germ cells (sperm or eggs, i.e., the "germ line") of the desired species. Nucleic acid constructs used for producing knockout non-human mammals can include a region of an endogenous nucleic acid that is being targeted and can also include a nucleic acid sequence encoding a selectable marker, which is generally used to interrupt a targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

An example of a targeting construct that can be used to generate PGRN knockout animals is a construct containing a 4.8 kb fragment of 5' homology and a 1.9 kb fragment of 3' homology flanking a floxed neomycin resistance (NEO) gene in reverse orientation (FIG. 9). The targeting vector can be linearized with a Pvu I restriction digest. Homology is placed such that exons 1-3 are removed in the initial targeting and replaced with the floxed NEO (FIG. 9). The loxP sites are placed such that the NEO cassette can be removed, following Cre expression, if its inclusion affects nearby genes (FIG. 9).

Figure 8:
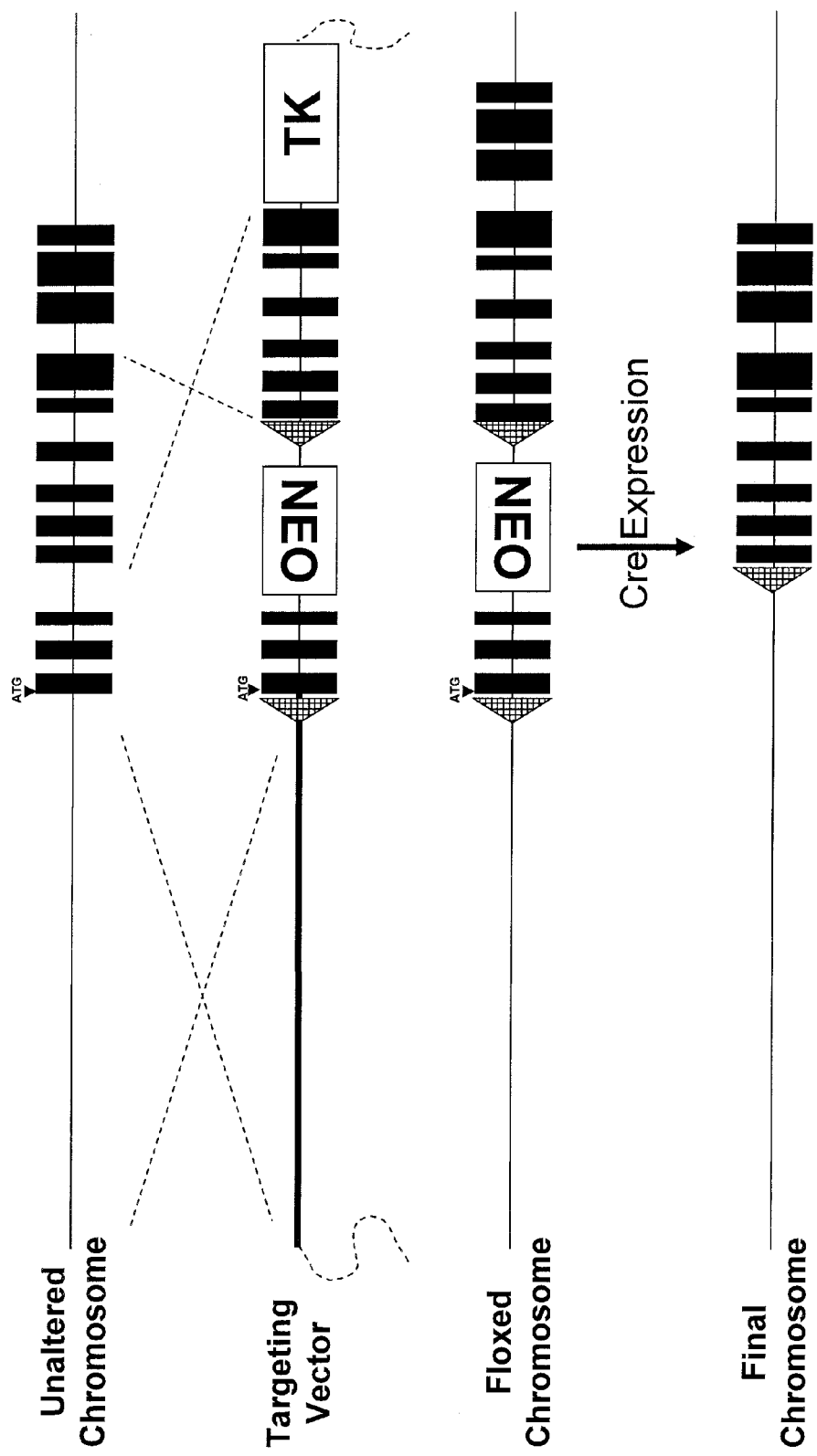
FIG. 8 is a schematic diagram depicting a targeting nucleic acid construct to create conditional PGRN knockout animals.

An example of a targeting construct that can be used to generate conditional PGRN knockout animals is a construct containing a floxed cassette containing 0.8 kb of coding sequence (exons 1-3) and a neomycin resistance (NEO) gene flanked by a 4.8 kb fragment of 5' homology and a 1.9 kb fragment of 3' homology (FIG. 8). The NEO gene can be placed in reverse orientation in the intron downstream of Exon 3. This specific orientation can reduce the possibility that the NEO gene within the floxed chromosome may interfere with normal gene function or result in aberrant transcripts that originate from the NEO start site. The location can be desirable due to the relatively large size of the chosen intron. The targeting vector can be linearized with a Pvu I restriction digest. The PGRN polypeptides produced from a floxed chromosome can be designed to be of normal composition and functionality. The floxed exons 1-3 and neomycin cassette can be removed following Cre-mediate recombination of the loxP sites, leaving a partial PGRN gene which lacks a start site and is predicted to be non-functional (FIG. 8).

Nucleic acid constructs for producing knockout non-human mammals can be introduced into the pronuclei of fertilized eggs by microinjection. Following pronuclear fusion, the developing embryo may carry the introduced nucleic acid in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with large cell populations and selection criteria that are characteristic of cultured cell systems. For production of knockout animals from an initial population of cultured cells, it is necessary that a cultured cell containing the desired knockout construct be capable of generating a whole animal. This is generally accomplished by placing the cell into a developing embryo environment.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem or "ES" cells) have been isolated by culture of cells derived from very young embryos (blastocysts). Such cells are capable, upon incorporation into an embryo, of differentiating into all cell types, including germ cells, and can be employed to generate animals lacking an endogenous PGRN nucleic acid or containing a partial PGRN nucleic acid. That is, cultured ES cells can be transformed with a knockout construct and cells can be selected in which a PGRN nucleic acid is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual*, second edition, Cold Spring Harbor Press, Plainview, N.Y. (1989).

To generate a knockout animal, ES cells having at least one inactivated PGRN allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo can be raised to sexual maturity and bred in order to obtain animals whose cells (including germ cells) carry the inactivated PGRN allele. If the original ES cell was heterozygous for the inactivated PGRN allele, several of these animals can be bred with each other to generate animals homozygous for the inactivated allele.

Direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 6 kb of homologous DNA into the targeting construct. It is also useful to prepare the knockout constructs from isogenic DNA.

Embryos derived from microinjected eggs can be screened for homologous recombination events in several ways. For example, if a targeted nucleic acid is interrupted by a coding region that produces a detectable (e.g., fluorescent) gene product, then the injected eggs can be cultured to the blastocyst stage and analyzed for presence of the indicator polypeptide. Embryos with fluorescing cells, for example, can then be implanted into a surrogate mother and allowed to develop to term. Injected eggs also can be allowed to develop, and DNA from the resulting pups can be analyzed by PCR or RT-PCR for evidence of homologous recombination.

Nuclear transplantation also can be used to generate non-human mammals. For example, fetal fibroblasts can be genetically modified such that they contain an inactivated endogenous PGRN nucleic acid, and then fused with enucleated oocytes. After activation of the oocytes, the eggs can be cultured to the blastocyst stage, and implanted into a recipient. See, Cibelli et al., *Science,* (1998) 280:1256-1258. Adult somatic cells, including, for example, cumulus cells and mammary cells, can be used to produce animals such as mice and sheep, respectively. See, for example, Wakayama et al., *Nature,* (1998) 394(6691):369-374; and Wilmut et al., *Nature*, (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient. Wakayama et al. 1998, supra.

Agents that can increase the level of a PGRN polypeptide can be identified or characterized using a non-human mammal that is the product of a cross between any non-human mammal described herein and any other non-human mammal of the same species. For example, any transgenic non-human mammal can be crossed with any of the knockout non-human mammals provided herein to create non-human mammals that can be used to identify or characterize agents that can increase the level of a PGRN polypeptide. A non-human mammal obtained by crossing a transgenic non-human mammal with a knockout non-human mammal provided herein also can be used to examine the effects of PGRN depletion on brain function and the impact of PGRN depletion on different neurodegenerative disease states.

In some cases, a backcross of tau transgenic (e.g., JNPL3) mice with PGRN knockout ($^{-/-}$) mice can be performed to generate (JNPL3)(PGRN$^{+/-}$) and (JNPL3)(PGRN$^{-/-}$) mice for use in determining the impact of depleting PGRN on the development of neurodegeneration linked to tau pathology, or for use in identifying or characterizing agents that can increase the level of a PGRN polypeptide. The mice can be maintained on the same background strain (e.g., C57BL/6) to minimize genetic differences. In a first round of breeding, hemizygous JNPL mice can be bred with PGRN null mice, resulting in 50% hemizygous (JNPL3)(PGRN$^{+/-}$) mice and 50% PGRN$^{+/-}$ mice. Hemizygous offspring (JNPL3)(PGRN$^{+/-}$) can be backcrossed to the PGRN$^{-/-}$ line, generating 25% (JNPL3)(PGRN$^{-/-}$), 25% (JNPL3)(PGRN$^{+/-}$), 25% PGRN$^{-/-}$, and 25% PGRN$^{+/-}$ mice. JNPL3 mice can also be crossed with PGRN$^{+/+}$ mice to generate (JNPL3)(PGRN$^{+/+}$) mice. Agents that can increase a PGRN polypeptide level can be identified or characterized by administering a candidate agent or vehicle alone to (JNPL3)(PGRN$^{+/-}$) mice, (JNPL3)(PGRN$^{-/-}$) mice, and/or (JNPL3)(PGRN$^{+/+}$) mice, measuring the level of a PGRN polypeptide in each mouse, and comparing the levels to determine whether or not administration of the candidate agent results in an increase in a level of a PGRN polypeptide.

In some cases, PGRN$^{-/-}$ non-human mammals can be crossed with transgenic non-human mammals expressing TAR DNA binding protein 43 (TDP-43) polypeptide to generate non-human mammals useful for studying the interaction between PGRN depletion and the formation of neuronal polypeptide inclusions containing TDP-43 polypeptide, as observed in patients with PGRN mutations and in patients with FTLD or ALS. Non-human mammals obtained by crossing PGRN$^{-/-}$ non-human mammals with transgenic non-human mammals expressing TDP-43 polypeptide also can be used to identify or characterize agents that can increase PGRN polypeptide levels. In some cases, PGRN$^{-/-}$ non-human mammals can be crossed with transgenic non-human mammals expressing amyloid precursor protein (APP; see, U.S. Pat. No. 5,877,399) to generate non-human mammals useful for studying the impact of PGRN depletion on amyloid deposition or for identifying or characterizing agents that can increase the level of a PGRN polypeptide in a mammal.

In some cases, agents that can increase the level of a PGRN polypeptide can be identified or characterized using a non-human mammal in which expression of a nucleic acid encoding a PGRN polypeptide is decreased using a vector such as a viral vector described herein. For example, a viral vector containing nucleic acid encoding an antisense or interfering RNA targeted to an endogenous nucleic acid encoding a PGRN polypeptide or a regulatory region of the endogenous nucleic acid can be administered to a non-human mammal to decrease expression of a PGRN polypeptide (e.g., by injecting a sufficient titer of recombinant viral particles into a mammal). The non-human mammals having a decreased level of expression of a PGRN polypeptide can be administered a candidate agent or vehicle alone and analyzed to determine if administration of the candidate agent results in an increase in the level of a PGRN polypeptide. In some cases, agents that can increase the level of a PGRN polypeptide can be identified or characterized using a non-human mammal in which a nucleic acid encoding a PGRN polypeptide with or without a mutation is expressed (e.g., overexpressed). A nucleic acid encoding a PGRN polypeptide with or without a mutation can be a transgene (e.g., in a transgenic non-human mammal), or can be delivered to a non-human mammal using a vector such as a viral vector described herein. For example, a viral vector containing a nucleotide sequence encoding a PGRN polypeptide can be used to express PGRN polypeptides (e.g., a human PGRN polypeptide having the amino acid sequence set forth in SEQ ID NO:1) in non-human mammals, and the non-human mammals can be used to identify or characterize agents that can increase the level of a PGRN polypeptide.

This document also provides non-mammalian PGRN knockout animals. Such animals can include C. elegans and zebrafish having at least one inactivated PGRN allele. Non-mammalian PGRN knockout animals can be used to examine the biological effects of PGRN depletion or to identify or characterize agents that can increase the level of a PGRN polypeptide.

A nucleic acid encoding a PGRN polypeptide, an agent having the ability to increase the level of a PGRN polypeptide in a mammal, a PGRN polypeptide (e.g., a biologically active PGRN polypeptide), or any combination thereof can be administered to a mammal identified as having a neurodegenerative disorder in order to reduce the severity of a symptom of the disorder or to reduce progression of the disorder. Additional examples of treatments for dementia that can be used in combination with the methods and materials provided herein include, without limitation, antipsychotics (e.g., drugs that can block the effects of dopamine), tranquilizers, and speech therapy to adjust to language difficulties and learn alternate ways of communicating.

A mammal that has been identified as having an elevated risk of developing dementia can be monitored for symptoms of dementia and can be assessed regularly for dementia using any appropriate diagnostic method such as a method provided herein, or any combination of methods provided herein. In addition, plans can be made for the care of a mammal having an elevated risk of developing dementia prior to the mammal developing dementia. A human identified as having an elevated risk of developing dementia also can receive counseling and can be educated about dementia. Once a mammal having an elevated risk of developing dementia develops symptoms of dementia, the mammal can be treated, e.g., to manage the symptoms. In some cases, a mammal being likely to develop dementia can be treated prophylactically, e.g., using one or more of the treatment methods provided herein. For example, a nucleic acid encoding a PGRN polypeptide, an agent having the ability to increase the level of a PGRN polypeptide in a mammal, a PGRN polypeptide (e.g., a biologically active PGRN polypeptide), or any combination thereof can be administered to a mammal identified as being susceptible to developing a neurodegenerative disorder in order to prevent or delay the onset of a neurodegenerative disorder or one or more symptoms thereof.

In some cases, a PPAR agonist, a NSAID, or any combination thereof can be administered to a mammal having or being susceptible to developing a neurodegenerative disorder. In some cases, a nucleic acid encoding a PGRN polypeptide can be administered to a mammal having a neurodegenerative disorder, or being susceptible to developing a neurodegenerative disorder, using a viral vector. In some cases, a nucleic acid encoding a PGRN polypeptide can be administered to a mammal in need of treatment along with one or more than one agent that can increase the level of a PGRN polypeptide in mammals (e.g., a PPAR agonist and/or a NSAID). In some cases, one or more than one agent having the ability to increase the level of a PGRN polypeptide can be administered along with a PGRN polypeptide to a mammal in need of treatment. In some cases, a PGRN polypeptide (e.g., a biologically active PGRN polypeptide) can be administered to a mammal having or being susceptible to developing a neurodegenerative disorder.

A nucleic acid encoding a PGRN polypeptide, an agent having the ability to increase the level of a PGRN polypeptide in a mammal, or a PGRN polypeptide (e.g., a biologically active PGRN polypeptide) can be administered to a mammal individually or in combination. For example, a composition containing a combination of agents, each of which can increase a PGRN polypeptide level, can be administered to a mammal in need of treatment for a neurodegenerative disorder. Such a composition can contain, without limitation, a NSAID and a PPAR agonist. A composition containing a combination of agents can contain additional ingredients including, without limitation, pharmaceutically acceptable vehicles. A pharmaceutically acceptable vehicle can be, for example, saline, water, lactic acid, or mannitol.

Nucleic acids, agents, and PGRN polypeptides (e.g., biologically active PGRN polypeptides) can be administered to mammals by any appropriate route, such as enterally (e.g., orally), parenterally (e.g., subcutaneously, intravenously, intradermally, intramuscularly, or intraperitoneally), intracerebrally (e.g., intraventricularly, intrathecally, or intracisternally) or intranasally (e.g., by intranasal inhalation). While direct administration into the brain of a mammal is one route of administration, a viral vector, an agent, or a PGRN polypeptide also can be administered, for example, intravenously, and targeted to the brain or engineered to cross the blood-brain barrier.

Any appropriate method can be used to target a viral vector to the brain. For example, a fiber knob of an adenovirus or an envelope protein of a lentivirus can be modified by attaching a ligand (e.g., an antibody or antibody fragment) that recognizes a brain-specific or neuron-specific receptor. Methods of enhancing transport of molecules across the blood-brain barrier can be used and can take advantage of passive diffusion (e.g., using sodium caprate) or receptor-mediated endocytosis (e.g., attachment of the virus particle to, for example, an anti-transferrin antibody or to putrescine). Expression of a viral vector carrying a nucleic acid encoding a PGRN polypeptide also can be targeted to the brain using a brain-specific or neuron-specific promoter and/or transcriptional regulatory elements (see, for example, U.S. Pat. No. 5,976,872 or 6,066,726). An example of a promoter that is useful for neuronal-specific expression of a nucleic acid encoding a PGRN polypeptide is a prion promoter.

Recombinant viruses and PGRN polypeptides can be administered in the presence or absence of agents that stabilize biological activity. For example, a recombinant virus or a PGRN polypeptide can be pegylated, acetylated, or both. In some cases, a PGRN polypeptide can be covalently attached to oligomers, such as short, amphiphilic oligomers that enable oral administration or improve the pharmacokinetic or pharmacodynamic profile of the conjugated polypeptide. The oligomers can include water soluble polyethylene glycol (PEG) and lipid soluble alkyls (short chain fatty acid polymers). See, for example, International Patent Application Publication No. WO 2004/047871.

A composition including a viral vector (e.g., containing a nucleic acid encoding a PGRN polypeptide), an agent (e.g., a candidate agent or an agent having the ability to increase the level of a PGRN polypeptide), a PGRN polypeptide (e.g., a biologically active PGRN polypeptide), or any combination thereof can be prepared for parenteral or intracerebral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Agents, nucleic acids, and polypeptides also can be prepared in solid (e.g., lyophilized) form for parenteral or intracerebral administration following addition of any appropriate diluent, such as a saline diluent (e.g., 0.4% or 0.9% sodium chloride, pH 7.4).

Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium hydrogen phosphate), lubricants (e.g., magnesium stearate, talc or silica), disintegrants (e.g., potato starch or sodium starch glycolate), or wetting agents (e.g., sodium lauryl sulfate). Tablets can be coated by methods known in the art. Preparations for oral administration can also be formulated to give controlled release of the agent.

Intranasal preparations can be presented in a liquid form (e.g., nasal drops or aerosols) or as a dry product (e.g., a powder). Both liquid and dry nasal preparations can be administered using a suitable inhalation device. Nebulized aqueous suspensions or solutions can also be prepared with or without a suitable pH and/or tonicity adjustment.

A nucleic acid encoding a PGRN polypeptide, an agent having the ability to increase the level of a PGRN polypeptide in a mammal, a PGRN polypeptide, or any combination thereof can be administered to a mammal in any amount, at any frequency, and for any duration effective to achieve a desired outcome (e.g., to reduce a symptom of a neurodegenerative disorder). In some cases, a nucleic acid encoding a PGRN polypeptide, an agent having the ability to increase the level of a PGRN polypeptide in a mammal, a PGRN polypeptide, or any combination thereof can be administered to a mammal to reduce a symptom of a neurodegenerative disorder by 5, 10, 25, 50, 75, 100, or more percent. Any appropriate method can be used to determine whether or not a symptom of a neurodegenerative disorder is reduced. For example, a test for cognitive impairment (e.g., the abbreviated mental test score (AMTS) or the mini mental state examination (MMSE)) can be used to determine whether or not a symptom of a neurodegenerative disorder (e.g., dementia) is reduced. In some cases, a nucleic acid encoding a PGRN polypeptide, an agent having the ability to increase the level of a PGRN polypeptide in a mammal, a PGRN polypeptide, or any combination thereof can be administered to a mammal to prevent or delay the onset of a neurodegenerative disorder. Any appropriate method can be used to determine whether or not the onset of a neurodegenerative disorder is prevented or delayed. For example, the age of onset of a neurodegenerative disorder, if onset occurs at all, can be compared to the median age of onset in mammals of the same species and same PGRN genotype or phenotype to determine whether or not the onset is delayed. In some cases, the age of onset can be compared to the median age of onset in mammals of the same species, sex, PGRN genotype, PGRN phenotype, and, in the case of humans, race, who did not receive any treatment for a neurodegenerative disorder prior to the onset of neurodegenerative symptoms.

An effective amount of a nucleic acid encoding a PGRN polypeptide, an agent having the ability to increase the level of a PGRN polypeptide, a PGRN polypeptide (e.g., a biologically active PGRN polypeptide), or any combination thereof can be any amount that reduces or prevents a symptom of a neurodegenerative disorder without producing significant toxicity to a mammal. Typically, an effective amount of an agent can be any amount greater than or equal to about 50 µg provided that that amount does not induce significant toxicity to the mammal upon administration. In some cases, the effective amount of an agent or a PGRN polypeptide can be between 100 and 500 µg, between 1 mg and 10 mg, between 5 mg and 20 mg, between 10 mg and 30 mg, between 50 mg and 100 mg, between 200 and 500 mg, between 200 and 800 mg, or between 150 and 900 mg. In some cases, an effective amount of a nucleic acid encoding a PGRN polypeptide can be from about $10^3$ to $10^{12}$ (e.g., about $10^8$) recombinant viral particles or plaque forming units (pfu) containing the nucleic acid. If a particular mammal fails to respond to a particular amount, then the amount can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment (e.g., the mammal's level of PGRN polypeptides or the mammal's cognitive state).

Various factors can influence the actual effective amount used for a particular application. For example, the frequency of administration, duration of treatment, use of multiple treatment agents, route of administration, and severity of the disorder may require an increase or decrease in the actual effective amount administered.

The frequency of administration of a nucleic acid encoding a PGRN polypeptide, an agent having the ability to increase the level of a PGRN polypeptide, a PGRN polypeptide, or any combination thereof can be any frequency that reduces or prevents a symptom of a neurodegenerative disorder without producing significant toxicity to the mammal. For example, the frequency of administration can be from about three times a day to about twice a month, or from about once a week to about once a month, or from about once every other day to about once a week, or from about once a month to twice a year, or from about four times a year to once every five years, or from about once a year to once in a lifetime. The frequency of administration can remain constant or can be variable during the duration of treatment. For example, an agent that modulates a PGRN polypeptide level can be administered daily, twice a day, five days a week, or three days a week. An agent can be administered for five days, 10 days, three weeks, four weeks, eight weeks, 48 weeks, one year, 18 months, two years, three years, or five years. In some cases, a viral vector can be administered as needed. A course of treatment can include rest periods. For example, an agent can be administered for five days followed by a nine-day rest period, and such a regimen can be repeated multiple times. As with the effective amount, various factors can influence the actual frequency of administration used for a particular application. For example, the effective amount, duration of treatment, use of multiple treatment agents, route of administration, and severity of disorder may require an increase or decrease in administration frequency.

An effective duration for administering an agent provided herein can be any duration that reduces or prevents a symptom of a neurodegenerative disorder or achieves a particular level of PGRN polypeptide expression without producing significant toxicity to the mammal. Thus, the effective duration can vary from several days to several weeks, months, or years. In general, the effective duration for the treatment of a disorder can range in duration from several days to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the disorder.

Before administering a nucleic acid encoding a PGRN polypeptide, an agent having the ability to increase the level of a PGRN polypeptide, a PGRN polypeptide, or any combination thereof to a mammal, the mammal can be assessed to determine whether or not the mammal has or is susceptible to developing a neurodegenerative disorder. For example, a mammal can be assessed as described herein to determine whether or not the mammal has a mutation (e.g., a mutation provided herein) in a PGRN nucleic acid, or to determine whether or not the mammal has a reduced level of PGRN RNA or polypeptide expression. Assays described herein for detecting PGRN RNA and polypeptide levels can be used to screen and identify individuals that have reduced levels of PGRN expression and are at risk for developing frontotemporal dementia or other neurodegenerative disorders. For example, lymphoblasts of patients with family members with frontotemporal dementia can be screened for PGRN polypeptide levels using a single assay, such as an ELISA, or a battery of biological assays, such as an ELISA, RT-PCR, and western blotting. Other genetic tests also can be used to assess mammals for neurodegenerative disorders, such as tests for determining the presence or absence of nucleic acid encoding ApoE4 in the mammal (see, for example, U.S. Pat. No. 5,508,167). Additional examples of diagnostic tests that can be used to assess mammals for neurodegenerative disorders include, without limitation, neurological exams, neurophysical testing, cognitive testing, and brain imaging. Any appropriate combination of diagnostic tests, such as a combination of tests described herein, also can be used to assess a mammal for a neurodegenerative disorder.

After administering a nucleic acid encoding a PGRN polypeptide, an agent having the ability to increase the level of a PGRN polypeptide, a PGRN polypeptide, or any combination thereof to a mammal having a neurodegenerative disorder, the mammal can be monitored to determine whether or not the disorder was treated. For example, a mammal having a neurodegenerative disorder can be assessed before and after treatment to determine whether or not a symptom (e.g., cognitive impairment) of the disorder was reduced (e.g., stopped). As described herein, any appropriate method can be used to assess symptoms of a neurodegenerative disorder. For example, cognitive testing can be performed before and after treatment to determine if cognitive function increased, decreased, or stayed the same with treatment. Imaging (e.g., MRI) also can be performed before and after treatment to determine if the treatment reduced progression of structural brain damage, for example. MRI brain scans taken before and after treatment also can be used to monitor the progression of a neurodegenerative disorder by mapping brain volume changes. Thought, memory, daily functioning, social conduct, social inhibitions, and/or personality of a mammal can be observed before, during, and after treatment to determine whether or not a symptom of a neurodegenerative order has improved or whether progression of a symptom has been reduced.

The effectiveness of a treatment for a neurodegenerative disorder provided herein (e.g., administration of an agent or a nucleic acid to increase a PGRN polypeptide level) also can be assessed by determining whether or not treatment of a mammal having a neurodegenerative disorder resulted in an increase in a PGRN polypeptide level in the mammal. A PGRN polypeptide level can be measured in a mammal using any appropriate method, such as a method described herein. For example, a level of a PGRN polypeptide can be measured in a sample of peripheral blood lymphocytes or cerebral spinal fluid from a mammal before and after treatment for a neurodegenerative disorder (e.g., treatment with an agent described herein) using an ELISA assay to determine if the level increased with treatment. Methods of monitoring the location or amount of a viral vector in a mammal are known and can include, for example, imaging a marker (e.g., a fluorophore), the product of a reporter gene (e.g., GFP), or a radioisotope (e.g., $^{99}$Tc) using methods known in the art, such as PET, nuclear, MR, or optical imaging. Levels of PGRN RNA or polypeptide can be measured in a mammal to monitor the level of expression of a viral vector delivering nucleic acid encoding a PGRN polypeptide.

In some cases, a mammal likely to develop a neurodegenerative disorder can be assessed during or after treatment with a nucleic acid encoding a PGRN polypeptide, an agent having the ability to increase the level of a PGRN polypeptide, a PGRN polypeptide (e.g., a biologically active PGRN polypeptide), or any combination thereof to determine whether or not the onset of a symptom of a neurodegenerative disorder is delayed, e.g., relative to the mean age of onset in mammals of the same species and, for example, the same PGRN genotype or phenotype that were not treated prior to manifestation of a symptom of the disorder. A mammal likely to develop a neurodegenerative disorder also can be assessed before and after treatment to determine whether or not a level of a PGRN polypeptide has increased in the mammal.

This document also provides methods and materials for identifying agents that can be used to treat a mammal having or being likely to develop a neurodegenerative disorder by increasing the level of a PGRN polypeptide in the mammal. For example, an animal model for dementia provided herein can be used to identify agents capable of increasing PGRN polypeptide levels. In some cases, animals generated by crossing PGRN$^{-/-}$ or PGRN$^{+/-}$ mice with JNPL3 or rTg4510 transgenic mice (Santacruz et al., *Science,* 309 (5733):476-81 (2005); Lewis et al., *Nat Genet,* 25(4):402-5 (2000)) can be used. In some cases, animals produced by crossing PGRN$^{-/-}$ or PGRN$^{+/-}$ mice with SOD1 mice (Hall et al., *J Neurosci Res,* 53(1):66-77 (1998)) can be used. In some case, animals generated by crossing PGRN$^{-/-}$ or PGRN$^{+/-}$ mice with triple-transgenic mice containing transgenes encoding PS1 (M146V), APP (Swe), and tau (P301L) polypeptides (Oddo et al., *Neuron,* 39(3):409-21 (2003)) can be used. Agents useful for treating neurodegenerative disorders also can be identified using any of the other non-human mammals described herein, or any mammals obtained by mating and propagating such mammals. For example, PGRN$^{-/-}$, PGRN$^{+/-}$, (JNPL3)(PGRN$^{-/-}$), and/or (JNPL3)(PGRN$^{+/-}$) non-human mammals can be used.

Typically, non-human mammals are treated with a candidate agent for increasing the level of a PGRN polypeptide after the mammals have developed one or more symptoms of a neurological disorder. Candidate agents for increasing the level of a PGRN polypeptide can be dissolved in a suitable vehicle prior to being administered to a non-human mammal. A vehicle can be an inert solvent in which an agent can be dissolved for administration. It is recognized that for any given agent, a vehicle suitable for non-human mammals may not be the same as the vehicle used for human treatment. Some examples of suitable vehicles include water, dimethyl sulfoxide, ethanol, and ethyl acetate. The concentration of agent to be tested can be determined based on the type of agent and in vitro data.

As described herein, a candidate agent can be administered to mammals in various ways. For example, a candidate agent can be dissolved in a suitable vehicle and administered directly using a medicine dropper or by injection. A candidate agent also can be administered as a component of drinking water or feed.

After treating non-human mammals with a candidate agent, one or more symptoms of a neurodegenerative disorder manifested in the mammals can be compared between treated and untreated mammals to determine whether or not the agent is effective for treating a neurodegenerative disorder (e.g., whether or not the agent reduces the severity of a symptom of a neurodegenerative disorder). For example, cognitive tests such as a water maze or object recognition test can be used to compare treated and untreated non-human mammals to determine whether or not the cognitive function of treated mammals is improved relative to that of the untreated mammals.

The efficacy of a candidate agent also can be assessed by comparing levels of PGRN polypeptides in plasma, CSF, and/or brain of treated and untreated mammals. Levels of PGRN polypeptides in plasma, cerebral spinal fluid (CSF), lymphocytes, and brain can be determined using any appropriate method such as those described herein. For example, levels of PGRN polypeptides can be determined using a sandwich ELISA or mass spectrometry in combination with internal standards or a calibration curve. Plasma and CSF can be obtained from mammals using standard methods. For example, lymphocytes and plasma can be obtained from blood by centrifugation, CSF can be collected by tapping the cisterna magna, and brain tissue can be obtained from sacrificed animals.

The invention will be further described in the following examples, which do not limit the scope of the invention described in the claims.

EXAMPLES

Example 1

Mutations in PGRN Cause Tau-Negative Frontotemporal Dementia Linked to Chromosome 17

Methods
PGRN Gene Sequencing:
Genomic DNA from members of each studied family was isolated from whole blood or brain tissue using standard protocols. All coding exons of the PGRN gene were amplified by PCR using primers designed to flanking intronic sequences (Table 2). Reactions contained each primer at a final concentration of 0.8 nM and 10% Q-solution (Qiagen, Valencia, Calif.), and were cycled using a 58-48° C. touchdown protocol. The resulting PCR products were purified with Multiscreen plates (Millipore, Billerica, Mass.), and sequenced in both directions on an ABI 3730 instrument using the relevant PCR primers and Big Dye chemistry following manufacturer's protocols (Applied Biosystems, Foster City, Calif.).

TABLE 2

PGRN sequencing and PCR primer sequences

| Name | Sequence | SEQ ID NO | Product size (bp) |
|---|---|---|---|
| GRN 1 F | GGGCTAGGGTACTGAGTGAC | 3 | 368 |
| GRN 1 R | AGTGTTGTGGGCCATTTG | 4 | |
| GRN 2 F | TGCCCAGATGGTCAGTTC | 5 | 537 |
| GRN 2 R | GCTGCACCTGATCTTTGG | 6 | |
| GRN 3 F | GGCCACTCCTGCATCTTTAC | 7 | 369 |
| GRN 3 R | TGAATGAGGGCACAAGGG | 8 | |
| GRN 4&5 F | TTAGTGTCACCCTCAAACC | 9 | 587 |
| GRN 4&5 R | ACTGGAAGAGGAGCAAAC | 10 | |
| GRN 6 F | GGGCCTCATTGACTCCAAGTGTA | 11 | 401 |
| GRN 6 R | GGTCTTTGTCACTTCCAGGCTCA | 12 | |
| GRN 7 F | TCCCTGTGTGCTACTGAG | 13 | 373 |
| GRN 7 R | AAGCAGAGAGGACAGGTC | 14 | |
| GRN 8 F | TACCCTCCATCTTCAACAC | 15 | 309 |
| GRN 8 R | TCACAGCACACAGCCTAG | 16 | |
| GRN 9 F | ATACCTGCTGCCGTCTAC | 17 | 457 |
| GRN 9 R | GAGGGCAGAAAGCAATAG | 18 | |
| GRN 10 F | TGTCCAATCCCAGAGGTATATG | 19 | 616 |
| GRN 10 R | ACGTTGCAGGTGTAGCCAG | 20 | |
| GRN 11 F | TGGACTGGAGAAGATGCC | 21 | 574 |
| GRN 11 R | CGATCAGCACAACAGACG | 22 | |
| GRN 12 F | CATGATAACCAGACCTGC | 23 | 387 |
| GRN 12 R | AGGGAGAATTTGGTTAGG | 24 | |
| RNA analysis (C31LfsX34 and R418X mutations) | | | |
| GRN c1F | AGACCATGTGGACCCTGG | 25 | 539 |
| GRN c1R | GTGATGCAGCGGGTGTGAACCAGG | 26 | |
| GRN c10F | ATACCTGCTGCCGTCTAC | 27 | |
| GRN c10R | ACGTTGCAGGTGTAGCCAG | 28 | 589 |

Mutation Validation and Control Screening:
The C31LfsX34 4 bp insert mutation was validated with a PCR/Genescan assay using the FAM-labeled forward primer 5'-GGGCTAGGGTACTGAGTGA-3' (SEQ ID NO:29), and the unlabeled reverse primer 5'-AGTGTT-GTGGGCCATTTG-3' (SEQ ID NO:30). Products run against the 400HD Rox standard (Applied Biosystems, Foster City, Calif.) exhibited two peaks, at 368 bp (wt allele) and 372 bp (mutant). All available samples of the UBC17 family and 550 North American control individuals were then screened with the same assay. Segregation analysis in the remaining families was carried out by sequencing of the relevant exon in each family, in order to check occurrence of the mutations with the disease. Sequence analysis of all PGRN coding exons was also used to screen 200 aged North American control individuals for all remaining mutations. Sequence analysis was also used to screen 150 Dutch and 95 UK control individuals for the Q125X (Dutch family 1083) and the Q468X (UK family F53) mutations, respectively.

Immunohistochemical Methods:
Immunohistochemistry was performed on formalin fixed, paraffin-embedded tissue sections of frontal cortex and hippocampus from two cases of familial FTD with proven PGRN mutations (UBC-17 and UBC-15), one case of Alzheimer's disease, and one age-matched neurologically normal control individual. Sections (5 nm) were deparaffinized and microwaved for antigen retrieval in citrate buffer, pH 6.0. Ubiquitin immunohistochemistry was performed using the Ventana ES automated staining system (Ventana, Tucson, Ariz.) with an ubiquitin primary antibody (anti-ubiquitin; DAKO, Glostrup, Denmark; 1:500) and developed using aminoethylcarbizole. For PGRN immunohistochemistry, sections were blocked with 2.5% horse serum (10 minutes), and incubated for one hour at room temperature with primary antibody (N-terminus, acrogranin N19; Santa Cruz Biotechnology, Santa Cruz, Calif.; 1:100; C-terminus acrogranin, S-15; Santa Cruz Biotechnology; 1:100; anti-PCDGF; Zymed, South San Francisco, Calif.; 1:100; entire human PGRN polypeptide, anti-human Progranulin; R&D Systems, Minneapolis, Minn.; 1:500) diluted in 2.5% blocking serum. Sections were then incubated with 5% biotinylated universal secondary antibody (Vector Laboratories, Burlingame, Calif.; 10 minutes), followed by incubation with streptavidin/peroxidase complex working solution (5 minutes), and were developed using diaminobenzidine (5 minutes). All sections were counterstained with Hematoxylin.

Analysis of PGRN Polypeptide in Lymphoblastoid Cell Lines:

Lymphoblastoid cells from patients and unaffected relatives were harvested by centrifugation at 5K g for 5 minutes. Pellets were resuspended in co-immunoprecipitation buffer (50 mM Tris-HCl pH 7.5, 100 mM NaCl, 15 mM EDTA, 0.1% Triton X-100, 1% SDS, and protease and phosphatase inhibitors), boiled at 100° C. for 5 minutes and sonicated for 15 seconds. For western blot analysis, equal amounts of total protein (40 µg) were resolved on 10% Tris-Glycine SDS-PAGE gels (Invitrogen, Carlsbad, Calif.) and transferred onto 0.45 µm PVDF membranes. Blots were blocked in 5% non-fat milk in TBS-T, hybridized with primary antibodies to human PGRN(N-terminus, acrogranin N-19; Santa Cruz Biotechnology; 1:200) followed by anti-goat HRP conjugated secondary antibody, and were visualized by Western Chemiluminescent ECL reagent (Pierce, Rockford, Ill.). PGRN levels were normalized to GAPDH (GAPDH monoclonal; Biodesign International, Saco, Me.; 1:3000). Band density from film exposed within linear range was measured using the Scion Image software package (Scion Corporation, Frederick, Md.).

Generation of R418X Mutant Polypeptide:

Site-directed mutagenesis was performed on a wild-type PGRN cDNA (intronless) construct (MGC clone id 2821810; Invitrogen) using the QuikChange Site-Directed Mutagenesis Kit (Stratagene; Agilent Technologies, Santa Clara, Calif.) according to the supplier's instructions. The wild-type and mutant PGRN cDNA constructs were transfected into HeLa cells using Lipofectamine 2000 Reagent (Invitrogen). After 24 hours, cells were harvested, and protein extracts were generated as described for the lymphoblast cells.

Analysis of PGRN RNA:

RNA was isolated from lymphoblastoid cells and brain (cerebellum) samples and analyzed by qRT-PCR using SYBR green as described elsewhere (Oosthuyse et al., Nat. Genet., 28:131-8 (2001)). Cerebellum was used since this region is unaffected in FTD-17, making it less likely for neuronal loss and microgliosis to influence PGRN RNA levels. To ensure that DNA contamination could not contribute to the detected signal, primers for PGRN were designed to span intron 1 (5'-GATGGTCAGTTCTGC-CCTGT-3' (forward; SEQ ID NO:31) and 5'-CCCT-GAGACGGTAAAGATGC-3' (reverse; SEQ ID NO:32); amplicon size=174 bp). Mass values for PGRN mRNA were normalized to 28S ribosomal RNA mass values and then divided by GAPDH mRNA to determine fold-change in expression. Values were expressed as a percentage of control individuals. RT-PCR fragment analysis was used to determine relative levels of mutant and wild-type PGRN RNA in C31LfsX34 (UBC17) lymphoblasts and brain tissue. RT-PCR was performed with 5' FAM-labeled 5'-GT-GAGCTGGGTGGCCTTAAC-3' (forward; SEQ ID NO:33) and 5'-GCAGAGCAGTGGGCATCAAC-3' (reverse; SEQ ID NO:34) primers. Amplicon sizes were analyzed on an ABI3100 (Applied Biosystems, Foster City, Calif.). The mutant C31LfsX34 RNA generated a product (196 bp) that was 4 bp longer than wild-type RNA. Sequence analysis of RT-PCR products (primers in Table 2) was further used to analyze levels of C31LfsX34 and R418X mutant RNAs compared to wild-type in relevant family brain tissues and lymphoblasts. PGRN RNA levels in lymphoblasts from the C31LfsX34 (UBC17) and the R418X (UBC15) families were analyzed with and without cycloheximide treatment (500 µM, 2-8 hours), a nonsense mediated decay (NMD) inhibitor.

Isolation of Detergent and Formic Acid Soluble and Insoluble Protein Fractions from FTD-17 and Normal Brain Tissue:

To study the presence and solubility of PGRN species in frozen frontal cortices and cerebellum of patients with the R418X (UBC15) and C31LfsX34 (UBC17) mutations, brain tissue was homogenized in 1 mL/250 mg THE buffer (10 mM Tris-HCl pH 7.5, 150 mM NaCl, 5 mM EDTA) containing 1:100 dilutions of Protease Inhibitor Cocktail, PMSF and Phosphatase Inhibitor Cocktails I and II (all obtained from Sigma, Saint Louis, Mo.). Brain homogenates from an unaffected control individual, an AD patient, and a PSP patient were included as controls. A portion of the homogenized extracts was solubilized by addition of 1% SDS and 15 second sonication, and was used as total SDS-soluble proteins. The remaining homogenate was centrifuged at 100K g for 30 minutes at 4° C. to obtain buffer soluble proteins. The pellet was re-homogenized in TNE containing 0.5% NP40 and centrifuged at 100K g for 30 minutes at 4° C. to obtain detergent soluble supernatant and insoluble pellet fractions. The pellet was further solubilized in TNE buffer containing 1% SDS and centrifuged at 100K g for 30 minutes at 4° C. Insoluble SDS pellet was resuspended in laemmli loading buffer. Frozen frontal cortices of patients were homogenized in 1 mL/150 mg RIPA buffer (50 mM Tris-HCl, 150 mM NaCl, 1% Triton X-100, 0.5% deoxycholate, and 0.1% SDS) containing protease and phosphatase inhibitors and centrifuged at 100K g for 60 minutes at 4° C. to generate RIPA-soluble fractions. The RIPA insoluble pellets were re-extracted with 70% formic acid, sonicated, and centrifuged at 100K g for 60 minutes at 4° C. The aqueous layer was collected, speedvaced to powder form, and resuspended in 1× laemmli loading buffer. Total, detergent and formic acid (soluble and insoluble) fractions were subsequently analyzed by western blotting as described for lymphoblastoid cell lines.

Results

Candidate genes within the 3.53 cM (6.19 Mb) critical region defined by haplotype analysis in reported families (D1751787-D175806) were examined. The coding exons of candidate genes were first sequenced in affected and unaffected members of UBC17 (Table 3), a large Canadian tau-negative FTD-17 family with highly significant evidence for linkage to chromosome 17q21 (2-point LOD 3.65). Analysis of over 80 genes (out of ~165 in the region) failed to identify a pathogenic mutation. However, when progranulin (PGRN) was sequenced, a 4 bp insertion mutation was detected in exon 1 (c.90_91insCTGC), causing a frameshift at codon 31 that is predicted to result in truncation of the encoded polypeptide after a read through of 34 residues (C31LfsX34). PGRN is a 593 amino acid (68.5 kDa) multifunctional growth factor that is composed of seven and a half tandem repeats of a 12-cysteine granulin motif. In contrast, the mutant (C31LfsX34) PGRN polypeptide is predicted to be only 65 residues in length, including the signal peptide (amino acids 1-17), and is predicted not to contain a single intact cysteinyl repeat (FIG. 1). The C31LfsX34 mutation segregated with disease in the UBC17 family (Table 3, FIG. 3) and was absent in 550 North American control individuals. These results indicated that this mutation was probably pathogenic.

To investigate the pathogenic mechanism of the mutations, immunohistochemistry was used to determine if PGRN accumulates in the ub-ir inclusions (NCI and NII) in the brains of FTD patients with PGRN mutations. Ubiquitin immunohistochemistry demonstrated neurites and neuronal cytoplasmic inclusions (NCI) in layer II of frontal neocortex, NCI in dentate granule cells of the hippocampus, and neuronal intranuclear inclusions (NII) in superficial neocortex. PGRN immunoreactivity was observed in a subset of cortical neurons in patients from multiple FTD families with PGRN mutations (UBC17, UBC15 and FTD129) as well as in aged control subjects. PGRN immunohistochemistry was positive in some neocortical neurons but did not stain NCI or NII in layer II cortex. Activated microglia exhibited strong PGRN expression in affected areas of FTD and around senile plaques in a control patient with Alzheimer's disease. Despite using a panel of antibodies that recognize all regions of the PGRN polypeptide, the ub-ir NCI and NII in the FTD-17 cases were negative for PGRN. Moreover, the

TABLE 3

Families with premature termination mutations in PGRN

| Family | Origin | Affecteds^ | Mean age onset | Mutation nucleotide | Mutation polypeptide |
|---|---|---|---|---|---|
| UBC17# | Canada | 17 (4) | 58 | c.90_91insCTGC | p.C31LfsX34 |
| 1083# | Netherlands | 19 (1) | 65 | c.373C > T | p.Q125X |
| UBC11 | Canada | 6 (1) | 68 | c.388_391delCAGT | p.Gln130fsX125 |
| F53 | UK | 3 (1) | 60 | c.388_391delCAGT | p.Gln130fsX125 |
| UBC19 | Canada | 9 (1) | 61 | c.IVS8 + 1G > A | p.V279GfsX4* |
| FTD129 | USA | 3 (2) | 54 | c.1145delC | p.T382SfsX29 |
| UBC4 | Canada | 7 (1) | 65 | c.1157G > A | p.W386X |
| UBC15 | Canada | 10 (4) | 60 | c.1252C > T | p.R418X |
| F337 | UK | 5 (1) | 59 | c.1402C > T | p.Q468X | families with previously published linkage to chr17.
^NII pathology confirmed in brackets.
*predicted effect of IVS8 + 1G > A mutation.

PGRN was sequenced in affected individuals from an additional 41 families with clinical and pathological features consistent with tau-negative FTD. Families were ascertained in Canada (7 families), the USA (8 families), the UK (17 families), the Netherlands (1 family), and Scandinavia (8 families). This analysis identified an additional seven PGRN mutations, in 8 of the 41 families (Table 3), each of which is predicted to cause premature termination of the coding sequence (FIG. 1). These mutations include four nonsense mutations (Q125X, W386X, R418X and Q468X), two frameshift mutations (Q130SfsX124 and T382SfsX29), and a mutation in the 5' splice site of exon 8 (IVS8+1G>A). The exon 8 splice site mutation (UBC19) is likely to lead to skipping of exon 8 from PGRN mRNA, resulting in a frameshift (V279 GfsX4). The Q130SfsX124 mutation was found in two FTD families ascertained independently in Canada (UBC11) and the UK (F53). All seven mutations segregated with disease in the relevant families (Table 3, FIG. 3) and were absent in 200 North American control individuals. In addition, the Q125X mutation (Dutch family 1083) was absent in 150 control individuals from the Netherlands, and the Q468X mutation (UK family F337) was absent in 95 UK controls.

The two FTD families with previously reported evidence for linkage to chromosome 17q21 (UBC17, and 1083) were both found to have mutations that cause premature termination in PGRN (FIG. 1). Significantly, all nine families with PGRN mutations also had neuropathological findings that included ub-ir NII.

truncated mutant PGRN species R418X (UBC15) and C31LfsX34 (UBC17) were not detected in total protein extracts of brain and lymphoblastoid cells from FTD-17 patients (FIG. 2C). There was also no evidence that insoluble PGRN species were accumulating in detergent or formic acid extractable fractions from patient brain tissue. Taken together these results suggest that the mutations are unlikely to cause aggregation of mutant or wild-type PGRN polypeptides.

Experiments were performed to determine whether premature termination of the PGRN coding sequence resulted in nonsense mediated decay (NMD) of the mutant RNAs since the location of the premature termination codon (PTC) created by each mutation was expected to trigger NMD. Quantitative-PCR analysis of RNA extracted from patient lymphoblasts carrying the R418X (UBC15) and C31LfsX34 (UBC17) mutations revealed that both were associated with about a 50% reduction in total PGRN RNA relative to lymphoblasts from unaffected individuals (FIG. 2A). In addition, PGRN RNA from both families consisted almost entirely of wild-type RNA with little of the mutant RNAs detected (FIG. 2B). Treatment of patient lymphoblasts with cycloheximide, a known inhibitor of NMD, resulted in an increase in levels of total PGRN RNA (FIG. 2A) that was associated with a selective increase in the R418X and C31LfsX34 mutant RNAs (FIG. 2B).

Similar results were obtained by sequence analysis of PGRN RNA from lymphoblasts containing the C31LfsX34 (UBC17) and R418X (UBC15) mutations. Sequence analysis of RT-PCR products from the lymphoblasts revealed single peaks over the mutation sites, indicating that the RNA consisted largely of wild-type species. After treating the lymphoblasts with cycloheximide (500 μM for eight hours), additional sequence peaks corresponding to increased levels of the two mutant RNA species were clearly visible, indicating that the mutant RNAs (C31LfsX34 and R418X) are normally subject to nonsense mediated decay. Furthermore, western blot analysis revealed that wild-type PGRN polypeptide was reduced in extracts from R418X and C31LfsX34 lymphoblasts (mean reduction 34%, p=0.01, t-test) relative to extracts from unaffected relatives (FIG. 2C). These results suggest that the observed premature termination mutations in PGRN cause tau-negative FTD-17 by creating null alleles, with the mutant RNAs likely being degraded by NMD. This results in loss of functional PGRN (haploinsufficiency) and can explain a lack of correlation between the location of the mutations and the clinical phenotype since each of the mutations has a similar effect, creation of a null allele.

Two additional mutations, Q415X and V452WfsX38, were identified in PGRN genes as described above. Both mutations are located in exon 10 of the PGRN gene, and both were found in cases of FTLD from the UK.

Results provided herein suggest that PGRN is essential for neuronal survival and that even partial loss of PGRN can lead to neurodegeneration. The identification of mutations in PGRN resolves a ten-year-old conundrum, namely the genetic basis for FTD linked to chromosome 17, and explains why multiple families linked to this region lack MAPT mutations. The fact that PGRN is located within 2 Mb of MAPT and yet mutations in both genes independently yield indistinguishable clinical phenotypes is presumably an extraordinary coincidence.

In patients with MND, probable loss-of-function mutations were found to affect another secreted factor, angiogenin (ANG). Tau-negative FTD and MND are closely related conditions. Up to 30% of MND patients develop frontal lobe deficits and a similar proportion of newly diagnosed FTD patients have findings diagnostic or suggestive of MND. The two diseases often coexist in the same family and both conditions have similar ub-ir pathology. Furthermore, PGRN and ANG are both potent inducers of angiogenesis and are linked with tumorigenesis. It appears that reduced levels of these functionally related growth factors represent a common mechanism of neurodegeneration in major subgroups of these two diseases. Moreover, the results provided herein indicate that replacement of these factors can be used as a novel therapeutic strategy in both devastating conditions.

Example 2

Mutations in PGRN are a Cause of Ubiquitin-Positive Frontotemporal Lobar Degeneration Patients and Methods FTLD Patients and Control Series for PGRN Mutation Screening:

The Mayo Clinic FTLD series had 378 patients, 210 clinically diagnosed FTLD patients and 168 pathologically confirmed FTLD patients. The mean onset age of dementia was 60±11 years (range 32-83). Among the 168 deceased patients, their mean age at death was 70±12 years (range 39-97). The main syndromic clinical diagnoses were FTD and PPA with rare occurrences of SD, CBS and FTD-MND. Among autopsied patients, FTLD-U was the major neuropathological subtype (N=105, 62.5%). The overall Mayo Clinic FTLD series had three patient subgroups: 15 FTLD patients from the Olmsted County community-based dementia series, 167 FTLD patients referred to NIH funded Alzheimer's disease Research Centers (ADRC-FTLD referral series), and 196 patients ascertained from multiple tertiary referral centers.

The Olmsted County Community-Based Dementia Series:

This series included 15 FTLD patients (7 clinical; 8 pathological) among 649 patients with clinical dementia collected in Olmsted County, Minn., USA. This series also contained 536 patients with possible or probable AD, 10 patients with vascular dementia, 36 patients with Lewy-body dementia (LBD) and 52 patients with other neurodegenerative forms of dementia. All FTLD patients (13 FTD and 2 PPA) were included in the mutation screening. The mean age at onset in the FTLD patients was 65±11 years (range 50 to 81), mean age at death was 79±12 years (range 54 to 96) and 67% (10/15) had a family history of dementia. The diagnoses were based on clinical findings and imaging.

The ADRC-FTLD Patient Referral Series:

This series had 167 FTLD patients ascertained by referral to five NIH ADRC-funded centers. The mean age at onset of dementia in this series was 59±10 years (range 32 to 83), and 38% had a positive family history of dementia. Primary clinical diagnoses included FTD, PPA, AD, CBS, FTD-MND, posterior cortical atrophy, and unspecified dementia. Pathological examination was performed in 28 of the 167 patients and the mean age at death in this group was 71±9 years (range 39-84). The FTLD-U pathological subtype was observed in 21 patients (75%). In addition, three patients were subsequently pathologically diagnosed with CBS, two with AD and one with atypical progressive supranuclear palsy (PSP)/LBD. All 167 patients included in the PGRN mutation screening received a clinical diagnosis of FTLD.

The Tertiary Referral Series:

A total of 196 FTLD (64 clinical, 132 pathological) patients were ascertained by multiple tertiary referral centers. The majority (N=112) of patients were obtained through nine brain banks within the U.S. The remaining 84 FTLD patients were ascertained internationally.

Control Individuals:

A total of 200 control individuals (mean age 76±10 years) were ascertained through the Mayo Clinics in Jacksonville, Fla. and Scottsdale, Ariz.

ALS Patient Series for PGRN Mutation Screening:

The ALS patient series comprised 48 patients, of which 27 were pathologically confirmed. ALS patients were recruited through the Neuromuscular Clinic, Mayo Clinic Jacksonville (N=17) and internationally (N=4). Pathologically confirmed ALS patients were obtained from the Neuropathological Core, Mayo Clinic Jacksonville (N=17), the Harvard Brain Bank (N=6), Northwestern University Feinberg School of Medicine (N=1) and Sun Health Research Institute (N=3). The mean age at onset of ALS was 57 years (range 30-75) and a family history of ALS was present in 40% of the patients.

PGRN Gene Sequencing:

The 12 coding exons of PGRN were amplified by PCR using primers and a protocol described elsewhere (Baker et al., *Nature*, 442:916-919 (2006)). In addition, PGRN PCR and sequencing primers were designed to amplify up to three PGRN exons in a single fragment, allowing for higher throughput analyses (Table 4). PCR primers flanking the non-coding exon 0 and the 3' UTR of PGRN were also generated (Table 4). Standard 25 μL PCR reactions were performed using Qiagen PCR products with addition of Q-solution for PGRN exons 1-3 and 7-9 (Qiagen, Valencia, Calif.) and primers at a final concentration of 0.8 µM each. The annealing temperature for PGRN exons 1-3 and 7-9 was 66° C., and for PGRN exons 4-6 and 10-12 was 64° C. The PGRN exon 0 and 3' UTR fragments were cycled using touchdown protocols of 70-55° C. and 58-48° C., respectively. PCR products were purified with Multiscreen plates (Millipore, Billerica, Mass.) and sequenced in both directions on an ABI 3730 instrument with the Big Dye chemistry following the manufacturer's protocol (Applied Biosystems, Foster City, Calif.).

TABLE 4

PGRN sequencing and PCR primers

| Name | Sequence | SEQ ID NO | Product size (bp) |
|---|---|---|---|
| GRN1-3F | GATTTCTGCCTGCCTGGACAGG | 35 | 864 |
| GRN1-3R | GATGCCACATGAATGAGGGCAC | 36 | |
| GRN4-6F | GTCACCCTCAAACCCCAGTAGC | 37 | 822 |
| GRN4-6R | CATGAACCCTGCATCAGCCAGG | 38 | |
| GRN7-9F | TTGCTGGGAGCCTGGCTGATGC | 39 | 1033 |
| GRN7-9R | CTCCTGCTTACAGCACCTCCAG | 40 | |
| GRN10-12F | CTGACAGATTCGTCCCCAGCTG | 41 | 1040 |
| GRN10-12R | ACCTCCCATGGTGATGGGGAGC | 42 | |
| GRNseq2-3F | GGTCATCTTGGATTGGCCAGAG | 43 | |
| GRNseq1-2R | TCTGCAGGTGGTAGAGTGCAGG | 44 | |
| GRNseq5-6F | AGGGGGTGAAGACGGAGTCAGG | 45 | |
| GRNseq4-5R | GAGGAGCAAACGTGAGGGGCAG | 46 | |
| GRNseq8-9F | TGATACCCCTGAGGGTCCCCAG | 47 | |
| GRNseq7-8R | GAAGAAGGGCAGGTGGGCACTG | 48 | |
| GRNseq11-12F | GCTAAGCCCAGTGAGGGGACAG | 49 | |
| GRNseq10-11R | GCCATACCCAGCCCCAGGATGG | 50 | |
| GRN 0F | CGCCTGCAGGATGGGTTAAGG | 51 | 507 |
| GRN 0R | GCGTCACTGCAATTACTGCTTCC | 52 | |
| RN 3'UTR F | AGCCAGGGGTACCAAGTGTTTG | 53 | 558 |
| GRN 3'UTR R | GGGGTAATGTGATACAGCCGATG | 54 | |

Genomic Characterization of PGRN:

The presence of internal PGRN genomic insertions/deletions or rearrangements was analyzed by long-range PCR of the complete 4 kb PGRN coding sequence in a single fragment using the Expand Long Template PCR System kit (Roche, Indianapolis, Ind.) and alternatively, by PCR of three overlapping 2 kb PGRN coding sequence fragments. Long-range PCR reactions were performed with primers GRN1-3F and GRN10-12R (Table 4) using the standard PCR protocol (buffer 1) and cycling conditions recommended by the manufacturer of the Expand Long Template PCR kit. A PvuII restriction enzyme digest was performed on the 4 kb PCR product resulting in nine fragments (1463, 608, 474, 445, 275, 271, 182, 142, and 63 bp) that could be readily sized. The smaller 2 kb PGRN coding sequence fragments that spanned exons 1-6, exons 4-9 and exons 7-12 were amplified using the GRN PCR primers developed for high throughput sequencing (GRN1-3F/GRN4-6R; GRN7-9F/GRN10-12R; GRN4-6F/GRN7-9R; Table 4). Standard 25 µL PCR reactions were performed using Qiagen PCR products with Q-solution and a 66-61° C. touchdown protocol for all primer sets and subsequent restriction enzyme digestion with RsaI (exons 1-6: 727, 588, 467, 79, and 66 bp; exons 4-9: 823, 316, 233, 207, 153, and 90 bp; exons 7-12: 1108, 266, 207, 153, 124, 90, and 83 bp). Agarose gel electrophoresis was performed on PvuII and RsaI digested fragments (2% gel) as well as on the undigested (1% gel) PCR products to detect aberrant banding patterns that might indicate the presence of a genomic abnormality. If an aberrant pattern was detected, the PCR reaction was repeated for confirmation, and sequencing analyses with internal PGRN primers were performed as described above.

PGRN Copy-Number Analyses:

To detect duplication or deletion mutations affecting the 5' or 3' end of the PGRN gene or the entire PGRN gene, semi-quantitative assessment of genomic copy number for exons 1 and 12 of PGRN was made relative to two endogenous genes; glyceraldehyde-3-phosphate dehydrogenase (GAPDH) and β-2-microglobulin ((β2M). Multiplexed PCR reactions contained fluorescently labeled primers (Table 5) designed to amplify the four products in a single reaction. This allowed relative peak heights to be measured in a linear phase PCR. Comparisons of peak heights of the two endogenous amplicons to each other served as a quality control, while ratios of exons 1 and 12 to both GAPDH and β2M were used to determine the relative copy-number of PGRN. PCR reactions were performed using 50 ng of DNA in 25 µL for 25 cycles at an annealing temperature of 65° C. Qiagen reagents (Qiagen, Valencia, Calif.) were used with Q-solution and a final primer concentration of 0.4 µM. Each sample was independently assessed in two separate PCR reactions, one using a 30 second extension time per cycle, the other using 2 minutes per cycle. Fluorescent amplicons were analyzed twice, on an ABI 3100 and an ABI3730 genetic analyzer, using GENEMAPPER and GENESCAN/GENOTYPER software (Applied Biosystems).

TABLE 5

Primers for PGRN copy-number analyses

| Name | Sequence | SEQ ID NO | Product size (bp) |
|---|---|---|---|
| GRNe1i-65'F | FAM-TGGCGTGGGCTTAAGCAGTTGCCAG | 55 | 291 bp |
| GRNe1i-R | AACCACAGACTTGTGCCTGGCGTCC | 56 | |
| GRNe12i-66'F | FAM-TGCTGTCCCTACCGCCAGGTCAG | 57 | 305 bp |
| GRNe12i-R | TGAGCAGAGGGCACCCTCCGAGTGG | 58 | |
| GAPDHi-65'F | FAM-GTCGGGACAAAGTTTAGGGCGTC | 59 | 263 bp |
| GAPDHi-R | GGCGCCTAGACGAAGTCCACAGC | 60 | |
| B2Mi-65'F | FAM-GCTTGGAGACAGGTGACGGTCCCTG | 61 | 328 bp |
| B2Mi-R | ATCCAGCCCTGGACTAGCCCCACG | 62 | |

Haplotype Sharing Studies:

Seven different PGRN mutations (c.26C>A (p.Ala9Asp); c.102delC (p.Gly35GlufsX19); c.154delA (p.Thr52HisfsX2); c.234_235delAG (p.Gly79AspfsX39); c.675_676delCA (p. Ser226TrpfsX28); c.1252C>T (p.Arg418X) and c.1477C>T (p.Arg493X)) were identified in multiple independently ascertained patients. To examine if the FTLD patients with the same PGRN mutation could have shared a common founder, seven STR markers spanning a region of 7.5 Mb flanking the PGRN gene at chromosome 17q21 were typed. All markers were amplified with one fluorescently labeled primer and PCR fragments were analyzed on an automated ABI3100 DNA-analyzer. Alleles were scored using the GENOTYPER software (Applied Biosystems). For six markers (D17S1814, D17S1299, D17S951, D17S934, D17S950 and D17S806), CEPH allele frequencies were used to estimate the allele frequency of the shared alleles in control individuals (CEPH genotype database; World Wide Web at cephb.fr/cephdb/). The marker TAUPROM was PCR amplified using TAUPROM-F: FAM-ACCGCGGCCAGCCATAACTCT (SEQ ID NO:63) and TAUPROM-R: ATCAAGGCACCTCAACATAATAAT (SEQ ID NO:64), and allele frequencies were estimated in a population of 180 unrelated control individuals.

APOE and MAPT Genotyping in PGRN Mutation Carriers:

PGRN mutation carriers were genotyped for the extended H1 and H2 MAPT haplotypes based on the H2 variant rs1052553 using a Taqman SNP genotyping assay on the 7900HT Fast Real Time PCR system (Rademakers et al., *Hum. Mol. Genet.*, 14:3281-3292 (2005)). Genotype calls were made using the SDS v2.2 software (Applied Biosystems). APOE alleles were determined as described elsewhere (Henderson et al., *Neurosci. Lett.*, 324:77-79 (2002)).

RT-PCR Analysis of PGRN RNA.

To determine if specific novel mutations in PGRN caused loss of the mutant RNA by NMD or a similar mechanism, PGRN RNA was analyzed where frozen brain tissue was available. Frontal brain tissue from patients NA05-064 (c.138+1G>A; IVS1+1G>A), NA99-175 (c.26C>A; p.Ala9Asp), UBC14-9 (c.463-1G>A; IVS4-1G>A), and A02-83 (c.708C>T; p.Asn236Asn) was homogenized and total RNA was isolated using Trizol Reagent (Invitrogen, Carlsbad, Calif.). First-strand cDNA was synthesized starting from total RNA with random hexamers and oligo-dT primers using the Superscript II First-Strand Synthesis System for RT-PCR kit (Invitrogen). PCR was performed on brain cDNA using primers spanning exon 1 in patients carrying mutations c.138+1G>A (IVS1+1G>A) and c.26C>A (p.Ala9Asp). The following primers were used: 5'-CAGGGAGGAGAGTGATTTG-3' (cEX0F; SEQ ID NO:65) and 5'-GCAGAGCAGTGGGCATCAAC-3' (cEX2R; SEQ ID NO:66), along with primers spanning exon 6 in patient A02-83 carrying the silent c.708C>T (p.Asn236Asn) mutation (5'-TGCTGTGTTATGGTCGATG-3' (cEX4F; SEQ ID NO:67) and 5'-GTACCCTTCTGCGTGTCAC-3' (cEX8R; SEQ ID NO:68)). The same cEX4F and cEX8R primers were used for cDNA analysis of patient UBC14-9, carrying the c.463-1G>A (1V54-1G>A) mutation in intron 4. In addition, PCR was performed on brain cDNA of patient UBC14-9 with primers spanning exon 10 to determine the number of transcribed alleles based on the presence of the c.1297C>T (p.Arg433Trp) missense mutation (5'-ATACCTGCTGCCGTCTAC-3' (cEX8F; SEQ ID NO:69) and 5'-ACGTTGCAGGTGTAGCCAG-3' (cEX11R; SEQ ID NO:70). RT-PCR products were analyzed on a 2% agarose gel and sequenced to determine the relative amounts of wild type and mutant mRNA.

Results

PGRN Sequencing Analyses in FTLD and ALS Patient Series:

Systematic screening of PGRN was performed in the FTLD and amyotrophic lateral sclerosis (ALS) patient series by direct sequencing of all 12 coding exons, the non-coding exon 0, the core promoter, and the complete 3' untranslated region (UTR). In the overall Mayo Clinic FTLD series (N=378), a total of 23 different pathogenic mutations were identified, defined as mutations that would clearly lead to loss of functional PGRN polypeptide consistent with mutations described elsewhere (Neary et al., *Neurology*, 51:1546-1554 (1998) and Ratnavalli et al., *Neurology*, 58:1615-1621 (2002)). Eighteen pathogenic mutations were found within the PGRN coding sequence, and five intronic mutations were predicted to destroy exonic splice-sites (Table 6). In addition, 13 coding sequence variants (7 missense and 6 silent mutations) were identified that likely represent non-disease related polymorphisms (Table 7). No pathogenic mutations were observed in ALS patients. An additional 8 non-pathogenic intronic sequence variants were identified (Table 8).

TABLE 6

Clinicopathological findings in FTLD families with pathogenic PGRN mutations

| | | Disease presentation[b] | | | | Mutation | | | |
|---|---|---|---|---|---|---|---|---|---|
| Patient | Origin[a] | Age at onset (years) | Age at death (years) | Pathological diagnosis [clinical] | Family history | Genomic[c] | Predicted cDNA[d] | Predicted polypeptide[e] | Location |
| F161-1 | USA | 55 | 66 | FTLD-U (NII) | ND | g.100068T > C | c.2T > C | p.Met? | EX1 |
| 11696 | USA[†] | 56 | N/A | [PPA] | Y | g.100092C > A | c.26C > A | p.Ala9Asp | EX1 |
| NA99-175 | USA | 48 | 56 | FTLD-U (NII) | N | g.100092C > A | c.26C > A | p.Ala9Asp | EX1 |
| NA03-140 | USA | 63 | 65 | FTLD-U (NII) | ND | g.100092C > A | c.26C > A | p.Ala9Asp | EX1 |
| 8536 | USA | 65 | N/A | [FTD] | Y | g.100129insC | c.63insC | p.Asp22ArgfsX43 | EX1 |
| UBC17-68 | Canada | 57 | 61 | FTLD-U (NII) | Y | g.100156_100157insCTGC | c.90_91insCTGC | p.Cys31LeufsX35 | EX1 |
| F159-1 | USA[†] | 83 | N/A | [PPA] | Y | g.100168delC | c.102delC | p.Gly35GlufsX19 | EX1 |
| 0179-90 | Sweden | ND | ND | FTLD[f] | ND | g.100168delC | c.102delC | p.Gly35GlufsX19 | EX1 |
| F149-1 | USA[†] | 56 | 63 | FTLD-U (NII) | Y | g.100205G > A | c.138 + 1G > A (IVS1 + 1G > A) | p.Met? | IVS1 |
| F142-1 | USA[†] | 69 | 76 | FTLD-U (NII) | Y | g.100343delA | c.154delA | p.Thr52HisfsX2 | EX2 |
| 367180 | USA[††] | 80 | 87 | FTLD-U (NII) | Y | g.100343delA | c.154delA | p.Thr52HisfsX2 | EX2 |
| 114209 | USA[††] | 61 | N/A | [PPA] | Y | g.100343delA | c.154delA | p.Thr52HisfsX2 | EX2 |

TABLE 6-continued

Clinicopathological findings in FTLD families with pathogenic PGRN mutations

| Patient | Origin[a] | Age at onset (years) | Age at death (years) | Pathological diagnosis [clinical] | Family history | Mutation Genomic[c] | Predicted cDNA[d] | Predicted polypeptide[e] | Location |
|---|---|---|---|---|---|---|---|---|---|
| 4504 | USA | 51 | 66 | FTLD-U (NII) | ND | g.100423_100424delAG | c.234_235delAG | p.Gly79AspfsX39 | EX2 |
| B3485 | USA | 61 | 68 | FTLD[f] | Y | g.100423_100424delAG | c.234_235delAG | p.Gly79AspfsX39 | EX2 |
| UBC11-1 | Canada | 66 | N/A | [FTD] | Y | g.101168_101171delCAGT | c.388_391delCAGT | p.Gln130SerfsX125 | EX4 |
| UBC14-9 | Canada | 55 | 60 | FTLD-U (NII) | Y | g.101343G > A | c.463 − 1G > A (IVS4 − 1G > A) | p.Ala155TrpfsX56 | IVS4 |
| A03-52 | USA | 56 | 61 | FTLD-U (NII) | N | g.101669_101670delCA | c.675_676delCA | p.Ser226TrpfsX28 | EX6 |
| B4301 | USA | 66 | 72 | FTLD[f] | Y | g.101669_101670delCA | c.675_676delCA | p.Ser226TrpfsX28 | EX6 |
| 97-35 | USA | 51 | 53 | FTLD-U (NII) | ND | g.101669_101670delCA | c.675_676delCA | p.Ser226TrpfsX28 | EX6 |
| B3802 | USA | 55 | 61 | FTLD[f] | Y | g.101703G > C | c.708 + 1G > C (IVS6 + 1G > C) | p.Val200GlyfsX18 | IVS6 |
| NP19870 | USA | 58 | 65 | FTLD-U | Y | g.101983_101984delTG | c.753_754delTG | p.Cys253X | EX7 |
| 12743 | USA | 56 | N/A | [CBS] | Y | g.102264G > C | c.836 − 1G > C (IVS7 − 1G > C) | p.Val279GlyfsX5 | IVS7 |
| F147-47 | USA[†] | 60 | 68 | FTLD-U (NII) | Y | g.102339_102340insTG | c.910_911insTG | p.Trp304LeufsX58 | EX8 |
| 4713 | USA | 56 | 65 | FTLD-U (NII) | Y | g.102340G > A | c.911G > A | p.Trp304X | EX8 |
| UBC19-1 | Canada | 55 | 61 | FTLD-U (NII) | Y | g.102363G > A | c.933 + 1G > A (IVS8 + 1G > A) | p.Val279GlyfsX5 | IVS8 |
| PPA1-1 | USA[†] | 65 | 73 | FTLD-U (NII) | Y | g.102516delG | c.998delG | p.Gly333ValfsX28 | EX9 |
| F129-2 | USA[†] | 56 | 63 | FTLD-U (NII) | Y | g.102663delC | c.1145delC | p.Thr382SerfsX30 | EX9 |
| UBC4-1 | Canada | 62 | 71 | FTLD-U (NII) | Y | g.102675G > A | c.1157G > A | p.Trp386X | EX9 |
| 01-01 | USA | 49 | 54 | FTLD-U (NII) | Y | g.102989C > T | c.1252C > T | p.Arg418X | EX10 |
| UBC15-16 | Canada | 60 | 77 | FTLD-U (NII) | Y | g.102989C > T | c.1252C > T | p.Arg418X | EX10 |
| F153-1 | USA[††] | 52 | 56 | FTLD-U (NII) | Y | g.103132_103133insC | c.1395_1396insC | p.Cys466LeufsX46 | EX10 |
| NA01-249 | USA | 66 | 75 | FTLD-U (NII) | Y | g.103306C > T | c.1477C > T | p.Arg493X | EX11 |
| PPA3-1 | USA | 65 | N/A | [PPA] | Y | g.103306C > T | c.1477C > T | p.Arg493X | EX11 |
| NA02-297 | USA | 56 | 59 | FTLD-U (NII) | Y | g.103306C > T | c.1477C > T | p.Arg493X | EX11 |
| F144-1 | USA[†] | 54 | N/A | [FTD] | Y | g.103306C > T | c.1477C > T | p.Arg493X | EX11 |
| 9118 | USA | 48 | N/A | [FTD] | Y | g.103306C > T | c.1477C > T | p.Arg493X | EX11 |
| A02-43 | USA | 57 | 61 | FTLD-U (NII) | Y | g.103306C > T | c.1477C > T | p.Arg493X | EX11 |
| 05-44 | USA | 53 | 56 | FTLD-U (NII) | Y | g.103306C > T | c.1477C > T | p.Arg493X | EX11 |
| NP12900 | USA | 69 | 72 | FTLD-U (NII) | Y | g.103306C > T | c.1477C > T | p.Arg493X | EX11 |

[a]† = FTLD-ADRC referral series; †† = Olmsted-County community-based dementia series
[b]FTLDU (NII) = Frontotemporal lobar degeneration with ubiquitin-positive intranuclear inclusions; ND = Not documented; N/A = Not applicable
[c]Numbering relative to the reverse complement of GenBank ® accession number AC003043.1 and starting at nucleotide 1
[d]Numbering according to GenBank ® accession number NM_002087.2 starting at the translation initiation codon
[e]Numbering according to GenPept ® accession number NP_002078.1
[f]Ubiquitin staining was not performed

TABLE 7

PGRN coding sequence variants with unknown significance

| Mutation Genomic[a] | Predicted cDNA | Predicted polypeptide | Location | rs number | Frequency Patients N (%) | Controls N (%) | Notes |
|---|---|---|---|---|---|---|---|
| g.100121C > T | c.55C > T | p.Arg19Trp | EX1 | | 1 (0.3) | — | |
| g.100165C > T' | c.99C > T | p.Asp33Asp | EX1 | | 3 (0.8) | 1 (0.4) | p.Gly79AspfsX39 in 1 patient |
| g.100453G > A | c.264G > A | p.Glu88Glu | EX2 | | 1 (0.3) | — | |
| g.100617T > C | c.313T > C | p.Cys105Arg | EX3 | | 1 (0.3) | — | Not segregating with disease |
| g.101164T > C | c.384T > C | p.Asp128Asp | EX4 | rs25646 | 17 (4.5) | 5 (2.2) | |
| g.101702C > T | c.708C > T | p.Asn236Asn | EX6 | | 1 (0.3) | — | Mutant RNA not subject to NMD |
| g.102290G > C | c.861G > C | p.Glu287Asp | EX8 | | 1 (0.3) | — | |
| g.102332G > A | c.903G > A | p.Ser301Ser | EX8 | | 1 (0.3) | — | |
| g.102488G > A | c.970G > A | p.Ala324Thr | EX9 | | 1 (0.3) | — | |
| g.102990G > A | c.1253G > A | p.Arg418Gln | EX10 | | 1 (0.3) | 1 (0.4) | |
| g.103034C > T | c.1297C > T | p.Arg433Trp | EX10 | | 5 (1.3) | — | p.Ala155TrpfsX56 in 1 patient |

TABLE 7-continued

PGRN coding sequence variants with unknown significance

| Genomic[a] | Predicted cDNA | Predicted polypeptide | Location | rs number | Patients N (%) | Controls N (%) | Notes |
|---|---|---|---|---|---|---|---|
| g.103251C > T | c.1422C > T | p.Cys474Cys | EX11 | | 1 (0.3) | — | |
| g.103373G > C | c.1544G > C | p.Gly515Ala | EX11 | rs25647 | 3 (0.8) | 1 (0.4) | p.Met1? in 1 patient |

[a]Numbering relative to the reverse complement of GenBank ® accession number AC003043.1 and starting at nucleotide 1
[b]Numbering according to GenBank ® accession number NM_002087.2 starting at the translation initiation codon
[c]Numbering according to GenPept ® accession number NP_002078.1

TABLE 8

List of intronic PGRN sequence variants identified in FTLD patients and control individuals

| Genomic mutation[a] | Predicted cDNA mutation[b] | Location | rs number |
|---|---|---|---|
| g.96164G > T | c.−80G > T | EX0 | |
| g.96281G > T | c.−8 + 45G > T (IVS0 + 45G > T) | IVS0 | |
| g.100460G > A | c.264 + 7G > A (IVS2 + 7G > A) | IVS2 | |
| g.100474G > A | c.264 + 21G > A (IVS2 + 21G > A) | IVS2 | rs9897526 |
| g.101082_101083insGTCA | c.350 − 48insAGTC (IVS3 − 48insAGTC) | IVS3 | |
| g.101266G > A | c.462 + 24G > A (IVS4 + 24G > A) | IVS4 | rs850713 |
| g.102072G > A | c.835 + 7G > A (IVS7 + 7G > A) | IVS7 | |
| g.103778C > T | c.*78C > T (3′UTR + 78C > T) | 3′UTR | rs5848 |

[a]Numbering relative to the reverse complement of GenBank ® accession number AC003043.1 and starting at nucleotide 1.
[b]Numbering according to GenBank ® accession number NM_002087.2 starting at the translation initiation codon.

Figure 4:
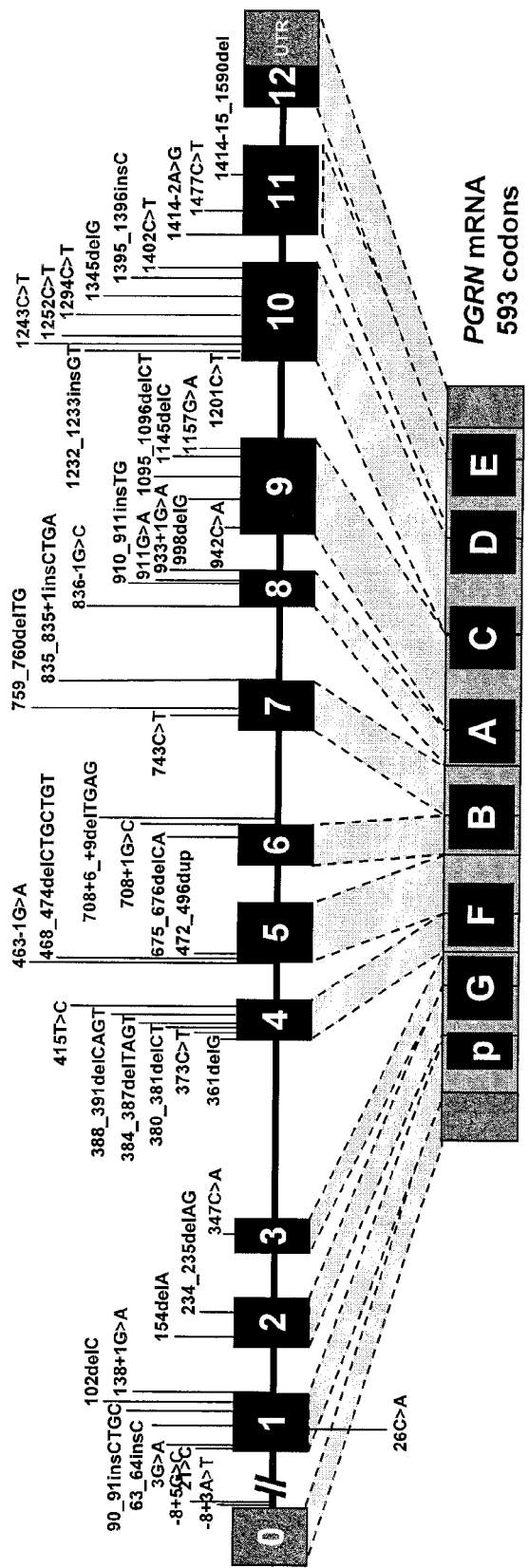
FIG. 4 is a schematic representation of a PGRN gene and mRNA encoding a PGRN polypeptide, showing identified PGRN mutations. Lettered boxes in the PGRN mRNA refer to individual granulin repeats. Mutations are numbered relative to the largest PGRN transcript (GenBank® accession number NM_002087.2; GI:60498993).
Figure 5:
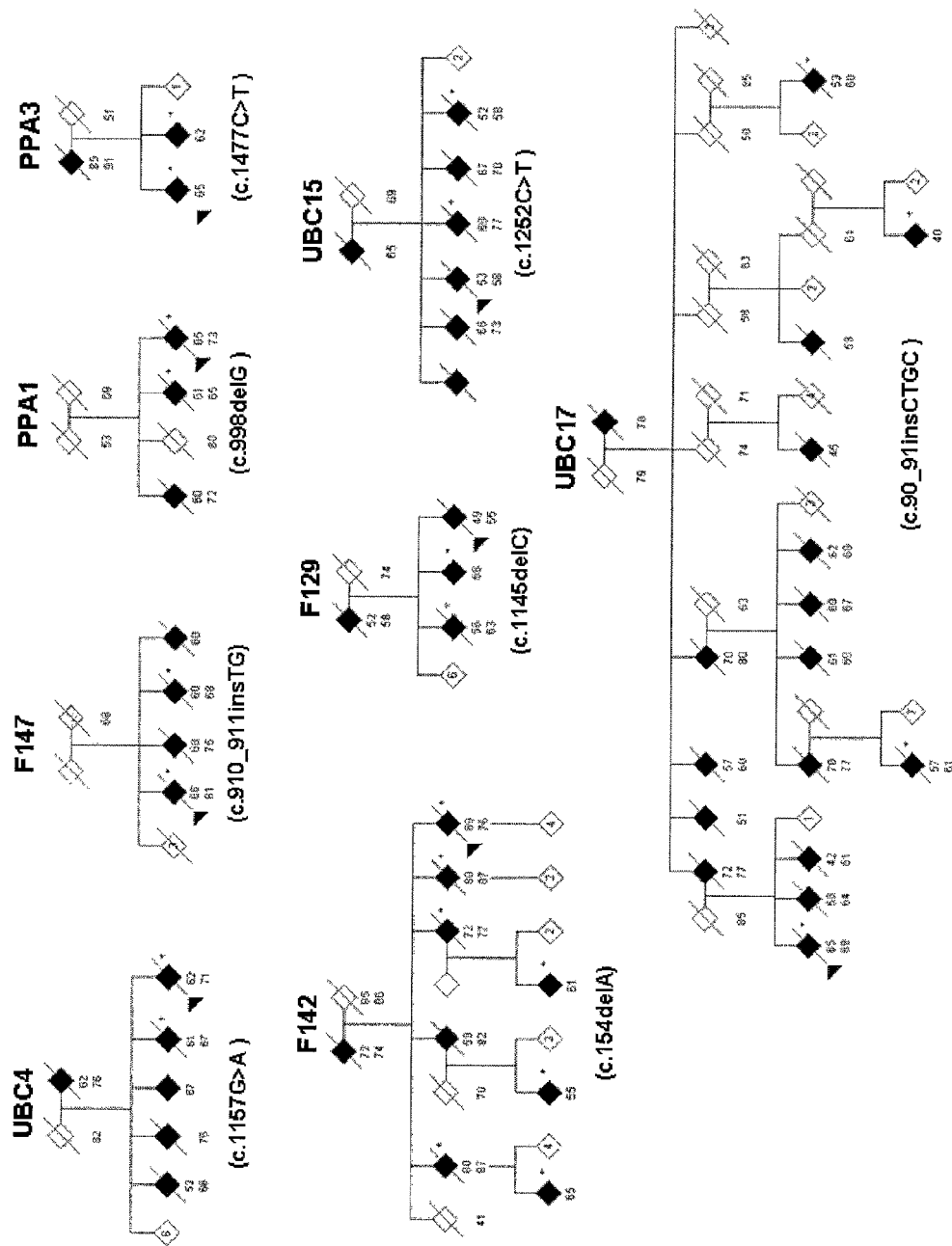
FIG. 5 contains family pedigrees revealing segregation of PGRN mutations with disease in eight FTLD families. To protect each patient's identity, all individuals are depicted as diamonds. The numbers within the diamonds represent the number of individual family members. Open symbols represent unaffected individuals, black symbols denote patients with clinical or pathological diagnosis of FTLD and grey symbols denote PD patients. The first number below the patient's symbol denotes age at onset (in years), followed by age at death (in years). The arrow indicates the proband. For patients, the presence of a PGRN mutation is shown with "+" right above the symbol.

The 23 pathogenic mutations included a total of 20 mutations that are predicted to result in premature termination of the PGRN coding sequence. This group of mutations included nonsense (N=4), frameshift (N=12), and splice-site (N=4) mutations. The truncating mutations were identified scattered over the PGRN gene in 9 different exons, but not in the 3′ end of exon 11 or in exon 12 (FIG. 4). Three additional mutations, two located in exon 1 and one located at the 5′ splice-site of exon 1, were identified that do not cause a simple truncation of the coding sequence, but are nonetheless almost certainly pathogenic. Mutation c.138+1G>A (IVS1+1G>A) is predicted to lead to the splicing out of exon 1, thereby removing the Met1 codon and all associated Kozac sequence, whereas c.2T>C (p.Met?) directly destroys the normal Kozac sequence by mutating the Met1 codon. The third mutation (c.26C>A; p.Ala9Asp) affects the hydrophobic core of the signal peptide sequence. None of the 23 pathogenic coding and splice-site mutations was observed by sequence analysis in 200 unrelated control individuals. Segregation analysis for eight different mutations was performed in FTLD families with at least one other affected family member available for genetic testing. This analysis showed segregation of the PGRN mutations with disease in all analyzed families (FIG. 5). Although all FTLD patients in these families carried the relevant PGRN mutation, five individuals from three different families carried a pathogenic PGRN mutation but had not developed disease by the age of 60, including one individual without symptoms at the age of 73.

In contrast to the pathogenic mutations, four of the 13 coding variants with unknown disease significance were observed in control individuals, including the silent mutation c.384T>C (p.Asp128Asp; rs25646) in exon 4 and the missense mutation c.1544G>C (p.Gly515Ala; rs25647) in exon 11, both reported in the NCBI dbSNP database (World Wide Web at ncbi.nih.gov/SNP; Table 7). Moreover, three variants were detected in patients already affected by another pathogenic PGRN mutation (Table 7). The missense mutation c.313T>C (p.Cys105Arg) was identified in the proband of FTLD family UBC20; however, sequence analyses of four affected and six unaffected relatives excluded segregation of this mutation with the FTLD phenotype in this family indicating that it is likely a rare benign variant.

Detection of Genomic Rearrangements in PGRN Region:

To assess the possible contribution of large genomic insertion/deletion mutations to the overall PGRN mutation frequency in FTLD, 100 patients from the ADRC-FTLD referral series and all FTLD patients (N=15) from the Olmsted County community-based dementia series were studied. In these patients long-range PCR analyses covering the complete PGRN coding region in either a single 4 kb fragment or in three 2 kb overlapping PCR fragments were performed to detect large internal PGRN mutations. No evidence for large internal genomic rearrangements in the PGRN gene was found in either patient series.

In addition, semi-quantitative PCR-based assays of exons 1 and 12 were performed in the complete FTLD population. These analyses have shown no evidence of PGRN copy-number alterations consistent with genomic deletions or multiplications affecting the 5′ or 3′ end of the PGRN gene or the entire gene.

Frequency of PGRN Mutations in the FTLD Patient Series:

Pathogenic mutations in the PGRN gene were detected in 39 patients or 10.5% of the Mayo Clinic FTLD series (N=378; Table 9). Within the subgroup of FTLD patients with a positive family history of a similar dementing disorder (N=144), the PGRN mutation frequency was considerably higher (Table 9). More than one fifth of the familial patients from the Mayo FTLD series (32 out of 144 analyzed patients or 22.2%) could be explained by mutations in the PGRN gene. Family history was not documented for five PGRN mutation carriers, while the FTD phenotype was considered sporadic in two patients (Table 6). Patient NA99-175 carrying mutation c.26C>A (p.Ala9Asp) in the signal peptide showed first symptoms of dementia at the early age of 48 years, while his parents died at the ages of 66 and 70 years without signs of dementia. For patient A03-52 (c.675_676delCA; p.Ser226TrpfsX28) with an onset age of 56 years, one parent died at the age of 56 years from an unrelated illness, which may explain the lack of a positive family history. A pathological confirmation of the FTLD diagnosis was available for 30 PGRN mutation carriers. In all mutation carriers with immunohistochemical data available (N=26), neuropathological findings were consistent with FTLD-U with NII, leading to an overall PGRN mutation frequency of 24.7% in the subpopulation of FTLD-U patients.

patients were not selected on the basis of family history or neuropathological subtype in this ADRC-FTLD series.

Founder Effects of PGRN Mutations:

A total of 23 different pathogenic mutations were identified in 39 independently ascertained patients from the Mayo Clinic FTLD series. The most frequently observed mutation was c.1477C>T (p.Arg493X) located in exon 11, which was identified in eight independently ascertained FTLD patients. Five other mutations were observed more than once: mutations c.26C>A (p.Ala9Asp), c.154delA (p.Thr52HisfsX2), and c.675_676delCA (p. Ser226TrpfsX28) were identified in three patients, and mutations c.102delC (p.Gly35GlufsX19), c.234_235delAG (p.Gly79AspfsX39), and c.1252C>T (p.Arg418X) were identified in two patients each (Table 6). To determine if patients carrying the same mutation could have had a common founder, haplotype analyses were performed with seven STR markers spanning a 7.5 Mb region around the PGRN gene. The common c.1477C>T

TABLE 9

Type and frequency of PGRN mutations in Mayo FTLD patient series

| | Total FTLD population | | | FTLD Community based dementia series | | | FTLD-ADRC series | | |
|---|---|---|---|---|---|---|---|---|---|
| Mutation type | All (N = 378) | FH+ (N = 144) | Ub+ (N = 105) | All (N = 15) | FH+ (N = 10) | Ub+ (N = 5) | All (N = 167) | FH+ (N = 64) | Ub+ (N = 21) |
| Frameshift | 18 | 14 | 11 | 3 | 3 | 2 | 5 | 5 | 4 |
| Nonsense | 12 | 12 | 9 | — | — | — | 1 | 1 | — |
| Splice-site | 5 | 5 | 3 | — | — | — | 1 | 1 | 1 |
| Missense | 3 | 1 | 2 | — | — | — | 1 | 1 | — |
| Kozac | 1 | — | 1 | — | — | — | — | — | — |
| Total | 39 (10.3%) | 32 (22.2%) | 26 (24.7%) | 3 (20.0%) | 3 (30.0%) | 2 (40.0%) | 8 (4.8%) | 8 (12.5%) | 5 (23.8%) |

FH+ = Positive family history of dementia
Ub+ = Pathological diagnosis of frontotemporal lobar degeneration with ubiquitin-positive inclusions In the 15 FTLD patients derived from the community-based dementia population collected in Olmsted County (Minnesota, USA) two different PGRN mutations were detected in a total of three FTLD patients. The two patients carrying the same c.154delA (p.Thr52HisfsX2) mutation were independently ascertained; however, genealogical studies revealed that they were second-degree relatives from the large F142 family (FIG. 5). The data obtained in this small FTLD subgroup from Olmsted County can be extrapolated to the entire community-based dementia series of 649 patients, resulting in a PGRN mutation frequency of ~0.5% in all types of dementia. In the ADRC-FTLD series, mutations were identified in eight FTLD patients (4.8% of 167), each carrying a different mutation (Table 9). Importantly, (p.Arg493X) mutation was identified in family PPA3, for which DNA of one additional affected and one unaffected individual was available, resulting in the unambiguous reconstruction of a disease haplotype in this family. When this haplotype was compared with individual genotype data of the seven additional patients carrying the c.1477C>T (p.Arg493X) mutation, shared alleles were observed between all patients for five consecutive STR markers spanning a 5.1 Mb region between D1751299 and TAU-PROM (Table 10). Shared haplotype analyses also supported a common genetic origin for each of the other six PGRN mutations that were observed in multiple independently ascertained FTLD patients.

TABLE 10

Shared haplotype analyses for PGRN p.Arg493X mutation in 8 FTLD families

| | | | PGRN p.Arg493X FTLD families | | | | | | | |
|---|---|---|---|---|---|---|---|---|---|---|
| Marker | Position (Mb) | Frequency (%) | PPA-3 | NA01-249 | NA02-297 | 6144472 | 9118 | A02-43 | NP12900 | 05-44 |
| D17S1814 | 35.70 | 21.4 | 162 | 161-161 | 161-161 | 150-162 | 166-162 | 154-162 | 164-162 | 155-161 |
| D17S1299 | 36.20 | 19.3 | 200 | 196-200 | 200-200 | 208-200 | 196-200 | 200-200 | 196-200 | 196-200 |
| D17S951 | 39.18 | 25.0 | 180 | 172-180 | 170-180 | 172-180 | 170-180 | 172-180 | 170-180 | 172-180 |
| c.1477C > T | 39.78 | | T | C-T | C-T | C-T | C-T | C-T | C-T | C-T |
| D17S934 | 40.41 | 16.1 | 180 | 180-180 | 174-180 | 180-180 | 184-180 | 182-180 | 176-180 | 174-180 |
| D17S950 | 40.62 | 11.1 | 190 | 190-190 | 184-190 | 190-190 | 180-190 | 192-190 | 178-190 | 188-190 |
| TAUPROM | 41.33 | 1.0 | 363 | 359-363 | 359-363 | 377-363 | 345-363 | 359-363 | 361-363 | 377-363 |
| D17S806 | 43.17 | 1.9 | 181 | 169-181 | 163-181 | 173-181 | 181-181 | 173-181 | 181-181 | 173-175 |

ND = Not determined

Figure 6:
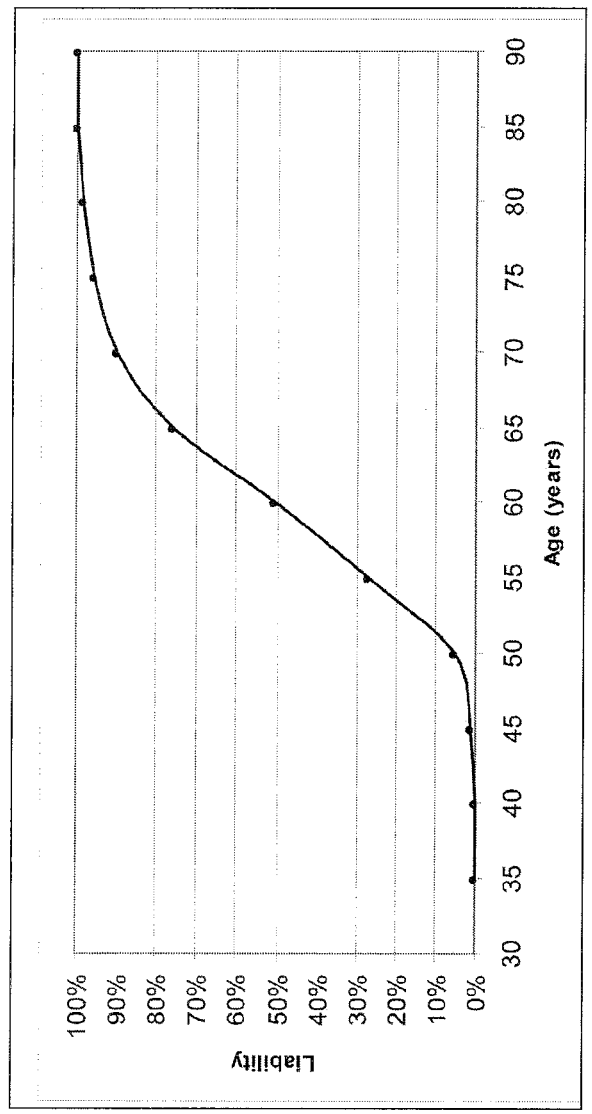
FIG. 6 is a liability curve for PGRN mutation carriers. The distribution of the age-related penetrance in PGRN mutation carriers is shown. The disease penetrance was calculated in age groups of 5 years starting at 30 years and ending at 85 years. A total of 69 affected and 16 non-affected PGRN mutation carriers were included in the analyses.

Phenotype of PGRN Mutation Carriers:

In the FTLD patients with pathogenic mutations in PGRN, the mean age at onset of dementia was 59±7 years (N=38) with a mean age at death of 65±8 years (N=29; Table 6). The clinical presentation was similar in the population of patients without PGRN mutations, although the age at death (70±12 years) was slightly later in non-carriers. As expected from the autosomal dominant FTLD-U families linked to chromosome 17 (Mackenzie et al., *Brain,* 129:853-867 (2006); Rademakers et al., *Mol. Psychiatry,* 7:1064-1074 (2002); and van der Zee et al., *Brain,* 129:841-852 (2006)), a broad age range was observed for both the onset of dementia (48 to 83 years) and the age at death (53 to 87 years). No obvious correlation was noted between the onset of the first clinical symptoms and the location of each mutation in PGRN. In fact, variable onset ages were also observed for patients carrying identical PGRN mutations, with onset ages ranging from 48 to 69 years for carriers of the c.1477C>T (p.Arg493X) mutation, and ranging from 48 to 63 years for the c.26C>A (p.Ala9Asp) mutation. Using information on 68 affected and 16 asymptomatic PGRN mutation carriers, a liability curve emphasizing the age-related disease penetrance for PGRN mutations was generated and showed that only 50% of mutation carriers were affected by the age of 60, while more than 90% of carriers were affected at 70 years of age (FIG. 6). Clinically, FTD (N=17) and PPA (N=7) were the most frequently observed diagnoses, and language dysfunction was a prominent presenting symptom in 24% of the mutation carriers, compared to only 12% of the patients not carrying PGRN mutations. Notably, one patient (who was alive) was clinically diagnosed with corticobasal syndrome (CBS). Two patients received a clinical diagnosis of Alzheimer's disease (AD) with seizures, and seven patients had a movement disorder (Parkinson disease (PD), parkinsonism, or FTD-MND); however, neuropathological autopsy findings for these nine patients were consistent with FTLD-U. Pathological confirmation of the clinical FTLD diagnoses was available for the majority of the mutation carriers (30/39, 77%), showing FTLD-U pathology with both cytoplasmic and intranuclear inclusions in patients for which immunohistochemical data were available (26/30, 87%).

The variable onset age of dementia observed for many PGRN mutations and the potential incomplete penetrance associated with the PGRN IVS0+5G>C mutation, reported in a Belgian FTD population (Cruts et al., *Nature,* 442:920-924 (2006)), emphasized the potential impact of modifying factors on the clinical presentation of FTLD in PGRN mutation carriers. Therefore, the effect of the genotypes of the Apolipoprotein E (APOE) gene and the extended H1 and H2 haplotypes of MAPT on the clinical presentation of FTLD was analyzed in all mutation carriers identified in this study. No obvious effect on age of onset or age at death could be observed for the MAPT haplotypes, either within extended FTLD families or when all FTLD patients with null mutations in PGRN were included in the analysis (mean age at onset for H1/H1 carriers was 59±8 years, and for H1/H2 carriers was 59±7 years). Unexpectedly, patients carrying at least one APOEε4 allele showed a significantly later disease onset (63±7 years; N=10) compared to APOEε3ε3 carriers (57±7 years; N=29; p=0.01, unpaired t-test).

Figure 7:
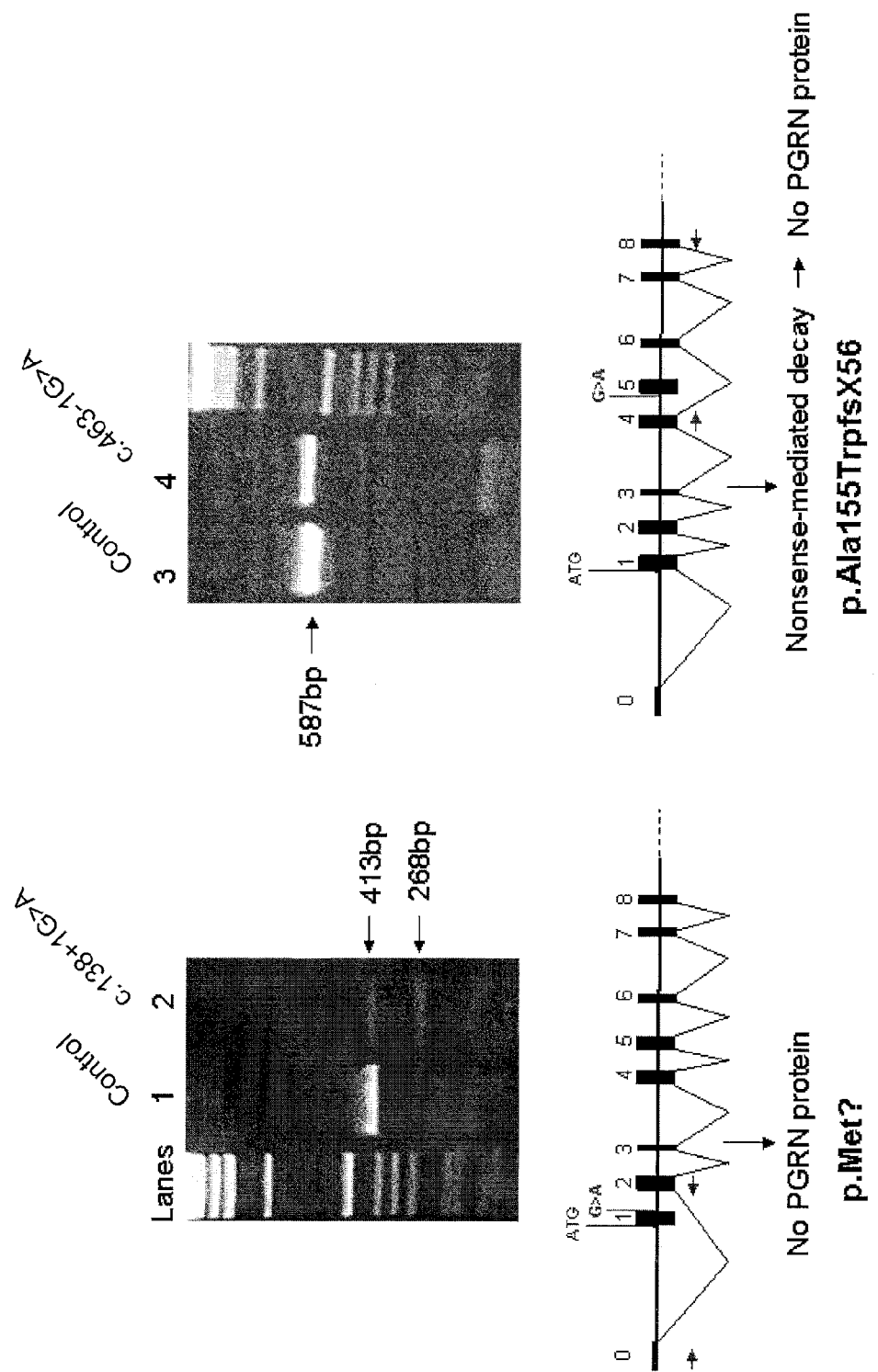
FIG. 7 contains images of agarose gels after electrophoresis of PGRN PCR amplicons obtained from first-strand cDNA prepared from frontal cortex of patients NA05-064 (c.138+1G>A; lane 2) and UBC14-9 (c.463-1G>A; lane 4). The analysis of a control individual is included to show the expected transcript lengths for PGRN cDNA exons 0-2 (413 bp, lane 1) and PGRN cDNA exons 4-8 (587 bp, lane 3). For each PGRN splice-site mutation, a schematic presentation of the predicted splicing of the mutant PGRN transcript is shown. The positions of the mutations and the locations of the PCR primers (arrows) are indicated.

Mechanistic Analyses of Novel PGRN Mutations:

Mutations affecting the splice-sites of PGRN were identified in five FTLD patients. These mutations are expected to lead to skipping of the affected exons, resulting in a frameshift and premature termination of the coding sequence. For the mutations affecting the 5' splice-site of exon 1 (c.138+1G>A; IVS1+1G>A) and the 3' splice-site of exon 5 (c.463-1G>A; IVS4-1G>A) frontal cortices of patients were available as a source of mRNA to study the effect of these mutations. RT-PCR transcript analyses in NA05-064 carrying the c.138+1G>A mutation showed evidence for an aberrant product corresponding to the skipping of exon 1 (268 bp) in addition to the wild-type transcript (413 bp; FIG. 7). The exclusion of exon 1 containing the start methionine codon from the PGRN mRNA is expected to block PGRN polypeptide from being generated, creating a functional null allele. In contrast, no aberrant transcript was identified for patient UBC14-9 carrying c.463-1G>A (IVS4-1G>A; FIG. 7). This mutation is likely to lead to skipping of exon 5 from the PGRN mRNA, resulting in a frameshift and a premature termination codon (PTC) in exon 6 (p.Ala155TrpfsX56; FIG. 7). To determine if the lack of an aberrant transcript for this mutation resulted from the specific degradation of mutant RNA (e.g., by NMD) it was determined whether the brain RNA in this patient was derived from both PGRN alleles. Brain mRNA from patient UBC14-9 was examined for the presence of the sequence variant c.1297C>T (p.Arg433Trp) in exon 10 that occurred on the opposite chromosome. Genomic DNA from patient UBC14-9 was heterozygous for this mutation with the C-allele segregating on the disease haplotype. Comparison of sequence traces of PGRN exon 10 in genomic DNA and mRNA prepared from frontal cortex of patient UBC14-9 confirmed the absence of mutant RNA (C-allele). The three additional splice-site mutations identified in this study are all predicted to cause frameshifts and premature termination of the coding sequence, and are therefore also likely to create null alleles through the degradation of the mutant RNAs. In this group of splice-site mutations, c.708+1G>C (IVS6+1G>C) is expected to result in skipping of exon 6, resulting in a frameshift and a PTC in exon 7 (Val200GlyfsX18), while mutations c.836-1G>C (IVS7-1G>C) and c.933+1G>A (IVS8+1G>A) are both predicted to lead to skipping of exon 8, resulting in a frameshift and premature termination of translation in exon 9 (Val279GlyfsX5).

The missense mutation c.26C>A (p.Ala9Asp) was identified in three independently ascertained FTLD patients and is located in the hydrophobic core of the PGRN signal peptide. To determine if the mutated PGRN signal peptide sequence resulted in a functional null allele, genomic DNA and brain cDNA sequence traces of PGRN exon 1 of patient NA99-175 carrying p.Ala9Asp were compared. Surprisingly, a substantial reduction in the amount of mutant RNA (A-allele) compared to wild-type RNA (C-allele) was detected.

Example 3

Mutations in PGRN are a Cause of Ubiquitin-Positive Frontotemporal Dementia Linked to Chromosome 17q21

Patients and Methods

Patients:

Belgian patients had pure FTD and were diagnosed using a standard protocol and established clinical criteria (Neary et al., *Neurology,* 51:1546-4554 (1998); Engelborghs et al., *Psychiatry,* 74:1148-1151 (2003)). In the series of 103 patients, 10 patients had a definite diagnosis of FTDU, two of dementia lacking distinctive histopathology (DLDH), and one of Pick's disease. Mutation analyses identified a MAPT mutation in three patients, Gly273Arg, Ser305Ser, and Arg406Trp, and one presenilin 1 (PSEN1) mutation, Gly183Val, in the patient with Pick's pathology (Dermaut et al., *Ann. Neurol.,* 55:617-626 (2004)). In the whole sample, mean onset age was 63.8±9.1 years (range 40-90 years). There were 50 females and 53 males, and 43 patients had a positive family history with at least one first-degree relative affected. The FTD series included eight probands sharing the same haplotype at 17q21, indicative of a common founder (van der Zee et al., *Brain,* 129:841-852 (2006)).

PGRN Gene Sequencing:

The sequence of non-coding exon 0 and coding exons 1-12 was determined in the 103 Belgian FTD patients and 190 neurologically healthy control individuals (mean age 52.4±13.3 years, range 37-85 years). For the PGRN exon 0 fragment containing the IVS0+5G>C mutation, 246 additional control individuals (mean age 67.0±12.8 years, range 40-92 years) were sequenced. Total genomic DNA was prepared from peripheral blood according to standard procedures. Standard 20 µL polymerase chain reaction (PCR) amplifications on genomic DNA were performed to amplify exons including exon-intron boundaries with primers designed using Primer 3 (Rozen and Skaletsky, *Methods Mol. Biol.,* 132:365-386 (2000); Cruts et al., *Nature,* 442:920-924 (2006)). Amplification products were purified with 1 U Antarctic phosphatase (New England Biolabs, Ipswich, Mass.) and 1 U exonuclease I (New England Biolabs) and sequenced in both directions using the Big Dye Terminator Cycle Sequencing kit v3.1 (Applied Biosystems) on an ABI3730 automated sequencer (Applied Biosystems). Sequences were analyzed with the Software Package NovoSNP (Weckx et al., *Genome Res.,* 15:436-442 (2005)).

PGRN mRNA and Polypeptide Analyses:

Epstein-Barr virus (EBV) transformed lymphoblasts were cultured and mRNA was isolated using the Chemagic mRNA Direct Kit (Chemagen, Baesweiler, Germany). Frontal brain tissue from the patients was homogenized and total RNA was extracted using the RiboPure Kit (Ambion, Austin, Tex.). First strand cDNA was synthesized starting from mRNA or total RNA with random hexamer primers using the SuperScript III First-Strand Synthesis System for RT-PCR kit (Invitrogen). PCR was performed on both lymphoblast and brain cDNA using primers amplifying the complete coding region of the PGRN transcript and primers amplifying part of the transcript encoding exon 5-6 to the 3' untranslated sequence (UTS). Primer sequences are provided elsewhere (Cruts et al., *Nature,* 442:920-924 (2006)). The resulting PCR products were sequenced to detect aberrant transcripts and to determine the number of transcribed alleles based on the presence of SNP rs5848.

Lymphoblasts were collected by centrifugation at 250 g and lysed in homogenization buffer. Samples were sonicated and cleared at 20,000 g. Protein aliquots (40 µg) were separated on a 4-12% Bis-Tris Nupage gel (Invitrogen) and were electroblotted to Hybond P polyvinylidene difluoride membrane (Amersham Biosciences, Piscataway, N.J.). Membranes were immunoblotted with anti-PGRN antibodies (acrogranin N-19 and 5-15) and detected with secondary antibody and the ECL plus chemiluminescent detection system (Amersham Biosciences, Piscataway, N.J.) with bands quantified on Kodak Imaging Station 440 (Eastman Kodak, Rochester, N.Y.). Quantitative data were normalized to the signal obtained for β-actin (clone AC-15; Sigma).

Results

In patients of the Belgian FTDU-17 founder family DR8, a G-to-C transversion was identified in intron 0 of PGRN at position +5 relative to the first non-coding exon 0 (IVS0+5G>C; Table 11, where IVS indicates intervening sequence), which segregated with disease (Cruts et al., *Nature,* 442:920-924 (2006)). The Belgian founder family was identified based on conclusive 17q21 linkage in one family (DR8; LOD score 3.49 at D175931; van der Zee et al., *Brain,* 129:841-852 (2006)) and subsequent haplotype sharing in seven apparently unrelated familial FTD patients (Cruts et al., *Nature,* 442:920-924 (2006)), indicative of a distant common ancestor (van der Zee, *Brain,* 129:841-852 (2006)). Mutation analysis of PGRN in 103 Belgian FTD patients identified the IVS0+5G>C mutation in the eight probands belonging to the different branches of the Belgian founder family and not in 436 control individuals. In both families, 1083 and DR8, the pathology showed the characteristic ubiquitin-immunoreactive neuronal cytoplasmic and nuclear inclusions in the temporal and frontal cortices (Rademakers et al., *Mol. Psychiatry,* 7:1064-1074 (2002); van der Zee et al., *Brain,* 129:841-852 (2006); Cruts et al., *Nature,* 442:920-924 (2006)). Rarely, inclusions also involved glia cells, but none of the inclusions was shown to have an appreciable presence for any polypeptide from almost 30 possible polypeptides tested (Pirici et al., *J. Neuropathol. Exp. Neurol.,* 65:289-301 (2006)). Patients of both families met the clinical criteria of FTD (Forman et al., *Ann. Neurol.,* 59:952-962 (2006); McKann et al., *Arch. Neurol.,* 58:1803-1809 (2001)), without associated signs of motor neuron disease (Rademakers et al., *Mol. Psychiatry,* 7:1064-1074 (2002); van der Zee et al., *Brain,* 129:841-852 (2006)).

TABLE 11

PGRN mutations identified in Belgian FTD patients

| | | Onset age in | | Mutation* | | |
|---|---|---|---|---|---|---|
| Patient/family | Pathology† | years | Genome‡ | Predicted RNA§ | Predicted polypeptide‖ | Location |
| DR8 | FTDU | 63.8 (n = 5) | g.96241G > C (IVS0 + 5G > C) | — | p.0 | IVS 0 |
| DR2 | Alive | 66.3 (n = 4) | g.96241G > C (IVS0 + 5G > C) | — | p.0 | IVS 0 |
| DR25 | FTDU | 69.5 (n = 2) | g.96241G > C (IVS0 + 5G > C) | — | p.0 | IVS 0 |
| DR26 | Alive | 65 | g.96241G > C (IVS0 + 5G > C) | — | p.0 | IVS 0 |
| DR27 | FTDU | 58 | g.96241G > C (IVS0 + 5G > C) | — | p.0 | IVS 0 |
| DR28 | FTDU | 57 | g.96241G > C (IVS0 + 5G > C) | — | p.0 | IVS 0 |
| SR31 | FTDU | 66 | g.96241G > C (IVS0 + 5G > C) | — | p.0 | IVS 0 |
| DR119 | Alive | 45 | g.96241G > C (IVS0 + 5G > C) | — | p.0 | IVS 0 |

TABLE 11-continued

PGRN mutations identified in Belgian FTD patients

| Patient/family | Pathology† | Onset age in years | Genome‡ | Predicted RNA§ | Predicted polypeptide‖ | Location |
|---|---|---|---|---|---|---|
| DR118 | Died without autopsy | 62 | g.100069G > A | c.3G > A | p.Met1?¶ | FX 1 |
| DR120 | Alive | 56 | g.101160_101161delCT | c.380_381delCT | p.Pro127ArgfsX2 | FX 4 |
| DR91 | Alive | 67 | g.102065_102066insCTGA | c.709_835del | p.Ala237TrpfsX4 | IVS 7 |

*Sequencing all 13 exons of PGRN in 190 control individuals did not identify these or other nonsense or frameshift mutations. Sequencing of exon 0 in 246 additional control individuals showed that the IVS0 + 5G > C mutation was absent.
†FTDU is an autopsied brain pathology diagnosis.
‡Numbering relative to the reverse complement of GenBank ® accession number AC003043 and starting at nucleotide 1.
§Numbering according to the largest PGRN transcript (GenBank ® accession number NM_002087.2) and starting at the translation initiation codon.
‖Numbering according to the largest PGRN isoform (GenPept ® accession number NP_002078.1).
¶Mutation in Met1 translation initiation codon.

The IVS0+5G>C mutation is located in the splice donor site of the first PGRN intron (intron 0) following the non-coding exon 0 (Table 11 and FIG. 4). In silico analysis predicted a marked drop in binding efficiency of the U1 snRNP complex. Furthermore, analysis of full-length PGRN complementary DNA in lymphoblasts and brain of probands DR8 (III-28) and DR27 (III-4) did not identify aberrant transcripts. However, DR8 III-28 and DR27 III-4, who were heterozygous C/T for single-nucleotide polymorphism (SNP) rs5848 located in the 3' untranslated sequence (UTS), with the C allele segregating on the disease haplotype, showed only the T allele when their lymphoblast and/or brain PGRN cDNA was sequenced (Cruts et al., Nature, 442:920-924 (2006)). In contrast, an unaffected relative was heterozygous for rs5848 in both genomic and cDNA sequences. These data support an absence of mutant PGRN mRNA transcript, most likely due to read-through of intron 0. Nuclear retention signals remaining on the unspliced transcript can prevent the transcript from leaving the nucleus, marking it for nuclear degradation (Vinciguerra and Stutz, Curr. Opin. Cell Biol., 16:285-292 (2004)). Western blot analysis of lymphoblast cell protein extracts from probands DR8 III-28 and DR27 III-4 supported these data and demonstrated a reduction of PGRN polypeptide levels (Cruts et al., Nature, 442:920-924 (2006)). Together, these data demonstrate that the DR8 founder haplotype carries a PGRN null allele that does not produce polypeptide. Robust PGRN immunoreactivity was observed in a subset of cortical neurons in patient DR8 III-28 (Cruts et al., Nature, 442:920-924 (2006)). However, despite using a panel of antibodies that recognize all regions of the PGRN polypeptide, the neuronal inclusions were negative for PGRN.

In addition to the IVS0+5G>C mutation in the eight probands of the Belgian FTDU-17 founder family, three other PGRN mutations were identified in three familial patients of the Belgian FTD series by genomic sequencing of all 13 exons and flanking intronic regions of PGRN (Table 11). In one FTD patient with an onset age of 62 years and a sister suffering from dementia who died at 64, a G>A transition was identified in exon 1 that destroyed the native Kozak sequence surrounding the Met1 translation initiation codon (c.3G>A). A U.S. patient who carried a different Met1 mutation (c.2T>C described above) showed a substantial reduction in expression level of the mutant transcript allele (Baker et al., Nature, 442:916-919 (2006)). In the two other familial patients, different frameshift mutations predicted carboxy-terminal-truncated polypeptides, Pro127ArgfsX2 and Ala237TrpfsX4, resulting from a dinucleotide deletion in exon 4 and a four nucleotide insertion affecting the intron 7 splice donor site and predicting exon 7 skipping (Table 11). As described above, PGRN frameshift mutations also produce null alleles through nonsense-mediated decay of mutant mRNA transcripts, lowering PGRN polypeptide levels (Baker et al., Nature, 442:916-919 (2006)). Together, the PGRN mutation data explained 10.7% (11 out of 103) of the genetic etiology of FTD and 25.6% (11 out of 43) of familial FTD in the Belgian patient series. In the same group, MAPT mutation frequencies were 2.9% (3 out of 103) overall and 7% (3 out of 43) in familial FTD, indicating that PGRN mutations are an approximately 3.5 times more frequent cause of FTD in Belgian patients.

In the Belgian founder family, the 16 patients carrying the IVS0+5G>C mutation had onset ages varying between 45 and 70 years (mean onset age 63.4±6.8 years; mean age at death 68.3±4.4 years). There were also four obligate carriers in generation II of family DR8 who died without symptoms of dementia. One died at a young age (II-1, 41 years), two at ages within the onset range (II-8 at 44 years and II-9 at 54 years), and one at 81 years (II-3; van der Zee, Brain, 129:841-852 (2006)). These highly variable onset ages and potential incomplete penetrance of the disease indicated that modifying factors are modulating onset age and as such contribute to a more complex genetic etiology for FTDU-17. Analysis of the apolipoprotein E gene (APOE) indicated that the APOE genotype has no effect on onset age. Interestingly, many of the FTDU-17 patients in the Belgian founder family had symptoms of non-fluent aphasia as a prominent feature of their disease (Cruts, Nature, 442:920-924 (2006); van der Zee, Brain, 129:841-852 (2006)).

The mutation data for PGRN explained linkage of FTDU-17 in Dutch family 1083 (Rademakers et al., Mol. Psychiatry, 7:1064-1074 (2002)) and the Belgian founder family DR8 (van der Zee et al., Brain, 129:841-852 (2006)). Although studies of nonsense and frameshift mutant transcripts indicated that they were probably degraded by nonsense-mediated mRNA decay (Baker et al., Nature, 942:916-919 (2006)), it could not be fully excluded that undetected low amounts of truncated polypeptides exerted their pathogenic effect through a dominant-negative or gain-of-function mechanism. Identification of a loss-of-allele mutation in intron 0 (IVS0+5G>C) provided convincing evidence that the pathogenic mechanism in FTDU-17 is indeed a loss of functional PGRN (haploinsufficiency). The IVS0+5G>C mutation may prevent splicing out of the first intron, intron 0, causing nuclear retention and degradation of the mutant transcript, or the mutant allele may not be transcribed. In either case, the mutant allele is nonfunctional and the result is a reduction in PGRN polypeptide.

Example 4

Mutations Other than Null Mutations Producing a Pathogenic Loss of Progranulin in Frontotemporal Dementia Experiments were performed to investigate the pathogenic nature of PGRN missense mutations and sequence variations in the 5' regulatory region identified in two studies, a Belgian (N=136) and a French (N=196) FTD patient series (Cruts et al., *Nature,* 442:920-924 (2006); Le Ber et al., *Human Mutat,* PMID: 17436289 (2007)), using in silico conservation and structural analyses to assess their effect on PGRN expression levels and the biological function of PGRN.

Subjects:

The Belgian patient sample consisted of 136 FTD patients who were diagnosed using a standard protocol and established clinical criteria as described elsewhere (Engelborghs et al., *J Neurol Neurosurg Psychiatry,* 74:1148-1151 (2003); Neary et al., *Neurology,* 51:1546-1554 (1998); Cruts et al., *Nature,* 442:920-924 (2006). For the French series, DNA samples from 196 index patients with FTD were collected through a French research network of neurologists (Le Ber et al., *Brain,* 129:3051-3065 (2006)). The diagnosis of FTD was based on the Lund and Manchester criteria as described elsewhere (The Lund and Manchester Groups, *J Neurol Neurosurg Psychiatry,* 57:416-418 (1994); Le Ber et al., *Human Mutat,* PMID: 17436289 (2007)). Mutation analyses identified a MAPT mutation in three Belgian and six French FTD patients, and a presenilin 1 (PSEN1; MIM#104311) mutation in one Belgian patient (van der Zee et al., *Brain,* 129:841-852 (2006); Dermaut et al., *Ann Neurol,* 55:617-626 (2004); Le Ber et al., *Human Mutat,* PMID: 17436289 (2007)). In addition to patients, 459 unrelated neurologically healthy Belgian and 187 French control individuals were analyzed for PGRN variations. Descriptives of the Belgian and French study populations are summarized in Table 12.

TABLE 12

Descriptions of Belgian and French study samples

|  | Belgian FTD patients N = 136 | French FTD patients N = 196 |
| --- | --- | --- |
| Mean AAO (range)[1] | 63.5 ± 9.2 (40-90) | 60.6 ± 7.9 (30-82) |
| Male/Female | 73/63 | 104/92 |
| Familial FTD[2] | 54 (40%) | 53 (27%) |
| FTD with MND | 9 (7%) | 37 (19%) |
| Pathological Diagnosis | 13 | 2 |
| FTDU | 10 | 2 |
| tauopathy | 1 | 0 |
| DLDH | 2 | 0 |

|  | Belgian control individuals N = 459 | French control individuals N = 187 |
| --- | --- | --- |
| Mean AAI (range)[3] | 58.6 ± 16.0 (19-92) | 67.0-11.4 (43-91) |
| Male/Female | 207/252 | 83/104 |

[1]AAO: age at onset in years ± the standard deviation;
[2]Positive family history was defined as having at least one first degree relative with dementia or FTD;
[3]AAI: age at inclusion in years ± the standard deviation.

PGRN Sequencing Analysis:

PGRN mutation analysis was performed in 136 Belgian patients and 190 French patients without MAPT mutations as well as in the French and Belgian control individuals as described elsewhere (Cruts et al., *Nature,* 442:920-924 (2006); Le Ber et al., *Human Mutat,* PMID: 17436289 (2007)). All PGRN exons and intron-exon boundaries were sequenced, including the non-coding exon 0 and a conserved region in intron 0 (g.96237-g.96983; numbering is relative to the reverse complement of GenBank® Accession Number AC003043 and starting at nt 1). Total genomic DNA was prepared from peripheral blood according to standard procedures. The exons and part of intron 0 were PCR amplified on genomic DNA (20 ng) using primers described elsewhere (Cruts et al., *Nature,* 442:920-924 (2006)) and an additional primer set for intron 0 (IVS0-F 5'-GGCCATGTG AGCTT-GAGGTT-3' (SEQ ID NO:85), IVS0-R 5'-GAGGGAG-TATAGTGTATGCTTC TACTGAATA-3' (SEQ ID NO:86)). Amplification products were purified with 1 U antarctic phosphatase (New England Biolabs, Ipswich, Mass., USA) and 1 U exonuclease I (New England Biolabs) and sequenced in both directions using the BigDye Terminator Cycle Sequencing kit v3.1 (Applied Biosystems, Foster City, Calif., USA) on an ABI3730 automated sequencer (Applied Biosystems). Sequences were analyzed using the Software Package novoSNP (Weckx et al., *Genome Res,* 15:436-442 (2005)).

Mutation Nomenclature:

Genomic DNA (gDNA) mutation numbering is relative to the reverse complement of GenBank® Accession Number AC003043.2 and starting at nt 1. Complementary DNA (cDNA) mutation numbering is relative to the largest PGRN transcript (GenBank® Accession Number NM_002087.2) and starting at translation initiation site +1. The polypeptide mutation numbering is according to the largest PGRN isoform (GenPept® Accession Number NP_002078.1).

Microsatellite Genotyping:

In Belgian patient DR121.1 and French patient F98/001, who both carried the PGRN c. 1294C>T, p.Arg432Cys mutation, 14 microsatellite (STR) markers spanning an 8 cM region around PGRN were genotyped for allele sharing analysis, as described elsewhere (van der Zee et al., *Brain,* 129:841-852 (2006)). Twenty ng genomic DNA was amplified in multiplex PCRs, at annealing temperature of 58° C., with fluorescently labeled primers. PCR products were sized on an ABI 3730 automated sequencer (Applied Biosystems), and genotypes were assigned using custom genotyping software.

In Silico Analyses:

Evolutionary conservation analysis was performed using the Sorting Intolerant From Tolerant (SIFT v.2) program (Ng and Henikoff, *Nucleic Acids Res,* 31:3812-3814 (2003)) to estimate the severity of amino acid mutations caused by single nucleotide polymorphisms (SNPs) by comparison to the evolutionary available pool and variability of amino acids at the mutated positions in an alignment of homologous sequences. Different inputs of selected homologues and their alignment were used: 61 unaligned sequences from BLink (Wheeler et al., *Nucleic Acids Res,* 32 Database issue:D35-D40 (2004)), SIFT aligns, remove 100% identical; ClustalX (Jeanmougin et al., *Trends Biochem Sci,* 23:403-405 (1998)) alignment of 61 sequences from BLink, remove 100% identical; Query sequence, SIFT finds homologues and aligns, remove 100% identical. Scores <0.05 are predicted to affect polypeptide function, scores ≥0.05 are predicted to be tolerated (Table 13).

TABLE 13

PGRN missense mutations in FTD patients

| Alias[1] | Variation | | | | Patients | | SIFT[6] | | |
| --- | --- | --- | --- | --- | --- | --- | --- | --- | --- |
| | Genome[2] | Predicted RNA[3] | Predicted polypeptide[4] | Origin | Family history[5] | Onset (years) | A | B | C |
| EX7 + 35C > T | g.101973C > T | c.743C > T | p.Pro248Leu | French | – | 71 | 0.02 | 0 | 0 |
| EX7 + 65G > A | g.102003G > A | c.773G > A | p.Ser258Asn | French | – | 53 | 0.14 | 0.24 | 0.03 |
| EX10 + 115C > T | g.103031C > T | c.1294C > T | p.Arg432Cys | French | +* | 65 | 0.19 | 0.02 | 0.19 |
| | | | | Belgian | – | 66 | | | |

Missense mutations were absent in 646 control individuals.
[1]EX: exon, exon numbering starts with noncoding first exon EX0.
[2]Numbering relative to the reverse complement of GenBank ® Accession Number AC003043.2 and starting at nt 1.
[3]Numbering according to the largest PGRN transcript (GenBank ® Accession Number NM_002087.2) and starting at translation initiation codon.
[4]Numbering according to the largest PGRN isoform (GenPept ® Accession Number NP_002078.1).
[5]A negative family history indicates that no first degree relatives were reported with dementia or FTD.
[6]SIFT consensus predictions (Ng and Henikoff, Nucleic Acids Res, 31: 3812-3814 (2003)): A) 61 unaligned sequences from BLink (Wheeler et al., Nucleic Acids Res, 32 Database issue: D35-D40 (2004)), SIFT aligns, remove 100% identical. B) ClustalX (Jeanmougin et al., Trends Biochem Sci, 23: 403-405 (1998)) alignment of 61 sequences from BLink, remove 100% identical. C) Query sequence, SIFT finds homologues and aligns, remove 100% identical. Scores <0.05 are predicted to affect polypeptide function (in bold), scores ≥0.05 are predicted to be tolerated.
*PGRN c.1294C > T, p.Arg432Cys was also detected in an affected cousin of the index patient.

Figure 2:
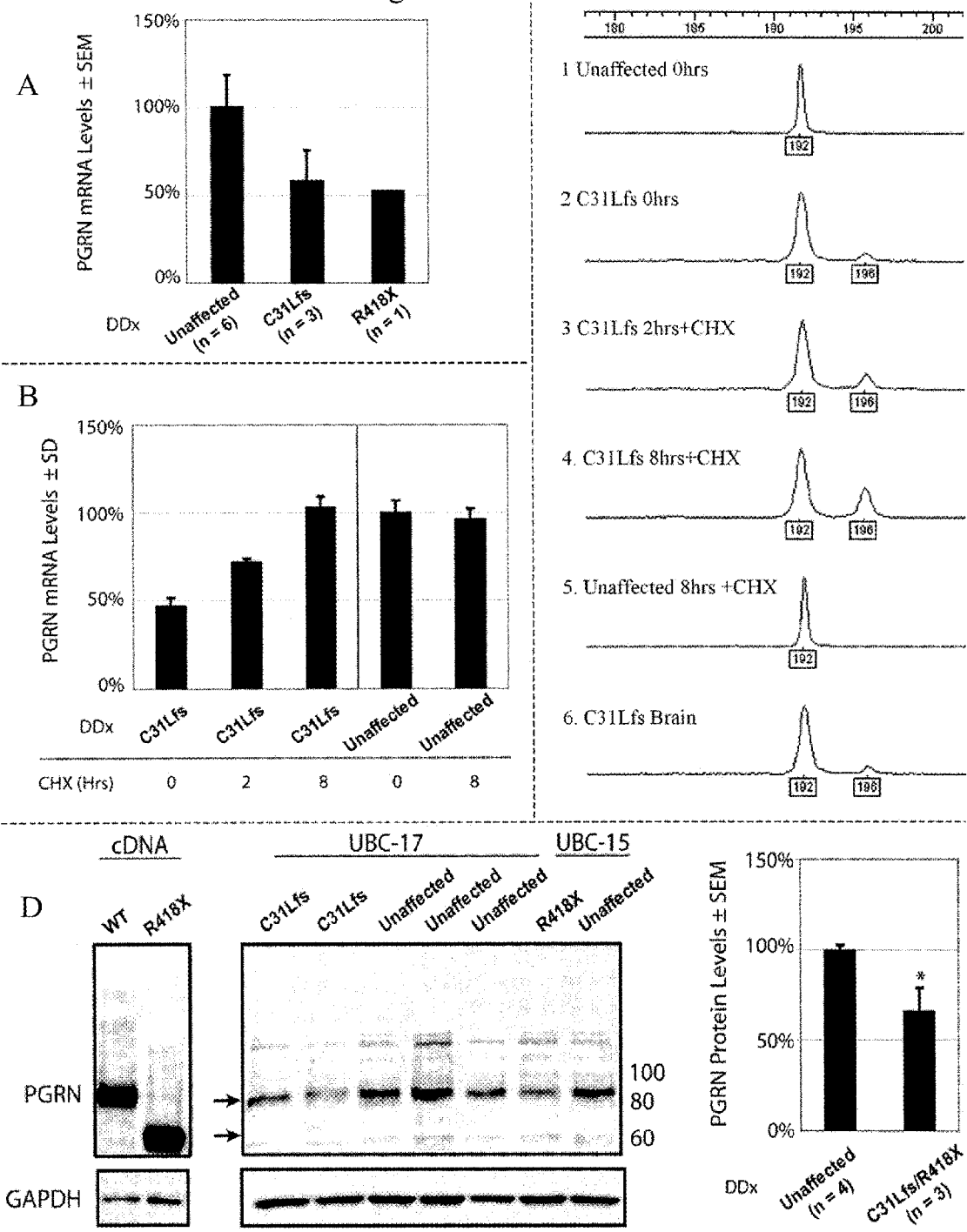
FIG. 2A is a bar graph plotting PGRN mRNA levels for lymphoblastoid cells from unaffected individuals or individuals carrying the C31LfsX34 (UBC17) or R418X (UBC15) mutations. PGRN RNA levels are shown as a percentage of levels in cells from unaffected individuals.
FIG. 2B is a graph plotting PGRN mRNA levels for the indicated cells treated with the NMD inhibitor cycloheximide (CHX; 500 µM) for the indicated number of hours. Treatment of C31LfsX34 cells with CHX for 2 hours and 8 hours resulted in a progressive increase in total PGRN RNA.
FIG. 2C contains traces of an RT-PCR fragment analysis in lymphoblastoid cells (1-5) and brain (6) from patients with the C31LfsX34 mutation, revealing that the mutant RNA (196 bp) is virtually absent. Treatment with CHX results in the selective increase in C31LfsX34 mutant RNA levels, but has no effect on PGRN RNA from control (unaffected) lymphoblasts.
FIG. 2D contains several photographs and a bar graph for an analysis of polypeptide extracts from lymphoblasts. Wild-type PGRN polypeptide levels are reduced in lymphoblasts from mutation (C31LfsX34 and R418X) carriers relative to unaffected relatives (mean reduction 34%, p=0.01, t-test). The C31LfsX34 (UBC17) and R418X (UBC15) mutant polypeptides are not detected. Arrows indicate the wild-type PGRN and the expected position of the R418X mutant polypeptide. R418X PGRN generated from an intronless cDNA construct (not subject to nonsense-mediated decay) expressed in HeLa cells (left hand panel) is included to demonstrate that the mutant polypeptide (if made) is stable.

To assess the effects of mutations on structure and stability of granulin domains, the full structures of individual granulin domains were modeled based on the repetitive occurrence of the disulfide connected beta-hairpin stack motif (crystal structure PDB 1g26 (Tolkatchev et al., Biochemistry, 39:2878-2886 (2000)) using SwissPDB-Viewer (Guex and Peitsch, Electrophoresis, 18:2714-2723 (1997)), Modeller (Fiser and Sali, Methods Enzymol, 374:461-491 (2003)), ProQ (Wallner and Elofsson, Protein Sci, 12:1073-1086 (2003)), and FoldX (Schymkowitz et al., Nucleic Acids Res, 33:W382-W388 (2005); FIG. 2). Differences in free energy resulting from the mutations were estimated using FoldX analogous to the SNPeffect method (Reumers et al., Bioinformatics, 22:2183-2185 (2006)), with the exception of an additional penalty for forming or breaking disulfide bonds (Czaplewski et al., Protein Eng Des Sel, 17:29-36 (2004)).

To estimate the effect of 5' regulatory region variations on putative transcription factor binding sites we performed a MatInspector analysis (World Wide Web at genomatix.de; Cartharius et al., Bioinformatics, 21:2933-2942 (2005)). A core similarity cut-off value of 1 and an optimized matrix similarity –0.05 were used (Table 14).

TABLE 14

PGRN 5' regulatory variations in FTD patients

| Alias[1] | Variation | | Patients | | | Effect on TFB sites (optimized threshold/matrix similarity)[4] | |
| --- | --- | --- | --- | --- | --- | --- | --- |
| | Genome[2] | Origin | Family history[3] | Onset (years) | loss | | gain |
| EX0 + 148G > T | g.96172G > T | Belgian | + | 51* | CDE (0.87/0.87) | | CDP (0.81/0.80) |
| IVS0 + 46G > T | g.96282G > T | Belgian | – | 49 | — | | Sp2 (0.80/0.85) |
| IVS0 + 189C > T | g.96425C > T | Belgian | + | 75 | EGR1 (0.86/0.82) | | PAX5 (0.73/0.71) |

Promoter mutations were absent in 646 control individuals.
[1]EX: exon, IVS: intron, exon numbering starts with noncoding first exon EX0;
[2]Numbering relative to the reverse complement of GenBank ® Accession Number AC003043.2 and starting at nt 1;
[3]A negative family history indicates that no first degree relatives were reported with dementia or FTD,
[4]MatInspector analysis (Cartharius et al., Bioinformatics, 21: 2933-2942 (2005)), a core similarity cut-off value of 1 and an optimized matrix similarity –0.05 were used.
*Neuropathological diagnosis at autopsy was conforming to FTDU.

Results

Apart from 13 reported null mutations (Cruts et al., Nature, 442:920-924 (2006); Le Ber et al., Human Mutat, PMID: 17436289 (2007)), extensive mutation analysis of PGRN in 332 FTD patients identified 11 exonic and five intronic variants, as well as ten variants in the 5' and two in the 3' regulatory regions of PGRN. Three missense mutations (Table 13, FIG. 11) and three sequence variations in the 5' regulatory region (Table 14) were detected only in patients and were absent in 1292 control chromosomes. Also, three silent mutations were unique to patients (Table 15). The remaining 19 variants were present in patients as well as control individuals and consisted of 11 rare (Table 16) and eight frequent polymorphisms (Table 17).

TABLE 15

PGRN silent mutations in FTD patients

Variation

| Alias[1] | Genome[2] | Predicted RNA[3] | Predicted polypeptide[4] |
|---|---|---|---|
| EX1 + 109C > T | g.100168C > T | c.102C > T | p.Pro34 |
| EX11 + 72C > T | g.103314C > T | c.1485C > T | p.Cys495 |
| EX12 + 51C > T | g.103613C > T | c.1695C > T | p.Cys565 |

Silent mutations were absent in 646 control individuals.
[1]EX: exon, exon numbering starts with noncoding first exon EX 0.
[2]Numbering relative to the reverse complement of GenBank® Accession Number AC003043.2 and starting at nt 1.
[3]Numbering according to the largest PGRN transcript (GenBank® Accession Number NM_002087.2) and starting at translation initiation codon.
[4]Numbering according to the largest PGRN isoform (GenPept® Accession Number NP_002078.1).

TABLE 16

Rare PGRN polymorphisms

Variation

| Alias[1] | Genome[2] | Predicted RNA[3] | Predicted protein[4] | rs number | FTD patients N = 332 (%) | Controls N = 646 (%) |
|---|---|---|---|---|---|---|
| EX0 + 175C > G | g.96199C > G | c.-3868C > G | — | — | 0.30 | 0.46 |
| IVS0 + 192G > A | g.96428G > A | c.-3639G > A | — | — | 0.90 | 0.15 |
| IVS0 + 236G > A | g.96472G > A | c.-3595G > A | — | — | 2.41 | 1.39 |
| IVS0 + 485A > G | g.96721A > G | c.-3346A > G | — | — | 0.60 | 1.24 |
| IVS0 + 583_584insG | g.96819_96820insG | c.-3248_-3247insG | — | — | 1.81 | 0.77 |
| EX1 + 106C > T | g.100165C > T | c.99C > T | p.Asp33 | — | 1.81 | 1.08 |
| IVS2 + 7G > A | g.100460G > A | c.264 + 7G > A | — | — | 0.30 | 0.77 |
| EX3 + 15G > A | g.100583G > A | c.279G > A | p.Gly93 | — | 0.30 | 0.15 |
| EX8 + 68G > A | g.102332G > A | c.903G > A | p.Ser301 | — | 0.30 | 0.62 |
| EX11 + 131G > C | g.103373G > C | c.1544G > C | p.Gly515Ala | rs25647 | 0.30 | 0.15 |
| 3' + 21G > A | g.104025G > A | — | — | — | 0.30 | 0.15 |

[1]EX: exon, IVS: intron, UTR: untranslated region, exon numbering starts with noncoding first exon EX0.
[2]Numbering relative to the reverse complement of GenBank® Accession Number AC003043.2 and starting at nt 1.
[3]Numbering according to the largest PGRN transcript (GenBank® Accession Number NM_002087.2) and starting at translation initiation codon.
[4]Numbering according to the largest PGRN isoform (GenPept® Accession Number NP_002078.1).

TABLE 17

Frequent PGRN polymorphisms

Variation

| Alias[1] | Genome[2] | Predicted RNA[3] | Predicted protein[4] | rs number | Controls N = 646 (%) |
|---|---|---|---|---|---|
| 5'-111delC | g.95914delC | — | — | rs17523519 | 25.93 |
| IVS0 + 561C > T | g.96797C > T | c.-3270C > T | — | rs3859268 | 26.32 |
| IVS2 + 21G > A | g.100474G > A | c.264 + 21G > A | — | rs9897526 | 10.99 |
| IVS3 - 47_-46insGTCA | g.101083_101084insGTCA | c.350 - 47_350 - 46insGTCA | — | — | 22.41 |
| EX4 + 35T > C | g.101164T > C | c.384T > C | p.Asp128 | rs25646 | 3.26 |
| IVS4 + 24G > A | g.101266G > A | c.462 + 24G > A | — | rs850713 | 22.72 |
| IVS7 + 7G > A | g.102011C > A | c.835 + 7G > A | — | — | 7.59 |
| 3'UTR + 78C > T | g.103778C > T | c.1860C > T | — | rs5848 | 27.19 |

[1]EX: exon, IVS: intron, UTR: untranslated region, exon numbering starts with noncoding first exon EX 0.
[2]Numbering relative to the reverse complement of GenBank® Accession Number AC003043.2 and starting at nt 1.
[3]Numbering according to the largest PGRN transcript (GenBank® Accession Number NM_002087.2) and starting at translation initiation codon.
[4]Numbering according to the largest PGRN isoform (GenPept® Accession Number NP_002078.1).

PGRN Missense Mutations:

The effect of c.743C>T, p.Pro248Leu; c.773G>A, p.Ser258Asn; and c.1294C>T, p.Arg432Cys on PGRN polypeptide sequence conservation and structure was investigated in silico (FIG. 11, Table 13). Two missense mutations, p.Pro248Leu and p.Arg432Cys, were predicted to be pathogenic. SIFT analysis predicted that Pro248Leu would dramatically perturb polypeptide function (p=0.00), which was in accordance with the structural modeling that revealed a significant destabilizing effect of 6.22±0.54 kcal/mol on the granulin domain. In the granulin domain structure, Pro248 is located in a loop connecting two β-hairpins where it is most likely essential to constrain a sharp and rigid turn (FIG. 11B). Moreover, Pro248 is adjacent to two Cys residues of the granulin B domain at a position which is 100% conserved between the seven granulin domains. Arg432Cys is located between granulin domains C and D (FIG. 11A). Depending on the parameters used, SIFT analysis predicted that this mutation perturbed the biological function of PGRN (p=0.02; Table 13). In addition, no Cys residues are normally observed between the granulin domains. Arg432Cys was detected in one Belgian (DR121.1, onset age 66 years) and one French FTD patient (F98/001, onset age 65 years). Allele sharing analysis using markers located in and around PGRN demonstrated that six consecutive STR markers in a region of 5.36 Mb centromeric of PGRN were shared as well as all intragenic PGRN SNPs. In 102 control individuals, EM estimation could not reveal this shared haplotype, neither was this allele combination observed.

Ser258Asn, located in granulin domain B, affects an amino acid residue that is conserved across orthologs but not between the granulin domains (FIG. 11A). SIFT analysis predicted a moderately significant effect for this mutation on polypeptide function (p=0.03; Table 13); however, structural modeling failed to show a destabilizing effect on the granulin domain.

PGRN Sequence Variations in 5' Regulatory Region:

The three promoter variants were analyzed using MatInspector to assess whether they potentially altered transcription factor binding (TFB) specificities (Table 14). MatInspector analysis predicted gain and/or loss of TFB sites for all three variations. One promoter mutation, g.96172G>T (EX0+148G>T) was predicted to create a CDP site and loss of a CDE site. CDP (CCAAT displacement protein) is a transcription factor for many diverse cellular genes that are involved in most cellular processes, including differentiation, development, and proliferation (Nishio and Walsh, *Proc Natl Acad Sci USA*, 101:11257-11262 (2004)), and CDE is able to regulate gene transcription in a cell cycle-dependent manner (Lange-zu et al., *FEBS Lett*, 484:77-81 (2000)). g.96282G>T (IVS0+46G>T) predicted gain of one Sp2 domain. Sp/XKLF proteins are shown to regulate transcription of genes involved in cell cycle control, oncogenesis, and differentiation (Moorefield et al., *J Biol Chem*, 279:13911-13924 (2004)). Finally, g.96425C>T (IVS0+189C>T) predicted loss of one EGR1 site and gain of one PAX5 site. EGR1 belongs to the early growth response family of zinc finger transcription factors and is involved in many processes related to growth, differentiation, and injury repair (McKee et al., *Brain Res*, 1088:1-11 (2006)). The PAX5 transcription factor has an important role in development of both B-lymphocytes and brain (Steinbach et al., *Int J Cancer*, 93:459-467 (2001)).

As described herein, three missense mutations, c.743C>T, p.Pro248Leu; c.773G>A, p.Ser258Asn; and c.1294C>T, p.Arg432Cys were identified in four patients (4/332 or 1.2%), and were absent in 1292 control chromosomes. In silico predictions based on evolutionary conservation and structure indicated that at least two mutations, p.Pro248Leu and p.Arg432Cys, are likely to be pathogenic since they significantly affect polypeptide structure and stability. Pro248, located in granulin domain B, is evolutionary conserved across PGRN orthologs including rodents and between all granulin domains. Further, molecular modeling indicated that Pro248 is located in a loop of the β-hairpin stack of granulin B.

p.Arg432Cys was observed in two independently ascertained FTD patients of Belgian (DR121.1) and French (F98/001) ancestry. These patients shared a common haplotype across the PGRN locus and flanking centromeric region of at least 5.36 Mb at 17q21, indicative of a common founder effect. Combined with the reported minimal candidate region for FTDU-17, this reduced the FTDU-17 locus to 3.18 Mb centromeric of PGRN and excluding MAPT. F98/001 had a positive family history of dementia and p.Arg432Cys was detected in another affected cousin, further supporting the pathogenic nature of the mutation. No familial anamnesis was reported for patient DR121.1. However, this patient was an only child which can explain why FTD presented as sporadic in this family.

Three patient-specific sequence variations of highly conserved nucleotides (3/332 or 0.9%) were observed in the 5' regulatory region of the PGRN gene. MatInspector analysis estimated changes in TFB sites for all three variants. g.96172G>T (EX0+148G>T) was identified in a Belgian patient diagnosed with familial FTD and onset age of 51 years. This patient died at the age of 55 years, and brain autopsy confirmed the diagnosis of FTD with ub-ir neuronal inclusions (FTDU). These data suggested that changes in PGRN transcriptional activities could be involved in risk for FTD.

In addition to patients, mutation analysis of PGRN in 646 control individuals revealed 25 sequence variations that were present only in control individuals (Table 18). Rare PGRN variants were detected in 11.3% (73/646) of control individuals versus 12.4% (41/332) of patients. This observation indicated the natural genetic variability of PGRN and that the pathogenic nature of a variation may depend on the impact of the variation on polypeptide structure and stability. A c.473G>A, p.Cys158Tyr mutation was found in an 82 year old control person. This variation may be either insufficient to cause disease or an example of non-penetrance. Non-penetrance of PGRN null mutations has been reported in the Belgian founder family DR8 segregating PGRN mutation g.96241G>C, IVS0+5G>C as well as in other American FTD families (Gass et al., *Hum Mol Genet*, 15:2988-3001 (2006)).

TABLE 18

Rare PGRN variants in control individuals

| | Variation | | | |
|---|---|---|---|---|
| Alias[1] | Genome[2] | Predicted RNA[3] | Predicted protein[4] | Controls N = 646 (%) |
| EX0 + 17G > C | g.96041G > C | c.-4026G > C | — | 0.15 |
| EX0 + 17G > A | g.96041G > A | c.-4026G > A | — | 0.15 |
| IVS0 + 401C > T | g.96637C > T | c.-3430C > T | — | 0.15 |
| IVS0 + 484T > C | g.96720T > C | c.-3347T > C | — | 0.15 |
| IVS0 + 516C > T | g.96752C > T | c.-3315C > T | — | 0.15 |
| IVS1 + 51G > A | g.100255G > A | c.138 + 51G > A | — | 0.15 |
| IVS2 − 43G > C | g.100526G > C | c.265–43G > C | — | 0.15 |
| EX3 + 53G > A | g.100621G > A | c.317G > A | p.Ser106Asn | 0.15 |
| IVS3 + 11G > C | g.100664G > C | c.349 + 11G > C | — | 0.15 |
| IVS3 + 52_+ 53delTG | g.100705_100706delTG | c.349 + 52__349 + 53delTG | — | 0.15 |
| EX5 + 11G > A | g.101354G > A | c.473G > A | p.Cys158Tyr | 0.15 |
| EX6 + 37G > A | g.101629G > A | c.635G > A | p.Arg212Gln | 0.15 |
| EX6 + 60A > T | g.101652A > T | c.658A > T | p.Thr220Ser | 0.15 |
| IVS6 + 57A > G | g.101759A > G | c.708 + 57A > G | — | 0.15 |
| EX7 + 73C > A | g.102011C > A | c.781C > A | p.Leu261Ile | 0.15 |
| EX7 + 96G > A | g.102034G > A | c.804G > A | p.Thr268 | 0.15 |
| EX9 + 63G > A | g.102514G > A | c.996G > A | p.Lys332 | 0.15 |
| IVS9 − 56G > A | g.102861G > A | c.1180 − 56G > A | — | 0.15 |
| IVS9 − 4C > A | g.102916C > A | c.1180 − 4C > A | — | 0.15 |
| EX10 + 74G > A | g.102990G > A | c.1253G > A | p.Arg418Gln | 0.15 |
| EX10 + 118C > T | g.103034C > T | c.1297C > T | p.Arg433Trp | 0.46 |

TABLE 18-continued

Rare PGRN variants in control individuals

Variation

| Alias[1] | Genome[2] | Predicted RNA[3] | Predicted protein[4] | Controls N = 646 (%) |
|---|---|---|---|---|
| EX10 + 230C > T | g.103146C > T | c.1409C > T | p.Pro470Leu | 0.15 |
| EX11 + 12C > T | g.103254C > T | c.1425C > T | p.Cys475 | 0.15 |
| EX12 + 4G > A | g.103566G > A | c.1648G > A | p.Val550Ile | 0.31 |
| 3'UTR + 268G > T | g.103968G > T | c.2050G > T | — | 0.15 |

[1]EX: exon, IVS: intron, UTR: untranslated region, exon numbering starts with noncoding first exon EX 0.
[2]Numbering relative to the reverse complement of GenBank ® Accession Number AC003043.2 and starting at nt 1.
[3]Numbering according to the largest PGRN transcript (GenBank ® Accession Number NM_002087.2) and starting at translation initiation codon.
[4]Numbering according to the largest PGRN isoform (GenPept ® Accession Number NP_002078.1).

PGRN mutations (nonsense, frameshift, missense, and promoter mutations) can account for 8.43% of FTD patients (28/332) and 18.69% of patients with a positive family history of FTD (20/107). In the group of patients with pathologically confirmed FTD, the PGRN mutation frequency would be 53.33% (8/15) and rise to 66.67% of patients with a FTDU diagnosis (8/12). These PGRN mutations most likely exert their pathogenic effect through reduced PGRN polypeptide levels by loss of transcript or reduced transcription (nonsense or frameshift transcripts and promoter mutations), loss of translation (Met1 mutations) or loss of polypeptide function (missense mutations).

Example 5

Progranulin Null Mutation Carriers Present with High Clinical Heterogeneity in an Extended Belgian Founder Family A mutation analysis of PGRN was performed in a large, well characterized Belgian Alzheimer's disease (AD) patient group and two independently ascertained Belgian Parkinson's disease (PD) populations. The AD patient group consisted of 666 AD patients (mean onset age 74.6±8.8 years, 65.5% female) derived from a large prospective study of neurodegenerative and vascular dementia in Flanders, Belgium (Engelborghs et al., *J Neurol Neurosurg Psychiatry*, 74:1148-51 (2003); Engelborghs et al., *Neurobiol Aging*, 27:285-92 (2006)). Each patient underwent a diagnostic neuropsychological examination, including a Mini Mental State Examination (MMSE; Folstein et al., *J Psychiatr Res*, 12:189-98 (1975)), structural neuroimaging consisting of brain computerized tomography (CT), and/or magnetic resonance imaging (MRI) and functional neuroimaging (single photon emission computed tomography (SPECT). Consensus diagnosis of possible or probable AD was given by at least two neurologists based on the National Institute of Neurological and Communicative Disorders and Stroke/Alzheimer Disease and Related Disorders Association (NINCDS/ADRDA) criteria (McKhann et al., *Neurology*, 34:939-44 (1984)). Most patients met the criteria for probable AD (N=627), whereas a small number of patients (N=39) were diagnosed as possible AD. In 48 probable AD patients who underwent autopsy, clinical diagnosis was confirmed neuropathologically. In 26.0% of patients, the disease was considered familial based on the occurrence of at least one first-degree relative suffering from dementia. Cerebrospinal fluid (CSF) was sampled in a subset of patients (N=365), and CSF levels of amyloid-β peptide ($A\beta_{1-42}$), total tau (T-tau), and tau phosphorylated at threonine 181 (P-tau$_{181P}$) were determined in duplicate by technicians who were blind to the clinical data using commercially available single parameter ELISA kits (Innogenetics, Gent, Belgium; Engelborghs et al., *Neurobiol Aging*, PMID: 17428581 (2007)).

Belgian PD patients (N=255, mean age at onset 59.4±10.9 years, 43.1% female) were derived from two independent studies. Eighty-two patients were selected from the same prospective study as the AD patients (Engelborghs et al., *J Neurol Neurosurg Psychiatry*, 74:1148-51 (2003)). A set of 173 PD patients was selected from a retrospective epidemiological study which was ascertained to assess the effect of environmental risk factors in PD (Pals et al., *Eur J Epidemiol*, 18:1133-42 (2003)). In both studies, a diagnosis of PD required three out of four of the following features to be present: (1) bradykinesia, (2) rigidity, (3) tremor, and (4) asymmetrical onset. Response to levodopa also was required to be present. Individuals had a positive family history of PD if at least one first degree relative presented with parkinsonism (3.5%).

The control group consisted of 459 unrelated, healthy, Dutch-speaking Belgian individuals (mean age at inclusion 58.6±16.0 years, 54.9% female). The control group included subjects (N=275) without neurological or psychiatric antecedents, or with neurological complaints without organic disease involving the central nervous system, and subjects (N=184) selected among married-in individuals in families with neurological diseases collected for genetic linkage studies.

After informed consent, blood samples of each proband were collected for genetic studies. For mutation carriers, additional relatives were collected for haplotype phase determination and segregation studies.

PGRN Sequencing:

Patients and control individuals were analyzed for mutations in coding exons 1 to 12 (Cruts et al., *Nature*, 442:920-4 (2006)) and non-coding exon 0. Primers were designed using Primer3 software (Rozen and Skaletsky, *Methods Mol Biol*, 132:365-86 (2000)). Twenty ng of genomic DNA were PCR amplified using individually optimized reaction conditions. Amplification products were purified using 1 U of antarctic phosphatase (New England Biolabs, Ipswich, Mass.) and 1 U of exonuclease I (New England Biolabs). Purified PCR products were sequenced in both directions using PCR primers or internal sequencing primers, and the Big Dye® Terminator v3.1 Cycle Sequencing kit (Applied Biosystems, Foster City, Calif.) according to manufacturer's protocol. Labeled products were separated on an Applied Biosystems 3730x1 DNA Analyzer (Applied Biosystems) and analyzed using NovoSNP (Weckx et al., *Genome Res*, 15:436-42 (2005)).

PGRN Transcript Analysis:

Lymphocytes were isolated from total blood using Ficoll density gradient centrifugation (Greiner Bio-One, Wemmel, Belgium), and mRNA was isolated from lymphocytes using the Chemagic mRNA Direct Kit (Chemagen, Baesweiler, Germany). First-strand cDNA was synthesized using the SuperScript III First-Strand Synthesis System for RT-PCR kit and random hexamer primers. After PCR amplification of part of the transcript (exon 5-6 to 3' UTR), genotypes at the mutated position were generated by direct sequencing as described elsewhere Cruts et al., Nature, 442:920-4 (2006)).

STR Genotyping:

In patients carrying IVS0+5G>C and additional family members, 12 STR markers located in the 8 cM ancestral PGRN haplotype observed in the Belgian DR8 founder family were genotyped (van der Zee et al., Brain, 129:841-52 (2006)). Twenty ng of genomic DNA were PCR amplified in four multiplex reactions (van der Zee et al., Brain, 129:841-52 (2006)). Fluorescently labeled products were resolved on an Applied Biosystems 3730x1 DNA Analyzer (Applied Biosystems). Genotypes were assigned using custom genotyping software. Allele frequencies for each STR marker were estimated in 102 unrelated Belgian control individuals (van der Zee et al., Brain, 129:841-52 (2006)).

Neuropathology:

A brain autopsy was performed on patient DR205.1. Brain hemispheres were fixed in buffered formalin, and tissues from the right and left frontal and parietal cortices, hippocampus, basal ganglia, midbrain, pons, medulla oblongata, and cerebellum were further processed for paraffin embedding. Ten μm thick sections were sliced and stained with hematoxylin and eosin, cresyl violet, Bodian and Gallyas. Five μm thick sections were also sliced from all brain regions and immunohistochemistry was performed with the following antibodies: 4G8 (anti-Aβ; Senetek, Napa, Calif.), AT8 (directed against abnormally phosphorylated PHF-tau; Innogenetics, Ghent, Belgium), ubiquitin (Dako, Glostrup, Denmark), α-synuclein (Dako), anti-glial fibrillary acidic protein (GFAP; Dako), and rabbit TAR DNA-binding protein-43 antisera (TDP-43; Proteintech Group, Chicago, Ill.). Antigen retrieval for Aβ immunohistochemistry was performed by treating sections with 98% formic acid for five minutes at room temperature for 4G8, α-synuclein, and TDP-43, and by boiling in citrate buffer (pH 6) for GFAP and ubiquitin. All dilutions were made in 0.1 M PBS with 0.1% bovine serum albumin. Staining was performed with appropriate secondary antibodies and strepta- vidin-biotin-horse-radish peroxidase (ABC/HRP) using chromogen 3'3' diaminobenzidine (DAB; Roche, Mannheim, Germany), as described elsewhere (Pirici et al., J Neuropathol Exp Neurol, 65:289-301 (2006)).

Results

PGRN Mutations in AD and PD Groups:

Direct genomic sequencing of PGRN in 666 AD patients, 255 PD patients, and 459 control individuals identified a nonsense mutation, p.Arg535X, in one AD patient and a null mutation, IVS0+5G>C, in two AD patients and one PD patient (Table 19).

TABLE 19

PGRN null mutations identified in Belgian AD and PD patients

| | | | | | Mutation | | | |
|---|---|---|---|---|---|---|---|---|
| Patient ID | Presentation | Onset age (years) | Family History[1] | Location[2] | Alias | Genomic[3] | Predicted RNA[4] | Predicted polypeptide[5] |
| DR142.1 | AD | 66 | ? | IVS 0 | IVS0 + 5G > C | g.96241G > C | — | p.0 |
| DR25.14 | AD | 76 | + | IVS 0 | IVS0 + 5G > C | g.96241G > C | — | p.0 |
| DR205.1 | PD | 54 | + | IVS 0 | IVS0 + 5G > C | g.96241G > C | — | p.0 |
| DR181.1 | AD | 72 | ? | EX 11 | EX11 + 190C > T | g.103432C > T | c.1690C > T | p.Arg535X |

Note:
[1] +: family history of dementia positive in first degree, ?: family history of dementia unknown;
[2] EX: exon, IVS: intron, exon numbering starts with non-coding first exon EX 0;
[3] Numbering relative to the reverse complement of GenBank® Accession Number AC003043 and starting at nt 1;
[4] Numbering according to the largest PGRN transcript (GenBank® Accession Number NM_002087.2) and starting at the translation initiation codon;
[5] Numbering according to the largest PGRN isoform (GenPept® Accession Number NP_002078.1).

The p.Arg535X nonsense mutation resulted in the formation of a premature termination codon (PTC) at position 535 (Table 19). To determine whether a transcript encoded by nucleic acid containing this mutation is degraded by the nonsense mediated decay (NMD) machinery, sequence analysis was performed on cDNA prepared from the patient's lymphocytes, and the results were compared to sequences obtained from the patient's genomic DNA (gDNA). The mutated allele was present in both gDNA and cDNA sequences, indicating that the mutant transcript is not degraded and suggesting that the mutant transcript is translated into a truncated polypeptide missing 59 C-terminal amino acids.

PGRN IVS0+5G>C Mutation Carriers in AD and PD Groups:

An intron 0 splice donor site mutation, IVS0+5G>C, was detected in two AD patients (DR25.14 and DR142.1) and one PD patient (DR205.1; Table 19). The IVS0+5G>C mutation was identified in eight probands of a large Belgian FTDU-17 founder family DR8 (Cruts et al., Nature, 442: 920-4 (2006); van der Zee et al., Brain, 129:841-52 (2006)).

Figure 12:
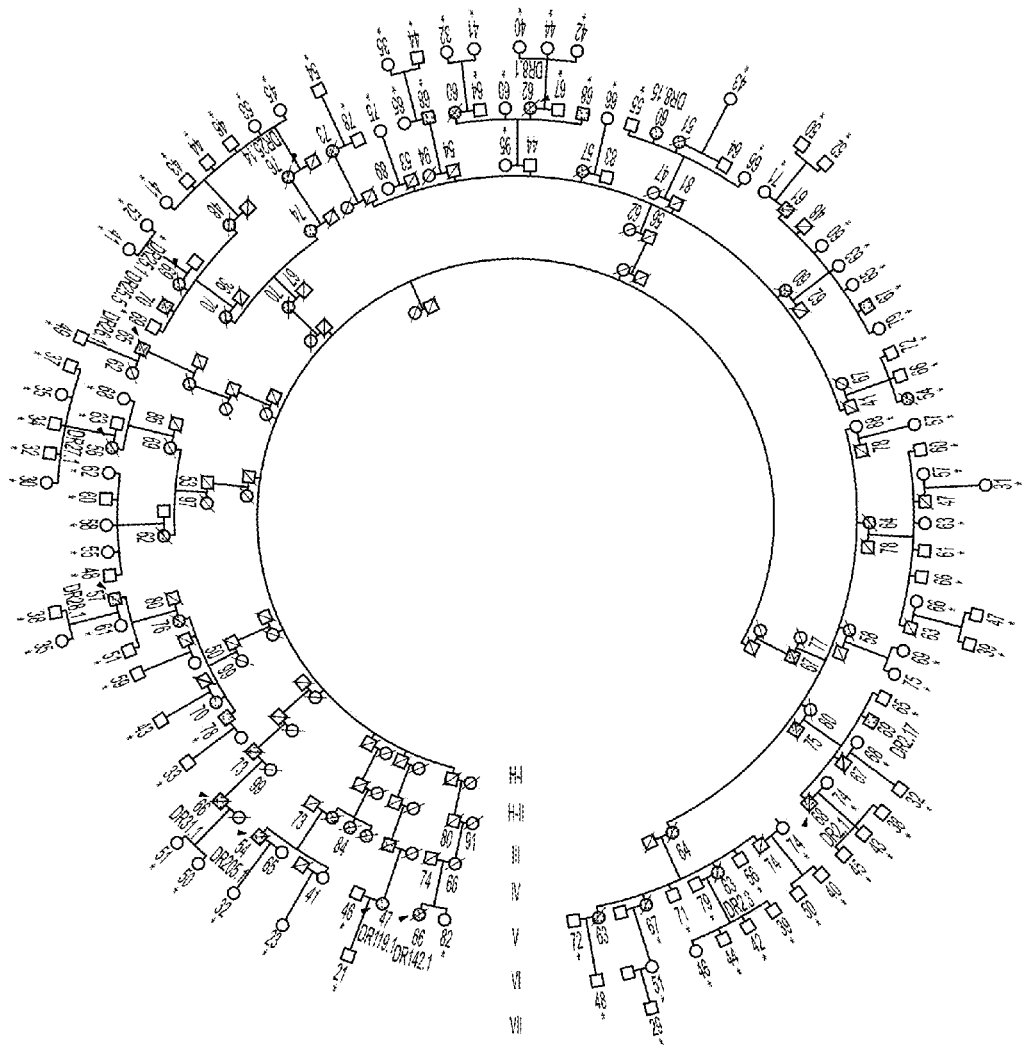
FIG. 12 contains a pedigree of the DR8 founder family showing ten different branches. Generations H-I and H-II are hypothetical generations. Black boxes represent patients, grey colored boxes are individuals for whom the affection status is unclear. Individuals for which DNA is available are indicated with asterisks. Patients represented with a DR number are those for which clinical and/or pathological information are available (Table 21). The index patient of each branch of the pedigree is indicated with an arrowhead.
Figure 13:
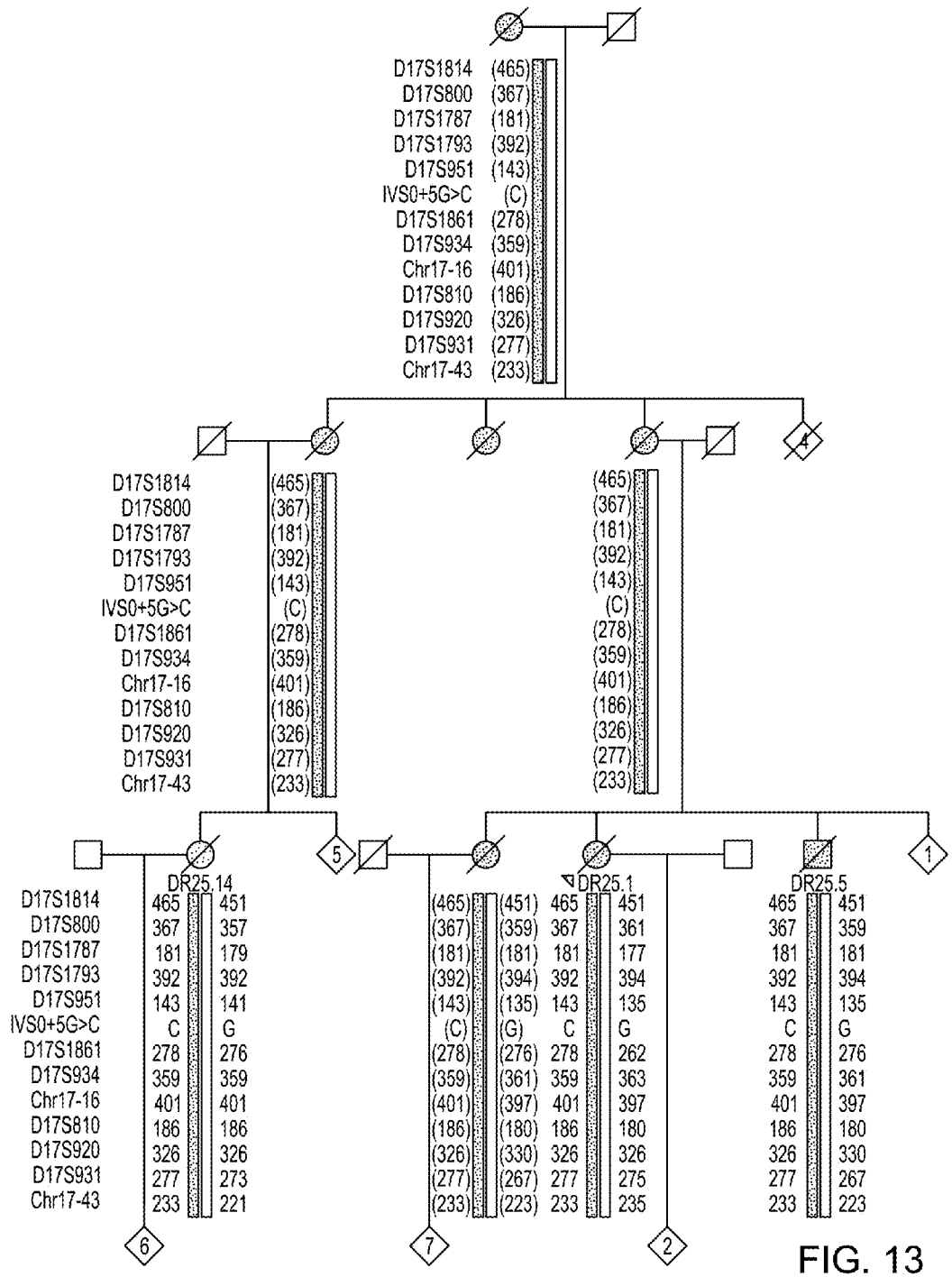
FIG. 13 is a pedigree diagram showing segregation of the DR8 founder haplotype in family DR25. The proband is indicated with an arrowhead. Filled symbols represent individuals with AD (grey) or FTLD (black). Allele lengths are shown in base pairs.

The three patients, DR25.14, DR142.1, and DR205.1, carried at least a part of the DR8 linked disease haplotype (Table 20), reducing the 8.0 cM founder haplotype to 1.61 cM (4.37 Mb) and excluding the gene encoding microtubule associated protein tau (MAPT). Genealogical examination indicated that there were no living affected (first or second degree) relatives available to demonstrate segregation of the mutation with dementia for mutation carriers DR142.1 and DR205.1 (FIG. 12). DR25.14 had a positive family history of dementia, with a mother and two maternal aunts suffering from late-onset dementia. Genealogical examination revealed that this patient is closely related to a branch, family DR25, of the Belgian DR8 founder family (FIGS. 12 and 13), e.g., the proband DR25.1 and her sibling DR25.5 being first cousins of DR25.14. Segregation of the disease haplotype in the extended pedigree of DR25 is shown in FIG. 13.

TABLE 20

Haplotype sharing of STR markers in IVS0 + 5G > C mutation carriers

| Marker | Genetic location (cM) | Physical location (Mb) | Linked allele[a] | Frequency linked allele (%)[b] | DR142.1 | DR25.14 | DR205.1 | |
|---|---|---|---|---|---|---|---|---|
| D17S1818 | 60.40 | 34.42 | — | — | 446 | 430 | 430 | |
| D17S1814 | 61.48 | 35.37 | 465 | 19 | 465 | 465 | 465 | |
| D17S800 | 62.01 | 36.31 | 367 | 10 | 361 | 367 | 367 | |
| D17S1787 | 62.01 | 36.98 | 181 | 35 | 181 | 181 | 181 | minimal |
| D17S1793 | 63.09 | 37.61 | 392 | 81 | 392 | 392 | 392 | founder |
| D17S951 | 63.62 | 39.18 | 143 | 23 | 143 | 143 | 143 | haplotype |
| PGRN | — | 39.78 | — | — | — | — | — | (1.61 cM) |
| D17S1861 | 63.62 | 40.16 | 278 | 6 | 278 | 278 | 278 | |
| D17S934 | 63.62 | 40.41 | 359 | 27 | 359 | 359 | 359 | |
| Chr17-16 | — | 40.68 | 401 | 22 | 401 | 401 | 399 | |
| D17S810 | 63.62 | 40.84 | 186 | 30 | 186 | 186 | 186 | |
| MAPT | — | 41.33 | — | — | — | — | — | |
| D17S920 | 64.16 | 42.17 | 326 | 64 | 326 | 326 | 326-332 | |
| D17S931 | 66.85 | 42.36 | 277 | 9 | 277 | 277 | 265 | |
| Chr17-43 | — | 42.68 | 233 | 47 | 233 | 233 | 239 | |
| D17S1795 | 68.44 | 45.28 | — | — | 399 | 397 | 391 | |

Linked alleles are represented in bold;
[a]ancestral haplotype identified in the DR8 founder family (van der Zee et al., Brain, 129: 841-52 (2006));
[b]allele frequencies were calculated in 92 control chromosomes. Genetic locations of the STR markers were obtained from the Marshfield gender-averaged map. Physical locations relative to NCBI genome build 35.

Clinical characteristics of the IVS0+5G>C carriers are summarized in Table 21. Both AD patients (DR25.14 and DR142.1) presented with complaints and symptoms of forgetfulness. In addition to severe impairment of recent memory, which first became apparent at age 76 years, patient DR25.14 had deficits of long-term memory. She had become apathetic, displaying a lack of initiative. Further, reduced verbal fluency was noted, but naming was unaffected. The patient was disoriented in both time and space, and displayed impaired problem solving. The CSF biomarker profile was typical for AD, with a decreased level of $A\beta_{142}$ and increased levels of total tau and P-tau$_{181P}$. In patient DR142.1, the early symptoms were first noted by members of her choir, who reported repetitive phone calls and repetition of stories and questions when patient DR142.1 was 66 years old. Disorientation in space caused her to get lost on several occasions. Towards the late stages of the disease, a loss of decorum became obvious. A year before death, communication through spontaneous speech was no longer possible, and she displayed verbal and motor stereotypies. The age at onset of AD varied considerably between both mutation carriers (66 and 76 years), which is in accordance with the wide range in onset ages seen in family DR8 (Cruts et al., Nature, 442:920-4 (2006); van der Zee et al., Brain, 129:841-5 (2006); Table 21). Both AD patients had a Middelheim Frontality Score (MFS) of 4 (De Deyn et al., Int J Geriatr Psychiatry, 20:70-9 (2005)).

TABLE 21

Overview of clinical and pathological characteristics of PGRN IVS0 + 5G > C carriers in the DR8 founder family

| Patient | Gender | Clinical diagnosis | Age at onset | Age at death (†)/current age | Presenting impairments | Additional features | Structural neuroimaging (CT/MRI) | Functional neuroimaging (SPECT/PET) | Pathology |
|---|---|---|---|---|---|---|---|---|---|
| DR2.1 | M | FTD | 66 | 71† | ↓memory, ↓concentration | disinhibition, ↓verbal fluency | Global mainly subcortical atrophy (CT) | NA | NA |
| DR2.3 | F | PNFA | 63 | 72† | PNFA, apathy | | Global cortico-subcortical atrophy R > L; PWML (MRI) | Relative bilateral frontal, parietal and temporal HP, R > L (SPECT) | FTLD-U + AD (Braak A-II (NFT max 20/mm², frequent SP)) |
| DR2.17 | M | FTD | 69 | 71 | ↓spontaneous speech, perseveration, dysarthria, apathy | | Global moderate cortical and subcortical atrophy (MRI) | Relative frontal and frontoparietal HP, L > R. Relative HP of left thalamus. Diastasis of frontal cortical activity (SPECT) | NA |
| DR8.1 | F | FTD | 62 | 69† | ↓word-finding, apathy, disinhibition, ↓memory | | Frontotemporoparietal cortical and subcortical atrophy L > R (MRI) | Relative bilateral frontal HP, L > R (SPECT) | FTLD-U + marked neuronal loss ZC SN, rare lewy bodies |
| DR8 III.18 | F | FTD | 51 | 55† | ↓spontaneous speech, echolalia, apathy, Δbehavior | ↓memory, control of emotions, loss of decorum | Global cortical and subcortical atrophy (CT) | Severe relative bifrontal HP, L > R (SPECT) | NA |
| DR8.15 | F | PPA | 63 | 64 | aphasia, verbal apraxia | | Postcontusional bilateral frontal and R temporal (MRI) | | NA |
| DR25.1 | F | FTD | 69 | 75† | ↓spontaneous speech, ↓initiative, hyperorality | repetitive movement of the hands | Cortical and subcortical frontal atrophy; periventricular white matter lesions (CT) | Severe relative bilateral frontal, parietal and temporal HP. Scintigraphic indications of subcortical loss (SPECT). | FTLD-U + marked neuronal loss ZC SN + few NFT (max 10/mm²) in hippocampus |
| DR25.5 | M | FTD | 70 | 74† | aphasia, apathy, Δbehavior, Δpersonality | | Cortical and subcortical atrophy, maximal frontally, L > R; PWML (MRI) | Bilateral frontal, parietal and temporal HP L > R; right cerebellar HP (PET) | FTLD-U |
| DR25.14 | F | AD | 76 | 78† | ↓memory, ↓verbal expression, apathy | CSF biomarker profile typical for AD | Cortico-subcortical atrophy. PWML. Lacunar infarctions in the basal ganglia bilaterally (CT) | Relative frontoparietal HP extending into both anterior temporal lobes. Preserved sensori-motor cortex activity (SPECT) | NA |
| DR26.1 | M | PNFA | 65 | 68† | progressive apraxia of speech | | Global subcortical and cortical atrophy maximal frontally and temporally, L > R (MRI) | Relative frontal, temporal and parietal HP P > R, relative HP of basal ganglia and lentiform nucleus. R cerebellar HP(SPECT) | NA |

TABLE 21-continued

Overview of clinical and pathological characteristics of PGRN IVS0 + 5G > C carriers in the DR8 founder family

| Patient | Gender | Clinical diagnosis | Age at onset | Age at death (†)/ current age | Presenting impairments | Additional features | Structural neuroimaging (CT/MRI) | Functional neuroimaging (SPECT/PET) | Pathology |
|---|---|---|---|---|---|---|---|---|---|
| DR27.1 | F | FTD | 58 | 64† | ↓behavior (decorum, aggression) | ↓verbal fluency, extrapyramidal rigidity | Corticosubcortical atrophy, maximal frontotemporally R > L; PWML (MRI) | Bilateral frontal, temporal and parietal HP R > L. Right HP at parieto-occipital transition. Left cerebellar HP (PET) | FTLD-U |
| DR28.1 | M | PNFA | 57 | 62† | PNFA | parkinsonism (tremor, rigidity) | NA | Relative frontal, temporal and parietal HP L > R (SPECT) | FTLD-U + mild neuronal loss ZC SN + few SP (max 40/mm$^2$), NFT |
| DR31.1 | M | PNFA | 66 | 70† | PNFA | | Global cortical and minor subcortical temporal atrophy L > R (MRI) | Marked relative bilateral frontal and temporal HP L > R, diastasis of frontal cortical activity (SPECT) | FTLD-U + neuronal loss ZC SN + rare perivascular Abeta deposits, NFT max 7/mm$^2$ |
| DR119.1 | F | PNFA | 45 | 47 | ↓word-finding, ↓verbal expression | | Anterior temporal atrophy L > R (MRI) | PET | NA |
| DR142.1 | F | AD | 66 | 76† | ↓memory | ↓spontaneous speech, loss of decorum | Slightly asymmetric (right > left) subcortical and cortical atrophy. PWML (CT) | Relative frontal, temporal and parietal HP, R > L. Diastasis of frontal cortical activity. Preserved sensori-motor cortex activity (SPECT) | NA |
| DR205.1 | M | PD + frontal dysfunction | 56 | 61† | resting tremor, rigidity, bradykinesia | mutism, echolalia, loss of judgment, disinhibition | NA | NA | FTLD-U + PD + DCP |

CT: computerized tomography;
MRI: magnetic resonance imaging;
SPECT: single photon emission computerized tomography;
PET: positron emission tomography;
PNFA: progressive non-fluent aphasia;
R: right;
L: left;
PWML: periventricular white matter lesions;
HP: hypoperfusion;
NFT: neurofibrillary tangle;
SP: senile plaques;
ZN: zona compacta;
SN: substantia nigra;
NA: not available.

PD patient DR205.1 was diagnosed with PD at age 56 years, one year after onset of symptoms. Symptoms included global and cogwheel rigidity, hypomimia, bradykinesia, shuffling gait, postural instability, and a discrete resting tremor. The patient responded well to levodopa treatment. Because of reported loss of concentration, a neuropsychological examination was performed one year after onset, which revealed no abnormalities. Three years after disease onset, progressive memory problems were noted, which were accompanied by apathy, hypophonia, and reduced verbal expression. Behavioral observation and neuropsychological testing then revealed loss of insight and judgment, changes in sexual behavior, impaired control of emotions, mutism, and echolalia, with comparatively spared memory and spatial abilities. These findings were compatible with pronounced frontal dysfunction in light of PD, or with frontotemporal dementia. DR205.1 had an MFS score of 6. Of interest, DR205.1 had a mother and two maternal aunts with late-onset dementia according to family informants, but no relatives with parkinsonism. At age 61, the patient died, and autopsy was performed.

Pathological Characteristics:

Pathological confirmation of the clinical diagnosis of both AD patients carrying IVS0+5G>C could not be obtained since both carriers died without autopsy; however, the proband of family DR25 (DR25.1) and her sibling (DR25.5) had pathologically confirmed FTLD-U (Cruts et al., *Nature*, 442:920-4 (2006); Table 21).

For DR205.1, who was clinically diagnosed with PD, autopsy was performed. On gross examination, a severe cortical atrophy, especially of the frontal lobe, was remarkable. The caudate nucleus was also atrophied and substantia nigra and locus coeruleus were severely depigmented. Histochemistry and immunohistochemical data showed a severe neuronal loss and gliosis in all neocortical regions analyzed, with many of the surviving neurons containing lipofuschin. Anti-ubiquitin immunoreactivity showed a huge burden of thread-like inclusions in layers II and III, as well as in deeper cortical layers and the white matter. Infrequent Lewy body inclusions were observed in brain stem, caudate nucleus, and occasionally in cortical regions. These inclusions were stained with ubiquitin and α-synuclein antibodies, but not with tau antibodies. In neocortical regions and basal ganglion, ubiquitin-positive and tau- and α-synuclein-negative inclusions were observed. Lenticular, cat-eye type of inclusions were especially abundant in the basal ganglion. Staining for the FTLD-U inclusion polypeptide TAR DNA-binding protein 43 (TDP-43; Neumann et al., *Science*, 314:130-3 (2006)) showed that the ubiquitin-positive inclusions (NII's and neuronal cytoplasmic inclusion (NCI's)) contained TDP-43. Normal nuclear staining was observed in unaffected neurons. Based on these findings, the patient was diagnosed as having a mixed pathology of diffuse Lewy body disease and FTLD-U. Interestingly, numerous Aβ-stained dense-core plaques were also observed in cortical and hippocampal regions.

The DR8 Founder Family:

Including the three mutation carriers, DR25.14, DR142.1, and DR205.1, the DR8 founder family comprises ten different branches extending over at least seven generations, and consists of at least 250 individuals. Genealogical information is available for 237 of the 250 individuals (FIG. 12). Of the 237 individuals, 44 are affected. The onset age is known for 39 patients, and the mean age of onset is 64.4 years, ranging from 45-78 years. Thirty five % of patients are male. In those patients (n=16) for whom detailed medical information was available, diagnosis was probable AD in two patients, PD with frontal dysfunction or frontotemporal dementia in one patient, and frontotemporal lobar degeneration in 13 patients, 11 of which were reported elsewhere, with a presenting diagnosis of progressive non-fluent aphasia (PNFA; 4/11) or FTD (7/11; van der Zee et al., *Brain*, 129:841-52 (2006); Table 21). Prominent presenting symptoms in these patients included language impairment (PNFA, reduced spontaneous speech) and behavioral and personality changes, of which apathy was most frequently noted (5/11). A first cousin of DR8.1 (DR8.15) carrying the IVS0+5G>C mutation developed a primary progressive aphasia at age 63 years. With unimpaired memory and activities of daily living, her language impairment was characterized by aphasia with reduced fluency, excessive phonological paraphasia of spoken and written language, verbal apraxia, and perseverations. One year after disease onset, the patient started displaying behavioral changes such as disinhibited laughter and stereotypic involuntary movements of tongue and jaw.

Through mutation analysis of PGRN in a sample of FTD patients, an additional IVS0+5G>C carrier was identified (DR119.1; Cruts et al., *Nature*, 442: 920-4 (2006)), defining a separate branch of the founder family. This patient presented with word finding difficulties and social withdrawal at age 45 years. Memory was preserved. Her speech was characterized by shortening and simplification of sentences and phonemic paraphasia, which led to a diagnosis of PNFA. The patient's father died at age 65 years after a 5-year period of progressive language impairment and behavioral changes.

In three out of 13 patients diagnosed with FTLD, impairment of memory was an early symptom. Parkinsonism was observed in one patient with a diagnosis of primary progressive aphasia (PPA, DR28.1), attributed to use of antipsychotic medication. Several siblings were reported to have had parkinsonian symptoms according to family informants.

Autopsy was performed in a total of eight patients, and confirmed the diagnosis of FTLD-U with ubiquitin-immunoreactive NII's in all cases, with a concurrent diagnosis of PD in DR205.1 and a concurrent diagnosis of early AD (Braak stage A-II) in DR2.3 (presenting symptoms: PNFA and behavioral changes). In three other brains, rare amyloid deposits or neurofibrillary tangles were observed, which were limited to hippocampal areas in DR31.1 and 25.1. In four patients other than DR205.1, mild to marked neuronal loss of the zona compacta of the substantia nigra was found, with melanin in astrocytic cytoplasm in three patients. Rare Lewy bodies were observed only in one patient.

In addition to null mutations, a number of mutations affecting the sequence of PGRN polypeptide were identified (Table 22). The majority of the missense mutations that were found in patients only (5/7) are located in domains encoding granulin polypeptides, suggesting that these mutations could interfere with the function of the granulin polypeptides in brain. Missense mutations also were identified in patients diagnosed with FTLD (van der Zee et al., *Hum Mutat*, 28:416 (2007)), of which two out of three (p.Pro248Leu and p.Arg432Cys) were predicted to have a substantial effect on PGRN polypeptide stability. Three of the missense mutations, p.Pro451Leu, p.Cys139Arg, and p.Arg564Cys, can have a similar effect on polypeptide structure, p.Pro451Leu abrogating a highly conserved Pro-residue, and p.Cys139Arg and p.Arg564Cys creating or destroying Cys-residues (Table 22).

TABLE 22

Mutations affecting PGRN polypeptide sequence

| Alias | Genome[1] | Predicted RNA[2] | Predicted polypeptide[3] | Location[4] | Patients | Control individuals |
|---|---|---|---|---|---|---|
| EX1 + 106C > A | g.100165C > A | c.99C > A | p.Asp33Glu | EX 1 | 2 (0.22) | — |
| EX4 + 66T > C | g.101195T > C | c.415T > C | p.Cys139Arg | EX 4 | 1 (0.11) | — |
| EX6 + 37G > A | g.101629G > A | c.635G > A | p.Arg212Gln | EX 6 | — | 1 (0.22) |
| EX7 + 73C > T | g.102072C > T | c.781C > T | p.Leu261Ile | EX 7 | 1 (0.11) | 1 (0.22) |
| EX9 + 37G > A | g.102488G > A | c.970G > A | p.Ala324Thr | EX 9 | 2 (0.22) | — |
| EX10 + 118C > T | g.103034C > T | c.1297C > T | p.Arg433Trp | EX 10 | 5 (0.54) | 1 (0.22) |
| EX10 + 173C > T | g.103089C > T | c.1352C > T | p.Pro451Leu | EX 10 | 1 (0.11) | — |
| EX11 + 127G > A | g.103369G > A | c.1540G > A | p.Val514Met | EX 11 | 2 (0.22) | — |
| EX11 + 131G > C | g.103373G > C | c.1544G > C | p.Gly515Ala | EX 11 | 2 (0.22) | — |
| EX12 + 46C > T | g.103608C > T | c.1690C > T | p.Arg564Cys | EX12 | 1 (0.11) | — |

[1]Numbering relative to the reverse complement of GenBank ® Accession Number AC003043 and starting at nt 1;
[2]Numbering according to the largest PGRN transcript (GenBank ® Accession Number NM_002087.2) and starting at the translation initiation codon;
[3]Numbering according to the largest PGRN isoform (GenPept ® Accession Number NP_002078.1);
[4]EX: exon, IVS: intron, exon numbering starts with non-coding first exon EX 0.

Additional mutations identified in PGRN nucleic acid are listed in Table 23. Polymorphisms identified in PGRN nucleic acid are listed in Table 24.

TABLE 23

Additional PGRN mutations

| Patient ID | Presentation | Onset age (years) | Family History | Alias | Genome[1] | Predicted RNA[2] | Predicted polypeptide[3] | Location[4] |
|---|---|---|---|---|---|---|---|---|
| d1397 | AD | 79 | − | 5'-34C > T | g.95991C > T | — | — | 5' Upstream |
| d2721 | PD | 55 | − | EX0 + 17G > C | g.96041G > C | — | — | EX 0 |
| d1343 | AD | 72 | − | EX0 + 111C > T | g.96135C > T | c.1-109C > T | — | EX 0 |
| d4796 | AD | 85 | − | EX0 + 164T > G | g;96188T > G | c.1-56T > G | — | EX 0 |
| d1399 | AD | 79 | + | IVS0 + 46G > T | g.96282G > T | — | — | IVS 0 |
| d2555 | PD | 52 | − | | | | | IVS 0 |
| d2654 | PD | 43 | + | | | | | IVS0 |
| DR148.1 | AD | 81 | + | EX1 + 106C > A | g.100165C > A | c.99C > A | p.Asp33Glu | EX 1 |
| d2631 | PD | 56 | − | | | | | EX 1 |
| DR197.1 | AD | 80 | − | EX4 + 66T > C | g.101195T > C | c.415T > C | p.Cys139Arg | EX 4 |
| d7675 | AD | ? | + | IVS4 + 15G > T | g.101257G > T | — | — | IVS 4 |
| d2634 | PD | 57 | − | IVS8 + 16G > A | g.102378G > A | — | — | IVS 8 |
| d5181 | AD | 72 | + | IVS8-40C > T | g.102115C > T | — | — | IVS 8 |
| DR196.1 | AD | 86 | − | EX9 + 37G > A | g.102488G > A | c.970G > A | p.Ala324Thr | EX 9 |
| d2657 | PD | 64 | − | | | | | EX 9 |
| d4504 | AD | 85 | − | IVS9 + 108G > A | g.102805G > A | — | — | IVS 9 |
| d1461 | AD | 69 | + | EX10 + 162C > T | g.103078C > T | c.1341C > T | p.His447 | EX 10 |
| DR152.1 | AD | 74 | − | EX10 + 173C > T | g.103089C > T | c.1352C > T | p.Pro451Leu | EX 10 |
| d5016 | AD | 84 | − | EX11 + 72C > T | g.103314C > T | c.1485C > T | c.Cys495 | EX 11 |
| DR165.1 | AD | 73 | + | EX11 + 127G > A | g.103369G > A | c.1540G > A | p.Val514Met | EX 11 |
| d5765 | PD | 70 | − | | | | | EX 11 |
| DR200.1 | AD | 74 | − | EX11 + 131G > C | g.103373G > C | c.1544G > C | p.Gly515Ala | EX 11 |
| DR201.1 | AD | 89 | − | | | | | EX 11 |
| d2597 | PD | 46 | − | EX11 + 141C > T | g.103383C > T | c. 1554C > T | c.Asp518 | EX 11 |
| DR144.1 | AD | 70 | + | EX12 + 46C > T | g.103608C > T | c.1690C > T | p.Arg564Cys | EX 12 |

[1]Numbering relative to the reverse complement of GenBank ® Accession Number AC003043 and starting at nt 1;
[2]Numbering according to the largest PGRN transcript (GenBank ® Accession Number NM_002087.2) and starting at the translation initiation codon;
[3]Numbering according to the largest PGRN isoform (GenPept ® Accession Number NP_002078.1);
[4]EX: exon, IVS: intron, UTR: untranslated region, exon numbering starts with non-coding first exon EX 0.

TABLE 24

PGRN polymorphisms in patients and/or control individuals

| Mutation | | | | | Number (%) | |
|---|---|---|---|---|---|---|
| Alias | Genome[1] | Predicted RNA[2] | Predicted polypeptide[3] | Location[4] | Patients | Control individuals |
| EX0 + 175C > G | g.96199C > G | c.1-45C > G | — | EX 0 | 1 (0.11) | 2 (0.44) |
| EX1 + 106C > T | g.100165C > T | c.99C > T | p.Asp33 | EX 1 | 11 (1.19) | 4 (0.87) |
| IVS2 + 7G > A | g.100460G > A | — | — | IVS 2 | 12 (1.30) | 3 (0.63) |
| IVS3 + 11G > C | g.100664G > C | — | — | IVS 3 | 0 (0.00) | 1 (0.22) |
| EX3 + 15G > A | g.100583G > A | c.279G > A | p.Gly93 | EX 3 | 8 (0.87) | 1 (0.22) |
| EX4 + 35T > C | g.101164T > C | c.384T > C | p.Asp128 | EX 4 | 43 (4.67) | 27 (5.88) |
| EX6 + 37G > A | g.101629G > A | c.635G > A | p.Arg212Gln | EX 6 | 0 (0.00) | 1 (0.22) |
| EX7 + 73C > T | g.102072C > T | c.781C > T | p.Leu261Ile | EX 7 | 1 (0.11) | 1 (0.22) |
| EX7 + 96G > A | g.102034G > A | c.804G > A | p.Thr268 | EX 7 | 0 (0.00) | 1 (0.22) |
| EX8 + 68G > A | g.102332G > A | c.903G > A | p.Ser301 | EX 8 | 3 (0.33) | 1 (0.22) |
| EX10 + 118C > T | g.103034C > T | c.1297C > T | p.Arg433Trp | EX 10 | 5 (0.54) | 1 (0.22) |
| EX11 + 12C > T | g.103254C > T | c.1425C > T | p.Cys475 | EX 11 | 0 (0.00) | 1 (0.22) |

[1]Numbering relative to the reverse complement of GenBank ® Accession Number AC003043 and starting at nt 1;
[2]Numbering according to the largest PGRN transcript (GenBank ® Accession Number NM_002087.2) and starting at the translation initiation codon;
[3]Numbering according to the largest PGRN isoform (GenPept ® Accession Number NP_002078.1);
[4]EX: exon, IVS: intron, exon numbering starts with non-coding first exon EX 0.

Example 6

Progranulin Modifies Onset Age and Survival in Amyotrophic Lateral Sclerosis

Study Groups:

A total of 230 sporadic ALS patients were recruited at the university hospitals of Leuven and Antwerpen, Belgium, with a diagnosis of definite, probable, or laboratory supported probable ALS (according to El Escorial criteria, available at on the World Wide Web at wfnals.org). The mean age of onset was 57.6±12.3 years and 146 (63%) of the patients were men. Of 219 patients, information on spinal or bulbar onset was available for 167 and 52 patients, respectively. Mean survival after first symptoms was 35±23 months (N=183). None of the patients carried a SOD1 mutation. The control group consisted of 436 community control persons, 192 men and 244 women, that were neurologically healthy and of Belgian descent. Mean age at examination of the control individuals was 58.7±15.8 years. The presence of population substructure was excluded based on 27 randomly selected microsatellite markers in Structure 2.1 (Pritchard et al., Genetics, 155(2):945-959 (2000)). DNA was obtained from 308 Dutch ALS patients who were diagnosed according to El Escorial criteria. The mean age at onset was 57.9±11.6 years, and 60.3% were male. Mean survival after first symptoms was 32.5±27.4 months (N=130). A Dutch control sample consisted of 345 individuals, of whom 45.8% were men, with a mean age at inclusion of 60±11.7 years.

PGRN Sequencing:

PGRN non-coding exon 0, coding exons 1 to 12, and a conserved 5' regulatory region in intron 0 were PCR amplified from 20 ng of genomic DNA using primers described elsewhere (Cruts et al., Nature, 442(7105):920-924 (2006)). Primers were designed using Primer3 software (Rozen and Skaletsky, Methods Mol Biol, 132:365-386 (2000)). Amplification products were purified using 1 U of antarctic phosphatase (New England Biolabs, Ipswich, Mass.) and 1 U of exonuclease I (New England Biolabs). Purified PCR products were sequenced in both directions using PCR primers or, if necessary, internal sequencing primers and the Big Dye® Terminator v3.1 Cycle Sequencing kit (Applied Biosystems, Foster City, Calif.) according to manufacturer's protocol. Labeled products were separated on an Applied Biosystems 3730x1 DNA Analyzer (Applied Biosystems).

PGRN SNP Genotyping:

Single nucleotide polymorphisms (SNPs; minor allele frequency >5%) except IVS4+24G>A ($r^2$=0.989 with IVS3-47-46insGTCA) were genotyped in a replication set in two MassARRAY iPlex assays, followed by Matrix-Assisted Laser Desorption/Ionization Time-Of-Flight (MALDI-TOF) mass spectrometry. PCR and extension primers were designed using Assay Design 3.1 software (Sequenom, Hamburg, Germany). Briefly, 20 ng of genomic DNA was PCR amplified using Titanium Taq DNA Polymerase (Clontech, Mountain View, Calif.) under standard conditions. PCR products were treated with shrimp alkaline phosphatase (SAP) for 20 minutes to remove unincorporated dNTPs. ThermoSequenase (Sequenom) was used for the base extension reactions. Primer extension products were cleaned and spotted onto chips that were subsequently scanned using a mass spectrometry workstation (MassARRAY Nanodispenser and MassARRAY compact analyzer; Sequenom). Spectrum analysis and genotype scoring was performed using Typer 3.3 software (Sequenom).

Allele Sharing Analysis:

Fourteen microsatellite markers spanning an 8 cM region around PGRN were genotyped in two ALS patients and one patient with Alzheimer dementia carrying the p.Ala324Thr mutation. Twenty ng of genomic DNA were PCR amplified in four multiplex reactions, as described elsewhere (van der Zee et al., Brain, 129(Pt 4):841-852 (2006)). Fluorescently labeled products were resolved on an Applied Biosystems 3730x1 DNA Analyzer (Applied Biosystems). Genotypes were assigned using custom genotyping software.

In Silico Prediction of Pathogenicity:

The effect of missense mutations on polypeptide function was estimated in silico using the Sorting Intolerant From Tolerant (SIFT v.2) program (Ng and Henikoff, Genome Res, 12(3):436-446 (2002)) based on sequence homology and physical properties of amino acids. Three different input methods were tested: (1) using both the automated SIFT homologue retrieval (from the SWISS-PROT 48.7 and TREMBL 31.7 databases) and alignment procedure, (2) applying the SIFT pruning and alignment protocol to 61 unaligned homologues sequences from NCBI's BLink database (Wheeler et al., Nucleic Acids Res, 34(Database issue):

D173-D180 (2006)), and (3) providing a curated ClustalX (Jeanmougin et al., *Trends Biochem Sci,* 23(10):403-405 (1998)) alignment of the 61 BLink sequences. For each input sequences 100% or 90% identical to the query were removed. An average score over the resulting six tests <0.05 was considered indicative of an effect on polypeptide function.

For structural modeling of mutations located in granulin domains, the full structure of a granulin domain was reconstructed based on the crystal structure of the N-terminal module of human granulin A (PDB 1g26; Tolkatchev et al., *Biochemistry,* 39(11):2878-2886 (2000)) using SwissPDB-Viewer (Guex and Peitsch, *Electrophoresis,* 18(15):2714-2723 (1997)), Modeller (Fiser and Sali, *Methods Enzymol,* 374:461-491 (2003)), ProQ (Wallner and Elofsson, *Protein Sci,* 12(5):1073-1086 (2003)), and FoldX (Schymkowitz et al., *Nucleic Acids Res,* 33(Web Server issue):W382-W388 (2005)). The effect of mutations on stability of granulin domains was evaluated using FoldX, introducing a penalty for forming or breaking disulfide bonds (Czaplewski et al., *Protein Eng Des Sel,* 17(1):29-36 (2004)). MatInspector analysis (Cartharius et al., *Bioinformatics,* 21(13):2933-2942 (2005)) was performed to estimate the effect of 5' regulatory variants on putative transcription factor binding sites. A core similarity cut off of 1 was used.

Statistical Analysis:

Deviations from Hardy-Weinberg equilibrium (HWE) were excluded using the HWE program for both Belgian and Dutch samples (Terwilliger and Ott, *Handbook of Human Genetic Linkage,* Johns Hopkins University Press, Baltimore, Md. (1994)). For SNPs with a minor allele frequency >5%, chi-square statistics and logistic regression analysis adjusted for age and gender were performed in SPPS 12.0 to examine the contribution of each detected common variant to the susceptibility to ALS. To study genotype-phenotype correlations, additional analyses were performed for patients with a spinal or bulbar onset of ALS. The effect of the polymorphisms on age at onset in patients was assessed in a univariate analysis of variance, adjusted for gender and site of onset. The effect of the polymorphisms on survival after onset of the first symptoms was tested with a Cox proportional hazards model. Hazard ratios (HR) were calculated with their 95% confidence intervals (95% CI) adjusted for gender, site of first symptoms, and age at first symptoms. Pairwise LD, computed in Haploview (Barrett et al., *Bioinformatics,* 21(2):263-265 (2005)) revealed two blocks of increased LD, one spanning the 5' regulatory region, the second covering intron 2 through to the 3' untranslated region. Haplotype frequencies were estimated in these LD blocks using a progressive EM insertion algorithm computing both maximum likelihood estimates of haplotype probabilities and posterior probabilities of pairs of haplotypes for each subject. Haplotype associations, based on these haplotype probabilities, were investigated with score statistics. A sliding window analysis was performed with 2-SNP windows. Both haplotype estimation and analysis were performed in Haplo Stats version 1.2.2. (Schaid et al., *Am J Hum Genet,* 70(2):425-434 (2002)). Simulation P-values were calculated based on 1000 random permutations of patient and control labels to control the type I error rate.

Results

PGRN Sequencing:

A systematic mutation analysis of PGRN was performed by direct sequencing of all coding exons, including exon-intron boundaries, and 5' and 3' regulatory regions in a series of 230 Belgian patients diagnosed with ALS, and in 436 control individuals. Seventeen rare variants (minor allele frequency <5%) were identified in 29 patients (9 exonic variants, 4 intronic variants, 3 variants in the 5' regulatory region, and 1 variant in the 3' regulatory region). Of these rare variants, 11 were absent from 872 control chromosomes (Tables 25, 26, and 27).

TABLE 25

PGRN missense mutations in ALS

| | Variation | | | | | |
|---|---|---|---|---|---|---|
| Alias | Genome[1] | Predicted RNA[2] | Predicted polypeptide[3] | Location[4] | Patients[5] | SIFT score[6] |
| EX3 + 65G > A | g.100633G > A | c.329G > A | p.Arg110Gln | EX 3 | 1/230 | 0.39 |
| EX4 + 22T > C | g.101151T > C | c.371T > C | p.Ile124Thr | EX 4 | 1/230 | 0.16 |
| EX9 + 37G > A | g.102488G > A | c.970G > A | p.Ala324Thr | EX 9 | 2/230 | 0.44 |
| EX10 + 74G > A | g.102990G > A | c.1253G > A | p.Arg418Gln | EX 10 | 1/230 | 0.27 |

[1]Numbering relative to the reverse complement of GenBank ® Accession Number AC003043 and starting at nt 1;
[2]Numbering according to the largest PGRN transcript (GenBank ® Accession Number NM_002087.2) and starting at the translation initiation codon;
[3]Numbering according to the largest PGRN isoform (GenPept ® Accession Number NP_002078.1);
[4]EX: exon, IVS: intron, exon numbering starts with non-coding first exon EX 0.
[6]Frequency of mutations in patients; absent from 436 healthy individuals.
[6]Average SIFT scores <0.05 are predicted to affect polypeptide function.

TABLE 26

Genetic variants in the PGRN 5' regulatory region

| Variation | | | Patients | Controls | TFBS alterations[3] |
|---|---|---|---|---|---|
| Alias | Genome[1] | Location[2] | (%; n = 230) | (%; n = 436) | (core/matrix similarity) |
| EX0 + 37A > G | g.96061A > G | EX 0 | 0.4 | 0 | −EVI1 (1/0.833) −PAX2 (1/0.798) −ISRE (1/0.819) +NFAT (1/0.96) |

TABLE 26-continued

Genetic variants in the PGRN 5' regulatory region

| Alias | Variation Genome[1] | Location[2] | Patients (%; n = 230) | Controls (%; n = 436) | TFBS alterations[3] (core/matrix similarity) |
|---|---|---|---|---|---|
| IVS0 + 236G > A | g.96472G > A | IVS 0 | 1.3 | 0.7 | +ELK1 (1/0.824) +ALM3 (1/0.936) |
| IVS0 + 485A > G | g.96721A > G | IVS 0 | 1.3 | 0.7 | No major changes |

[1]Numbering relative to the reverse complement of GenBank ® Accession Number AC003043 and starting at nt 1;
[2]EX: exon, IVS: intron, exon numbering starts with non-coding first exon EX 0.
[3]TFBS: transcription factor binding site; MatInspector prediction.

TABLE 27

Rare PGRN silent and intronic variations

| Alias | Genome[1] | Predicted RNA[2] | Predicted polypeptide[3] | Location[4] | Patients (%; n = 230) | Control (%; n = 436) |
|---|---|---|---|---|---|---|
| EX1 + 106C > T | g.100165C > T | c.99C > T | p.Asp33 | EX 1 | 1.7 | 0.9 |
| IVS2 + 7G > A | g.100460G > A | — | — | IVS 2 | 1.3 | 0.7 |
| EX4 + 35T > C | g.101164T > C | c.384T > C | p.Asp128 | EX 4 | 5.6 | 6 |
| EX4 + 65G > A | g.101194G > A | c.414G > A | p.Thr138 | EX 4 | 0.4 | 0 |
| IVS6 + 57A > G | g.101759A > G | — | — | IVS 6 | 0.4 | 0 |
| EX7 + 96G > A | g.102034G > A | c.804G > A | p.Thr268 | EX 7 | 0.4 | 0.2 |
| EX8 + 68G > A | g.102332G > A | c.903G > A | p.Ser301 | EX 8 | 0.4 | 0.2 |
| IVS8 − 40C > T | g.102412C > T | — | — | IVS 8 | 0.4 | 0 |
| IVS9 + 101C > T | g.102798C > T | — | — | IVS 9 | 0.4 | 0 |
| EX10 + 162C > T | g.103078C > T | c.1341C > T | p.His447 | EX 10 | 0.9 | 0 |
| 3' + 21G > A | g.104025G > A | — | — | 3' Downstream | 0.9 | 0 |

[1]Numbering relative to the reverse complement of GenBank ® Accession Number AC003043 and starting at nt 1;
[2]Numbering according to the largest PGRN transcript (GenBank ® Accession Number NM_002087.2) and starting at the translation initiation codon;
[3]Numbering according to the largest PGRN isoform (GenPept ® Accession Number NP_002078.1);
[4]EX: exon, IVS: intron; exon numbering starts with non-coding first exon EX 0.

Missense Mutations:

The nine exonic sequence variants included four missense mutations that were absent from Belgian control individuals (Table 25): c.329G>A (Arg110Gln), c.371T>C (Ile124Thr), c.970G>A (Ala324Thr), and c.1253G>A (Arg418Gln). All four missense mutations were located in or at the border of a granulin domain. Arg110Gln is located in the C-terminal end of the granulin G domain, but the wild type residue is not conserved between granulin domains. SIFT analysis predicted that Arg110Gln is unlikely to affect polypeptide function (average SIFT score 0.39), based on evolutionary conservation of homologous sequences. Arg418Gln is located at the C-terminal border of granulin C. SIFT analysis predicted that Arg418Gln might be tolerated in polypeptide function (average SIFT score 0.27). Ile124Thr is located at the N-terminal border of the granulin F domain, at a position that is conserved between granulin domains, containing either an Ile or a Val residue. SIFT analysis predicted that Ile124Thr would affect polypeptide function in four out of six tests, but directly providing a ClustalX alignment of 61 homologous sequences from BLink to SIFT predicted that Ile124Thr would be tolerated. Limiting the SIFT analysis to 13 sequences specifically validated for human PGRN revealed a SIFT score of 0.01, predicting an intolerant change. Ile124Thr was estimated to have an average effect of −0.35±0.03 kcal/mol on the stability of the granulin domain, being weakly stabilizing. Ala324Thr is located in the granulin A domain, at a non-conserved position. SIFT analysis predicted that Ala324Thr would be tolerated, and structural modeling of the mutation revealed a weakly destabilizing effect of 0.36±0.01 kcal/mol on the granulin domain. Interestingly, Ala324Thr was also detected in one Belgian patient with Alzheimer dementia. Allele sharing revealed that both ALS patients share alleles of microsatellite markers flanking PGRN, spanning a shared region of maximum 2.8 Mb. One ALS patient shared alleles at seven consecutive markers with the Alzheimer patient, spanning about 6 Mb (Table 28).

TABLE 28

Allele sharing analysis in p.Ala324Thr mutation carriers

| Marker | Physical position (Mb) | Frequency of shared allele (%)[1] | ALS ALS165.01 | ALS ALS236.01 | Alzheimer d4833 |
|---|---|---|---|---|---|
| D17S1818 | 34.42 | 20 | 438-442 | 438-442 | 436-438 |
| D17S1814 | 35.37 | 18.9 | 457-463 | 455-457 | 459-463 |
| D17S800 | 36.31 | 46.1 | 359-361 | 361-361 | 361-361 |
| D17S1787 | 36.98 | 23.8 | 177-181 | 179-181 | 171-177 |
| D17S1793 | 37.61 | 78.8 | 392-392 | 394-394 | 392-394 |
| D17S951 | 39.18 | 40.2 | 135-145 | 135-135 | 135-137 |
| p.Ala324Thr | 39.78 | | G-A | G-A | G-A |
| D17S1861 | 40.16 | 9.0 | 262-264 | 262-280 | 262-262 |
| D17S934 | 40.41 | 4.5 | 359-361 | 367-373 | 373-377 |

Shared alleles are represented in bold;
[1]frequency of shared allele based on 102 Belgian control individuals.

Regulatory Variants:

Three variants were detected in the 5' regulatory region, of which one in non-coding exon 0 was absent from control chromosomes (Table 26). MatInspector analysis predicted that this variant (g.96061A>G) is likely to abolish EVI1, PAX2 and ISRE transcription factor binding sites, and create a NFAT binding site. No major changes in transcription factor binding sites were predicted for g.96721A>G, whereas g.96472G>A may create an ELK1 or ALM3 binding site. The latter two variants were present in three patients (1.3%) and three control individuals each (0.7%), and thus their frequency did not differ significantly between patients and control individuals (OR 1.9 (95% CI 0.4-9.5; p-value 0.4)).

Clinical Phenotype:

Of the five mutations identified only in patients and affecting polypeptide function or expression, four were identified in five women, and one (Ile124Thr) was identified in a man. All women had a spinal onset of the disease, whereas the male patient had a bulbar onset. The onset ages varied between patients, ranging from 53 years (Ala324Thr) to 74 years (Arg110Gln). Likewise, disease duration varied from 16 months (Ile124Thr) to >88 months (Ala324Thr). Even between the two patients carrying Ala324Thr, onset age and disease duration varied widely. One patient showed first symptoms at age 62 years and died after 28 months. The other patient had first symptoms at age 53 years and was still alive after 88 months. The two patients share a 2.8 Mb haplotype with a man who was diagnosed with probable Alzheimer dementia at 86 years, suggesting a distant common ancestor.

Common PGRN Polymorphisms:

Genotype data of eight frequent SNPs (minor allele frequency >5%) were extracted from the sequencing data obtained in both Belgian patients and Belgian control individuals for genetic association analyses (Table 29). Genotype frequencies did not differ between patients and control individuals for any of the individual SNPs, neither in crude nor in age or gender adjusted logistic regression analyses (Table 29). Haplotype based association analysis was performed in the two distinct blocks of PGRN with high LD. No statistically significant global or haplotype-specific differences were observed between ALS patients and control individuals in either LD block (global p-value 0.34 and 0.63, respectively).

TABLE 29

Genotype frequencies of PGRN SNPs in ALS patients and control individuals

| Variation | | | | | ALS | Control | | |
|---|---|---|---|---|---|---|---|---|
| Alias | Genome[1] | rs number | Location[2] | Genotype | (%) | (%) | p-value | OR (95% CI) |
| 5'-111delC | g.95914delC | rs17523519 | 5'upstream | wt/wt | 54.4 | 54.0 | 0.8 | Ref |
| | | | | del/wt | 36.8 | 38.6 | | 0.9 (0.6-1.3) |
| | | | | del/del | 8.8 | 7.4 | | 1.1 (0.6-2.1) |
| IVS0 + 561C > T | g.96797C > T | rs3859268 | IVS 0 | CC | 52.6 | 51.0 | 0.6 | Ref |
| | | | | CT | 38.2 | 41.5 | | 0.8 (0.6-1.2) |
| | | | | TT | 9.2 | 7.6 | | 1.2 (0.6-2.1) |
| IVS2 + 21G > A | g.100474G > A | rs9897526 | IVS 2 | GG | 85.6 | 80.3 | 0.2 | Ref |
| | | | | GA | 14.0 | 18.5 | | 0.7 (0.5-1.1) |
| | | | | AA | 0.4 | 1.2 | | 0.3 (0.04-2.8) |
| IVS3-47-46insGTCA | g.101083_101084 insGTCA | rs34424835 | IVS 3 | wt/wt | 62.4 | 59.5 | 0.6 | Ref |
| | | | | ins/wt | 33.6 | 35.0 | | 0.9 (0.6-1.3) |
| | | | | ins/ins | 4.0 | 5.5 | | 0.7 (0.3-1.6) |
| EX4 + 35 T > C | g.101164T > C | rs25646 | EX 4 | TT | 94.7 | 93.4 | 0.5 | Ref |
| | | | | TC | 5.3 | 6.6 | | 0.8 (0.4-1.6) |
| | | | | CC | 0 | 0 | | — |
| IVS4 + 24 G > A | g.101266G > A | rs850713 | IVS 4 | GG | 62.6 | 58.7 | 0.5 | Ref |
| | | | | AG | 33.5 | 35.6 | | 0.9 (0.6-1.2) |
| | | | | AA | 4.0 | 5.7 | | 0.7 (0.3-1.5) |
| IVS7 + 7 G > A | g.102072G > A | — | IVS 7 | GG | 85.5 | 86.6 | 0.8 | Ref |
| | | | | GA | 14.0 | 13.2 | | 1.0 (0.6-1.6) |
| | | | | AA | 0.5 | 0.2 | | 3.2 (0.2-51.9) |
| 3'UTR + 78 C > T | g.103778C > T | rs5848 | 3' UTR | CC | 57.3 | 50.9 | 0.3 | Ref |
| | | | | CT | 36.6 | 42.1 | | 0.8 (0.6-1.1) |
| | | | | TT | 6.2 | 6.9 | | 0.8 (0.4-1.6) |

[1]Numbering relative to the reverse complement of GenBank ® Accession Number AC003043 and starting at nt 1;
[2]EX: exon, IVS: intron, UTR: untranslated region; exon numbering starts with non-coding first exon EX 0.

Figure 14:
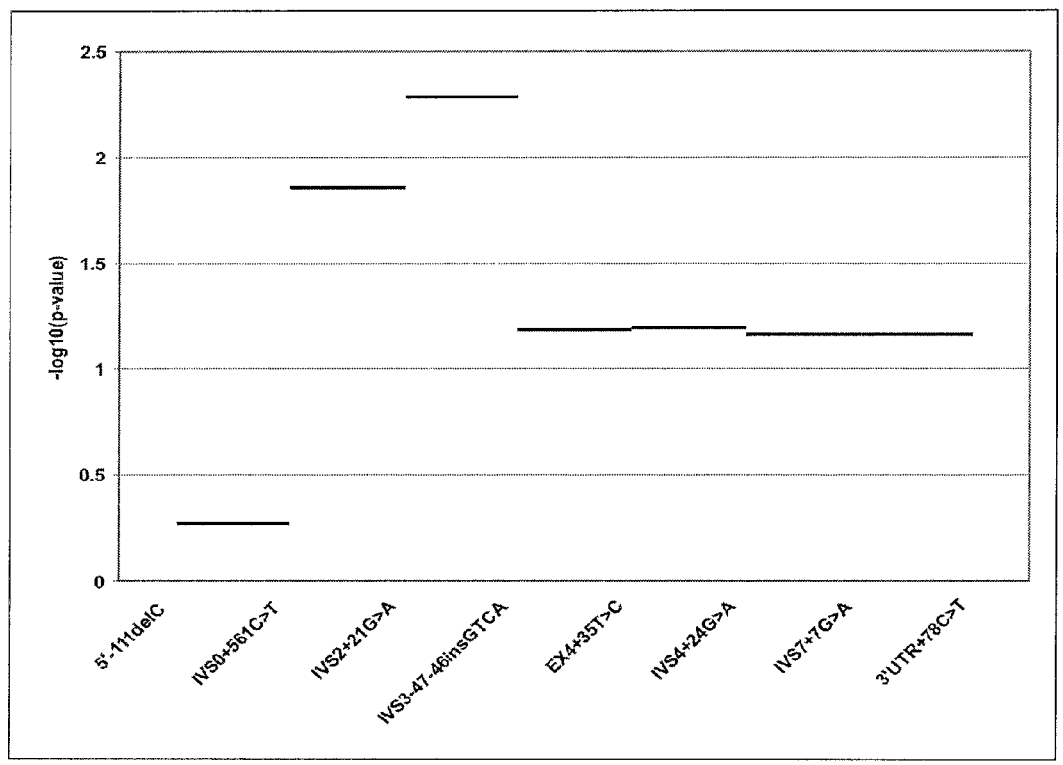
FIG. 14 is a graph plotting the −log 10 of the global p-value of a score statistic examining the association between subsequent 2-SNP haplotypes and age at onset for all common PGRN variants with minor allele frequency >0.05. The y-axis denotes the −log 10 p-value, and the x-axis depicts the common variants in order of location.
Figure 15:
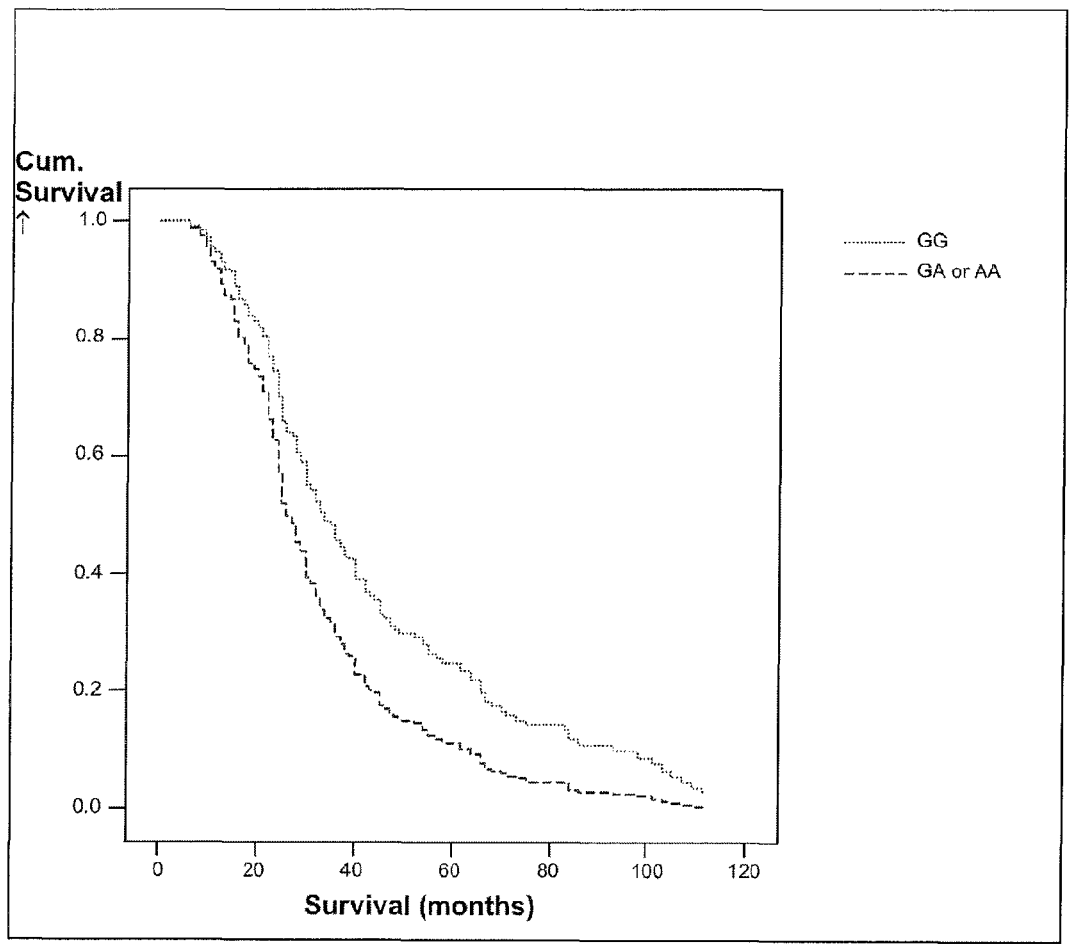
FIG. 15 is a graph plotting survival after disease onset by IVS2+21G>A genotype. A survival function is given for patients homozygous for the wild type GG (dotted line) and carriers of the A allele (dashed line). The y-axis denotes cumulative survival, and the x-axis denotes survival time in months after disease onset (t=0). Patients still alive at last examination were censored.

Genotype-Phenotype Correlation:

Given the clinical heterogeneity of ALS, the effect of PGRN SNPs on site of onset (bulbar or spinal), age at onset, and survival was evaluated. No association was observed between a single SNP or haplotype and site of onset. However, age at onset was significantly reduced in carriers of the rare allele IVS2+21G>A (mean difference: 7.7 years (95% CI: 3.2-12.1 years; p=0.001)), and to a lesser extent in carriers of the rare allele IVS3-47-46insGTCA and IVS4+24G>A (pairwise $r^2$=0.989; mean difference: 4.1 years (95% CI: 0.9-7.4 years; p=0.013). In a haplotype based setting, sliding window analysis indicated that a 2-SNP window of IVS2+21G>A and IVS3-47-46insGTCA was significantly associated with age at onset (p=0.005; FIG. 14). Moreover, carriers of the rare allele of IVS2+21G>A had a significantly shorter survival after onset of ALS (HR 1.70 (95% CI 1.10-2.64; p=0.017); FIG. 15). Although non-significant, an HR of similar magnitude was observed for carriers of the rare allele of IVS3-47-46insGTCA and IVS4+24G>A (HR 1.82 (95% CI 0.84-3.95; p=0.1)). To confirm these findings, we replicated the association analysis in a Dutch sample of ALS patients and controls. As in the Belgian sample, no statistically significant association was observed between single SNPs or haplotypes and disease status or site of onset, but patients homozygous for the rare allele at IVS3-47-46insGTCA had a significantly shorter survival after onset of ALS (HR 2.29 (95% CI 1.15-4.55; p=0.018)).

Example 7

Genomic Progranulin Deletions are a Frequent Cause of Frontotemporal Dementia The contribution of genomic PGRN deletions to the etiology of FTD was assessed in a series of 103 unrelated Belgian patients with pure FTD (Cruts et al., *Nature,* 442: 920-924 (2006)). Four PGRN null mutations were identified in 11 of the 103 patients, as described elsewhere (Cruts et al., *Nature,* 442:920-924 (2006)).

Figure 16A:
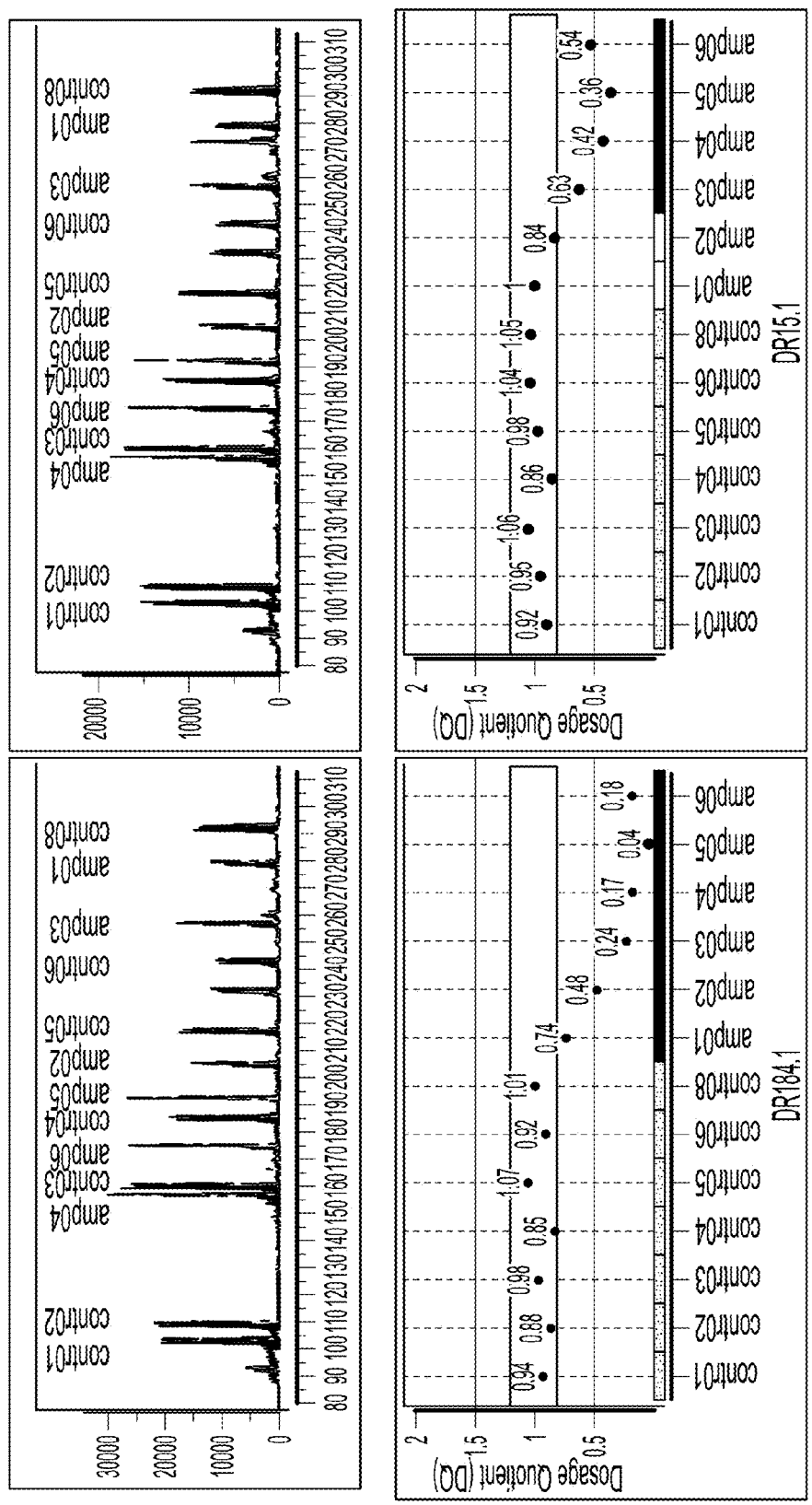
FIG. 16A contains MAQ results of patients DR184.1 (left) and DR15.1 (right) generated by the MAQs program. The upper panel contains chromatograms comparing samples from a patient and control individuals. Test (amp) and reference amplicons (contr) are indicated above the peaks. The x-axis shows the length of the amplicons in base pairs, and the y-axis indicates the peak heights. The lower panel contains dosage plots showing DQ values for reference (left side) and test amplicons (right side). Test amplicons with a DQ value below 0.75 are indicated with a black bar. The grey area represents normal variation (DQ=0.8-1.2). In patient DR184.1, the peak areas of all test amplicons are clearly reduced compared to the control individuals, resulting in DQ values below 0.75 for all test amplicons. Patient DR15.1 shows reduced DQs only for test amplicons 3 to 6.
Figure 16B:
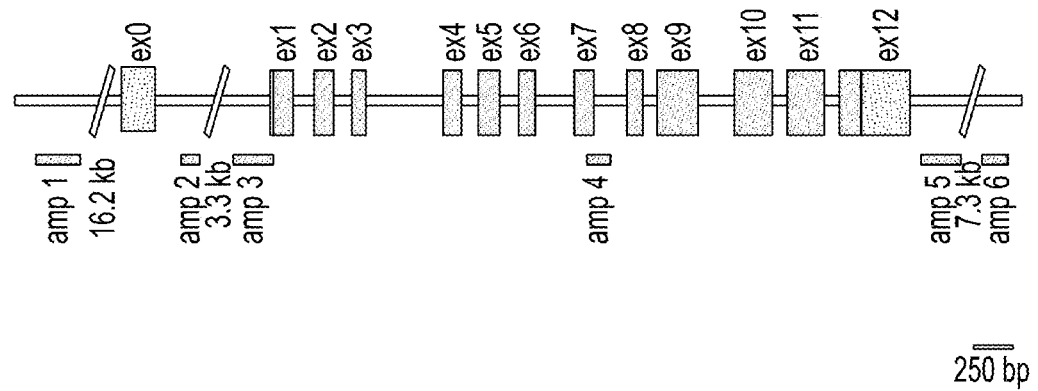
FIG. 16B is a schematic representation of the PGRN gene and flanking regions with MAQ test amplicons indicated. PGRN coding regions are shown in dark grey, non-coding regions in light grey.

To detect PGRN copy number changes, the FTD series was screened with Multiplex Amplicon Quantification (MAQ; Suls et al., *Hum Mutat,* 27:914-920 (2006)). The MAQ technique involves quantification of a number of fluorescently labeled test and reference amplicons obtained in one multiplex PCR reaction. The PGRN MAQ assay contained six test amplicons located in and around PGRN and seven reference amplicons located at randomly selected genomic positions (FIG. 16B). These 13 fragments were simultaneously amplified using 20 ng of genomic DNA in one PCR reaction with optimized reaction conditions. Peak areas of the test amplicons were normalized to those of the reference amplicons. Comparison of normalized peak areas of test amplicons between a patient and control individuals resulted in a dosage quotient (DQ) for each test amplicon, calculated by the MAQ software (MAQs) package (on the World Wide Web at vibgeneticservicefacility.be/MAQ.htm). DQ values below 0.75 indicated a deletion. MAQ analysis of 103 FTD patients revealed the presence of two deletions of more than one test amplicon in two FTD patients (FIG. 16A). In patient DR184.1, DQs of all test amplicons were reduced below 0.75, indicating a genomic deletion of PGRN including 5' and 3' flanking regions. In patient DR15.1, only test amplicons 3 to 6 showed DQs below 0.75, suggesting a partial deletion of the gene not including exon 0 and only telomerically extending beyond PGRN (FIGS. 16A and 16B). Deletions were excluded in 267 neurologically healthy Belgian control individuals (mean age 58.4±16.0 years, range 25-92 years) using the MAQ assay.

Figure 16C:
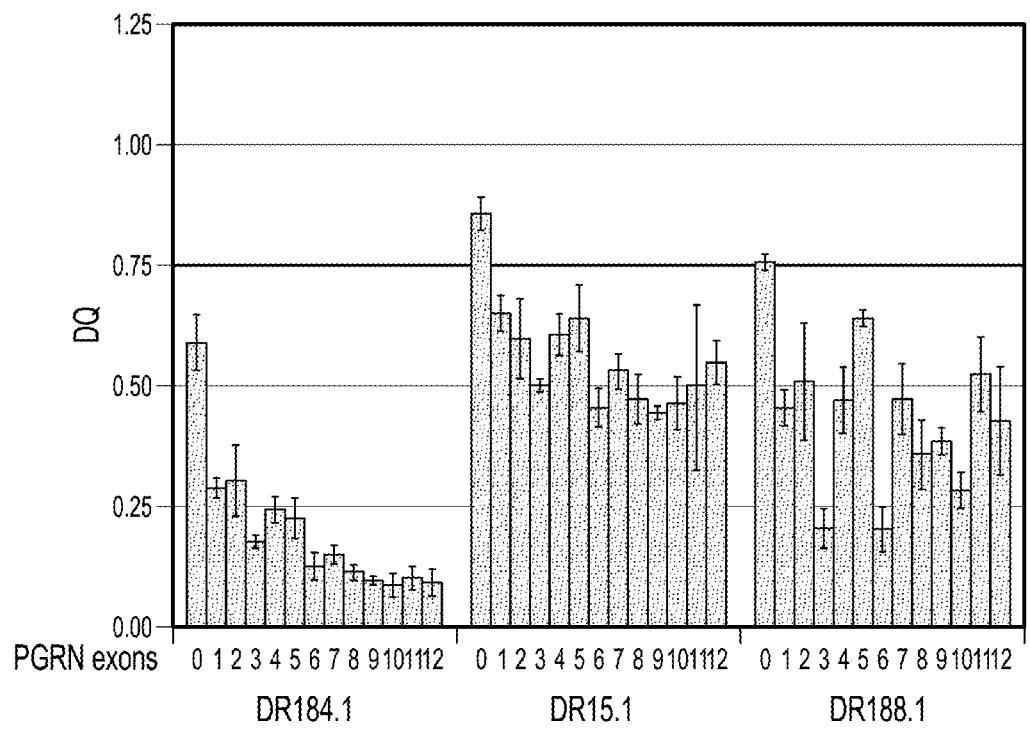
FIG. 16C is a graph of qPCR SYBR Green results of all 13 PGRN exons for patients DR184.1, DR15.1, and DR188.1. The plot shows the DQ values with standard error for each PGRN exon, indicated on the x-axis. Each DQ value represents the mean of DQs obtained for housekeeping genes hB2M and hUBC, measured in duplicate. In DR184.1, all PGRN exons show a DQ lower than 0.75, while in patients DR15.1 and DR188.1, only exons 1 to 12 are deleted, although exon 0 of DR188.1 is only slightly increased.

Real time PCR allele quantification (qPCR) was performed to quantify the copy number of PGRN using SYBR® Green I assays on the ABI Prism 7900HT Sequence Detection System (Applied Biosystems, Foster City, Calif.). Primers for one amplicon in each PGRN exon and for one amplicon in human ubiquitin C (hUBC) and human β2-microglobulin (hB2M) were designed with PrimerExpress software (Applied Biosystems). The primer sequences are listed in Table 30. Twenty ng of genomic DNA from patients and control individuals were amplified in duplicate using the universal amplification protocol (Applied Biosystems) as described elsewhere (Sleegers et al, *Brain,* 129:2977-2983 (2006)). DQs were calculated by comparing normalized quantities between patient and control individuals. qPCR of the amplicon in PGRN exon 11 was compared to hUBC and hB2M in the whole FTD sample, and 33 patients were identified with a DQ below 0.75, including DR184.1 and DR15.1. These patients were further analyzed for the 12 remaining PGRN exons, resulting in identification of three patients with a large PGRN deletion. In DR184.1, DQs of all PGRN exons were below 0.75, and in DR15.1, DQs of PGRN exons 1 to 12 were below 0.75 (FIG. 16C). These results were in agreement with the MAQ results. One additional patient (DR188.1) was observed to carry a deletion of a region including all PGRN exons other than exon 0, similar to the deletion in DR15.1 (FIG. 16C). qPCR data were further confirmed using a TaqMan assay designed to amplify a region in PGRN exon 11. The probe sequence is listed in Table 30.

TABLE 30

Primers and probe sequences for PGRN qPCR

| Gene/Region | Name | Sequence | Amplicon size in bp |
|---|---|---|---|
| PGRN | | | |
| exon 0 | ex0F | GAGTAGAAAAGAAACACAGCATTCCA (SEQ ID: 87) | 69 |
|  | ex0R | CCGCTCCCATTGGCTACTTA (SEQ ID: 88) | |
| exon 1 | ex1F | GCCAGACGTTCCTTGGTACTTT (SEQ ID: 89) | 79 |
|  | ex1R | CCACCAGCCCTGCTGTTAAG (SEQ ID: 90) | |
| exon 2 | ex2F | CAAATGGCCCACAACACTGA (SEQ ID: 91) | 64 |
|  | ex2R | AGAGCAGTGGGCATCAACCT (SEQ ID: 92) | |
| exon 3 | ex3F | ATGCAGGTTTCTCTGTGTTCCA (SEQ ID: 93) | 121 |
|  | ex3R | CCCAGCTGCACCTGATCTTT (SEQ ID: 94) | |
| exon 4 | ex4F | TCCCTGAGTGGGCTGGTAGT (SEQ ID: 95) | 62 |
|  | ex4R | GCACCCACGGAGTTGTTACCT (SEQ ID: 96) | |
| exon 5 | ex5F | GAAGACGGAGTCAGGACCATTT (SEQ ID: 97) | 61 |
|  | ex5R | AGCAGTGCACCCTGTCTTCA (SEQ ID: 98) | |
| exon 6 | ex6F | TGTCCAGCTCGGTCATGTGT (SEQ ID: 99) | 111 |
|  | ex6R | CACTCACGTTGGGCATTGG (SEQ ID: 100) | |
| exon 7 | ex7F | CACCTGCTGCTCCGATCAC (SEQ ID: 101) | 58 |
|  | ex7R | GATCAGGTCACACACAGTGTCTTG (SEQ ID: 102) | |
| exon 8 | ex8F | TCCTCTCTGCTTCCCTCACAGT (SEQ ID: 103) | 85 |
|  | ex8R | TGTAGACGGCAGCAGGTATAGC (SEQ ID: 104) | |
| exon 9 | ex9F | GCCTGCCAGACCCACAAG (SEQ ID: 105) | 65 |
|  | ex9R | GGAGGGACAGCTGCTGACAT (SEQ ID: 106) | |
| exon 10 | ex10F | CTGCCAGTTGCCCCATGT (SEQ ID: 107) | 82 |
|  | ex10R | CATTATGTTCCTGTCCCCTCACT (SEQ ID: 108) | |
| exon 11 | ex11F | GCTGGCTACACCTGCAACGT (SEQ ID: 109) | 58 |
|  | ex11R | GGGCAGAGACCACTTCCTTCT (SEQ ID: 110) | |
|  | probe | AGGCTCGATCCTGC (SEQ ID: 111) | |

TABLE 30 -continued

Primers and probe sequences for PGRN qPCR

| Gene/ Region | Name | Sequence | Amplicon size in bp |
|---|---|---|---|
| exon 12 | ex12F | CTGGGACGCCCCTTTGA (SEQ ID: 112) | 73 |
|  | ex12R | GGGCTGCAGAGTCTTCAGTACTG (SEQ ID: 113) |  |
| Housekeeping Genes ||||
| hB2M exon 3 | ex3F | TTACTGAAGAATGGAGAGAGAATTGAAA (SEQ ID: 114) | 68 |
|  | ex3R | GACCAGTCCTTGCTGAAAGACA (SEQ ID: 115) |  |
| hUBC | hUBC-F | GGGTCAATATGTAATTTTCAGTGTTAG (SEQ ID: 116) | 80 |
|  | hUBC-R | TTGTCTAACAAAAAAGCCAAAAACG (SEQ ID: 117) |  |

Figure 17:
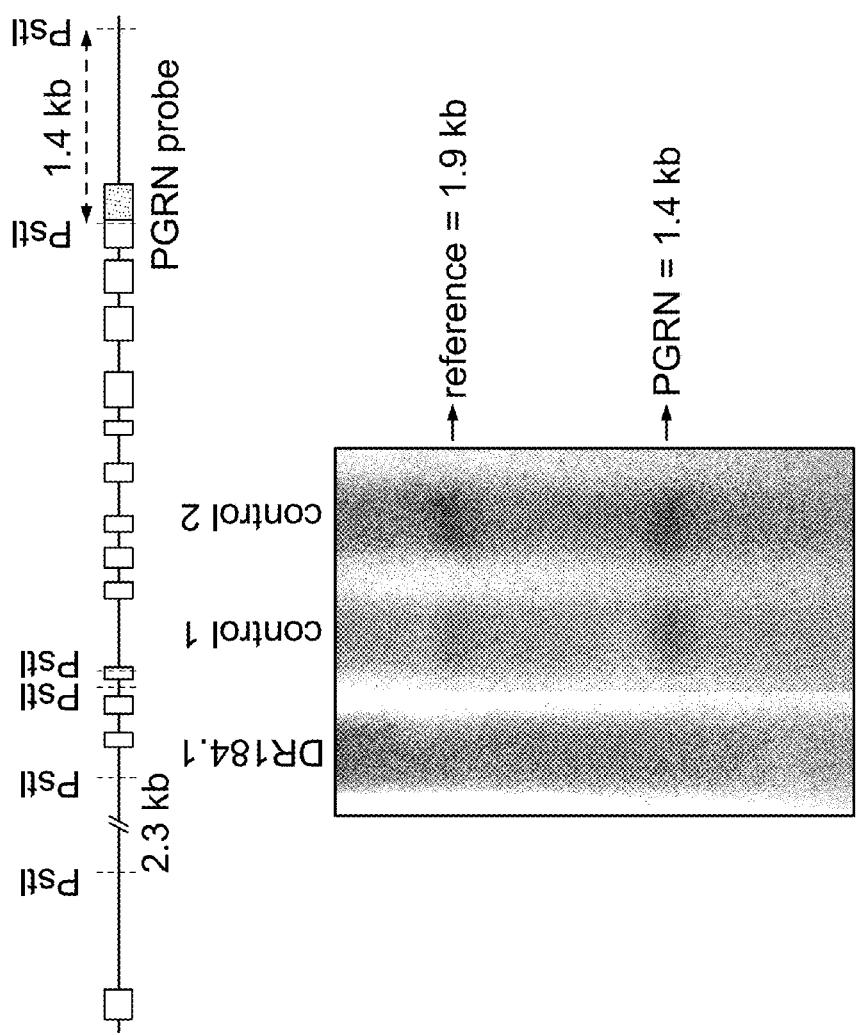
FIG. 17, upper panel is a schematic representation of PGRN with PstI restriction sites indicated with dotted vertical lines. The PGRN probe, hybridizing to a restriction fragment of 1.4 kb, contains part of PGRN 3' UTR and downstream sequence. The lower panel is a Southern blot of samples from patient DR184.1 and two control individuals hybridized with a PGRN probe and a reference probe. Bands resulting from the PGRN probe and the reference probe are indicated. The signal intensity of the PGRN fragment (1.4 kb) is lower than that of the reference fragment (1.9 kb) in the patient compared to the two control individuals. No bands of other sizes can be observed.
Figure 18:
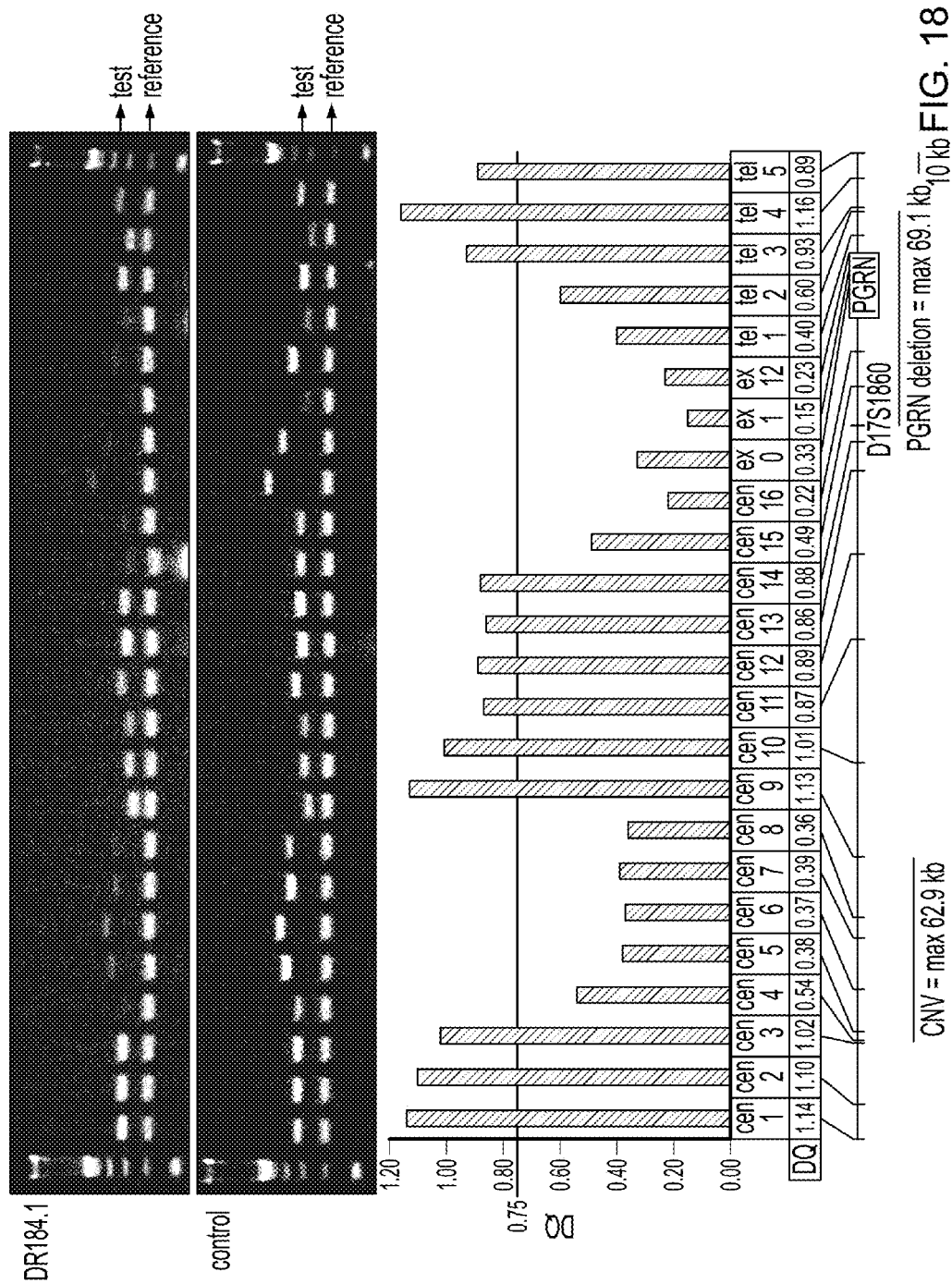
FIG. 18 contains an agarose gel showing co-amplification of a series of selected test fragments in and flanking PGRN with a reference fragment in patient DR184.1 and a control individual. The resulting bands were quantified on a Kodak Imaging Station 440. The graph in the lower panel shows the DQ value obtained for each fragment, indicated on the x-axis. DQ values below 0.75 indicate a deletion. A genomic segment of chromosome 17q21 is shown below the graph with the position of the amplified test fragments indicated with vertical bars. Two regions with lowered DQs can be observed: a PGRN-containing deletion and a deletion more upstream of PGRN, assumed to be a CNV. Minimal deleted regions are indicated with a grey line, and breakpoint regions are indicated with a black line. Marker D1751860 is shown since it was used to further reduce the centromeric breakpoint region of the PGRN-containing deletion.
Figure 19:
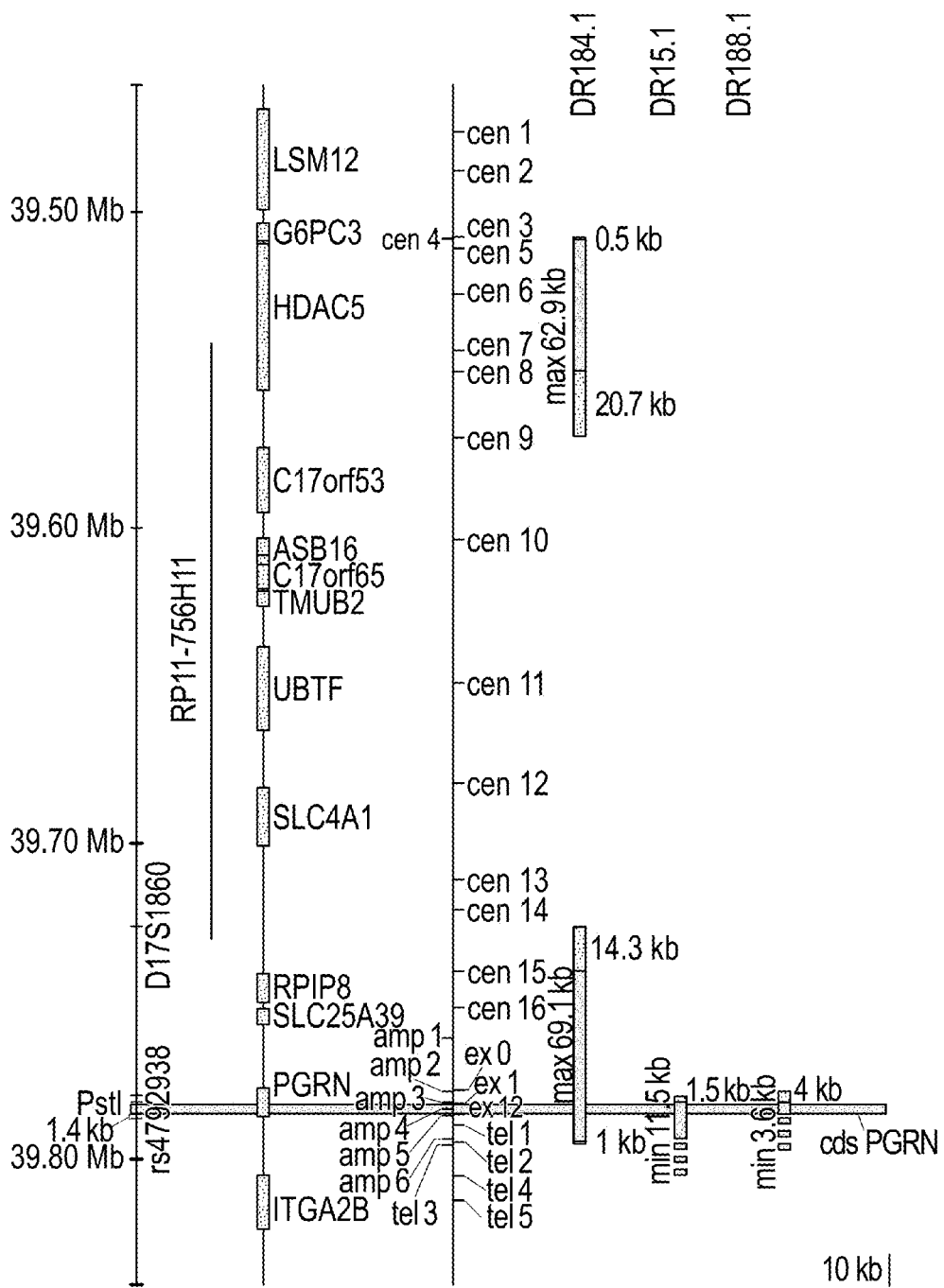
FIG. 19 contains a map of the 17q21 genomic region containing the identified deletions showing gene annotation, STR markers, SNPs, PstI restriction sites in PGRN, location of BAC RP11-756H11, and location of MAQ amplicons and fragments used in the multiplex mapping panel. For each of the patients, the minimal deleted regions are shown in dark grey and the breakpoint regions are indicated in light grey. The PGRN coding sequence is indicated with a light grey horizontal bar showing that it is included in each of the three minimal deleted regions. Dotted bars in patients DR15.1 and DR188.1 indicate that the telomeric breakpoint regions in these patients are not defined.

Restriction mapping was performed using DNA from patient DR184.1 to validate the MAQ and qPCR results and to further map the deleted region. Ten μg of DNA from DR184.1 and two control individuals was digested with 30 U of PstI and separated on a 0.7% agarose gel together with a 1 kb plus DNA ladder as a size standard (Invitrogen, Carlsbad, Calif.). After Southern blotting, a fragment containing part of PGRN 3' UTR and downstream sequence in combination with a reference fragment for normalization, were hybridized as described elsewhere (Cruts et al, Hum Mol Genet, 14:1753-1762 (2005)). The signal intensity of the 1.4 kb PstI restriction fragment hybridized with the PGRN probe was lower than the 1.9 kb PstI restriction fragment hybridized with the reference probe in the patient compared to the control individuals (FIG. 17). Bands were quantified using the Kodak Imaging Station 440 (Eastman Kodak, Rochester, N.Y.) and comparison of normalized band intensities between samples from the patient and the control individuals confirmed the loss of one PGRN allele (FIG. 17). No differently sized bands were observed, suggesting the absence of junction fragments in this region and preventing further mapping of the deletion with this technique. To delineate the size of the deletion in patient DR184.1, a mapping panel was generated which consisted of more than one hundred semi-quantitative multiplex PCRs of selected fragments in and flanking PGRN co-amplified with an arbitrarily chosen reference fragment. The primers are listed in Table 31. The resulting bands were quantified on the Kodak Imaging Station 440 (Eastman Kodak), and DQs were calculated as the ratio of the normalized band intensities in the patient to a control individual. This analysis resulted in delineation of the PGRN-containing deletion spanning a maximal region of 74.3 kb and in the finemapping of the breakpoint regions, centromerically to 19.4 kb between fragments cen 14 and cen 15 and telomerically to about 1 kb between fragments tel 2 and tel 3 (FIGS. 18 and 19). Between fragments cen 14 and cen 15, a heterozygous STR marker D17S1860 was located, further finemapping the centromeric breakpoint region to 14.3 kb and resulting in a final maximal deleted region of 69.1 kb that could not be further reduced (FIGS. 18 and 19). In addition to PGRN, this region comprises two other known genes: RPIP8 and SLC25A39 (NCBI Build 35; on the World Wide Web at genome.ucsc.edu/cgi-bin/hgGateway?org=Human&db=hg17; FIGS. 18 and 19) of which 50% may be sufficient to execute normal function since the patient showed no symptoms other than characteristic FTD features. Moreover, each of these two genes belongs to a gene family suggesting that, if necessary, gene loss may be compensated by other family members. The mapping panel also revealed a second deleted region in DR184.1, about 77 kb upstream of the PGRN deletion (FIGS. 18 and 19). The second deleted region was mapped to a maximal size of 62.9 kb containing RefSeq gene HDAC5 and part of G6PC3 with a centromeric breakpoint region of about 0.5 kb between fragments cen 3 and cen 4 and a telomeric breakpoint region of 20.7 kb between fragments cen 8 and cen 9 (FIGS. 18 and 19). The deletion most likely represents the copy number variation (CNV) identified by BAC array-CGH in 8 of 95 unrelated healthy individuals (Wong et al, Am J Hum Genet, 80:91-104 (2007); database of genomic variants on the World Wide Web at projects.tcag.ca/variation/), implying loss of BAC RP11-756H11 (FIG. 19) although these individuals only have a deleted region of 29.6 kb in common. This can be explained by the resolution of BAC array-CGH, which is too low to exactly map CNV boundaries, or by the occurrence of several CNVs with different sizes in this region. Neither of these two deletions was identified in an unaffected sibling of DR184.1. In addition, genotyping STR markers at 17q21 showed that the two siblings shared one haplotype. These two observations demonstrated that the two deleted regions in DR184.1 were located in cis.

TABLE 31

Primer sequences for the semi-quantitative multiplex PCR mapping panel

| Primers | | Amplicon |
|---|---|---|
| Name | Sequence | size in bp |
| cen 1F | GTCATGTCTGTTCCTTCACTGCC (SEQ ID: 118) | 301 |
| cen 1R | TCATGGGTCTGAAGAGTCTCCAG (SEQ ID: 119) |  |
| cen 2F | AGGTAGAATTTGCTTCAATCTCCAG (SEQ ID: 120) | 301 |
| cen 2R | ATTGCTGAGCCCAGGTGAGT (SEQ ID: 121) |  |
| cen 3F | CCCATAATGACGGCCCTGT (SEQ ID: 122) | 301 |
| cen 3R | CAACCGCCAAAAGGAAGGT (SEQ ID: 123) |  |
| cen 4F | ATTCTCTTGCCAAGCTGCAC (SEQ ID: 124) | 294 |
| cen 4R | CTAGGTGCAGGCGAGATAGG (SEQ ID: 125) |  |
| cen 5F | CAGAGTGCGTGAGGACACGTAGAG (SEQ ID: 126) | 374 |
| cen 5R | AAGCACAGGGGAGGGTATTGAGTG (SEQ ID: 127) |  |
| cen 6F | CGGAACAAGGAGAAGAGCAAAGAG (SEQ ID: 128) | 402 |
| cen 6R | GAATGAGGAAATAAACCAGGGATGG (SEQ ID: 129) |  |
| cen 7F | ACCACCTTCCCTTCGGTCTGCT (SEQ ID: 130) | 341 |
| cen 7R | CCAGCCCTGTGTATTCTCAACAAAA (SEQ ID: 131) |  |

TABLE 31 -continued

Primer sequences for the semi-quantitative multiplex PCR mapping panel

| Name | Sequence | Amplicon size in bp |
|---|---|---|
| cen 8F | GGTCTCCTTCGACTCTCAGATTCCT (SEQ ID: 132) | 351 |
| cen 8R | CCTGGAAGGGAAACCCACACAG (SEQ ID: 133) | |
| cen 9F | ATGACTCACATGCCACTGGA (SEQ ID: 134) | 261 |
| cen 9R | GCAGTGAATCAGCCTGACAA (SEQ ID: 135) | |
| cen 10F | CAACCAAAGGGTATCGGCAG (SEQ ID: 136) | 281 |
| cen 10R | GGAAGGTCTCTCTTGCCATGG (SEQ ID: 137) | |
| cen 11F | GTAGTATACCCCCATCTTATAACGGG (SEQ ID: 138) | 281 |
| cen 11R | TGGTCTTGAGCCAAACAGCC (SEQ ID: 139) | |
| cen 12F | GATCTGCAGCTGCTGTGTGT (SEQ ID: 140) | 325 |
| cen 12R | TGCTTACCCTCATCCTGGTC (SEQ ID: 141) | |
| cen 13F | AAGAGAATGAAGTGGTCAGGGAAG (SEQ ID: 142) | 301 |
| cen 13R | TGACTTGGTCATTTTGAACCCC (SEQ ID: 143) | |
| cen 14F | ATACCACTCCCTGCCACCCT (SEQ ID: 144) | 301 |
| cen 14R | CCCATTAGACGTGGCCATTAAT (SEQ ID: 145) | |
| cen 15F | ACCAAGGTTGAGGTCCCAGA (SEQ ID: 146) | 301 |
| cen 15R | CCCTTAGGAACATCCCTCCC (SEQ ID: 147) | |
| cen 16F | AGGTCAGGCAGCACTAGCAT (SEQ ID: 148) | 296 |
| cen 16R | TTGCTTAACTGCCAGGCTCT (SEQ ID: 149) | |
| PGRN ex 0F | CTGTCAATGCCCCAGACACG (SEQ ID: 150) | 499 |
| PGRN ex 0R | CCCCCAAGGAGTTTCAGTAAGC (SEQ ID: 151) | |
| PGRN ex 1F | TTGAGAAGGCTCAGGCAGTC (SEQ ID: 152) | 400 |
| PGRN ex 1R | GGCCATTTGTCCTAGAAAGACAGG (SEQ ID: 153) | |
| PGRN ex 12F | TGGGACGCCCCTTTGAGG (SEQ ID: 154) | 274 |
| PGRN ex 12R | CACAGGGTCCACTGAAACG (SEQ ID: 155) | |
| tel 1F | GGGCTTAGCGTTCAGGTGTA (SEQ ID: 156) | 340 |
| tel 1R | TGGAGATTTGACCCCAAGAG (SEQ ID: 157) | |
| tel 2F | TCTAGTGGGGGTTGGGTATG (SEQ ID: 158) | 283 |
| tel 2R | AGGAGCAGAGAGCGAGAGTG (SEQ ID: 159) | |
| tel 3F | TCGAAGCCTGACATTCCATATAGTAT (SEQ ID: 160) | 302 |
| tel 3R | GAGCAAGACCCTGACAACACATC (SEQ ID: 161) | |
| tel 4F | CACCTACCACCCCAACTCTG (SEQ ID: 162) | 256 |
| tel 4R | CATTGGGTCCTCTTGGTGTC (SEQ ID: 163) | |
| tel 5F | GACACATTGAGGCTGAGCAC (SEQ ID: 164) | 312 |
| tel 5R | ACCACCCTGAACCTGGATCT (SEQ ID: 165) | |
| reference F | GGCTCAGCACCAACCTTCCC (SEQ ID: 166) | 183 |
| reference R | GCCTGGTTCCACTCTCCCTCTG (SEQ ID: 167) | |

Five known SNPs in intron 0 (rs3859268, rs2879096, rs3785817, rs4792938, and rs4792939) were genotyped since MAQ and/or qPCR data suggested that PGRN exon 0 was excluded from the deleted region. Only the most 3' SNP rs4792939 was homozygous in DR15.1, enabling further delimitation of the deletion at the centromeric end to a breakpoint region of 1.5 kb between rs4792938 in intron 0 and MAQ amplicon 3 (FIG. 19). In contrast, the centromeric breakpoint region of the deletion in DR188.1 remained about 4 kb, defined by qPCR amplicons of exon 0 and exon 1 (FIG. 19). The telomeric breakpoint regions were not identified in either of these two patients; therefore, only the minimal size of the deletions could be estimated: about 11.5 kb in DR15.1 from MAQ amplicon 3 to MAQ amplicon 6, and about 3.6 kb in DR188.1 from qPCR exon 1 to qPCR exon 12 (FIG. 19). Based on the estimated minimal sizes, the deletions did not contain genes other than PGRN. It is, however, possible that the extent of the deletion in DR188.1 is greater than estimated since the DQ of qPCR exon 0 was only slightly above 0.75, suggesting that the centromeric breakpoint in DR188.1 may be located more upstream of PGRN as in DR184.1.

The three patients carrying a genomic PGRN deletion presented with typical FTD symptoms including language impairment. They had a late onset of disease and disease duration of more than ten years, except for patient DR184.1 who died after four years of disease, suggesting that a deletion of a larger region may result in a more severe disease course. A positive family history of dementia was recorded for patient DR15.1, whose father was affected. No affected relatives of any of the three patients were available to perform segregation analyses.

Genomic deletions explain at least 2.9% of the genetic etiology of FTD and at least 2.3% of familial FTD in the Belgian sample. Together with the null mutations identified in 11 patients as described elsewhere (Cruts et al., Nature, 442:920-924 (2006)), PGRN mutations account for about 13.6% of all FTD patients and about 27.9% of FTD patients with a positive family history, rising to about 17.4% and 32.6%, respectively, when potential missense and promoter mutations also are considered (van der Zee et al., Hum Mutat, 28:416 (2007)).

Example 8

Identifying Agents that can Alter PGRN Polypeptide Levels

All-trans-retinoic acid and inflammatory events were observed to be major regulators of PGRN expression (He and Bateman, *J Mol Med*, 81:600-612 (2003); He et al., *Cancer Res*, 62:5590-5596 (2002), Ong et al., *Am J Physiol Regul Integr Comp Physiol*, 291:R1602-1612 (2006)). These data suggested that certain classes of agents (e.g., NSAIDs and PPAR compounds) related to these biochemical pathways may influence PGRN production. Studies were performed using a variety of cell lines and several compounds in the NSAID and PPAR compound families to examine the ability of these agents to modulate PGRN polypeptide production in cell culture systems.

Materials and Methods

Cell cultures were maintained in standard cell culture media supplemented with 5% fetal bovine serum and 100 U/mL penicillin/streptomycin (Life Technologies, Karlsruhe, Germany). Cell cultures consisted of Chinese hamster ovary (CHO) cells; human HeLa cells (HeLa); BE(2)-M17, human neuroblastoma (M17); N2A, mouse neuroblastoma; and human lymphoblasts.

The following NSAIDs were dissolved in the vehicle DMSO: ibuprofen (Biomol, Plymouth Meeting, Pa.), indomethacin (Biomol), diclofenac (Cayman Chemical, Ann Arbor, Mich.), naproxen (Cayman Chemical), and aspirin (ICN Biomedicals, Irvine, Calif.). Cells were cultured in serum-containing media and treated for 24 hours in serum-free media with a specific NSAID. NSAID toxicity was examined using a standard MTT-assay (3-(4,5-Dimethyl-2-thiazolylyl)-2,5-diphenyl-2H-tetrazolium Bromide). For cell toxicity studies, cells were treated with NSAIDS at concentrations up to 100 micromolar.

The following PPAR activators were dissolved in DMSO: ciglitazone (Calbiochem, San Diego, Calif.), fenofibrate (Sigma-Aldrich, Saint Louis, Mo.), clofibrate (Calbiochem), and L165041 (Calbiochem). Cells were cultured in serum-containing media and treated for 24 hours in serum-free media with a specific PPAR agonist.

Curcumin (Sigma-Aldrich) and resveratrol (Sigma-Aldrich) were dissolved in DMSO. Cells were cultured in serum-containing media and treated for 24 hours in serum-free media with curcumin or resveratrol.

Antibodies that were used included a monoclonal human progranulin antibody (Zymed, South San Francisco, Calif.) directed against full length progranulin polypeptide, a mouse progranulin antibody (R&D Systems, Minneapolis, Minn.) directed against full length progranulin polypeptide, and an anti-GAPDH antibody (Sigma-Aldrich).

Results

Figure 20:
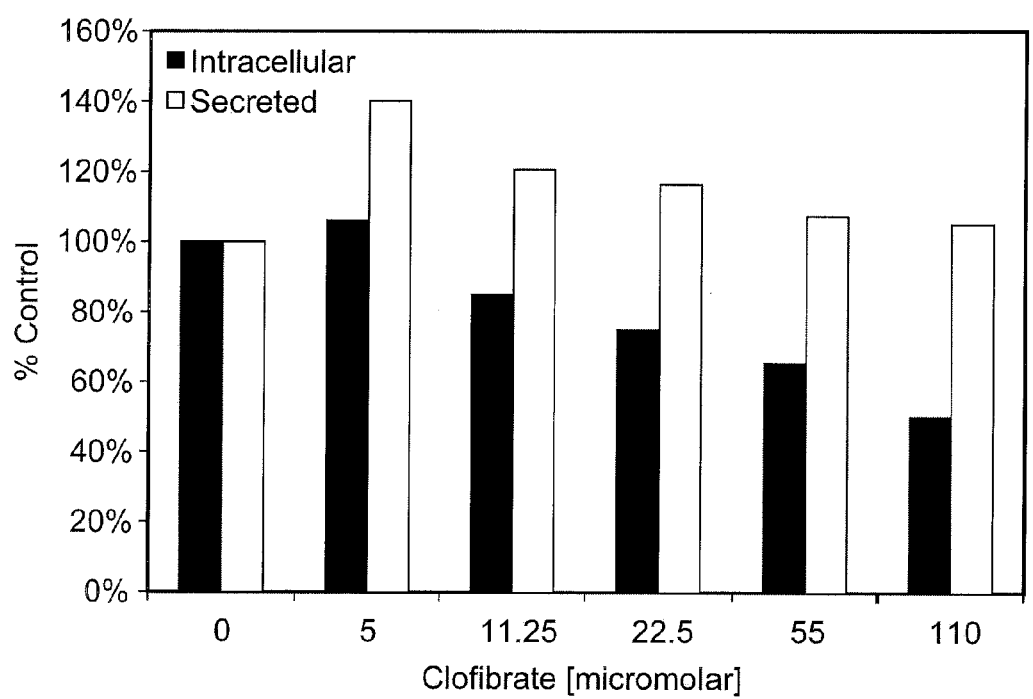
FIG. 20 is a graph plotting intracellular and secreted PGRN polypeptide levels in clofibrate treated M17 cell cultures relative to DMSO treated cells. Intracellular=intracellular PGRN polypeptide levels, and Secreted=PGRN polypeptide levels detected in serum free media. The results presented are averages of two or three experiments performed in duplicate.

PPARα Activators Increase Intracellular and Secreted PGRN Polypeptide Levels:

Cell cultures were treated with increasing concentrations of the PPARα activator clofibrate or with DMSO. Levels of PGRN polypeptide in culture supernatants and in cell lysates were analyzed using Western blotting. The levels of intracellular and secreted forms of PGRN polypeptide were compared in clofibrate treated M17 cell cultures and DMSO treated M17 cell cultures (FIG. 20). Treatment with clofibrate caused an initial increase and then a decrease in the levels of both intracellular and secreted forms of PGRN polypeptide after 24 hours. Cell cultures treated with 5 micromolar clofibrate showed a 140% increase in the level of secreted PGRN polypeptide. No significant effect on GAPDH polypeptide expression was observed. These results indicate that treatment of M17 cells with clofibrate selectively elevated secreted PGRN polypeptide levels.

Figure 21:
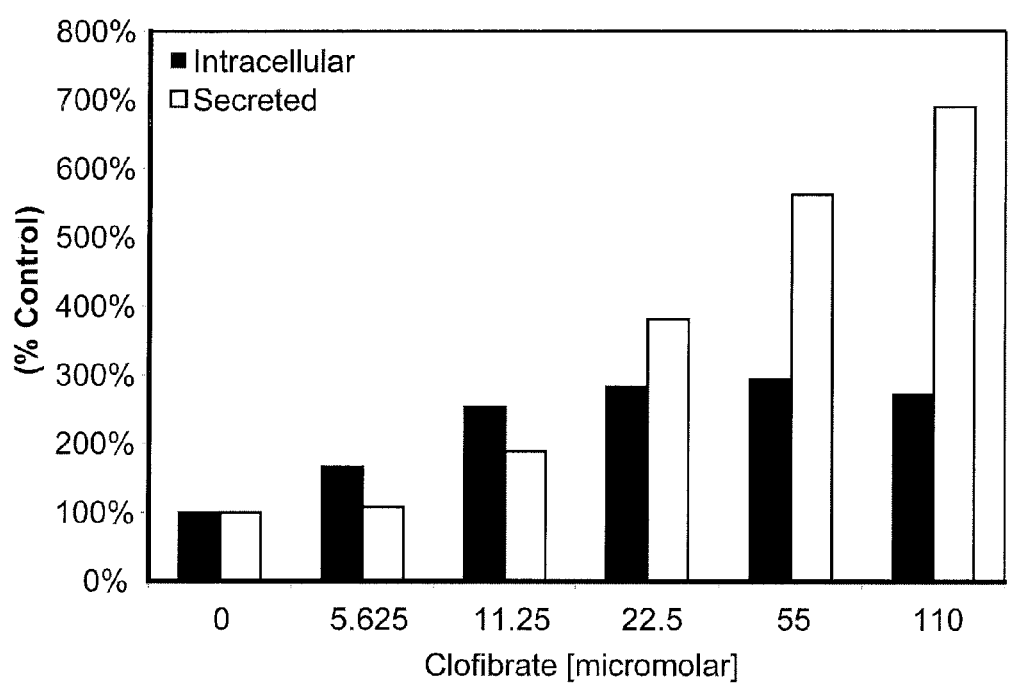
FIG. 21 is a graph plotting intracellular and secreted PGRN polypeptide levels in clofibrate treated lymphoblast cell cultures relative to DMSO treated cells. Intracellular=intracellular PGRN polypeptide levels, and Secreted=PGRN polypeptide levels detected in serum free media. The results presented are averages of two or three experiments performed in duplicate.

The levels of intracellular and secreted forms of PGRN polypeptide also were compared in clofibrate treated human lymphoblast cell cultures and DMSO treated lymphoblast cell cultures (FIG. 21). Cell cultures treated with 110 micromolar clofibrate showed a 700% increase in the level of secreted PGRN polypeptide. No significant effect on GAPDH polypeptide expression was observed. These results indicate that treatment of human lymphoblasts with clofibrate selectively elevated secreted and intracellular PGRN polypeptide levels in a dose-dependent manner. No cell toxicity was observed with clofibrate treatment.

Figure 22:
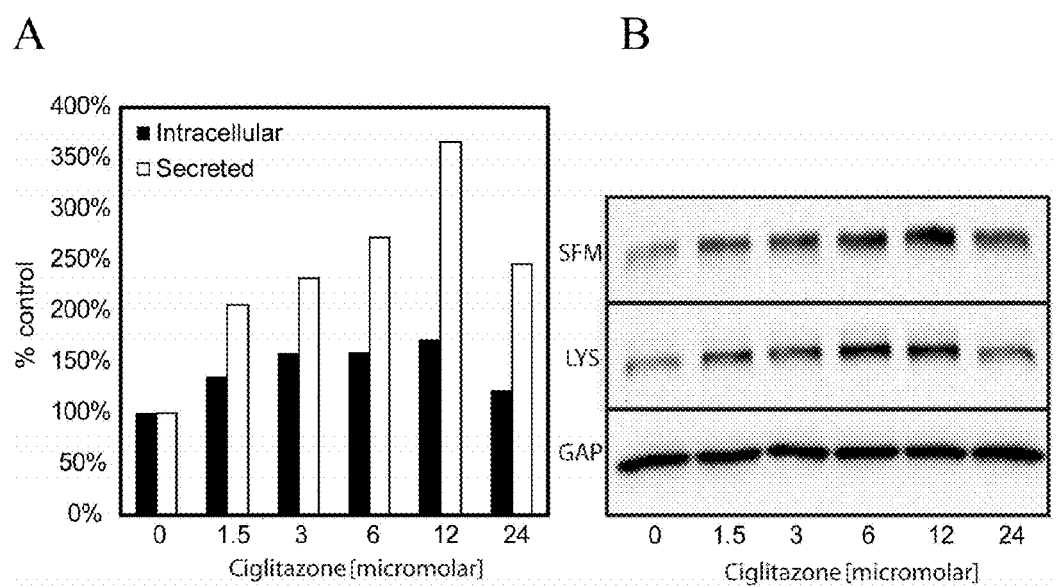
FIG. 22A is a graph plotting PGRN polypeptide levels in cell lysates (Intracellular) and culture supernatants (Secreted) from M17 cells that were treated with the indicated concentrations of ciglitazone. The PGRN polypeptide levels are plotted as a percent of control levels in cell lysates or culture supernatants from M17 cells treated with DMSO.
FIG. 22B contains Western blots analyzing PGRN polypeptide expression in cell lysates (LYS) and culture supernatants (SFM) from M17 cells treated with the indicated concentrations of ciglitazone (upper two rows).

PPARγ Activators Increase Intracellular and Secreted PGRN Polypeptide Levels:

Cell cultures were treated with increasing concentrations of the PPARγ activator ciglitazone. Levels of PGRN polypeptide in culture supernatants and in cell lysates were analyzed using Western blotting. The levels of PGRN polypeptide in supernatants and in cell lysates of M17 cells treated with ciglitazone were compared to the corresponding levels in supernatants and cell lysates, respectively, of M17 cells treated with DMSO (FIGS. 22A and B). Cell cultures treated with 1.5 to 24 micromolar ciglitazone showed a 200% to 350% increase in the level of secreted PGRN polypeptide and an approximately 110% to 170% increase in the level of intracellular PGRN polypeptide. No significant effect on GAPDH polypeptide expression was observed. These results indicated that treatment of M17 cells with ciglitazone selectively elevated intracellular PGRN polypeptide and secreted PGRN polypeptide levels in a dose-dependent manner.

Figure 23:
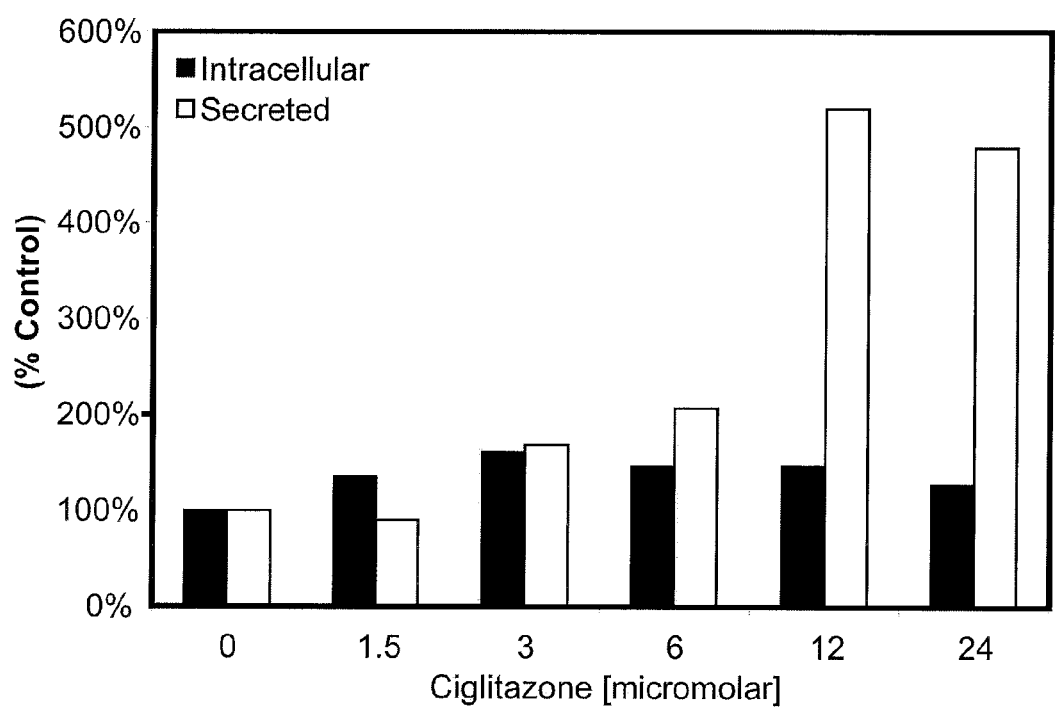
FIG. 23 is a graph plotting intracellular and secreted PGRN polypeptide levels in ciglitazone treated human lymphoblast cell cultures relative to DMSO treated cells. Intracellular=intracellular PGRN polypeptide levels, and Secreted=PGRN polypeptide levels detected in serum free media. The results presented are averages of two or three experiments performed in duplicate.

The levels of PGRN polypeptide in supernatants and in cell lysates of human lymphoblast cells treated with ciglitazone also were compared to the corresponding levels in supernatants and cell lysates, respectively, of human lymphoblast cells treated with DMSO (FIG. 23). Cell cultures treated with 12 micromolar ciglitazone showed an approximately 500% increase in the level of secreted PGRN polypeptide. No significant effect on GAPDH polypeptide expression was observed. These results indicated that treatment of human lymphoblasts with clofibrate selectively elevated secreted and intracellular PGRN polypeptide levels. No cell toxicity was observed with clofibrate treatment.

Figure 24:
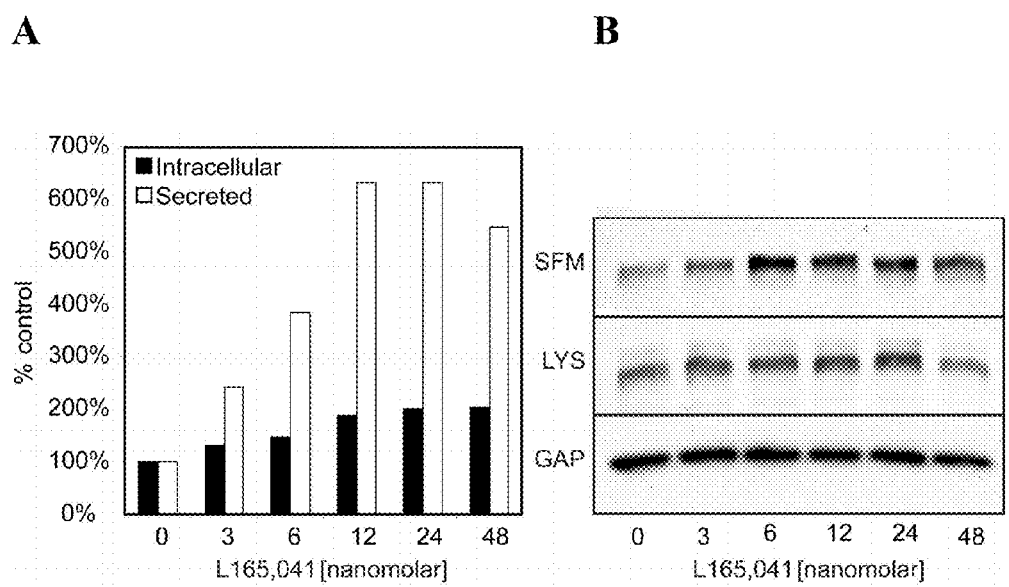
FIG. 24A is a graph plotting PGRN polypeptide levels in cell lysates (Intracellular) and culture supernatants (Secreted) from human lymphoblast cells that were treated with the indicated concentrations of L165,041. The PGRN polypeptide levels are plotted as a percent of control levels in cell lysates or culture supernatants from human lymphoblast cells treated with DMSO.
FIG. 24B contains Western blots analyzing PGRN polypeptide expression in cell lysates (LYS) and culture supernatants (SFM) from human lymphoblast cells treated with the indicated concentrations of L165, 041 (upper two rows).

PPARδ Activators Increase Intracellular and Secreted PGRN Polypeptide Levels:

Cell cultures were treated with various concentrations of the PPARδ activator L165,041. Levels of PGRN in culture supernatants and in cell lysates were analyzed using Western blotting. Intracellular and secreted PGRN polypeptide levels in human lymphoblasts treated with various concentrations of L165,041 were compared to the corresponding levels in human lymphoblasts treated with DMSO (FIGS. 24A and B). Substantial increases in both intracellular and secreted forms of PGRN polypeptide were observed 24 hours after treating human lymphoblasts with 3 to 12 nM L165,041. Cell cultures treated with 12 to 48 nM of L165,041 showed an approximately 600% increase in the level of secreted PGRN polypeptide and an approximately 200% increase in the level of intracellular PGRN polypeptide. No significant effect on GAPDH polypeptide expression was observed. These results indicate that treatment of human lymphoblasts with L165,041 selectively elevated intracellular and secreted PGRN polypeptide levels in a dose-dependent manner.

Figure 25:
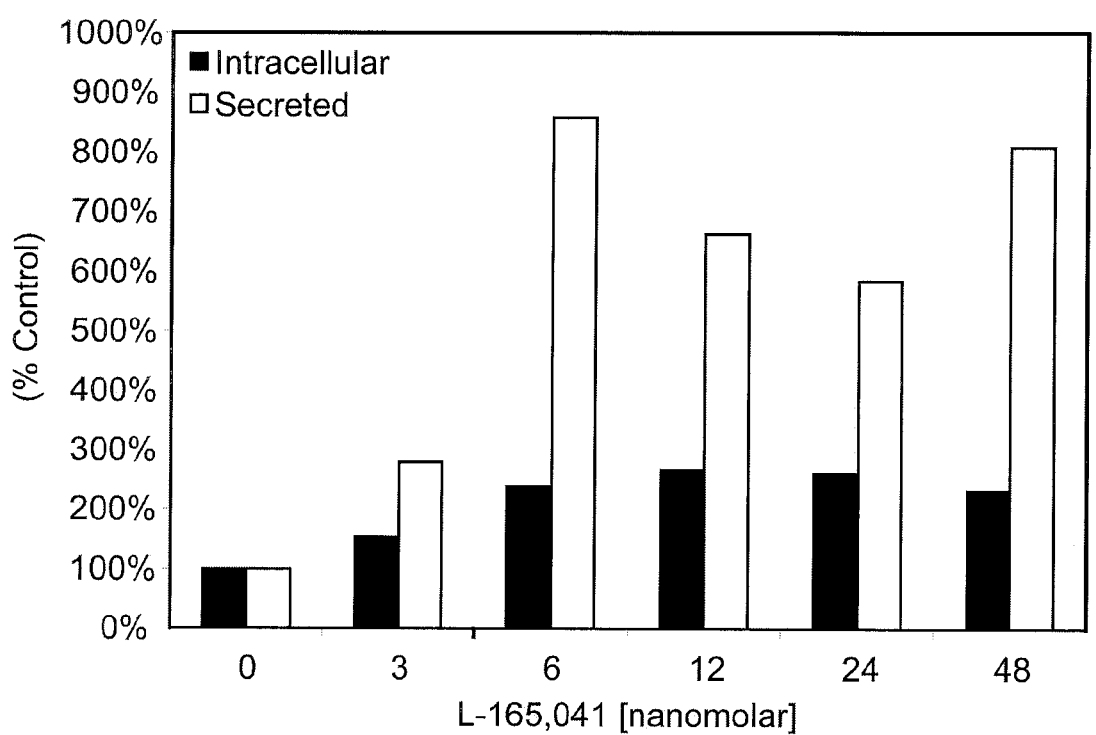
FIG. 25 is a graph plotting intracellular and secreted PGRN polypeptide levels in L165,041 treated M17 cell cultures relative to DMSO treated cells. Intracellular=intracellular PGRN polypeptide levels, and Secreted=PGRN polypeptide levels detected in serum free media. The results presented are averages of two or three experiments performed in duplicate.

Levels of PGRN polypeptide in cell culture supernatants and cell lysates of M17 cells treated with various concentrations of L165,041 also were compared to corresponding PGRN polypeptide levels in M17 cells treated with DMSO (FIG. 25). Treatment of M17 cells with 3 to 24 nM L165,041 significantly increased both intracellular and secreted PGRN polypeptide levels after 24 hours. No cell toxicity was observed following treatment with L165,041 at concentrations up to 48 nM.

The PPARδ agonist, GW501516, also was observed to elevate PGRN polypeptide levels in M17 and N2A cell lines.

NSAIDs Modulate Intracellular and Secreted PGRN Polypeptide Levels:

HeLa cell cultures (N=4 for all studies) were treated with various concentrations of NSAIDs, including ibuprofen, naproxen, indomethacin, meclofenamic acid, and acetylsalicylic acid for 24 hours in serum free media. Levels of PGRN polypeptide in culture supernatants and in cell lysates were analyzed using Western blotting.

Figure 26:
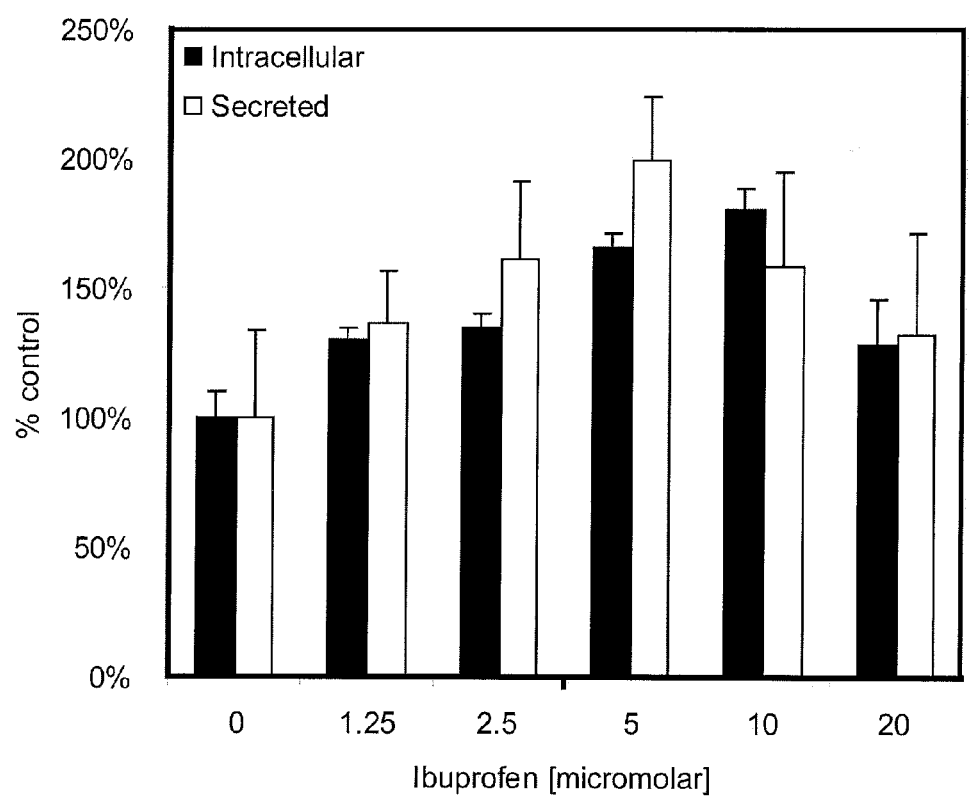
FIG. 26 is a graph plotting PGRN polypeptide levels in cell lysates (Intracellular) and culture supernatants (Secreted) from HeLa cells that were treated with the indicated concentrations of ibuprofen. The PGRN polypeptide levels are plotted as a percent of control levels in cell lysates or culture supernatants from HeLa cells treated with DMSO. The averages of the results from four experiments are plotted.

Treated and untreated HeLa cells were analyzed for PGRN polypeptide expression using immunohistochemistry. Perinuclear expression of PGRN polypeptide was observed in untreated cells. Treatment with ibuprofen (2.5 μM for 24 hours) increased PGRN polypeptide expression in the Golgi of HeLa cells. Levels of PGRN polypeptide in cell culture supernatants and cell lysates of HeLa cells treated with various concentrations of ibuprofen were compared to corresponding PGRN polypeptide levels in HeLa cells treated with DMSO (FIG. 26). Cell cultures treated with 1.25 to 20 micromolar ibuprofen showed an approximately 150% to 200% increase in the level of secreted PGRN polypeptide and an approximately 150% increase in the level of intracellular PGRN polypeptide. No significant effect on GAPDH polypeptide expression was observed. These results indicate that treatment of HeLa cells with ibuprofen selectively elevated intracellular and secreted PGRN polypeptide levels in a dose-dependent manner.

Figure 27:
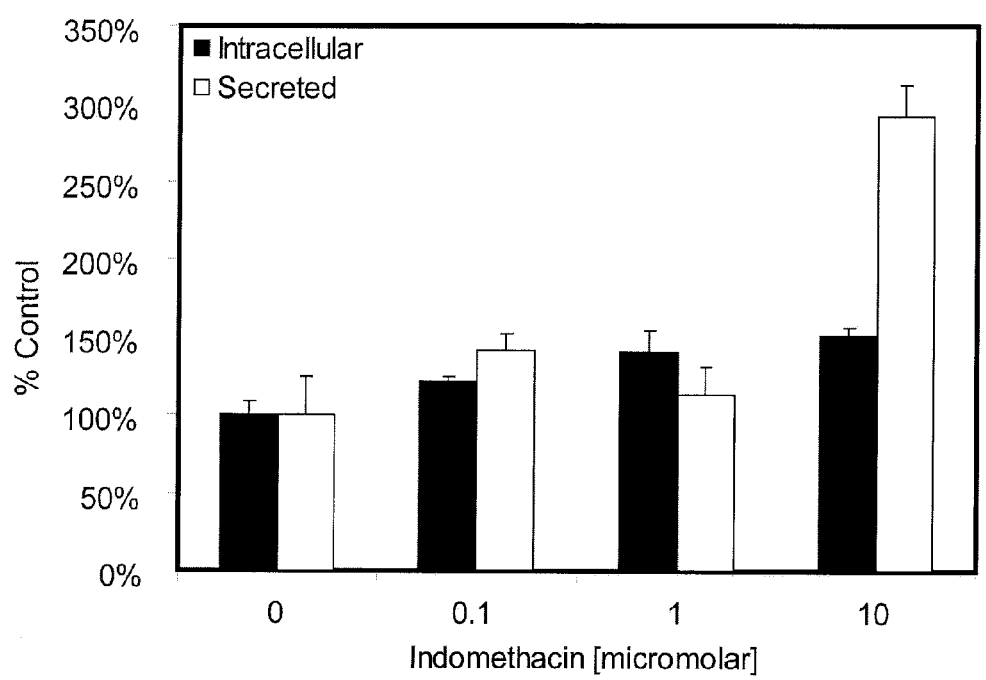
FIG. 27 is a graph plotting PGRN polypeptide levels in cell lysates and culture supernatants from HeLa cells that were treated with the indicated concentrations of indomethacin. The PGRN polypeptide levels are plotted as a percent of control levels in cell lysates or culture supernatants from HeLa cells treated with DMSO. Intracellular=intracellular PGRN polypeptide levels, and Secreted=PGRN polypeptide levels detected in serum free media.
Figure 28:
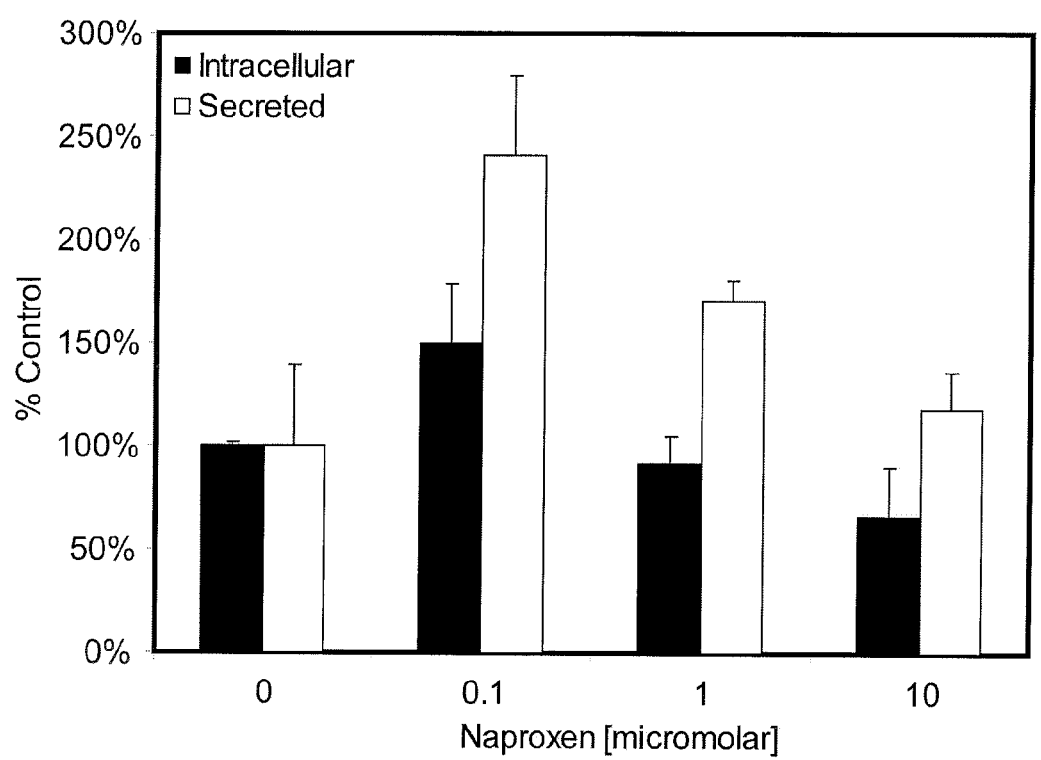
FIG. 28 is a graph plotting PGRN polypeptide levels in cell lysates and culture supernatants from HeLa cells that were treated with the indicated concentrations of naproxen. The PGRN polypeptide levels are plotted as a percent of control levels in cell lysates or culture supernatants from HeLa cells treated with DMSO. Intracellular=intracellular PGRN polypeptide levels, and Secreted=PGRN polypeptide levels detected in serum free media.
Figure 29:
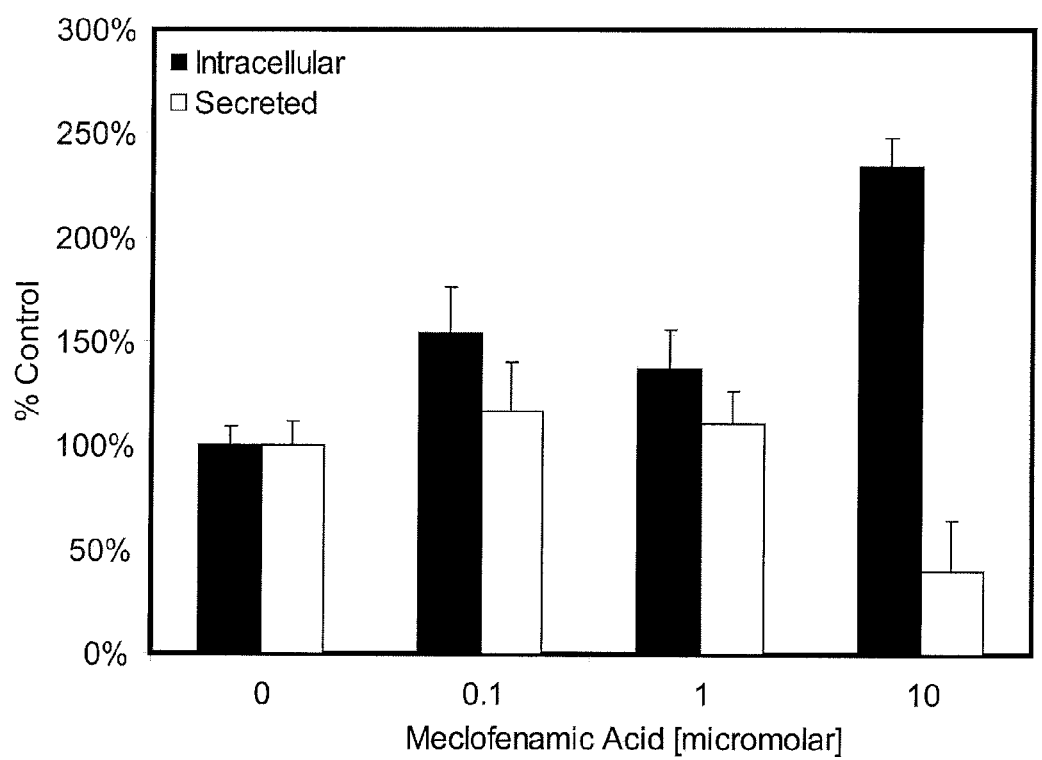
FIG. 29 is a graph plotting PGRN polypeptide levels in cell lysates and culture supernatants from HeLa cells that were treated with the indicated concentrations of meclofenamic acid. The PGRN polypeptide levels are plotted as a percent of control levels in cell lysates or culture supernatants from HeLa cells treated with DMSO. Intracellular=intracellular PGRN polypeptide levels, and Secreted=PGRN polypeptide levels detected in serum free media.
Figure 30:
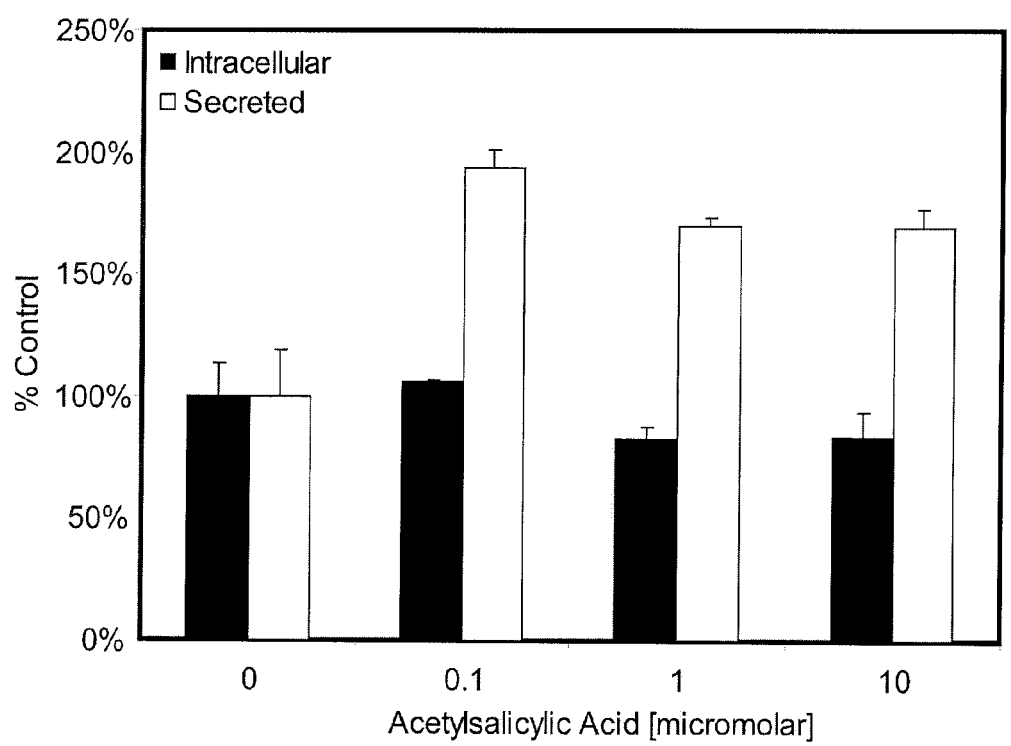
FIG. 30 is a graph plotting PGRN polypeptide levels in cell lysates and culture supernatants from HeLa cells that were treated with the indicated concentrations of acetylsalicyclic acid. The PGRN polypeptide levels are plotted as a percent of control levels in cell lysates or culture supernatants from HeLa cells treated with DMSO. Intracellular=intracellular PGRN polypeptide levels, and Secreted=PGRN polypeptide levels detected in serum free media.

Dose-response studies of other NSAIDs, including indomethacin, naproxen, meclofenamic acid, and acetylsalicylic acid (FIGS. 27-30) showed that these agents similarly elevate intracellular and/or secreted PGRN polypeptide levels. In particular, treatment with indomethacin increased intracellular and secreted PGRN polypeptide levels in HeLa cells (FIG. 27). Treatment with naproxen also increased intracellular and secreted PGRN polypeptide levels in HeLa cells (FIG. 28), as did treatment with meclofenamic acid (FIG. 29). The highest concentration of meclofenamic acid tested (10 μM) caused a significant decrease in the level of secreted PGRN polypeptide (FIG. 29). Treatment with acetylsalicylic acid was observed to increase secreted PGRN polypeptide levels in HeLa cells (FIG. 30).

Other cell lines, including M17 and N2A, treated with ibuprofen show similar responses to those observed in HeLa cells, with increases in PGRN polypeptide expression up to 600% following treatment with ibuprofen at concentrations ranging from 1 to 5 μM.

Figure 31:
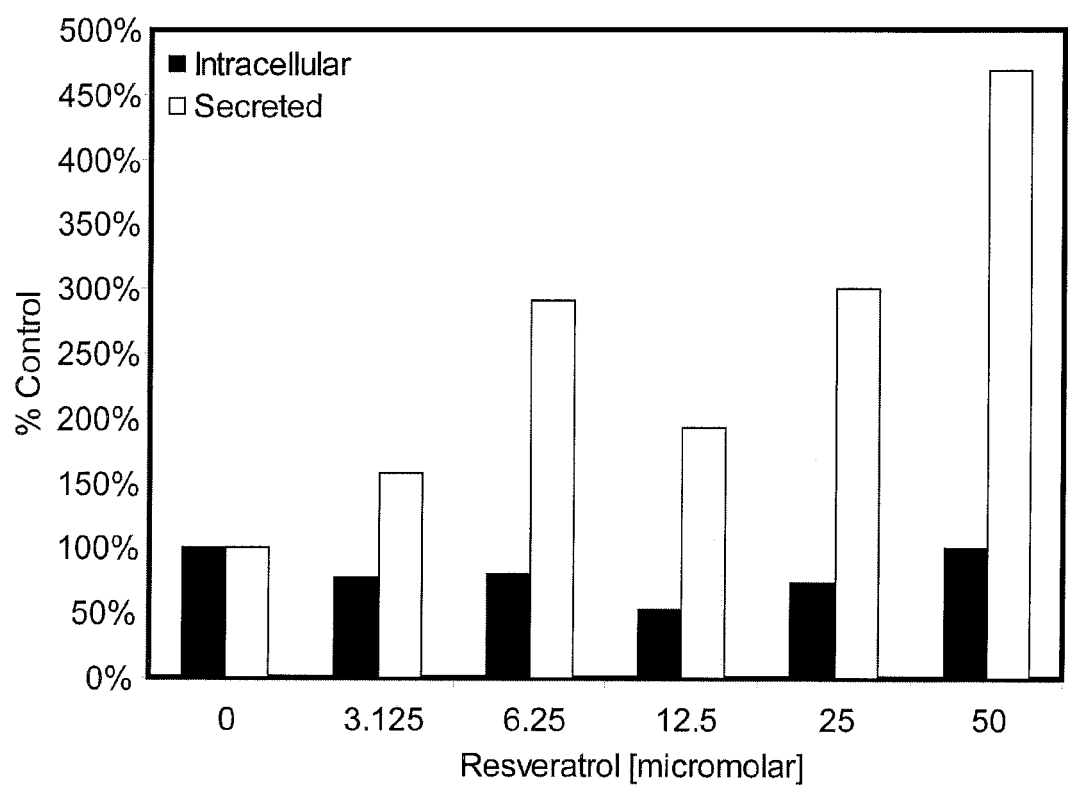
FIG. 31 is a graph plotting PGRN polypeptide levels in cell lysates and culture supernatants from M17 cells that were treated with the indicated concentrations of resveratrol. The PGRN polypeptide levels are plotted as a percent of control levels in corresponding cell lysates or culture supernatants from M17 cells treated with DMSO. Intracellular=intracellular PGRN polypeptide levels, and Secreted=PGRN polypeptide levels detected in serum free media.

Curcumin and Resveratrol Modulate Intracellular and Secreted PGRN Polypeptide Levels:

M17 cell cultures (N=4) were treated with various concentrations of curcumin and resveratrol for 24 hours in serum free media. Levels of PGRN polypeptide in culture supernatants and cell lysates were analyzed using Western blotting. Levels of PGRN polypeptide in cell culture supernatants and cell lysates of M17 cells treated with various concentrations of resveratrol were compared to corresponding PGRN polypeptide levels in M17 cells treated with DMSO (FIG. 31). Cell cultures treated with 3.125 to 50 micromolar resveratrol showed an approximately 150% to 450% increase in the level of intracellular PGRN polypeptide and no increase in the level of secreted PGRN polypeptide. No significant effect on GAPDH polypeptide expression was observed.

Figure 32:
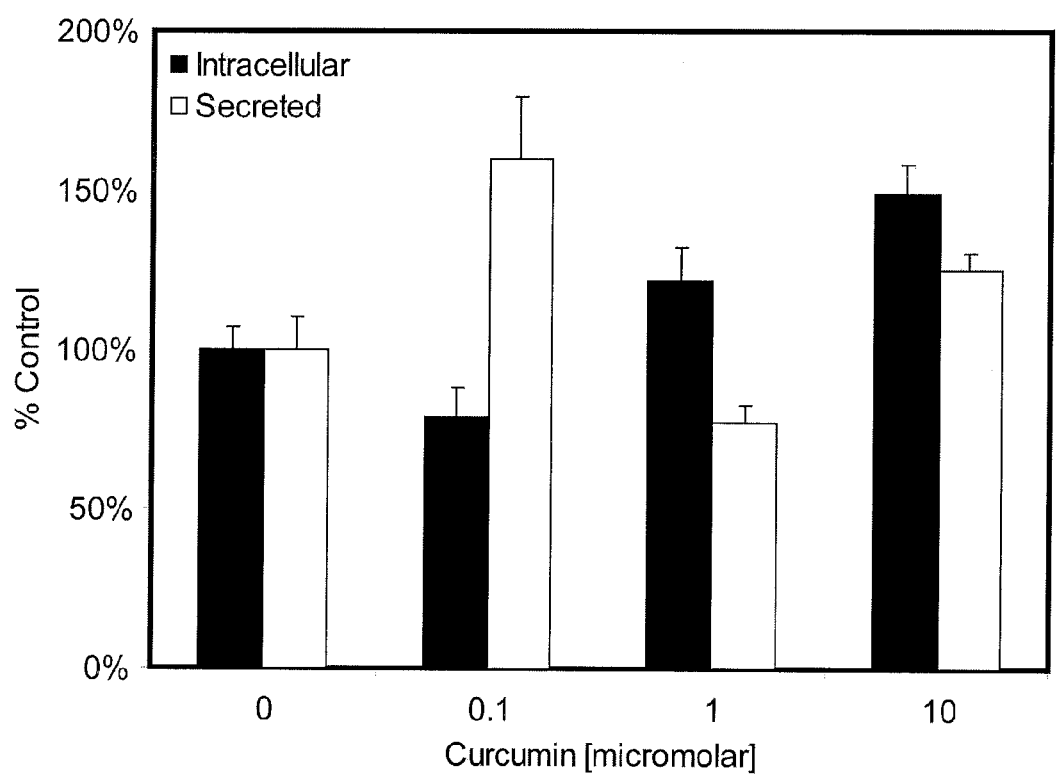
FIG. 32 is a graph plotting PGRN polypeptide levels in cell lysates and culture supernatants from M17 cells that were treated with the indicated concentrations of curcumin. The PGRN polypeptide levels are plotted as a percent of control levels in corresponding cell lysates or culture supernatants from M17 cells treated with DMSO. Intracellular=intracellular PGRN polypeptide levels, and Secreted=PGRN polypeptide levels detected in serum free media.

Levels of PGRN polypeptide in cell culture supernatants and cell lysates of M17 cells treated with various concentrations of curcumin also were compared to corresponding PGRN polypeptide levels in M17 cells treated with DMSO (FIG. 32). Cell cultures treated with 0.1 micromolar curcumin showed an approximately 150% increase in the level of secreted PGRN polypeptide. No significant effect on GAPDH polypeptide expression was observed.

Example 9

Characterizing the Distribution of PGRN Polypeptide Expression

A number of studies were performed to assess the extent of the distribution of PGRN polypeptide in human and mouse brain. PGRN polypeptide was ubiquitously expressed in all regions throughout human as well as mouse CNS tissue. Double immunofluorescence studies showed that PGRN expression is restricted to neurons and microglia. Double immunofluorescence micrographs were taken of hippocampus endplate in mouse brain. PGRN polypeptide was strongly expressed in neurons, but not in astrocytes stained for GFAP. There was a lack of colocalization between oligodendrocytes and PGRN polypeptide. PGRN polypeptide strongly colocalized with the microglial marker IBA-1.

The subcellular distribution of PGRN polypeptide was evaluated using cell culture models. Double immunofluorescence studies using Be(2)-M17 (human neuroblastoma) and N2A (mouse neuroblastoma) cell lines showed that PGRN polypeptide was distributed throughout the cell, but was substantially concentrated within the perinuclear compartment. Studies using a battery of antibodies demonstrated that PGRN polypeptide was predominately colocalized with Golgi (anti-58K). Double immunofluorescence micrographs were taken of Be(2)-M17 (human) and N2A (mouse) neuroblastoma cell lines stained with anti-PGRN polypeptide antibodies and anti-58K (a marker for Golgi). A high degree of colocalization was observed between PGRN polypeptide and 58K in Be(2)-M17 cells at a magnification of 40×. A significant overlap also was observed between PGRN polypeptide and 58K in N2A cells. Double immunofluorescence studies failed to find an association between PGRN polypeptide and peroxisomes (anti-PMP-70), lysosomes (anti-LAMP1; anti-LAMP2) or secretory vesicles (anti-synaptobrevin 2).

The expression of PGRN polypeptide was examined in both human and transgenic mouse models that develop the hallmark pathology described in Alzheimer's disease and frontotemporal dementia. Tissues also were stained for NFTs using a CP13 antibody to detect hyperphosphorylated tau, and nuclei were stained blue using DAPI. PGRN polypeptide was enriched around amyloid plaques in both human tissue and transgenic models. However, in contrast to the significant overlap between PGRN polypeptide and amyloid plaques, a significant dissociation between the accumulation of neurofibrillary tangles and the accumulation of PGRN polypeptide was observed in both human Alzheimer's disease and transgenic mouse tissue. PGRN polypeptide did not directly co-localize with neurofibrillary tangles, but was strongly upregulated with the onset of tau pathology. These results indicate that in human and mouse models of Alzheimer's disease, PGRN polypeptide is strongly upregulated in dystrophic neurons and reactive microglia that surround plaques, but PGRN polypeptide expression did not appear to be elevated in neurons with neurofibrillary tangle pathology. These results also indicate that changes in PGRN polypeptide expression are dramatic with the onset of pathology in both humans and mice.

PGRN polypeptide expression was examined in the JNPL3 mouse line. A series of photomicrographs were taken of tissues from non-transgenic JNPL3 siblings showing that PGRN polypeptide expression increases from 2-10 months of age. Tissue from spinal cord with omit of the primary antibody served as a control. Photomicrographs of tissues from a two month old mouse showed light PGRN polypeptide positive staining. Relatively little staining was observed in the ramified microglia, although there appeared to be light immunoreactivity. By ten months of age, there was a significant increase in neuropil immunoreactivity. Both neurons and microglia had detectable PGRN polypeptide immunoreactivity. Results of these experiments indicate that PGRN polypeptide levels gradually increase with age in both microglial and neuronal populations in the absence of pathology.

Studies of JNPL3 mice indicated that there was an increase in PGRN polypeptide staining that strongly correlated with increasing motor impairment and increasing tau pathology. A series of photomicrographs were taken demonstrating that PGRN polypeptide expression increases according to pathological stage. Photomicrographs of tissue from an unaffected 2 month old JNPL3 mouse indicated that there was slightly more PGRN polypeptide immunoreactivity than was seen in 10-month old non-transgenic mice. Photomicrographs of tissue from an 8 month old mouse having mild motor impairment showed increased neuropil staining and an increase in the number of PGRN polypeptide positive microglia. Photomicrographs of tissue from a 14 month old mouse having moderate motor impairment indicated significant microglial activation and an increase in neuropil staining. Photomicrographs of tissue from 10 month old mouse having late/end stage pathology showed a significant increase in the number of PGRN polypeptide-positive activated microglia and increased neuropil staining. Results of these studies indicate that PGRN polypeptide expression is upregulated significantly at the onset of neurodegenerative phenotypes in the JNPL3 mouse model of tauopathy, consisting of increased microglial and neuronal PGRN polypeptide expression.

Example 10

Characterizing the Biochemical Pathways that Elevate PGRN Polypeptide Expression Experiments are performed to determine how PPAR agonists and NSAIDs regulate PGRN polypeptide expression. The hypothesis of this study is that PGRN polypeptide expression depends on activity and co-factors within the PPAR nuclear receptor pathways, and that PPAR agonists and NSAIDs target the same pathways. In addition to studies demonstrating that PPAR agonists can regulate PGRN polypeptide expression, studies of the promoter region of the PGRN gene suggested the presence of putative PPAR binding sites and PPAR response elements (Bhandari et al., *Endocrinology*, 133:2682-2689 (1993); Bhandari et al., *Biochem J*, 319 (Pt 2):441-447 (1996)). Experimental work with myeloid cells showed that all trans-retinoic acid, which associates with retinoic acid receptors and significantly enhances PPAR receptor activity, results in an upregulation of PGRN mRNA (Ong et al., *Am J Physiol Regul Integr Comp Physiol*, 291:R1602-1612 (2006)). NSAIDs may also function as PPAR agonists (Jaradat et al., *Biochem Pharmacol*, 62:1587-1595 ((2001); Lehmann et al., *J Biol Chem*, 272:3406-3410 (1997)). Kojo et al. (*J Pharmacol Sci*, 93:347-355 (2003)) showed that ibuprofen and other NSAIDS may selectively activate PPAR receptor activity at $1 \times 10e^{-9}$ M and higher concentrations in in vitro assays.

It is hypothesized that increased PGRN polypeptide expression is caused by the activation of PPAR receptors by both PPAR compounds and by NSAIDs, such as ibuprofen, indomethacin, and diclofenac, that are thought to activate PPARδ and PPARγ, but not PPARα, receptors (Kojo et al., *J Pharmacol Sci*, 93:347-355 (2003)). Activated receptors bind to a PPAR responsive element (PPRE) within the PGRN promoter, resulting in increased mRNA transcription and translation. The hypothesis is tested using two studies. In one study, dose-response assays for PGRN polypeptide are performed using a combination of pharmacological manipulation and RNA-interference. In another study, the functional peroxisome-proliferator responsive element is identified in human GRN.

Studies to address the regulation of PGRN mRNA and polypeptide by pharmacological manipulation of PPAR receptors are initially addressed use a series of agonist-antagonist dose-response studies. Highly selective PPARα (GW7647), PPARδ (L165,041), and PPARγ (GW1929) agonists that are active in the low nM range are obtained from commercial vendors, such as Calbiochem. PPAR antagonists, including compounds that are selective for the PPARγ receptor subtype with an $IC_{50}$ in the low nM range, also are obtained. In addition, compounds such as GW9662 (2-Chloro-5-nitro-N-phenylbenzamide), are obtained. Such compounds can block PPARα receptors in the low nM range and PPARδ receptors in the low micromolar range and can be used as pan-PPAR inhibitors at higher concentrations (Leesnitzer et al., *Biochemistry*, 41:6640-6650 (2002)).

Pharmacological studies are performed with both PPAR agonists and NSAIDs, including ibuprofen, indomethacin, and diclofenac, to elevate PGRN production. GW9662 is used as a pan-PPAR inhibitor to show that both PPAR agonists and NSAIDs exert functional activity on PGRN expression through the PPAR nuclear transcription pathway. Northern blot analysis and real-time RT-PCR are used to quantitate mRNA levels of PGRN. Western blotting is used to quantitate intracellular and secreted PGRN polypeptide levels. To validate the assays, PPAR transcription factor activity induced by NSAIDs and PPAR agonists is determined in these experiments through the use of the PPARα, δ, γ Complete Transcription Factor Assay Kit (Cayman Chemical). This kit allows for quantitative detection of PPAR-DNA binding. Follow up studies in BE(2)-M17 human neuroblastoma cell lines employ a siRNA approach. These studies use siRNA to selectively downregulate PPARα, PPARγ, and PPARδ receptors, which allows for a careful dissection of each pathway in the regulation of PGRN expression. Validated siRNA sequences against PPARα, PPARγ, and PPARδ receptors are available from Invitrogen.

To investigate the hypothesis that the PGRN promoter contains a functional PPRE, protocols described elsewhere are used (Chen et al., *Biochem Biophys Res Commun*, 347:821-826 (2006)). Briefly, PCR amplification is used to perform serial deletions of the 5' flanking region of the human GRN promoter sequence. Serial deleted promoter sequences are subcloned into a luciferase expression vector (Promega), and the promoter-reporter sequences are confirmed by DNA sequencing. One hour prior to transfection, Be(2)-M17 cells are pretreated with PPARα, PPARγ, or PPARδ agonists at an appropriate $EC_{50}$ concentration. M17 cells lines are transiently transfected with promoter-reporter vectors, and monitored for luciferase expression with treatment. As a positive control, p-RL (*Renilla luciferase* expression vector) plasmid is co-transfected as a transfection efficiency control. Forty-eight hours after transfection, both the Firefly and *Renilla luciferase* activities are quantified using a Dual-Luciferase reporter assay system (Promega, Madison, Wis.). To confirm that the promoter-reporter is activated by PPAR receptors on positive hits, an active promoter-reporter sequence is transiently co-transfected with PPARγ and RXRα expression vectors to show activation of luciferase expression in the presence or absence of PPAR agonists. Electrophoretic mobility shift assays are used to determine whether specific polypeptide-DNA complexes are formed when cells that have been transiently transfected with promoter-reporter vectors are treated with PPAR agonists. In this analysis, nuclear extracts of transiently transfected and treated cells are prepared with a Nuclear Extract Kit (Active Motif, Carlsbad, Calif.). Consensus PPRE and PPRE-like sequence double-stranded oligonucleotides that are used in EMSA competition assays are labeled with $\gamma$-$^{32}$P-ATP by polynucleotide kinase enzyme (Promega) and purified using a Sephadex G-25 spin column (Amersham, Piscataway, N.J.). The oligonucleotide probes used in this experiment correspond to a PPRE-like probe (which is obtained from an active promoter-reporter vector) and a competitive consensus PPRE probe that is common to all PPRE elements (Schachtrup et al., *Biochem J*, 382:239-245 (2004)): 5'-CAAAACTAGGTCAAAGGTCA-3' (SEQ ID NO:71). Unlabeled probes are used in 100-fold excess concentration for competition experiments. In some experiments, a LightShift Chemiluminescent EMSA kit (Pierce) is used to perform the EMSA assays.

To perform Western blot analysis of PGRN polypeptide expression, cells are lysed in a mild detergent buffer containing protease inhibitor, sonicated, and centrifuged to remove cellular debris. Progranulin levels are assessed in brain tissue by probing blots using an anti-mouse PGRN antibody (R&D Systems), followed by a sheep anti-mouse secondary antibody (Sigma-Aldrich). GAPDH polypeptide expression is used as a marker to normalize polypeptide levels.

The Transcription Factor Assay Kit (Cayman Chemical) is used to detect PPAR-DNA binding. Briefly, nuclear lysates prepared from treated cells are added to a 96-well plate coated with a dsDNA sequence containing PPREs. PPAR bind to the PPRE elements, plates are washed, and PPARα, PPARγ, and PPARδ receptors are detected using primary and secondary antibodies.

A quantitative real-time PCR assay is used to measure GRN expression. Total RNA is extracted from M17 cells using Trizol Reagent (GIBCO-BRL/Life Technologies, Invitrogen). RNA is treated with RQ1 DNase (Promega) and then reverse transcribed using moloney murine leukemia virus RT (GIBCO-BRL/Life Technologies). Expression values are normalized to β-actin expression. The primer pairs used for the GRN transcript are 5'-GGACAGTACT-GAAGACTCTG-3' (forward primer; SEQ ID NO:72) and 5'-GGATGGCAGCTTGTAATGTG-3' (reverse primer; SEQ ID NO:73); the primers for β-actin are 5'-GAAGTGT-GACGTGGACATCC-3' (forward primer; SEQ ID NO:74) and 5'-CCGATCCACACGGAGTACTT-3' (reverse primer; SEQ ID NO:75; GIBCO-BRL/Life Technologies). Amplification reaction mixtures are prepared according to the LightCycler FastStart DNA Master SYBR Green I kit instructions (Roche Applied Science, Penzberg, Germany) with a final primer concentration of 0.5 μM for each reaction. The amplifications are performed in duplicates using the following conditions: hot start step (denaturation) at 95° C. for 10 minutes, followed by 45 cycles of 95° C. for 10 seconds, 66° C. for 10 seconds, and 72° C. for 10 seconds.

To perform Northern blotting, total RNA is isolated from $10^7$ cells using TriZol Reagent. RNA samples, 10 or 15 μg, are denatured with glyoxal at 50° C. for 1 hour and subjected to electrophoresis using a 1% agarose gel in 10 mM $NaH_2PO_4$, pH 7. RNA is transferred to a nylon blotting membrane (Bio-Rad, Hercules, Calif.) and fixed by baking. Membranes are hybridized at 65° C. in 0.5 M $NaH_2PO_4$ for 24 hours using a radiolabeled complementary sequence to the 5' end of PGRN, and then stringently washed. Autoradiograms are obtained by exposing these blots to X-Omat film with intensifying screens. Densitometry is performed using ImageJ software (NIH, Bethesda, Md.) and normalized to the 28S ribosomal RNA bands. Statistical analyses are performed with ANOVA.

Example 11

Determining if PGRN Polypeptide Alters Neurodegeneration In Vivo

Studies are performed to determine how alterations in the level of PGRN polypeptide can modulate neurodegeneration in the JNPL3 mouse line, a tauopathy model. Two different animal models (JNPL3 and PGRN$^{-/-}$ mice) are used to test whether different levels of PGRN polypeptide can modulate a neurodegenerative phenotype. PGRN polypeptide expression was observed to correlate positively with neuropathology in the JNPL3 line, but it is not known whether this is a primary or secondary response. Given the modulatory role of PGRN polypeptide on inflammatory processes in peripheral tissues, experiments are performed to determine if JNPL3 mice lacking PGRN have an accelerated neurodegenerative phenotype. Studies also are performed to determine whether elevated PGRN levels can slow the neurodegenerative phenotype in JNPL3 mice.

Compared with a relatively modest age-related increase in PGRN expression in non-transgenic siblings, there is a significant upregulation of PGRN expression in both white and gray matter in JNPL3 mice. Although there is only modest evidence for pathology in young PGRN$^{-/-}$ mice (below), a 50% reduction in PGRN expression leads to full-blown FTD in human patients (Baker et al., *Nature*, 442:916-919 (2006); Cruts et al., *Nature*, 442:920-924 (2006)). In addition, PGRN is an important factor in wound healing (He and Bateman, *J Mol Med*, 81:600-612 (2003); He et al., *Nat Med*, 9:225-229 (2003); He et al., *Cancer Res*, 62:5590-5596 (2002)). The loss of PGRN may impair healing processes and promote inflammation, leading to an acceleration of tauopathy, advanced synaptic degeneration, increased microglial activation and gliosis, and a shortened life span in the JNPL3 model.

A backcross of JNPL3 mice with PGRN$^{-/-}$ mice is performed to generate (JNPL3)(PGRN$^{+/-}$), and (JNPL3) (PGRN$^{-/-}$) mice. (JNPL3)(PGRN$^{+/+}$) mice also are generated for comparison studies. Thirty mice of each line are allowed to age until reaching a "severe" motor deficit stage, as assessed by formal motor tests given on a weekly basis. Mice are sacrificed upon reaching this threshold. A Kaplan-Meier survival curve and median survival time are developed from this data and compared across groups. Brains and spinal cord are harvested from euthanized mice and evaluated for alterations in levels of hyperphosphorylated tau, PGRN, microglial activation, gliosis and inflammatory markers, and numbers of neurons, glial and oligodendrocytes. Since PGRN is expressed in neurons and is likely to be an important survival factor that can affect synaptic function, the synaptic architecture is characterized by evaluating the anterior horn cells from the mice. JNPL3 mice show an altered synaptic number with the onset of tau pathology (Katsuse et al., *Neurosci Lett*, 409:95-99 (2006)). Synaptic number is evaluated using double immunofluorescence staining for pre- and post-synaptic densities. Dendritic spine number is characterized by visualizing neurons with DiOlistic labeling (ballistic delivery of lipophilic dye), followed by quantification of dendrites and spines with the Metamorph imaging system. These data indicate whether PGRN helps to maintain functional neuronal connects in the presence of ongoing neuropathology.

JNPL3 transgenic mice are on the C57BL/6 background strain. These animals are hemizygous for the 0N4R tau isoform with the P301L mutation in exon 10, driven by the MoPrP promoter (Lewis et al., *Nat Genet*, 25:402-405 (2000)). Expression in hemizygotes is almost equivalent to that of endogenous mouse tau, and these mice develop neurofibrillary tangles, neuronal loss, and motor deficits as early as 6 months of age, with up to a fifty-percent neuronal loss in the spinal cord. Onset of severe neuropathology typically begins from 12-14 months of age. In these mice, neurofibrillary tangles in neuronal cell bodies are composed mainly of straight tau filaments, and are concentrated in the spinal cord, brain stem, and some regions of the midbrain of the P301L animals. Pre-tangles in the mice have a much wider distribution. Neurofibrillary tangles, similar to those found in human tauopathies, are positive for thioflavin S, Congo red, and Gallyas, Bielschowsky, and Bodian silver stains, and can be stained with numerous antibodies for tau hyperphosphorylation.

A colony of PGRN knockout mice on the C57BL/6 background strain (The Jackson Laboratory, Bar Harbor, Me.) was established (Charles River Laboratories, Wilmington, Mass.). A targeted disruption of the genomic region of PGRN from exon 2 to exon 13 was performed by replacement with a PGK-Neo-pA cassette. The targeted disruption knocks out 3.7 kb of the PGRN genomic locus and results in complete deletion of PGRN. Both hemizygous ($^{+/-}$) and homozygous ($^{-/-}$) mice were viable.

An initial characterization of PGRN wild-type ($^{+/+}$), heterozygous ($^{+/-}$) and homozygote ($^{-/-}$) knockout mice at 1 and 8 months of age has been performed. PGRN expression was detected in the wild-type (WT) mice, was observed to a lesser extent in the PGRN$^{+/-}$ mice, and was completely absent in the null mice. In wild-type mice, PGRN immunoreactivity was most pronounced in the hippocampus. Expression was also high in the cortex and in Purkinje cells of the cerebellum. It was noted that GFAP immunoreactivity, a marker for astrocytes and astrogliosis, was significantly greater in the 8-month PGRN$^{-/-}$ mice compared with all other groups. These results suggest that the mice have a subtle form of pathology.

To generate a null PGRN background in the JNPL3 line, JNPL3 mice are backcrossed onto the PGRN$^{-/-}$ background over two rounds of breeding. All mice are maintained on a C57BL/6 background strain (The Jackson Laboratory) to minimize genetic differences between groups. In the first round, hemizygous JNPL are bred with PGRN null mice (JNPL3)(PGRN$^{-/-}$), resulting in 50% hemizygous (JNPL3)(PGRN$^{+/-}$) and 50% PGRN$^{+/-}$. Hemizygous offspring (JNPL3)(PGRN$^{+/-}$) are backcrossed to the PGRN$^{-/-}$ line, generating 25% (JNPL3)(PGRN$^{-/-}$), 25% (JNPL3)(PGRN$^{+/-}$), 25% PGRN$^{-/-}$, and 25% PGRN$^{+/-}$ mice. JNPL3 mice on a wild-type PGRN background are used for comparison.

Synapses and dendritic Spine Number are evaluated. Changes in presynaptic vesicles associated with tauopathy are examined using an antibody to synaptophysin (STN clone SY38, Chemicon). Additionally, changes in the active zone of synapses are examined by dual fluorescent labeling of the pre-synaptic protein (Bassoon) and post-synaptic protein (SAP-102; Christopherson et al., *Cell*, 120:421-433 (2005); Dresbach et al., *Mol Cell Neurosci*, 23:279-291 (2003)). "DiOlistic" labeling, or particle-mediated ballistic delivery of lipophilic dyes (Gan et al., *Neuron*, 27:219-225 (2000)), is used to rapidly and differentially label brain cells in transgenic mice to examine neuronal architecture. Tungsten particles coated with DiI (1,1-dioctadecyl-3,3,3',3'-tetramethyl-indocarbocyanine perchlorate) are shot into fixed brain sections (200 µm) using a gene gun (Bio-Rad, Hercules, Calif.) and allowed to diffuse into cells. Labeled dendritic arbors and axons are typically visible over several hundred microns. For example, an image of a neuron was acquired following DiOlistic labeling. The image represented a collapsed view of 100 confocal planes covering 50 µm of depth. A high magnification image of an apical dendrite after DiOlistic labeling showed dendritic spines. These results indicate that clear labeling of dendritic spines is possible using this method. For each neuron, the number of spines along five random stretches of apical dendrite at least 10 µm in length is counted using Metamorph automated quantitation software (Molecular Devices, Sunnyvale, Calif.). The density of spines is calculated by normalizing the value for the number of spines for a 10 µm segment length. For each experimental group, a minimum of 2,000 spines per animal are analyzed with the investigators blind to genotype.

Immunohistochemistry is used to assess tauopathy phenotype. Standard tau antibodies used in this study include AT8 and PHF-1 for abnormal tau phosphorylation and MC1 for abnormal tau conformation (Lewis et al., *Nat. Genet.*, 25:402-405 (2000)). Additionally, the following antibodies are used to detect neurons (NeuN; Chemicon, Millipore, Billerica, Mass.), oligodendrocytes (CAII; Ghandour), microglia (CD11B; Serotec/CD45 Serotec, Raleigh, N.C.), astrocytes (GFAP, Astrazenica), and progranulin (R&D Systems). Neuronal number is quantitated in spinal cord using an unbiased stereological approach (the single section dissector method; Moller et al., *J Microsc*, 159 (Pt 1):61-71 (1990)).

Biochemistry is applied to characterize the tau species present in different treatment groups. Regional dissections of spinal cord, cortex and cerebellum are sequentially extracted through a typical tau sarkosyl fractionation protocol that separates soluble and insoluble tau species in treatment groups (Ramsden et al., *J Neurosci*, 25:10637-10647 (2005)). Brain tissue is homogenized in 10 volumes (g/mL) of TBS containing protease and phosphatase inhibitors and spun at 100,000 g for one hour. The TBS supernatant is analyzed for soluble tau. The pellet is re-extracted with TBS containing 10% sucrose and 0.8 M sodium chloride. The sucrose supernatant is adjusted to 1% sarkosyl and incubated at 37° C. for one hour. The sarkosyl pellet is collected by spinning the sucrose supernatant at 100,000 for two hours. The pellet is then solubilized in Laemmli buffer. The protein is electrophoresed and western blotted by standard protocol. Polypeptide loading on western blots is determined by polypeptide quantification for the soluble fraction (S1) and by initial tissue input for the insoluble fraction (P3). The western blots of soluble and insoluble tau are probed with antibodies that recognize human tau (E1), mouse and human tau (WKS46), and phosphorylated tau. Screening is carried out for numerous tau phosphoepitopes (e.g., phospho-202/205, phospho-231/235, and phospho-396/404). Western blots are probed with tau antibodies sensitive to phosphorylation and conformationally dependent epitopes, as well as with an anti-mouse PGRN antibody (R&D Systems).

Motor performance is evaluated in transgenic mice. A basic SHIRPA protocol, consisting of primary and secondary screens, is used to comprehensively evaluate mouse motor behavior (Rogers et al., *Mamm Genome*, 8:711-713 (1997)). This battery of simple tests begins with procedures that are most sensitive to physical manipulation. Additional screens include the assessment of sensorimotor deficits using rotarod, wire hang testing, and gait analysis. Motor function is monitored twice a week by wire hang, beam walk, and flight reflex tests. Animals are monitored daily when signs of motor impairments become evident. Based on performance, animals are categorized as "unaffected," "initial," "moderate," and "severe" motor phenotype. Animals failing at least two consecutive motor tests for two consecutive days and scored as a severe phenotype are sacrificed. The statistical significance between groups is assessed by a one-way ANOVA followed by a Fisher's post-hoc test.

In some experiments, established tau transgenic lines, such as htau mice, are used.

Example 12

Determining if Agents that Elevate PGRN Polypeptide Expression are Neuroprotective In Vivo Two studies are performed to (1) identify agents that can elevate PGRN polypeptide levels using cell-based and cortical slice screens, and (2) to validate the neuroprotective effects of the best candidate agents in vivo using the (JNPL3)(PGRN) mouse cross. Screening is performed using agents that are closely related to the anti-inflammatory and PPAR drugs identified in vitro as PPAR elevating compounds. Agents that elicit robust increases in PGRN polypeptide in cortical slice cultures are tested in transgenic mice.

Figure 33:
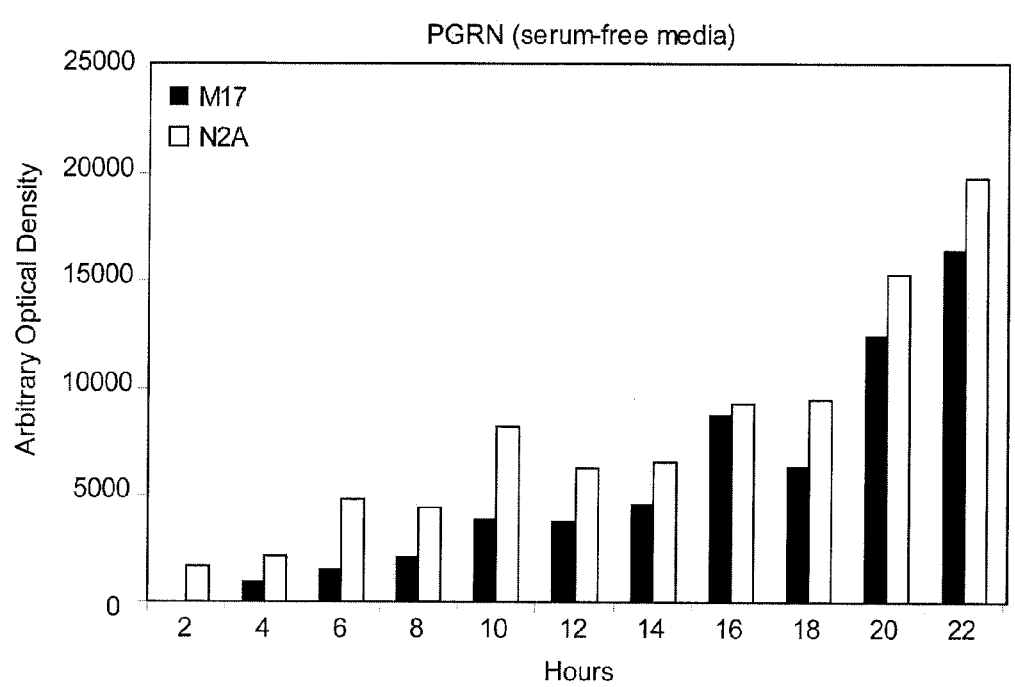
FIG. 33 is a graph plotting levels of PGRN polypeptide secreted by M17 and N2A cells at the indicated time points. The graph indicates that secreted PGRN polypeptide accumulates linearly over 22 hours in both cell lines.

Agents are screened to identify prospective candidates that can elevate production of PGRN polypeptide in vivo (FIG. 33). Agents that are screened include (a) non-steroidal anti-inflammatory drugs (30 compounds, including COX-1 and COX-2 inhibitors), (b) PPAR agonists (10 compounds), (c) HMG-CoA reductase inhibitors (8 compounds), (d) anti-histamines (5 compounds), (e) and a limited collection of 20 natural products and derivatives of natural products, including curcumin, ginseng, ginko biloba, resveratrol, green tea extracts (epigallocatechin gallate, epigallocatechin, epicatechin gallate, epicatechin and gallic acid) and anthocyanins. Agents that are screened include drugs that are reported to have protective effects in Alzheimer's disease (Vardy et al., *Expert Rev Neurother*, 6:695-704 (2006)). Compounds are purchased from commercial sources, including Calbiochem and Sigma-Aldrich. A screening system for PGRN polypeptide was developed to test the agents. The screening system yielded highly reproducible results and was used to identify drug candidates. Agents are screened in BE(2)-M17 (human neuroblastoma) and N2A (mouse neuroblastoma) cells over a 6-log order concentration ($1\times10e^{-9}$-$1\times10e^{-5}$) in four replicates. Media and lysates are collected and analyzed by Western blot for alterations in PGRN polypeptide levels. Agents also are screening using a standard MTT assay to eliminate non-specific effects from toxicity.

Agents exhibiting activity in cell-culture based screens are tested in (JNPL3)(PGRN$^{+/+}$) organotypic cortical slices to evaluate PGRN polypeptide elevating activity in an ex vivo system that contains a relatively intact neuronal architecture with neurons and microglia before performing in vivo studies. Slices are prepared from brains of mice in the fourth week of postnatal development and are maintained for periods of a month or more (Gahwiler et al., *Trends Neurosci*, 20:471-477 (1997)). The slices have preserved adult-like characteristics. The slices also retain much of the connective organization found in vivo as well as the potential for synaptic plasticity (long term potentiation) and responsiveness to pathological insults. Long-term organotypic slice cultures are well suited for studying changes in brain physiology and pathology associated with tau expression and drug treatments. The organotypic slices are accessible to a variety of experimental manipulations that are independent of the blood brain barrier, and consequently represent a good model system to screen potential agents for regulation of PGRN polypeptide expression. Cortical slices are primarily used in these studies to validate the cell culture effects of short term agent treatment on both intracellular and secreted PGRN polypeptide levels using dose-response curves.

Two lead agents that are confirmed to elevate PGRN polypeptides levels in cortical slices are further evaluated for an effect on neurodegenerative processes and survival. As an initial in vivo screen, up to six potential candidate agents are selected for long-term treatment by performing pilot studies with an initial escalating dose-response trial design in order to select the most promising agent for long-term treatment. Groups of one month old (JNPL3)(PGRN$^{+/-}$) mice are treated via the oral administration route in short-term (one week) studies using a dose-escalating study design. Actual doses used for each agent are based on dose-responses seen in the cortical slice system. Up to five different agents are tested in this design. Brain and spinal cord tissue are analyzed for PGRN polypeptide levels by Western blotting. Two agents that show the greatest increase are selected for long-term studies.

Mice are chronically treated using a dietary strategy that assumes an average daily consumption of food (and incorporated agents). Agents are homogenously incorporated into kibble. JNPL3 mice are backcrossed onto the PGRN$^{-/-}$ lines to generate three groups of 30 mice with each of the following genotypes: (JNPL3)(PGRN$^{+/-}$), (JNPL3) (PGRN$^{-/-}$) and (JNPL3)(PGRN$^{+/+}$), for comparison studies. Mice are placed on the diet immediately after weaning and are allowed to age until reaching a "severe" motor deficit stage, as assessed by formal motor tests given on a weekly basis. Mice are sacrificed upon reaching this threshold in order to generate a Kaplan-Meier survival curve and median survival time. Brains and spinal cord are harvested from euthanized mice and evaluated by immunohistochemical and biochemical means for alterations in hyperphosphorylated tau, endogenous PGRN levels, microglial activation, inflammatory markers and neuronal cell number. A PGRN knockout background on the JNPL3 line allows a specific PGRN-protective response to be distinguished from a response that occurs because of a general neuroprotective effect.

Organotypic slice cultures are prepared using a modified protocol described elsewhere (Xiang et al., *J Neurosci Methods*, 98:145-154 (2000)). Brains from transgenic mice 25-30 days postnatal are aseptically removed and sagittally hemisected. Each hemi brain is sliced into 400-μm-thick sections using a McIllwain tissue chopper (Brinkman Instruments, Westbury, N.Y.). Sections are allowed to rest for one hour in a highly oxygenated, balanced salt solution. Sections are then plated onto membrane inserts (Millipore) in six-well plates (three slices/well). Cultures are maintained in one mL of elevated potassium slice culture media (25% horse serum (GIBCO-Life Technologies), 50% Basal Essential Media-Eagles, 25% Earle's balanced salt solution (EBSS), 25 mM NaHEPES, 1 mM glutamine, 28 mM glucose, pH 7.2) and incubated at 32° C. in a 5% $CO_2$ atmosphere. After three days, culture media is switched to a physiological concentration of potassium (25% horse serum, 50% Basal Essential Media-Eagles, and EBSS modified so that the potassium concentration is 2.66 mM). After five days in vitro, cultures are maintained in physiological potassium slice culture medium containing a reduced serum level (5%), and the temperature is raised to 35° C. Slices are fed from the bottom of the culture every three days. Experimental agents are either added to the culture media, or added dropwise to the surface of the culture.

Mice are weighed and evaluated for weekly food consumption. Based on quantity of kibble consumed (typically 10-14% body weight per day), candidate agents that elevate PGRN polypeptide levels are homogenously incorporated into Harlan Teklad 7102 kibble diet by Research Diets (New Brunswick, N.J.) at a concentration shown to elevate the level of PGRN polypeptide in brain. Chronic drug dosing is performed, and consumption of kibble and body weight are monitored on a weekly basis.

Animal breeding, biochemistry, immunohistochemistry, motor evaluation, and statistical analysis are performed as described herein to evaluate the effects of drug treatment on the development of neurodegenerative phenotype.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the level of a PGRN polypeptide within a mammal having frontotemporal dementia, wherein the genome of said mammal comprises a null mutation in a PGRN nucleic acid, wherein said method comprises administering, to said mammal, a nucleic acid comprising a nucleic acid sequence that encodes said PGRN polypeptide.

2. The method of claim 1, wherein said mammal is a human.

3. The method of claim 1, wherein said nucleic acid comprises the nucleotide sequence set forth in SEQ ID NO:2.

4. The method of claim 1, wherein said nucleic acid encodes a polypeptide comprising the amino acid sequence set forth in SEQ ID NO:1.

5. The method of claim 1, wherein said nucleic acid is administered using a viral vector.

6. The method of claim 5, wherein said viral vector is selected from the group consisting of an adeno-associated virus vector, a lentivirus vector, and an adenovirus vector.

* * * * *

UNITED STATES PATENT AND TRADEMARK OFFICE
CERTIFICATE OF CORRECTION

PATENT NO. : 9,486,541 B2  
APPLICATION NO. : 13/932727  
DATED : November 8, 2016  
INVENTOR(S) : Hutton et al.

Page 1 of 1

It is certified that error appears in the above-identified patent and that said Letters Patent is hereby corrected as shown below:

On the Title Page

Item [73], delete "Universteit" and insert -- Universiteit --, therefor.

Signed and Sealed this
Twenty-fifth Day of April, 2017

Michelle K. Lee
*Director of the United States Patent and Trademark Office*

SEQUENCE LISTING

```
<160> NUMBER OF SEQ ID NOS: 167

<210> SEQ ID NO 1
<211> LENGTH: 593
<212> TYPE: PRT
<213> ORGANISM: Homo sapiens

<400> SEQUENCE: 1

Met Trp Thr Leu Val Ser Trp Val Ala Leu Thr Ala Gly Leu Val Ala
 1               5                  10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205
```

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
        355                 360                 365

Val Ser Ser Cys Pro Ser Ser Asp Thr Cys Cys Gln Leu Thr Ser Gly
    370                 375                 380

Glu Trp Gly Cys Cys Pro Ile Pro Glu Ala Val Cys Cys Ser Asp His
385                 390                 395                 400

Gln His Cys Cys Pro Gln Arg Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Gly Ser Leu Ser His Pro Arg Asp Ile Gly Cys Asp Gln His Thr
        435                 440                 445

Ser Cys Pro Val Gly Gly Thr Cys Cys Pro Ser Gln Gly Gly Ser Trp
    450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
        515                 520                 525

Asp Asn Gln Thr Cys Cys Arg Asp Asn Arg Gln Gly Trp Ala Cys Cys
    530                 535                 540

Pro Tyr Ala Gln Gly Val Cys Cys Ala Asp Arg Arg His Cys Cys Pro
545                 550                 555                 560

Ala Gly Phe Arg Cys Ala Arg Arg Gly Thr Lys Cys Leu Arg Arg Glu
                565                 570                 575

Ala Pro Arg Trp Asp Ala Pro Leu Arg Asp Pro Ala Leu Arg Gln Leu
        580                 585                 590

Leu

<210> SEQ ID NO 2
<211> LENGTH: 2095
<212> TYPE: DNA

<213> ORGANISM: Homo sapiens

<400> SEQUENCE: 2

```
cgcaggcaga ccatgtggac cctggtgagc tgggtggcct aacagcagg gctggtggct      60
ggaacgcggt gcccagatgg tcagttctgc cctgtggcct gctgcctgga ccccggagga    120
gccagctaca gctgctgccg tccccttctg acaaatggc ccacaacact gagcaggcat     180
ctgggtggcc cctgccaggt tgatgcccac tgctctgccg ccactcctg catctttacc     240
gtctcaggga cttccagttg ctgccccttc ccagaggccg tggcatgcgg ggatggccat    300
cactgctgcc cacggggctt ccactgcagt gcagacgggc gatcctgctt ccaaagatca    360
ggtaacaact ccgtgggtgc catccagtgc cctgatagtc agttcgaatg cccggacttc    420
tccacgtgct gtgttatggt cgatggctcc tggggtgct gccccatgcc caggcttcc     480
tgctgtgaag acagggtgca ctgctgtccg cacggtgcct tctgcgacct ggttcacacc    540
cgctgcatca cacccacggg cacccacccc ctggcaaaga agctccctgc ccagaggact    600
aacagggcag tggccttgtc cagctcggtc atgtgtccgg acgcacggtc ccggtgccct    660
gatggttcta cctgctgtga gctgcccagt gggaagtatg gctgctgccc aatgcccaac    720
gccacctgct gctccgatca cctgcactgc tgccccaag acactgtgtg tgacctgatc    780
cagagtaagt gcctctccaa ggagaacgct accacggacc tcctcactaa gctgcctgcg    840
cacacagtgg gcgatgtgaa atgtgacatg gaggtgagct gccagatgg ctatacctgc    900
tgccgtctac agtcgggggc ctggggctgc tgcccttta cccaggctgt gtgctgtgag    960
gaccacatac actgctgtcc cgcggggttt acgtgtgaca cgcagaaggg tacctgtgaa   1020
caggggcccc accaggtgcc ctggatggag aaggccccag ctcacctcag cctgccagac   1080
ccacaagcct tgaagagaga tgtcccctgt gataatgtca gcagctgtcc ctcctccgat   1140
acctgctgcc aactcacgtc tggggagtgg ggctgctgtc aatcccaga ggctgtctgc   1200
tgctcggacc accagcactg ctgccccag cgatacacgt gtgtagctga ggggcagtgt   1260
cagcgaggaa gcgagatcgt ggctggactg gagaagatgc ctgcccgccg cggttcctta   1320
tcccacccca gagacatcgg ctgtgaccag cacaccagct gcccggtggg cggaacctgc   1380
tgcccgagcc agggtgggag ctgggcctgc tgccagttgc ccatgctgt gtgctgcgag   1440
gatcgccagc actgctgccc ggctggctac acctgcaacg tgaaggctcg atcctgcgag   1500
aaggaagtgg tctctgccca gcctgccacc ttcctggccc gtagccctca cgtgggtgtg   1560
aaggacgtgg agtgtgggga aggacacttc tgccatgata accagacctg ctgccgagac   1620
aaccgacagg gctgggcctg ctgtccctac gccagggcg tctgttgtgc tgatcggcgc   1680
cactgctgtc ctgctggctt ccgctgcgca cgcagggta ccaagtgttt gcgcaggag   1740
gccccgcgct gggacgcccc tttgagggac ccagccttga cagctgct gtgagggaca    1800
gtactgaaga ctctgcagcc ctcgggaccc cactcggagg gtgccctctg ctcaggcctc   1860
cctagcacct cccctaacc aaattctccc tggaccccat tctgagctcc ccatcaccat   1920
gggaggtggg gcctcaatct aaggccttc cctgtcagaa gggggttgag gcaaaagccc    1980
attacaagct gccatcccct cccgtttca gtggaccctg tggccaggtg cttttcccta   2040
tccacagggg tgtttgtgtg ttgggtgtgc tttcaataaa gtttgtcact ttctt         2095
```

<210> SEQ ID NO 3
<211> LENGTH: 20
<212> TYPE: DNA
<213> ORGANISM: Artificial Sequence

```
<220> FEATURE:
<223> OTHER INFORMATION: oligonucleotide

<400> SEQUENCE: 3
gggctagggt actgagtgac                                               20

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
agtgttgtgg gccatttg                                                 18

<210> SEQ ID NO 5
<211> LENGTH: 18
<212> TYPE: DNA
<213> ORGANISM: Artificial Sequence
<220> FEATURE:
<223> OTHER INFORMATION: oligonucleotide

<400> SEQUENCE: 5
tgcccagatg gtcagttc                                                 18

<210> SEQ ID NO 6
<211> LENGTH: 18
<212> TYPE: DNA
<213> ORGANISM: Artificial Sequence
<220> FEATURE:
<223> OTHER INFORMATION: oligonucleotide

<400> SEQUENCE: 6
gctgcacctg atctttgg                                                 18

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
ggccactcct gcatctttac                                               20

<210> SEQ ID NO 8
<211> LENGTH: 18
<212> TYPE: DNA
<213> ORGANISM: Artificial Sequence
<220> FEATURE:
<223> OTHER INFORMATION: oligonucleotide

<400> SEQUENCE: 8
tgaatgaggg cacaaggg                                                 18

<210> SEQ ID NO 9
<211> LENGTH: 19
<212> TYPE: DNA
<213> ORGANISM: Artificial Sequence
<220> FEATURE:
<223> OTHER INFORMATION: oligonucleotide

<400> SEQUENCE: 9
ttagtgtcac cctcaaacc                                                19
```

<210> SEQ ID NO 10
<211> LENGTH: 18
<212> TYPE: DNA
<213> ORGANISM: Artificial Sequence
<220> FEATURE:
<223> OTHER INFORMATION: oligonucleotide

<400> SEQUENCE: 10
actggaagag gagcaaac                                                 18

<210> SEQ ID NO 11
<211> LENGTH: 23
<212> TYPE: DNA
<213> ORGANISM: Artificial Sequence
<220> FEATURE:
<223> OTHER INFORMATION: oligonucleotide

<400> SEQUENCE: 11
gggcctcatt gactccaagt gta                                           23

<210> SEQ ID NO 12
<211> LENGTH: 23
<212> TYPE: DNA
<213> ORGANISM: Artificial Sequence
<220> FEATURE:
<223> OTHER INFORMATION: oligonucleotide

<400> SEQUENCE: 12
ggtctttgtc acttccaggc tca                                           23

<210> SEQ ID NO 13
<211> LENGTH: 18
<212> TYPE: DNA
<213> ORGANISM: Artificial Sequence
<220> FEATURE:
<223> OTHER INFORMATION: oligonucleotide

<400> SEQUENCE: 13
tccctgtgtg ctactgag                                                 18

<210> SEQ ID NO 14
<211> LENGTH: 18
<212> TYPE: DNA
<213> ORGANISM: Artificial Sequence
<220> FEATURE:
<223> OTHER INFORMATION: oligonucleotide

<400> SEQUENCE: 14
aagcagagag gacaggtc                                                 18

<210> SEQ ID NO 15
<211> LENGTH: 19
<212> TYPE: DNA
<213> ORGANISM: Artificial Sequence
<220> FEATURE:
<223> OTHER INFORMATION: oligonucleotide

<400> SEQUENCE: 15
taccctccat cttcaacac                                                19

<210> SEQ ID NO 16
<211> LENGTH: 18
<212> TYPE: DNA
<213> ORGANISM: Artificial Sequence
<220> FEATURE:
<223> OTHER INFORMATION: oligonucleotide

```
<400> SEQUENCE: 16
tcacagcaca cagcctag                                          18

<210> SEQ ID NO 17
<211> LENGTH: 18
<212> TYPE: DNA
<213> ORGANISM: Artificial Sequence
<220> FEATURE:
<223> OTHER INFORMATION: oligonucleotide

<400> SEQUENCE: 17
atacctgctg ccgtctac                                          18

<210> SEQ ID NO 18
<211> LENGTH: 18
<212> TYPE: DNA
<213> ORGANISM: Artificial Sequence
<220> FEATURE:
<223> OTHER INFORMATION: oligonucleotide

<400> SEQUENCE: 18
gagggcagaa agcaatag                                          18

<210> SEQ ID NO 19
<211> LENGTH: 22
<212> TYPE: DNA
<213> ORGANISM: Artificial Sequence
<220> FEATURE:
<223> OTHER INFORMATION: oligonucleotide

<400> SEQUENCE: 19
tgtccaatcc cagaggtata tg                                     22

<210> SEQ ID NO 20
<211> LENGTH: 19
<212> TYPE: DNA
<213> ORGANISM: Artificial Sequence
<220> FEATURE:
<223> OTHER INFORMATION: oligonucleotide

<400> SEQUENCE: 20
acgttgcagg tgtagccag                                         19

<210> SEQ ID NO 21
<211> LENGTH: 18
<212> TYPE: DNA
<213> ORGANISM: Artificial Sequence
<220> FEATURE:
<223> OTHER INFORMATION: oligonucleotide

<400> SEQUENCE: 21
tggactggag aagatgcc                                          18

<210> SEQ ID NO 22
<211> LENGTH: 18
<212> TYPE: DNA
<213> ORGANISM: Artificial Sequence
<220> FEATURE:
<223> OTHER INFORMATION: oligonucleotide

<400> SEQUENCE: 22
cgatcagcac aacagacg                                          18

<210> SEQ ID NO 23
```

```
<211> LENGTH: 18
<212> TYPE: DNA
<213> ORGANISM: Artificial Sequence
<220> FEATURE:
<223> OTHER INFORMATION: oligonucleotide

<400> SEQUENCE: 23
catgataacc agacctgc                                                  18

<210> SEQ ID NO 24
<211> LENGTH: 18
<212> TYPE: DNA
<213> ORGANISM: Artificial Sequence
<220> FEATURE:
<223> OTHER INFORMATION: oligonucleotide

<400> SEQUENCE: 24
agggagaatt tggttagg                                                  18

<210> SEQ ID NO 25
<211> LENGTH: 18
<212> TYPE: DNA
<213> ORGANISM: Artificial Sequence
<220> FEATURE:
<223> OTHER INFORMATION: oligonucleotide

<400> SEQUENCE: 25
agaccatgtg gaccctgg                                                  18

<210> SEQ ID NO 26
<211> LENGTH: 24
<212> TYPE: DNA
<213> ORGANISM: Artificial Sequence
<220> FEATURE:
<223> OTHER INFORMATION: oligonucleotide

<400> SEQUENCE: 26
gtgatgcagc gggtgtgaac cagg                                           24

<210> SEQ ID NO 27
<211> LENGTH: 18
<212> TYPE: DNA
<213> ORGANISM: Artificial Sequence
<220> FEATURE:
<223> OTHER INFORMATION: oligonucleotide

<400> SEQUENCE: 27
atacctgctg ccgtctac                                                  18

<210> SEQ ID NO 28
<211> LENGTH: 19
<212> TYPE: DNA
<213> ORGANISM: Artificial Sequence
<220> FEATURE:
<223> OTHER INFORMATION: oligonucleotide

<400> SEQUENCE: 28
acgttgcagg tgtagccag                                                 19

<210> SEQ ID NO 29
<211> LENGTH: 19
<212> TYPE: DNA
<213> ORGANISM: Artificial Sequence
<220> FEATURE:
<223> OTHER INFORMATION: oligonucleotide

<400> SEQUENCE: 29
```
gggctagggt actgagtga                                          19

<210> SEQ ID NO 30
<211> LENGTH: 18
<212> TYPE: DNA
<213> ORGANISM: Artificial Sequence
<220> FEATURE:
<223> OTHER INFORMATION: oligonucleotide

<400> SEQUENCE: 30
agtgttgtgg gccatttg                                           18

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
gatggtcagt tctgccctgt                                         20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
ccctgagacg gtaaagatgc                                         20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
gtgagctggg tggccttaac                                         20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
gcagagcagt gggcatcaac                                         20

<210> SEQ ID NO 35
<211> LENGTH: 22
<212> TYPE: DNA
<213> ORGANISM: Artificial Sequence
<220> FEATURE:
<223> OTHER INFORMATION: oligonucleotide

<400> SEQUENCE: 35
gatttctgcc tgcctggaca gg                                      22

<210> SEQ ID NO 36
<211> LENGTH: 22
<212> TYPE: DNA

```
<213> ORGANISM: Artificial Sequence
<220> FEATURE:
<223> OTHER INFORMATION: oligonucleotide

<400> SEQUENCE: 36
gatgccacat gaatgagggc ac                                          22

<210> SEQ ID NO 37
<211> LENGTH: 22
<212> TYPE: DNA
<213> ORGANISM: Artificial Sequence
<220> FEATURE:
<223> OTHER INFORMATION: oligonucleotide

<400> SEQUENCE: 37
gtcaccctca aacccagta gc                                           22

<210> SEQ ID NO 38
<211> LENGTH: 22
<212> TYPE: DNA
<213> ORGANISM: Artificial Sequence
<220> FEATURE:
<223> OTHER INFORMATION: oligonucleotide

<400> SEQUENCE: 38
catgaaccct gcatcagcca gg                                          22

<210> SEQ ID NO 39
<211> LENGTH: 22
<212> TYPE: DNA
<213> ORGANISM: Artificial Sequence
<220> FEATURE:
<223> OTHER INFORMATION: oligonucleotide

<400> SEQUENCE: 39
ttgctgggag cctggctgat gc                                          22

<210> SEQ ID NO 40
<211> LENGTH: 22
<212> TYPE: DNA
<213> ORGANISM: Artificial Sequence
<220> FEATURE:
<223> OTHER INFORMATION: oligonucleotide

<400> SEQUENCE: 40
ctcctgctta cagcacctcc ag                                          22

<210> SEQ ID NO 41
<211> LENGTH: 22
<212> TYPE: DNA
<213> ORGANISM: Artificial Sequence
<220> FEATURE:
<223> OTHER INFORMATION: oligonucleotide

<400> SEQUENCE: 41
ctgacagatt cgtccccagc tg                                          22

<210> SEQ ID NO 42
<211> LENGTH: 22
<212> TYPE: DNA
<213> ORGANISM: Artificial Sequence
<220> FEATURE:
<223> OTHER INFORMATION: oligonucleotide

<400> SEQUENCE: 42
acctcccatg gtgatgggga gc                                          22
```

<210> SEQ ID NO 43
<211> LENGTH: 22
<212> TYPE: DNA
<213> ORGANISM: Artificial Sequence
<220> FEATURE:
<223> OTHER INFORMATION: oligonucleotide

<400> SEQUENCE: 43
ggtcatcttg gattggccag ag                                              22

<210> SEQ ID NO 44
<211> LENGTH: 22
<212> TYPE: DNA
<213> ORGANISM: Artificial Sequence
<220> FEATURE:
<223> OTHER INFORMATION: oligonucleotide

<400> SEQUENCE: 44
tctgcaggtg gtagagtgca gg                                              22

<210> SEQ ID NO 45
<211> LENGTH: 22
<212> TYPE: DNA
<213> ORGANISM: Artificial Sequence
<220> FEATURE:
<223> OTHER INFORMATION: oligonucleotide

<400> SEQUENCE: 45 aggggggtgaa gacggagtca gg                                             22

<210> SEQ ID NO 46
<211> LENGTH: 22
<212> TYPE: DNA
<213> ORGANISM: Artificial Sequence
<220> FEATURE:
<223> OTHER INFORMATION: oligonucleotide

<400> SEQUENCE: 46
gaggagcaaa cgtgaggggc ag                                              22

<210> SEQ ID NO 47
<211> LENGTH: 22
<212> TYPE: DNA
<213> ORGANISM: Artificial Sequence
<220> FEATURE:
<223> OTHER INFORMATION: oligonucleotide

<400> SEQUENCE: 47
tgatacccct gagggtcccc ag                                              22

<210> SEQ ID NO 48
<211> LENGTH: 22
<212> TYPE: DNA
<213> ORGANISM: Artificial Sequence
<220> FEATURE:
<223> OTHER INFORMATION: oligonucleotide

<400> SEQUENCE: 48
gaagaagggc aggtgggcac tg                                              22

<210> SEQ ID NO 49
<211> LENGTH: 22
<212> TYPE: DNA
<213> ORGANISM: Artificial Sequence
<220> FEATURE:

<223> OTHER INFORMATION: oligonucleotide

<400> SEQUENCE: 49
gctaagccca gtgaggggac ag                                          22

<210> SEQ ID NO 50
<211> LENGTH: 22
<212> TYPE: DNA
<213> ORGANISM: Artificial Sequence
<220> FEATURE:
<223> OTHER INFORMATION: oligonucleotide

<400> SEQUENCE: 50 gccatacccca gccccaggat gg                                         22

<210> SEQ ID NO 51
<211> LENGTH: 21
<212> TYPE: DNA
<213> ORGANISM: Artificial Sequence
<220> FEATURE:
<223> OTHER INFORMATION: oligonucleotide

<400> SEQUENCE: 51
cgcctgcagg atgggttaag g                                           21

<210> SEQ ID NO 52
<211> LENGTH: 23
<212> TYPE: DNA
<213> ORGANISM: Artificial Sequence
<220> FEATURE:
<223> OTHER INFORMATION: oligonucleotide

<400> SEQUENCE: 52
gcgtcactgc aattactgct tcc                                         23

<210> SEQ ID NO 53
<211> LENGTH: 22
<212> TYPE: DNA
<213> ORGANISM: Artificial Sequence
<220> FEATURE:
<223> OTHER INFORMATION: oligonucleotide

<400> SEQUENCE: 53
agccaggggt accaagtgtt tg                                          22

<210> SEQ ID NO 54
<211> LENGTH: 23
<212> TYPE: DNA
<213> ORGANISM: Artificial Sequence
<220> FEATURE:
<223> OTHER INFORMATION: oligonucleotide

<400> SEQUENCE: 54
ggggtaatgt gatacagccg atg                                         23

<210> SEQ ID NO 55
<211> LENGTH: 25
<212> TYPE: DNA
<213> ORGANISM: Artificial Sequence
<220> FEATURE:
<223> OTHER INFORMATION: oligonucleotide

<400> SEQUENCE: 55
tggcgtgggc ttaagcagtt gccag                                       25

```
<210> SEQ ID NO 56
<211> LENGTH: 25
<212> TYPE: DNA
<213> ORGANISM: Artificial Sequence
<220> FEATURE:
<223> OTHER INFORMATION: oligonucleotide

<400> SEQUENCE: 56
aaccacagac ttgtgcctgg cgtcc                                               25

<210> SEQ ID NO 57
<211> LENGTH: 23
<212> TYPE: DNA
<213> ORGANISM: Artificial Sequence
<220> FEATURE:
<223> OTHER INFORMATION: oligonucleotide

<400> SEQUENCE: 57
tgctgtccct accgccaggt cag                                                 23

<210> SEQ ID NO 58
<211> LENGTH: 25
<212> TYPE: DNA
<213> ORGANISM: Artificial Sequence
<220> FEATURE:
<223> OTHER INFORMATION: oligonucleotide

<400> SEQUENCE: 58
tgagcagagg gcaccctccg agtgg                                               25

<210> SEQ ID NO 59
<211> LENGTH: 23
<212> TYPE: DNA
<213> ORGANISM: Artificial Sequence
<220> FEATURE:
<223> OTHER INFORMATION: oligonucleotide

<400> SEQUENCE: 59
gtcgggacaa agtttagggc gtc                                                 23

<210> SEQ ID NO 60
<211> LENGTH: 23
<212> TYPE: DNA
<213> ORGANISM: Artificial Sequence
<220> FEATURE:
<223> OTHER INFORMATION: oligonucleotide

<400> SEQUENCE: 60
ggcgcctaga cgaagtccac agc                                                 23

<210> SEQ ID NO 61
<211> LENGTH: 25
<212> TYPE: DNA
<213> ORGANISM: Artificial Sequence
<220> FEATURE:
<223> OTHER INFORMATION: oligonucleotide

<400> SEQUENCE: 61
gcttggagac aggtgacggt ccctg                                               25

<210> SEQ ID NO 62
<211> LENGTH: 24
<212> TYPE: DNA
<213> ORGANISM: Artificial Sequence
<220> FEATURE:
<223> OTHER INFORMATION: oligonucleotide
```

<400> SEQUENCE: 62
atccagccct ggactagccc cacg                                    24

<210> SEQ ID NO 63
<211> LENGTH: 21
<212> TYPE: DNA
<213> ORGANISM: Artificial Sequence
<220> FEATURE:
<223> OTHER INFORMATION: oligonucleotide

<400> SEQUENCE: 63
accgcggcca gccataactc t                                       21

<210> SEQ ID NO 64
<211> LENGTH: 24
<212> TYPE: DNA
<213> ORGANISM: Artificial Sequence
<220> FEATURE:
<223> OTHER INFORMATION: oligonucleotide

<400> SEQUENCE: 64
atcaaggcac ctcaacataa taat                                    24

<210> SEQ ID NO 65
<211> LENGTH: 19
<212> TYPE: DNA
<213> ORGANISM: Artificial Sequence
<220> FEATURE:
<223> OTHER INFORMATION: oligonucleotide

<400> SEQUENCE: 65
cagggaggag agtgatttg                                          19

<210> SEQ ID NO 66
<211> LENGTH: 20
<212> TYPE: DNA
<213> ORGANISM: Artificial Sequence
<220> FEATURE:
<223> OTHER INFORMATION: oligonucleotide

<400> SEQUENCE: 66
gcagagcagt gggcatcaac                                         20

<210> SEQ ID NO 67
<211> LENGTH: 19
<212> TYPE: DNA
<213> ORGANISM: Artificial Sequence
<220> FEATURE:
<223> OTHER INFORMATION: oligonucleotide

<400> SEQUENCE: 67
tgctgtgtta tggtcgatg                                          19

<210> SEQ ID NO 68
<211> LENGTH: 19
<212> TYPE: DNA
<213> ORGANISM: Artificial Sequence
<220> FEATURE:
<223> OTHER INFORMATION: oligonucleotide

<400> SEQUENCE: 68
gtacccttct gcgtgtcac                                          19

<210> SEQ ID NO 69
<211> LENGTH: 18

```
<212> TYPE: DNA
<213> ORGANISM: Artificial Sequence
<220> FEATURE:
<223> OTHER INFORMATION: oligonucleotide

<400> SEQUENCE: 69
atacctgctg ccgtctac                                                    18

<210> SEQ ID NO 70
<211> LENGTH: 19
<212> TYPE: DNA
<213> ORGANISM: Artificial Sequence
<220> FEATURE:
<223> OTHER INFORMATION: oligonucleotide

<400> SEQUENCE: 70
acgttgcagg tgtagccag                                                   19

<210> SEQ ID NO 71
<211> LENGTH: 20
<212> TYPE: DNA
<213> ORGANISM: Artificial Sequence
<220> FEATURE:
<223> OTHER INFORMATION: oligonucleotide

<400> SEQUENCE: 71
caaaactagg tcaaaggtca                                                  20

<210> SEQ ID NO 72
<211> LENGTH: 20
<212> TYPE: DNA
<213> ORGANISM: Artificial Sequence
<220> FEATURE:
<223> OTHER INFORMATION: oligonucleotide

<400> SEQUENCE: 72
ggacagtact gaagactctg                                                  20

<210> SEQ ID NO 73
<211> LENGTH: 20
<212> TYPE: DNA
<213> ORGANISM: Artificial Sequence
<220> FEATURE:
<223> OTHER INFORMATION: oligonucleotide

<400> SEQUENCE: 73
ggatggcagc ttgtaatgtg                                                  20

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74
gaagtgtgac gtggacatcc                                                  20

<210> SEQ ID NO 75
<211> LENGTH: 20
<212> TYPE: DNA
<213> ORGANISM: Artificial Sequence
<220> FEATURE:
<223> OTHER INFORMATION: oligonucleotide

<400> SEQUENCE: 75
```

```
ccgatccaca cggagtactt                                                       20
```

<210> SEQ ID NO 76
<211> LENGTH: 17
<212> TYPE: PRT
<213> ORGANISM: Homo sapiens

<400> SEQUENCE: 76

```
Met Trp Thr Leu Val Ser Trp Val Ala Leu Thr Ala Gly Leu Val Ala
 1               5                  10                  15

Gly
```

<210> SEQ ID NO 77
<211> LENGTH: 41
<212> TYPE: PRT
<213> ORGANISM: Homo sapiens

<400> SEQUENCE: 77

```
Thr Arg Cys Pro Asp Gly Gln Phe Cys Pro Val Ala Cys Cys Leu Asp
 1               5                  10                  15

Pro Gly Gly Ala Ser Tyr Ser Cys Cys Arg Pro Leu Leu Asp Lys Trp
             20                  25                  30

Pro Thr Thr Leu Ser Arg His Leu Gly
             35                  40
```

<210> SEQ ID NO 78
<211> LENGTH: 65
<212> TYPE: PRT
<213> ORGANISM: Homo sapiens

<400> SEQUENCE: 78

```
Gly Pro Cys Gln Val Asp Ala His Cys Ser Ala Gly His Ser Cys Ile
 1               5                  10                  15

Phe Thr Val Ser Gly Thr Ser Ser Cys Cys Pro Phe Pro Glu Ala Val
             20                  25                  30

Ala Cys Gly Asp Gly His His Cys Cys Pro Arg Gly Phe His Cys Ser
             35                  40                  45

Ala Asp Gly Arg Ser Cys Phe Gln Arg Ser Gly Asn Asn Ser Val Gly
         50                  55                  60

Ala
65
```

<210> SEQ ID NO 79
<211> LENGTH: 81
<212> TYPE: PRT
<213> ORGANISM: Homo sapiens

<400> SEQUENCE: 79

```
Ile Gln Cys Pro Asp Ser Gln Phe Glu Cys Pro Asp Phe Ser Thr Cys
 1               5                  10                  15

Cys Val Met Asp Gly Ser Trp Gly Cys Cys Pro Met Pro Gln Ala Ser
             20                  25                  30

Cys Cys Glu Asp Arg Val His Cys Cys Pro His Gly Ala Phe Cys Asp
             35                  40                  45

Leu Val His Thr Arg Cys Ile Thr Pro Thr Gly Thr His Pro Leu Ala
         50                  55                  60

Lys Lys Leu Pro Ala Gln Arg Thr Asn Arg Ala Val Ala Leu Ser Ser
65                  70                  75                  80

Ser
```

-continued

<210> SEQ ID NO 80
<211> LENGTH: 76
<212> TYPE: PRT
<213> ORGANISM: Homo sapiens

<400> SEQUENCE: 80

Val Met Cys Pro Asp Ala Arg Ser Arg Cys Pro Asp Gly Ser Thr Cys
1               5                   10                  15

Cys Glu Leu Pro Ser Gly Lys Tyr Gly Cys Cys Pro Met Pro Asn Ala
            20                  25                  30

Thr Cys Cys Ser Asp His Leu His Cys Cys Pro Gln Asp Thr Val Cys
        35                  40                  45

Asp Leu Ile Gln Ser Lys Cys Leu Ser Lys Glu Asn Ala Thr Thr Asp
    50                  55                  60

Leu Leu Thr Lys Leu Pro Ala His Thr Val Gly Asp
65                  70                  75

<210> SEQ ID NO 81
<211> LENGTH: 82
<212> TYPE: PRT
<213> ORGANISM: Homo sapiens

<400> SEQUENCE: 81

Val Lys Cys Asp Met Glu Val Ser Cys Pro Asp Gly Tyr Thr Cys Cys
1               5                   10                  15

Arg Leu Gln Ser Gly Ala Trp Gly Cys Cys Pro Phe Thr Gln Ala Val
            20                  25                  30

Cys Cys Glu Asp His Ile His Cys Cys Pro Ala Gly Phe Thr Cys Asp
        35                  40                  45

Thr Gln Lys Gly Thr Cys Glu Gln Gly Pro His Gln Val Pro Trp Met
    50                  55                  60

Glu Lys Ala Pro Ala His Leu Ser Leu Pro Asp Pro Gln Ala Leu Lys
65                  70                  75                  80

Arg Asp

<210> SEQ ID NO 82
<211> LENGTH: 78
<212> TYPE: PRT
<213> ORGANISM: Homo sapiens

<400> SEQUENCE: 82

Val Pro Cys Asp Asn Val Ser Ser Cys Pro Ser Ser Asp Thr Cys Cys
1               5                   10                  15

Gln Leu Thr Ser Gly Glu Trp Gly Cys Cys Pro Ile Pro Glu Ala Val
            20                  25                  30

Cys Cys Ser Asp His Gln His Cys Cys Pro Gln Arg Tyr Thr Cys Val
        35                  40                  45

Ala Glu Gly Gln Cys Gln Arg Gly Ser Glu Ile Val Ala Gly Leu Glu
    50                  55                  60

Lys Met Pro Ala Arg Arg Ala Ser Leu Ser His Pro Arg Asp
65                  70                  75

<210> SEQ ID NO 83
<211> LENGTH: 77
<212> TYPE: PRT
<213> ORGANISM: Homo sapiens

<400> SEQUENCE: 83

```
Ile Gly Cys Asp Gln His Thr Ser Cys Pro Val Gly Gln Thr Cys Cys
1               5                   10                  15

Pro Ser Leu Gly Gly Ser Trp Ala Cys Cys Gln Leu Pro His Ala Val
            20                  25                  30

Cys Cys Glu Asp Arg Gln His Cys Cys Pro Ala Gly Tyr Thr Cys Asn
        35                  40                  45

Val Lys Ala Arg Ser Cys Glu Lys Glu Val Val Ser Ala Gln Pro Ala
    50                  55                  60

Thr Phe Leu Ala Arg Ser Pro His Val Gly Val Lys Asp
65                  70                  75

<210> SEQ ID NO 84
<211> LENGTH: 75
<212> TYPE: PRT
<213> ORGANISM: Homo sapiens

<400> SEQUENCE: 84

Val Glu Cys Gly Glu Gly His Phe Cys His Asp Asn Gln Thr Cys Cys
1               5                   10                  15

Arg Asp Asn Arg Gln Gly Trp Ala Cys Cys Pro Tyr Arg Gln Gly Val
            20                  25                  30

Cys Cys Ala Asp Arg Arg His Cys Cys Pro Ala Gly Phe Arg Cys Ala
        35                  40                  45

Ala Arg Gly Thr Lys Cys Leu Arg Arg Glu Ala Pro Arg Trp Asp Ala
    50                  55                  60

Pro Leu Arg Asp Pro Ala Leu Arg Gln Leu Leu
65                  70                  75

<210> SEQ ID NO 85
<211> LENGTH: 20
<212> TYPE: DNA
<213> ORGANISM: Artificial Sequence
<220> FEATURE:
<223> OTHER INFORMATION: oligonucleotide

<400> SEQUENCE: 85
ggccatgtga gcttgaggtt                                            20

<210> SEQ ID NO 86
<211> LENGTH: 31
<212> TYPE: DNA
<213> ORGANISM: Artificial Sequence
<220> FEATURE:
<223> OTHER INFORMATION: oligonucleotide

<400> SEQUENCE: 86
gagggagtat agtgtatgct tctactgaat a                               31

<210> SEQ ID NO 87
<211> LENGTH: 26
<212> TYPE: DNA
<213> ORGANISM: Artificial Sequence
<220> FEATURE:
<223> OTHER INFORMATION: oligonucleotide

<400> SEQUENCE: 87
gagtagaaaa gaaacacagc attcca                                     26

<210> SEQ ID NO 88
<211> LENGTH: 20
<212> TYPE: DNA
```

```
<213> ORGANISM: Artificial Sequence
<220> FEATURE:
<223> OTHER INFORMATION: oligonucleotide

<400> SEQUENCE: 88
ccgctcccat tggctactta                                               20

<210> SEQ ID NO 89
<211> LENGTH: 22
<212> TYPE: DNA
<213> ORGANISM: Artificial Sequence
<220> FEATURE:
<223> OTHER INFORMATION: oligonucleotide

<400> SEQUENCE: 89
gccagacgtt ccttggtact tt                                            22

<210> SEQ ID NO 90
<211> LENGTH: 20
<212> TYPE: DNA
<213> ORGANISM: Artificial Sequence
<220> FEATURE:
<223> OTHER INFORMATION: oligonucleotide

<400> SEQUENCE: 90
ccaccagccc tgctgttaag                                               20

<210> SEQ ID NO 91
<211> LENGTH: 20
<212> TYPE: DNA
<213> ORGANISM: Artificial Sequence
<220> FEATURE:
<223> OTHER INFORMATION: oligonucleotide

<400> SEQUENCE: 91
caaatggccc acaacactga                                               20

<210> SEQ ID NO 92
<211> LENGTH: 20
<212> TYPE: DNA
<213> ORGANISM: Artificial Sequence
<220> FEATURE:
<223> OTHER INFORMATION: oligonucleotide

<400> SEQUENCE: 92
agagcagtgg gcatcaacct                                               20

<210> SEQ ID NO 93
<211> LENGTH: 22
<212> TYPE: DNA
<213> ORGANISM: Artificial Sequence
<220> FEATURE:
<223> OTHER INFORMATION: oligonucleotide

<400> SEQUENCE: 93
atgcaggttt ctctgtgttc ca                                            22

<210> SEQ ID NO 94
<211> LENGTH: 20
<212> TYPE: DNA
<213> ORGANISM: Artificial Sequence
<220> FEATURE:
<223> OTHER INFORMATION: oligonucleotide

<400> SEQUENCE: 94
cccagctgca cctgatcttt                                               20
```

<210> SEQ ID NO 95
<211> LENGTH: 20
<212> TYPE: DNA
<213> ORGANISM: Artificial Sequence
<220> FEATURE:
<223> OTHER INFORMATION: oligonucleotide

<400> SEQUENCE: 95
tccctgagtg ggctggtagt                                           20

<210> SEQ ID NO 96
<211> LENGTH: 21
<212> TYPE: DNA
<213> ORGANISM: Artificial Sequence
<220> FEATURE:
<223> OTHER INFORMATION: oligonucleotide

<400> SEQUENCE: 96
gcacccacgg agttgttacc t                                         21

<210> SEQ ID NO 97
<211> LENGTH: 22
<212> TYPE: DNA
<213> ORGANISM: Artificial Sequence
<220> FEATURE:
<223> OTHER INFORMATION: oligonucleotide

<400> SEQUENCE: 97
gaagacggag tcaggaccat tt                                        22

<210> SEQ ID NO 98
<211> LENGTH: 20
<212> TYPE: DNA
<213> ORGANISM: Artificial Sequence
<220> FEATURE:
<223> OTHER INFORMATION: oligonucleotide

<400> SEQUENCE: 98
agcagtgcac cctgtcttca                                           20

<210> SEQ ID NO 99
<211> LENGTH: 20
<212> TYPE: DNA
<213> ORGANISM: Artificial Sequence
<220> FEATURE:
<223> OTHER INFORMATION: oligonucleotide

<400> SEQUENCE: 99
tgtccagctc ggtcatgtgt                                           20

<210> SEQ ID NO 100
<211> LENGTH: 19
<212> TYPE: DNA
<213> ORGANISM: Artificial Sequence
<220> FEATURE:
<223> OTHER INFORMATION: oligonucleotide

<400> SEQUENCE: 100
cactcacgtt gggcattgg                                            19

<210> SEQ ID NO 101
<211> LENGTH: 19
<212> TYPE: DNA
<213> ORGANISM: Artificial Sequence
<220> FEATURE:

-continued

<223> OTHER INFORMATION: oligonucleotide

<400> SEQUENCE: 101
cacctgctgc tccgatcac                                                19

<210> SEQ ID NO 102
<211> LENGTH: 24
<212> TYPE: DNA
<213> ORGANISM: Artificial Sequence
<220> FEATURE:
<223> OTHER INFORMATION: oligonucleotide

<400> SEQUENCE: 102
gatcaggtca cacacagtgt cttg                                          24

<210> SEQ ID NO 103
<211> LENGTH: 22
<212> TYPE: DNA
<213> ORGANISM: Artificial Sequence
<220> FEATURE:
<223> OTHER INFORMATION: oligonucleotide

<400> SEQUENCE: 103
tcctctctgc ttccctcaca gt                                            22

<210> SEQ ID NO 104
<211> LENGTH: 22
<212> TYPE: DNA
<213> ORGANISM: Artificial Sequence
<220> FEATURE:
<223> OTHER INFORMATION: oligonucleotide

<400> SEQUENCE: 104
tgtagacggc agcaggtata gc                                            22

<210> SEQ ID NO 105
<211> LENGTH: 18
<212> TYPE: DNA
<213> ORGANISM: Artificial Sequence
<220> FEATURE:
<223> OTHER INFORMATION: oligonucleotide

<400> SEQUENCE: 105
gcctgccaga cccacaag                                                 18

<210> SEQ ID NO 106
<211> LENGTH: 20
<212> TYPE: DNA
<213> ORGANISM: Artificial Sequence
<220> FEATURE:
<223> OTHER INFORMATION: oligonucleotide

<400> SEQUENCE: 106
ggagggacag ctgctgacat                                               20

<210> SEQ ID NO 107
<211> LENGTH: 18
<212> TYPE: DNA
<213> ORGANISM: Artificial Sequence
<220> FEATURE:
<223> OTHER INFORMATION: oligonucleotide

<400> SEQUENCE: 107
ctgccagttg ccccatgt                                                 18

```
<210> SEQ ID NO 108
<211> LENGTH: 23
<212> TYPE: DNA
<213> ORGANISM: Artificial Sequence
<220> FEATURE:
<223> OTHER INFORMATION: oligonucleotide

<400> SEQUENCE: 108
cattatgttc ctgtcccctc act                                            23

<210> SEQ ID NO 109
<211> LENGTH: 20
<212> TYPE: DNA
<213> ORGANISM: Artificial Sequence
<220> FEATURE:
<223> OTHER INFORMATION: oligonucleotide

<400> SEQUENCE: 109
gctggctaca cctgcaacgt                                                20

<210> SEQ ID NO 110
<211> LENGTH: 21
<212> TYPE: DNA
<213> ORGANISM: Artificial Sequence
<220> FEATURE:
<223> OTHER INFORMATION: oligonucleotide

<400> SEQUENCE: 110
gggcagagac cacttccttc t                                              21

<210> SEQ ID NO 111
<211> LENGTH: 14
<212> TYPE: DNA
<213> ORGANISM: Artificial Sequence
<220> FEATURE:
<223> OTHER INFORMATION: oligonucleotide

<400> SEQUENCE: 111
aggctcgatc ctgc                                                      14

<210> SEQ ID NO 112
<211> LENGTH: 17
<212> TYPE: DNA
<213> ORGANISM: Artificial Sequence
<220> FEATURE:
<223> OTHER INFORMATION: oligonucleotide

<400> SEQUENCE: 112
ctgggacgcc cctttga                                                   17

<210> SEQ ID NO 113
<211> LENGTH: 23
<212> TYPE: DNA
<213> ORGANISM: Artificial Sequence
<220> FEATURE:
<223> OTHER INFORMATION: oligonucleotide

<400> SEQUENCE: 113
gggctgcaga gtcttcagta ctg                                            23

<210> SEQ ID NO 114
<211> LENGTH: 28
<212> TYPE: DNA
<213> ORGANISM: Artificial Sequence
<220> FEATURE:
<223> OTHER INFORMATION: oligonucleotide
```

```
<400> SEQUENCE: 114
ttactgaaga atggagagag aattgaaa                                          28

<210> SEQ ID NO 115
<211> LENGTH: 22
<212> TYPE: DNA
<213> ORGANISM: Artificial Sequence
<220> FEATURE:
<223> OTHER INFORMATION: oligonucleotide

<400> SEQUENCE: 115
gaccagtcct tgctgaaaga ca                                                22

<210> SEQ ID NO 116
<211> LENGTH: 27
<212> TYPE: DNA
<213> ORGANISM: Artificial Sequence
<220> FEATURE:
<223> OTHER INFORMATION: oligonucleotide

<400> SEQUENCE: 116
gggtcaatat gtaattttca gtgttag                                           27

<210> SEQ ID NO 117
<211> LENGTH: 25
<212> TYPE: DNA
<213> ORGANISM: Artificial Sequence
<220> FEATURE:
<223> OTHER INFORMATION: oligonucleotide

<400> SEQUENCE: 117
ttgtctaaca aaaaagccaa aaacg                                             25

<210> SEQ ID NO 118
<211> LENGTH: 23
<212> TYPE: DNA
<213> ORGANISM: Artificial Sequence
<220> FEATURE:
<223> OTHER INFORMATION: oligonucleotide

<400> SEQUENCE: 118
gtcatgtctg ttccttcact gcc                                               23

<210> SEQ ID NO 119
<211> LENGTH: 23
<212> TYPE: DNA
<213> ORGANISM: Artificial Sequence
<220> FEATURE:
<223> OTHER INFORMATION: oligonucleotide

<400> SEQUENCE: 119
tcatgggtct gaagagtct ccag                                               23

<210> SEQ ID NO 120
<211> LENGTH: 25
<212> TYPE: DNA
<213> ORGANISM: Artificial Sequence
<220> FEATURE:
<223> OTHER INFORMATION: oligonucleotide

<400> SEQUENCE: 120
aggtagaatt tgcttcaatc tccag                                             25

<210> SEQ ID NO 121
<211> LENGTH: 20
```

```
<212> TYPE: DNA
<213> ORGANISM: Artificial Sequence
<220> FEATURE:
<223> OTHER INFORMATION: oligonucleotide

<400> SEQUENCE: 121
attgctgagc ccaggtgagt                                                  20

<210> SEQ ID NO 122
<211> LENGTH: 19
<212> TYPE: DNA
<213> ORGANISM: Artificial Sequence
<220> FEATURE:
<223> OTHER INFORMATION: oligonucleotide

<400> SEQUENCE: 122
cccataatga cggccctgt                                                   19

<210> SEQ ID NO 123
<211> LENGTH: 19
<212> TYPE: DNA
<213> ORGANISM: Artificial Sequence
<220> FEATURE:
<223> OTHER INFORMATION: oligonucleotide

<400> SEQUENCE: 123
caaccgccaa aaggaaggt                                                   19

<210> SEQ ID NO 124
<211> LENGTH: 20
<212> TYPE: DNA
<213> ORGANISM: Artificial Sequence
<220> FEATURE:
<223> OTHER INFORMATION: oligonucleotide

<400> SEQUENCE: 124
attctcttgc caagctgcac                                                  20

<210> SEQ ID NO 125
<211> LENGTH: 20
<212> TYPE: DNA
<213> ORGANISM: Artificial Sequence
<220> FEATURE:
<223> OTHER INFORMATION: oligonucleotide

<400> SEQUENCE: 125
ctaggtgcag gcgagatagg                                                  20

<210> SEQ ID NO 126
<211> LENGTH: 24
<212> TYPE: DNA
<213> ORGANISM: Artificial Sequence
<220> FEATURE:
<223> OTHER INFORMATION: oligonucleotide

<400> SEQUENCE: 126
cagagtgcgt gaggacacgt agag                                             24

<210> SEQ ID NO 127
<211> LENGTH: 24
<212> TYPE: DNA
<213> ORGANISM: Artificial Sequence
<220> FEATURE:
<223> OTHER INFORMATION: oligonucleotide

<400> SEQUENCE: 127
```

```
aagcacaggg gagggtattg agtg                                          24

<210> SEQ ID NO 128
<211> LENGTH: 24
<212> TYPE: DNA
<213> ORGANISM: Artificial Sequence
<220> FEATURE:
<223> OTHER INFORMATION: oligonucleotide

<400> SEQUENCE: 128
cggaacaagg agaagagcaa agag                                          24

<210> SEQ ID NO 129
<211> LENGTH: 25
<212> TYPE: DNA
<213> ORGANISM: Artificial Sequence
<220> FEATURE:
<223> OTHER INFORMATION: oligonucleotide

<400> SEQUENCE: 129
gaatgaggaa ataaaccagg gatgg                                         25

<210> SEQ ID NO 130
<211> LENGTH: 22
<212> TYPE: DNA
<213> ORGANISM: Artificial Sequence
<220> FEATURE:
<223> OTHER INFORMATION: oligonucleotide

<400> SEQUENCE: 130
accaccttcc cttcggtctg ct                                            22

<210> SEQ ID NO 131
<211> LENGTH: 25
<212> TYPE: DNA
<213> ORGANISM: Artificial Sequence
<220> FEATURE:
<223> OTHER INFORMATION: oligonucleotide

<400> SEQUENCE: 131
ccagccctgt gtattctcaa caaaa                                         25

<210> SEQ ID NO 132
<211> LENGTH: 25
<212> TYPE: DNA
<213> ORGANISM: Artificial Sequence
<220> FEATURE:
<223> OTHER INFORMATION: oligonucleotide

<400> SEQUENCE: 132
ggtctccttc gactctcaga ttcct                                         25

<210> SEQ ID NO 133
<211> LENGTH: 22
<212> TYPE: DNA
<213> ORGANISM: Artificial Sequence
<220> FEATURE:
<223> OTHER INFORMATION: oligonucleotide

<400> SEQUENCE: 133
cctggaaggg aaacccacac ag                                            22

<210> SEQ ID NO 134
<211> LENGTH: 20
<212> TYPE: DNA
<213> ORGANISM: Artificial Sequence
```

```
<220> FEATURE:
<223> OTHER INFORMATION: oligonucleotide

<400> SEQUENCE: 134
atgactcaca tgccactgga                                              20

<210> SEQ ID NO 135
<211> LENGTH: 20
<212> TYPE: DNA
<213> ORGANISM: Artificial Sequence
<220> FEATURE:
<223> OTHER INFORMATION: oligonucleotide

<400> SEQUENCE: 135
gcagtgaatc agcctgacaa                                              20

<210> SEQ ID NO 136
<211> LENGTH: 20
<212> TYPE: DNA
<213> ORGANISM: Artificial Sequence
<220> FEATURE:
<223> OTHER INFORMATION: oligonucleotide

<400> SEQUENCE: 136
caaccaaagg gtatcggcag                                              20

<210> SEQ ID NO 137
<211> LENGTH: 21
<212> TYPE: DNA
<213> ORGANISM: Artificial Sequence
<220> FEATURE:
<223> OTHER INFORMATION: oligonucleotide

<400> SEQUENCE: 137
ggaaggtctc tcttgccatg g                                            21

<210> SEQ ID NO 138
<211> LENGTH: 26
<212> TYPE: DNA
<213> ORGANISM: Artificial Sequence
<220> FEATURE:
<223> OTHER INFORMATION: oligonucleotide

<400> SEQUENCE: 138
gtagtatacc cccatcttat aacggg                                       26

<210> SEQ ID NO 139
<211> LENGTH: 20
<212> TYPE: DNA
<213> ORGANISM: Artificial Sequence
<220> FEATURE:
<223> OTHER INFORMATION: oligonucleotide

<400> SEQUENCE: 139
tggtcttgag ccaaacagcc                                              20

<210> SEQ ID NO 140
<211> LENGTH: 20
<212> TYPE: DNA
<213> ORGANISM: Artificial Sequence
<220> FEATURE:
<223> OTHER INFORMATION: oligonucleotide

<400> SEQUENCE: 140
gatctgcagc tgctgtgtgt                                              20
```

<210> SEQ ID NO 141
<211> LENGTH: 20
<212> TYPE: DNA
<213> ORGANISM: Artificial Sequence
<220> FEATURE:
<223> OTHER INFORMATION: oligonucleotide

<400> SEQUENCE: 141
tgcttaccct catcctggtc                                               20

<210> SEQ ID NO 142
<211> LENGTH: 24
<212> TYPE: DNA
<213> ORGANISM: Artificial Sequence
<220> FEATURE:
<223> OTHER INFORMATION: oligonucleotide

<400> SEQUENCE: 142
aagagaatga agtggtcagg gaag                                          24

<210> SEQ ID NO 143
<211> LENGTH: 22
<212> TYPE: DNA
<213> ORGANISM: Artificial Sequence
<220> FEATURE:
<223> OTHER INFORMATION: oligonucleotide

<400> SEQUENCE: 143
tgacttggtc attttgaacccc                                             22

<210> SEQ ID NO 144
<211> LENGTH: 20
<212> TYPE: DNA
<213> ORGANISM: Artificial Sequence
<220> FEATURE:
<223> OTHER INFORMATION: oligonucleotide

<400> SEQUENCE: 144
ataccactcc ctgccaccct                                               20

<210> SEQ ID NO 145
<211> LENGTH: 22
<212> TYPE: DNA
<213> ORGANISM: Artificial Sequence
<220> FEATURE:
<223> OTHER INFORMATION: oligonucleotide

<400> SEQUENCE: 145
cccattagac gtggccatta at                                            22

<210> SEQ ID NO 146
<211> LENGTH: 20
<212> TYPE: DNA
<213> ORGANISM: Artificial Sequence
<220> FEATURE:
<223> OTHER INFORMATION: oligonucleotide

<400> SEQUENCE: 146
accaaggttg aggtcccaga                                               20

<210> SEQ ID NO 147
<211> LENGTH: 20
<212> TYPE: DNA
<213> ORGANISM: Artificial Sequence
<220> FEATURE:
<223> OTHER INFORMATION: oligonucleotide

```
<400> SEQUENCE: 147
cccttaggaa catccctccc                                            20

<210> SEQ ID NO 148
<211> LENGTH: 20
<212> TYPE: DNA
<213> ORGANISM: Artificial Sequence
<220> FEATURE:
<223> OTHER INFORMATION: oligonucleotide

<400> SEQUENCE: 148
aggtcaggca gcactagcat                                            20

<210> SEQ ID NO 149
<211> LENGTH: 20
<212> TYPE: DNA
<213> ORGANISM: Artificial Sequence
<220> FEATURE:
<223> OTHER INFORMATION: oligonucleotide

<400> SEQUENCE: 149
ttgcttaact gccaggctct                                            20

<210> SEQ ID NO 150
<211> LENGTH: 20
<212> TYPE: DNA
<213> ORGANISM: Artificial Sequence
<220> FEATURE:
<223> OTHER INFORMATION: oligonucleotide

<400> SEQUENCE: 150
ctgtcaatgc cccagacacg                                            20

<210> SEQ ID NO 151
<211> LENGTH: 22
<212> TYPE: DNA
<213> ORGANISM: Artificial Sequence
<220> FEATURE:
<223> OTHER INFORMATION: oligonucleotide

<400> SEQUENCE: 151
cccccaagga gtttcagtaa gc                                         22

<210> SEQ ID NO 152
<211> LENGTH: 20
<212> TYPE: DNA
<213> ORGANISM: Artificial Sequence
<220> FEATURE:
<223> OTHER INFORMATION: oligonucleotide

<400> SEQUENCE: 152
ttgagaaggc tcaggcagtc                                            20

<210> SEQ ID NO 153
<211> LENGTH: 24
<212> TYPE: DNA
<213> ORGANISM: Artificial Sequence
<220> FEATURE:
<223> OTHER INFORMATION: oligonucleotide

<400> SEQUENCE: 153
ggccatttgt cctagaaaga cagg                                       24

<210> SEQ ID NO 154
```

```
<211> LENGTH: 18
<212> TYPE: DNA
<213> ORGANISM: Artificial Sequence
<220> FEATURE:
<223> OTHER INFORMATION: oligonucleotide

<400> SEQUENCE: 154
tgggacgccc ctttgagg                                                   18

<210> SEQ ID NO 155
<211> LENGTH: 19
<212> TYPE: DNA
<213> ORGANISM: Artificial Sequence
<220> FEATURE:
<223> OTHER INFORMATION: oligonucleotide

<400> SEQUENCE: 155
cacagggtcc actgaaacg                                                  19

<210> SEQ ID NO 156
<211> LENGTH: 20
<212> TYPE: DNA
<213> ORGANISM: Artificial Sequence
<220> FEATURE:
<223> OTHER INFORMATION: oligonucleotide

<400> SEQUENCE: 156
gggcttagcg ttcaggtgta                                                 20

<210> SEQ ID NO 157
<211> LENGTH: 20
<212> TYPE: DNA
<213> ORGANISM: Artificial Sequence
<220> FEATURE:
<223> OTHER INFORMATION: oligonucleotide

<400> SEQUENCE: 157
tggagatttg accccaagag                                                 20

<210> SEQ ID NO 158
<211> LENGTH: 20
<212> TYPE: DNA
<213> ORGANISM: Artificial Sequence
<220> FEATURE:
<223> OTHER INFORMATION: oligonucleotide

<400> SEQUENCE: 158
tctagtgggg gttgggtatg                                                 20

<210> SEQ ID NO 159
<211> LENGTH: 20
<212> TYPE: DNA
<213> ORGANISM: Artificial Sequence
<220> FEATURE:
<223> OTHER INFORMATION: oligonucleotide

<400> SEQUENCE: 159
aggagcagag agcgagagtg                                                 20

<210> SEQ ID NO 160
<211> LENGTH: 26
<212> TYPE: DNA
<213> ORGANISM: Artificial Sequence
<220> FEATURE:
<223> OTHER INFORMATION: oligonucleotide

<400> SEQUENCE: 160
``` tcgaagcctga cattccatat agtat                                    26

<210> SEQ ID NO 161
<211> LENGTH: 23
<212> TYPE: DNA
<213> ORGANISM: Artificial Sequence
<220> FEATURE:
<223> OTHER INFORMATION: oligonucleotide

<400> SEQUENCE: 161
gagcaagacc ctgacaacac atc                                       23

<210> SEQ ID NO 162
<211> LENGTH: 20
<212> TYPE: DNA
<213> ORGANISM: Artificial Sequence
<220> FEATURE:
<223> OTHER INFORMATION: oligonucleotide

<400> SEQUENCE: 162
cacctaccac cccaactctg                                           20

<210> SEQ ID NO 163
<211> LENGTH: 20
<212> TYPE: DNA
<213> ORGANISM: Artificial Sequence
<220> FEATURE:
<223> OTHER INFORMATION: oligonucleotide

<400> SEQUENCE: 163
cattgggtcc tcttggtgtc                                           20

<210> SEQ ID NO 164
<211> LENGTH: 20
<212> TYPE: DNA
<213> ORGANISM: Artificial Sequence
<220> FEATURE:
<223> OTHER INFORMATION: oligonucleotide

<400> SEQUENCE: 164
gacacattga ggctgagcac                                           20

<210> SEQ ID NO 165
<211> LENGTH: 20
<212> TYPE: DNA
<213> ORGANISM: Artificial Sequence
<220> FEATURE:
<223> OTHER INFORMATION: oligonucleotide

<400> SEQUENCE: 165
accaccctga acctggatct                                           20

<210> SEQ ID NO 166
<211> LENGTH: 20
<212> TYPE: DNA
<213> ORGANISM: Artificial Sequence
<220> FEATURE:
<223> OTHER INFORMATION: oligonucleotide

<400> SEQUENCE: 166
ggctcagcac caaccttccc                                           20

<210> SEQ ID NO 167
<211> LENGTH: 22
<212> TYPE: DNA

```
<213> ORGANISM: Artificial Sequence
<220> FEATURE:
<223> OTHER INFORMATION: oligonucleotide

<400> SEQUENCE: 167
gcctggttcc actctccctc tg                                      22
```